(12) United States Patent
Estrada et al.

(10) Patent No.: US 11,072,618 B2
(45) Date of Patent: Jul. 27, 2021

(54) COMPOUNDS, COMPOSITIONS AND METHODS

(71) Applicant: Denali Therapeutics Inc., South San Francisco, CA (US)

(72) Inventors: Anthony A. Estrada, South San Francisco, CA (US); Jianwen A. Feng, South San Francisco, CA (US); Brian Fox, South San Francisco, CA (US); Cheng Hu, South San Francisco, CA (US); Maksim Osipov, South San Francisco, CA (US); Zachary K. Sweeney, South San Francisco, CA (US); Javier de Vicente Fidalgo, South San Francisco, CA (US); Arun Thottumkara, South San Francisco, CA (US)

(73) Assignee: DENALI THERAPEUTICS INC., South San Francisco, CA (US)

(*) Notice: Subject to any disclaimer, the term of this patent is extended or adjusted under 35 U.S.C. 154(b) by 0 days.

(21) Appl. No.: 16/434,533

(22) Filed: Jun. 7, 2019

(65) Prior Publication Data
US 2019/0300537 A1 Oct. 3, 2019

Related U.S. Application Data

(63) Continuation of application No. PCT/US2017/065368, filed on Dec. 8, 2017.

(60) Provisional application No. 62/526,942, filed on Jun. 29, 2017, provisional application No. 62/432,412, filed on Dec. 9, 2016.

(51) Int. Cl.
| | | |
|---|---|---|
| C07D 487/04 | (2006.01) | |
| G01N 33/50 | (2006.01) | |
| C07K 14/00 | (2006.01) | |
| G01N 33/574 | (2006.01) | |
| G01N 33/68 | (2006.01) | |

(52) U.S. Cl.
CPC ............ *C07D 487/04* (2013.01); *C07K 14/00* (2013.01); *G01N 33/50* (2013.01); *G01N 33/5091* (2013.01); *G01N 33/574* (2013.01); *G01N 33/6893* (2013.01)

(58) Field of Classification Search
CPC .... C07D 487/04; G01N 33/50; G01N 33/574; G01N 33/6893; G01N 33/5091
USPC ....................................................... 514/248
See application file for complete search history.

(56) References Cited

U.S. PATENT DOCUMENTS

| | | | |
|---|---|---|---|
| 4,477,464 A | 10/1984 | Slade et al. | |
| 4,871,842 A | 10/1989 | Sugihara et al. | |
| 5,055,464 A | 10/1991 | Murakami et al. | |
| 5,206,234 A | 4/1993 | Bock et al. | |
| 5,206,235 A | 4/1993 | Fisher et al. | |
| 5,283,241 A | 2/1994 | Bochis et al. | |
| 5,284,841 A | 2/1994 | Chu et al. | |
| 5,310,737 A | 5/1994 | Fisher et al. | |
| 5,330,987 A | 7/1994 | Allen et al. | |
| 5,420,271 A | 5/1995 | Warshawsky et al. | |
| 5,428,158 A | 6/1995 | Warshawsky et al. | |
| 5,457,196 A | 10/1995 | Warshawsky et al. | |
| 5,484,917 A | 1/1996 | Lowe, III | |
| 5,596,000 A | 1/1997 | Esser et al. | |
| 5,606,054 A | 2/1997 | Fisher et al. | |
| 5,672,596 A | 9/1997 | Wyvratt et al. | |
| 5,710,153 A | 1/1998 | Ohmoto et al. | |
| 5,712,273 A | 1/1998 | Schnorrenberg et al. | |
| 5,726,307 A | 3/1998 | Schoen et al. | |
| 5,747,235 A | 5/1998 | Farid et al. | |
| 5,783,573 A | 7/1998 | Rozsa et al. | |
| 5,789,587 A | 8/1998 | Fisher et al. | |
| 5,958,924 A | 9/1999 | McCort et al. | |
| 6,028,195 A | 2/2000 | Cho et al. | |
| 6,211,174 B1 | 4/2001 | Devita et al. | |
| 6,335,363 B1 | 1/2002 | Gerlach et al. | |
| 6,350,741 B1 | 2/2002 | Golec et al. | |
| 6,376,484 B1 | 4/2002 | Ohmoto et al. | |
| 7,098,235 B2 | 8/2006 | Sher et al. | |
| 7,109,357 B2 | 9/2006 | Wannamaker et al. | |
| 7,208,600 B2 | 4/2007 | Cottrell et al. | |
| 7,491,743 B2 | 2/2009 | Cuny et al. | |
| 7,842,686 B2 | 11/2010 | Anderson et al. | |
| 7,884,074 B2 | 2/2011 | Petzelbauer et al. | |
| 8,088,890 B2 | 1/2012 | Petzelbauer et al. | |
| 8,242,150 B2 | 8/2012 | Fischer et al. | |
| 8,569,286 B2 | 10/2013 | Hipskind et al. | |
| 8,586,732 B2 | 11/2013 | Corkey et al. | |
| 9,062,002 B2 | 6/2015 | Takhi et al. | |
| 9,062,075 B2 | 6/2015 | Takhi et al. | |

(Continued)

FOREIGN PATENT DOCUMENTS

| | | |
|---|---|---|
| CN | 103664904 | 3/2014 |
| EP | 0322779 | 7/1989 |

(Continued)

OTHER PUBLICATIONS

Shen Kun et al., Copper-catalyzed aminoalkynylation of alkenes with hypervalent iodine reagents, Chemical Science (2017), 8(12), 8265-8270.*
B Testa et al., Prodrug Design in, 5 Encyclopedia of Pharmaceutical Technology, 3008-3014 (J. Swarbrick ed., 3rd ed., 2007).*
Bacqué et al., "Tin-free radical cyclizations for the synthesis of 7-azaoxindoles, 7-azaindolines, tetrahydro[1,8]naphthyridines, and tetrahydro-5H-pyrido[2,3-b]azepin-8-ones", Org Lett. 2004, 6(21), 3671-3674.
Berger et al., "Characterization of GSK'963: a structurally distinct, potent and selective inhibitor of RIP1 kinase", Cell Death Discovery, 2015, 1, 15009. (7 pages).

(Continued)

*Primary Examiner* — Tracy Vivlemore
*Assistant Examiner* — Ebenezer O Sackey
(74) *Attorney, Agent, or Firm* — McNeill Baur PLLC

(57) ABSTRACT

The present disclosure relates generally to methods and compositions for preventing or arresting cell death and/or inflammation.

17 Claims, No Drawings

(56) References Cited

U.S. PATENT DOCUMENTS

| | | |
|---|---|---|
| 2003/0191049 A1 | 10/2003 | Amblard et al. |
| 2004/0002495 A1 | 1/2004 | Sher et al. |
| 2004/0142938 A1 | 7/2004 | Sher et al. |
| 2006/0004013 A1 | 1/2006 | Kimura et al. |
| 2007/0010428 A1 | 1/2007 | McMurray et al. |
| 2007/0117839 A1 | 5/2007 | Kimura et al. |
| 2009/0048213 A1* | 2/2009 | Kimura ............... C07D 401/10 514/80 |
| 2009/0203967 A1 | 8/2009 | Kimura et al. |
| 2011/0046195 A1 | 2/2011 | Blackwell et al. |
| 2011/0135600 A1 | 6/2011 | Stieber et al. |
| 2011/0152253 A1 | 6/2011 | Motoki et al. |
| 2011/0230414 A1 | 9/2011 | Hendricks et al. |
| 2011/0306626 A1 | 12/2011 | Selnick et al. |
| 2012/0315247 A1 | 12/2012 | Xi |
| 2013/0165446 A1 | 6/2013 | Fujita et al. |
| 2015/0315210 A1 | 11/2015 | Hu et al. |
| 2015/0353533 A1 | 12/2015 | Bandyopadhyay et al. |
| 2015/0374662 A1 | 12/2015 | Bode et al. |
| 2017/0008878 A1 | 1/2017 | Bandyopadhyay et al. |
| 2020/0079784 A1* | 3/2020 | Bonanomi ............... A61P 25/16 |

FOREIGN PATENT DOCUMENTS

| | | |
|---|---|---|
| EP | 0462800 | 12/1991 |
| EP | 0703222 | 3/1996 |
| EP | 0728746 | 8/1996 |
| EP | 1939187 | 7/2008 |
| EP | 2493888 | 4/2016 |
| EP | 3017825 | 5/2016 |
| ES | 2081747 | 3/1996 |
| GB | 2272439 | 5/1994 |
| JP | 334977 | 2/1991 |
| JP | 5-239065 | 9/1993 |
| JP | 9-295996 | 11/1997 |
| JP | 10-251295 | 9/1998 |
| JP | 2000-256318 | 9/2000 |
| JP | 2005-035933 | 2/2005 |
| WO | WO-1992/016524 | 10/1992 |
| WO | WO-1994/001421 | 1/1994 |
| WO | WO-1994/004531 | 3/1994 |
| WO | WO-1994/007483 | 4/1994 |
| WO | WO-1994/007486 | 4/1994 |
| WO | WO-1994/08683 | 4/1994 |
| WO | WO-1994/024149 | 10/1994 |
| WO | WO-1995/003290 | 2/1995 |
| WO | WO-1995/016692 | 6/1995 |
| WO | WO-1995/028419 | 10/1995 |
| WO | WO-1995/030687 | 11/1995 |
| WO | WO-1996/005195 | 2/1996 |
| WO | WO-1996/011691 | 4/1996 |
| WO | WO-1996/011701 | 4/1996 |
| WO | WO-1996/011940 | 4/1996 |
| WO | WO-1996/016008 | 5/1996 |
| WO | WO-1996/040653 | 12/1996 |
| WO | WO-1996/040654 | 12/1996 |
| WO | WO-1996/040655 | 12/1996 |
| WO | WO-1996/040656 | 12/1996 |
| WO | WO-1997/022619 | 6/1997 |
| WO | WO-1998/000402 | 1/1998 |
| WO | WO-1999/007731 | 2/1999 |
| WO | WO-2000/005246 | 2/2000 |
| WO | WO-2001/074783 | 10/2001 |
| WO | WO-2001/074784 | 10/2001 |
| WO | WO-2001/079261 | 10/2001 |
| WO | WO-2001/090084 | 11/2001 |
| WO | WO-2001/092235 | 12/2001 |
| WO | WO-2002/018382 | 3/2002 |
| WO | WO-2002/020500 | 3/2002 |
| WO | WO-2003/007945 | 1/2003 |
| WO | WO-2003/010141 | 2/2003 |
| WO | WO-2003/014377 | 2/2003 |
| WO | WO-2003/031376 | 4/2003 |
| WO | WO-2004/002960 | 1/2004 |
| WO | WO-2004/055008 | 7/2004 |
| WO | WO-2004/082602 | 9/2004 |
| WO | WO-2004/098589 | 11/2004 |
| WO | WO-2005/056577 | 6/2005 |
| WO | WO-2006/031606 | 3/2006 |
| WO | WO-2006/044449 | 4/2006 |
| WO | WO-2006/044504 | 4/2006 |
| WO | WO-2006/059164 | 6/2006 |
| WO | WO-2006/063178 | 6/2006 |
| WO | WO-2006/071775 | 7/2006 |
| WO | WO-2006/079077 | 7/2006 |
| WO | WO-2006/103559 | 10/2006 |
| WO | WO-2006/105222 | 10/2006 |
| WO | WO-2006/113432 | 10/2006 |
| WO | WO-2006/116713 | 11/2006 |
| WO | 2006133147 A2 | 12/2006 |
| WO | WO-2007/035935 | 3/2007 |
| WO | WO-2007/067416 | 6/2007 |
| WO | WO-2007/109251 | 9/2007 |
| WO | WO-2007/126871 | 11/2007 |
| WO | WO-2007/145922 | 12/2007 |
| WO | WO-2008/009122 | 1/2008 |
| WO | WO-2008/040778 | 4/2008 |
| WO | WO-2008/045484 | 4/2008 |
| WO | WO-2008/080056 | 7/2008 |
| WO | WO-2008/106077 | 9/2008 |
| WO | WO-2008/135525 | 11/2008 |
| WO | WO-2008/156580 | 12/2008 |
| WO | WO-2009/019115 | 2/2009 |
| WO | WO-2009/085256 | 7/2009 |
| WO | WO-2009/095759 | 8/2009 |
| WO | WO-2009/095788 | 8/2009 |
| WO | WO-2009/095789 | 8/2009 |
| WO | WO-2009/103432 | 8/2009 |
| WO | WO-2009/105348 | 8/2009 |
| WO | WO-2009/140549 | 11/2009 |
| WO | WO-2010/019899 | 2/2010 |
| WO | WO-2010/083725 | 7/2010 |
| WO | WO-2011/035019 | 3/2011 |
| WO | WO-2011/133964 | 10/2011 |
| WO | WO-2011/149963 | 12/2011 |
| WO | WO-2012/061408 | 5/2012 |
| WO | WO-2013/000994 | 1/2013 |
| WO | WO-2013/012918 | 1/2013 |
| WO | WO-2013/013826 | 1/2013 |
| WO | WO-2013/059791 | 4/2013 |
| WO | WO-2013/151739 | 10/2013 |
| WO | WO-2013/189241 | 12/2013 |
| WO | WO-2014/009495 | 1/2014 |
| WO | WO-2014/023708 | 2/2014 |
| WO | WO-2014/072930 | 5/2014 |
| WO | WO-2014/125444 | 8/2014 |
| WO | WO-2014/144547 | 9/2014 |
| WO | WO-2014/155016 | 10/2014 |
| WO | WO-2014/170892 | 10/2014 |
| WO | 2014210456 A1 | 12/2014 |
| WO | WO-2015/027137 | 2/2015 |
| WO | WO-2015/103583 | 7/2015 |
| WO | WO-2015/104677 | 7/2015 |
| WO | WO-2015/184257 | 12/2015 |
| WO | WO-2016/023918 | 2/2016 |
| WO | WO-2016/027253 | 2/2016 |
| WO | WO-2016/055028 | 4/2016 |
| WO | WO-2016/101885 | 6/2016 |
| WO | WO-2016/101887 | 6/2016 |
| WO | WO-2016/113668 | 7/2016 |
| WO | WO-2016/128936 | 8/2016 |
| WO | WO-2016/168014 | 10/2016 |
| WO | WO-2017/004500 | 1/2017 |
| WO | WO-2017/022962 | 2/2017 |
| WO | WO-2017/069279 | 4/2017 |
| WO | WO-2017/109724 | 6/2017 |

OTHER PUBLICATIONS

Berger et al., "Drilling into RIP1 biology: what compounds are in your toolkit?", Cell Death and Disease, 2015, 6:E1889, 2 pages.
Bolin et al., "Peptide and Peptide Mimetic Inhibitors of Antigen Presentation by HLA-DR Class II MHC Molecules, Design, Structure-

(56) References Cited

OTHER PUBLICATIONS

Activity Relationships, and X-ray Crystal Structures", J. Med. Chem., 2000, 43, 2135-2148.
CAS RN 1222532-89-9 Registry, 1-Piperidinecarboxamide, 4-(1,4-dihydro-2-oxo-3(2H)-quinazoliny1)-N-[2,3,4,5-tetrahydro-1-(1-methylethyl)-2-oxo-1H-1-benzazepin-3-yl]-(CA Index Name), Entered STN: May 12, 2010, Database: ChEBI (European Bioinformatics Institute). (1 page).
Cristau et al. "Reaction of lithium diphenylphosphonium di(methylide) with carbonic acid derivatives. A novel access to polyfunctional unsaturated esters and amides", Heteroatom Chemistry, 1992, 3(4), 415-422.
Degterev et al., "Identification of RIP1 kinase as a specific cellular target of necrostatins." Nature Chemical Biology, 2008, 4, 313-321.
Dhanik et al., "Binding Modes of Peptidomimetics Designed to Inhibit STAT3", PLoS ONE 7(12): e51603 (2012). (18 pages).
Fischer et al., "Discovery of novel triazolobenzazepinones as ?-secretase modulators with central Aβ42 lowering in rodents and rhesus monkeys." Bioorganic & Medicinal Chemistry Letters, 2015, 25(17), 3488-3494.
GlaxoSmithKline, "A Safety and Tolerability Study of GSK2982772, in Single (in Both Fed and Fasted States) and Repeat Oral Doses in Healthy Male Subjects." ClinicalTrials.gov, record processed Aug. 2, 2016. (14 pages).
GlaxoSmithKline, "Safety, Tolerability, Pharmacokinetics, Pharmacodynamics, and Efficacy of Repeat Doses of GSK2982772." ClinicalTrials.gov, record processed Aug. 2, 2016. (14 pages).
Harris et al., "Discovery of a First-in-Class Receptor Interacting Protein 1 (RIP1) Kinase Specific Clinical Candidate (GSK2982772) for the Treatment of Inflammatory Diseases." J Med Chem., 2017, 60(4), 1247-1261.
Harris et al., "DNA-Encoded Library Screening Identifies Benzo[b][1,4]oxazepin-4-ones as Highly Potent and Monoselective Receptor Interacting Protein 1 Kinase Inhibitors." J. Med. Chem., 2016, 59(5), 2163-2178.
Herpin et al., "Directed sorting approach for the synthesis of large combinatorial libraries of discrete compounds." Methods Enzymol., 2003, 369, 75-99.
Hoyt et al., "Benzazepinone Nav1.7 blockers: potential treatments for neuropathic pain." Bioorganic & Medicinal Chemistry Letters, 2007, 17(22), 6172-6177.
International Search Report and Written Opinion for International Application No. PCT/US2017/016509, dated Aug. 7, 2017. (26 pages).
Klapars et al., "Synthesis of medium ring nitrogen heterocycles via a tandem copper-catalyzed C-N bond formation-ring-expansion process." J Am Chem Soc., 2004, 126(11), 3529-33.
Mandal et al., "Conformationally Constrained Peptidomimetic Inhibitors of Signal Transducer and Activator of Transcription 3: Evaluation and Molecular Modeling." J. Med. Chem., 2009, 52(8), 2429-2442.
Ofengeim et al., "Activation of necroptosis in multiple sclerosis." Cell Rep., 2015, 10(11), 1836-1849.
Paone et al., "Orally bioavailable imidazoazepanes as calcitonin gene-related peptide (CGRP) receptor antagonists: Discovery of MK-2918," Bioorganic & Medicinal Chemistry Letters, 2011, 21, 2683-2686.

Rosauer et al., "Novel 3,4-Dihydroquinolin-2(1H)-one inhibitors of human glycogen phosphorylase a." Bioorganic & Medicinal Chemistry Letters, 2003, 13(24), 4385-4388.
Rosloniec et al., "Second-generation peptidomimetic inhibitors of antigen presentation effectively treat autoimmune diseases in HLA-DR-transgenic mouse models." J Autoimmun., 2006, 27(3), 182-195.
Sarabu et al., "Oxazole-and Imidazole-Based Ser-Leu Dipeptide Mimetics in Potent Inhibitors of Antigen Presentation by MHC Class II DR Molecules." Drug Design and Discovery, 2002, 18(1), 3-7.
Teng et al., "Structure activity relationship and liver microsome stability studies of pyrrole necroptosis inhibitors." Bioorg Med Chem Lett., 2008, 18(11), 3219-3223.
Teng et al., "Structure-activity relationship study of [1,2,3]thiadiazole necroptosis inhibitors." Bioorganic & Medicinal Chemistry Letters, 2007, 17(24), 6836-6840.
Teng et al., "Structure-activity relationship study of novel necroptosis inhibitors." Bioorganic & Medicinal Chemistry Letters 2005, 15, 5039-5044.
Wei et al., "Modeling Ligand-Receptor Interaction for Some MHC Class II HLA-DR4 Peptide Mimetic Inhibitors Using Several Molecular Docking and 3D QSAR Techniques." J. Chem. Inf. Model., 2005, 45(5), 1343-1351.
Williams et al., "Characterization of a New Class of Potent Inhibitors of the Voltage-Gated Sodium Channel Nav1.7." Biochemistry, 2007, 46(50), 14693-14703.
Xie et al., "Structural basis of RIP1 inhibition by necrostatins." Structure, 2013, 21(3), 493-499.
Belskaya et al., "Synthesis and (3+2) cycloaddition reactions of N,N'-and C,N-cyclic azomethine imines," Chemistry of Heterocyclic Compounds, Nov. 11, 2016, vol. 52, pp. 627-636.
International Search Report and Written Opinion of International Application No. PCT/US2017/065368, dated Feb. 22, 2018 (8 pages).
Wrobleski et al., "Intramolecular Reactions of Benzylic Azides with Ketones:. Competition between Schmidt and Mannich Pathways," The Journal of Organic Chemistry, Jan. 5, 2001, vol. 66, pp. 886-889.
Chemical Abstracts Service, RN: 138036-07-04; 138036-05-2 (Jan. 1, 1992).
Harris et al., "Discovery of Small Molecule RIP1 Kinase Inhibitors for the Treatment of Pathologies Associated with Necroptosis", ACS Medicinal Chemistry Letters, 4(12), pp. 1238-1243 (Dec. 12, 2013).
Khan et al., "Design and synthesis of nonpeptide mimetics of jaspamide", International Journal of Peptide & Protein Research, 38(4), pp. 324-334 (1991).
Supplementary European Search Report issued in corresponding European Application No. EP 17877524, dated May 27, 2020 (10 pages).
Thomas et al., "Reaction of novel imide reducing reagents with pyrrolizidinediones", Journal of Organic Chemistry, 54 (19), pp. 4535-4543 (Sep. 1, 1989).

* cited by examiner

COMPOUNDS, COMPOSITIONS AND METHODS

CROSS REFERENCE TO RELATED APPLICATIONS

This application is a United States non-provisional continuation application filed under 35 U.S.C. § 111(a) of International Patent Application No. PCT/US2017/065368, filed on Dec. 8, 2017, which claims priority under 35 U.S.C. § 119(e) of U.S. Provisional Application No. 62/432,412, filed Dec. 9, 2016, and U.S. Provisional Application No. 62/526,942, filed on Jun. 29, 2017. The entire contents of each of these applications are incorporated by reference in their entirety into this application.

FIELD

The present disclosure relates generally to methods and compositions for preventing or arresting cell death and/or inflammation.

BACKGROUND

Programmed necrotic cell death, also called necroptosis, is a form of cell death in which various stimuli such as TNFα, certain toll-like receptor (TLR) agonists and ischemia can induce cellular necrosis. Necroptosis is a highly inflammatory form of cell death and is thought to be an important contributor to pathology in multiple degenerative and inflammatory diseases. These diseases include neurodegenerative diseases, stroke, coronary heart disease and myocardial infarction, retinal degenerative diseases, inflammatory bowel disease, kidney disease, liver disease and others.

Necrosis is characterized by cell membrane and organelle disruption, cell swelling and mitochondrial impairment, followed by cell lysis. Also, cell lyses typically are accompanied by an inflammatory response. Some of the underlying biochemical events in this process are now understood and the activity of receptor interacting protein kinase 1 has been shown to be important for cells to undergo necroptosis. Furthermore, this activity is also known to promote the release of inflammatory mediators such as TNF alpha from cells which can induce inflammation and also promote further necroptosis. Therefore, identifying and preparing low molecular weight molecules that prevent necrotic cell death and/or inflammation by inhibiting this or by other mechanisms can provide useful compounds for therapeutic intervention in diseases characterized by necrotic cell death and/or inflammation.

While progress has been made, there remains a need in the art for improved compounds for preventing and treating diseases involving cell death and/or inflammation. The present disclosure provides this and related benefits.

SUMMARY

Provided herein are compounds that are useful as inhibitors of receptor interacting protein kinase 1. The disclosure also provides compositions, including pharmaceutical compositions, kits that include the compounds, and methods of using (or administering) and making the compounds. The disclosure further provides compounds or compositions thereof for use in a method of treating a disease, disorder, or condition that is mediated by receptor interacting protein kinase 1. Moreover, the disclosure provides uses of the compounds or compositions thereof in the manufacture of a medicament for the treatment of a disease, disorder or condition that is mediated by (or mediated, at least in part, by) receptor interacting protein kinase 1.

In certain aspects, provided is a compound of any of Formulas I-XX, or subformula thereof, or a pharmaceutically acceptable salt, prodrug, stereoisomer or a mixture of stereoisomers thereof. In certain aspects, provided is a compound as shown in Table 1 or a pharmaceutically acceptable salt, prodrug, stereoisomer or a mixture of stereoisomers thereof. In certain aspects, provided is a compound as shown in Table 2 or a pharmaceutically acceptable salt, prodrug, stereoisomer or a mixture of stereoisomers thereof. Also provided herein is a pharmaceutical composition comprising a compound as described herein, or a pharmaceutically acceptable salt, prodrug, stereoisomer or a mixture of stereoisomers thereof, and an excipient.

Provided herein are compounds and compositions for use in medicine. In certain embodiments, the compounds and compositions are for use in the treatment of a receptor interacting protein kinase 1-mediated disease or disorder.

Provided herein is a method of treating a receptor interacting protein kinase 1-mediated disease or disorder comprising administering a therapeutically effective amount of a compound or pharmaceutical composition disclosed herein to a subject in need thereof.

In certain embodiments, the disease or disorder is inflammatory bowel disease, Crohn's disease, ulcerative colitis, psoriasis, retinal detachment, retinitis pigmentosa, macular degeneration, pancreatitis, atopic dermatitis, rheumatoid arthritis, spondyloarthritis, gout, SoJIA, systemic lupus erythematosus, Sjogren's syndrome, systemic scleroderma, anti-phospholipid syndrome, vasculitis, osteoarthritis, non-alcohol steatohepatitis, alcohol steatohepatitis, autoimmune hepatitis autoimmune hepatobiliary diseases, primary sclerosing cholangitis, nephritis, Celiac disease, autoimmune ITP, transplant rejection, ischemia reperfusion injury of solid organs, sepsis, systemic inflammatory response syndrome, cerebrovascular accident, myocardial infarction, Huntington's disease, Alzheimer's disease, Parkinson's disease, allergic diseases, asthma, atopic dermatitis, multiple sclerosis, type I diabetes, Wegener's granulomatosis, pulmonary sarcoidosis, Behcet's disease, interleukin-1 converting enzyme associated fever syndrome, chronic obstructive pulmonary disease, tumor necrosis factor receptor-associated periodic syndrome, or peridontitis. In certain embodiments, the disease or disorder is trauma, ischemia, stroke, cardiac infarction, infection, Gaucher's disease, Krabbe disease, sepsis, Parkinson's disease, Alzheimer's disease, amyotrophic lateral sclerosis, Huntington's disease, HIV-associated dementia, retinal degenerative disease, glaucoma, age-related macular degeneration, rheumatoid arthritis, psoriasis, psoriatic arthritis or inflammatory bowel disease. In certain embodiments, the disease or disorder is Alzheimer's disease, amyotrophic lateral sclerosis (ALS), Friedreich's ataxia, Huntington's disease, Lewy body disease, Parkinson's disease, or spinal muscular atrophy. In certain embodiments, the disease or disorder is brain injury, spinal cord injury, dementia, stroke, Alzheimer's disease, amyotrophic lateral sclerosis (ALS/Lou Gehrig's Disease), Parkinson's disease, Huntington's disease, multiple sclerosis, diabetic neuropathy, polyglutamine (polyQ) diseases, stroke, Fahr disease, Menke's disease, Wilson's disease, cerebral ischemia, or a prion disorder.

DETAILED DESCRIPTION

The following description sets forth exemplary embodiments of the present technology. It should be recognized, however, that such description is not intended as a limitation on the scope of the present disclosure but is instead provided as a description of exemplary embodiments.

1. Definitions

As used in the present specification, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, —C(O)NH$_2$ is attached through the carbon atom. A dash at the front or end of a chemical group is a matter of convenience; chemical groups may be depicted with or without one or more dashes without losing their ordinary meaning. A wavy line or a dashed line drawn through a line in a Formula indicates a specified point of attachment of a group. Unless chemically or structurally required, no directionality or stereochemistry is indicated or implied by the order in which a chemical group is written or named.

The prefix "$C_{u-v}$" indicates that the following group has from u to v carbon atoms. For example, "$C_{1-6}$ alkyl" indicates that the alkyl group has from 1 to 6 carbon atoms.

Reference to "about" a value or parameter herein includes (and describes) embodiments that are directed to that value or parameter per se. In certain embodiments, the term "about" includes the indicated amount±10%. In certain embodiments, the term "about" includes the indicated amount±5%. In certain embodiments, the term "about" includes the indicated amount±1%. Also, to the term "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Alkyl" refers to an unbranched or branched saturated hydrocarbon chain. As used herein, alkyl has 1 to 20 carbon atoms (i.e., $C_{1-20}$ alkyl), 1 to 12 carbon atoms (i.e., $C_{1-12}$ alkyl), 1 to 8 carbon atoms (i.e., $C_{1-8}$ alkyl), 1 to 6 carbon atoms (i.e., $C_{1-6}$ alkyl) or 1 to 4 carbon atoms (i.e., $C_{1-4}$ alkyl). Examples of alkyl groups include methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl and 3-methylpentyl. When an alkyl residue having a specific number of carbons is named by chemical name or identified by molecular formula, all positional isomers having that number of carbons may be encompassed; thus, for example, "butyl" includes n-butyl (i.e., —(CH$_2$)$_3$CH$_3$), sec-butyl (i.e., —CH(CH$_3$)CH$_2$CH$_3$), isobutyl (i.e., —CH$_2$CH(CH$_3$)$_2$) and tert-butyl (i.e., —C(CH$_3$)$_3$); and "propyl" includes n-propyl (i.e., —(CH$_2$)$_2$CH$_3$) and isopropyl (i.e., —CH(CH$_3$)$_2$).

Certain commonly used alternative chemical names may be used. For example, a divalent group such as a divalent "alkyl" group, a divalent "aryl" group, etc., may also be referred to as an "alkylene" group or an "alkylenyl" group, an "arylene" group or an "arylenyl" group, respectively. Also, unless indicated explicitly otherwise, where combinations of groups are referred to herein as one moiety, e.g. arylalkyl or aralkyl, the last mentioned group contains the atom by which the moiety is attached to the rest of the molecule.

"Alkenyl" refers to an alkyl group containing at least one carbon-carbon double bond and having from 2 to 20 carbon atoms (i.e., $C_{2-20}$ alkenyl), 2 to 8 carbon atoms (i.e., $C_{2-8}$ alkenyl), 2 to 6 carbon atoms (i.e., $C_{2-6}$ alkenyl) or 2 to 4 carbon atoms (i.e., $C_{2-4}$ alkenyl). Examples of alkenyl groups include ethenyl, propenyl, butadienyl (including 1,2-butadienyl and 1,3-butadienyl).

"Alkynyl" refers to an alkyl group containing at least one carbon-carbon triple bond and having from 2 to 20 carbon atoms (i.e., $C_{2-20}$ alkynyl), 2 to 8 carbon atoms (i.e., $C_{2-8}$ alkynyl), 2 to 6 carbon atoms (i.e., $C_{2-6}$ alkynyl) or 2 to 4 carbon atoms (i.e., $C_{2-4}$ alkynyl). The term "alkynyl" also includes those groups having one triple bond and one double bond.

"Alkoxy" refers to the group "alkyl-O—". Examples of alkoxy groups include methoxy, ethoxy, n-propoxy, iso-propoxy, n-butoxy, tert-butoxy, sec-butoxy, n-pentoxy, n-hexoxy and 1,2-dimethylbutoxy.

"Alkoxyalkyl" refers to the group "alkyl-O-alkyl".

"Alkylthio" refers to the group "alkyl-S—".

"Acyl" refers to a group —C(O)R, wherein R is hydrogen, alkyl, alkenyl, alkynyl, cycloalkyl, heterocyclyl, aryl, heteroalkyl or heteroaryl; each of which may be optionally substituted, as defined herein. Examples of acyl include formyl, acetyl, cyclohexylcarbonyl, cyclohexylmethyl-carbonyl and benzoyl.

"Amido" refers to both a "C-amido" group which refers to the group —C(O)NR$^y$R$^z$ and an "N-amido" group which refers to the group —NR$^y$C(O)R$^z$, wherein R$^y$ and R$^z$ are independently hydrogen, alkyl, alkenyl, alkynyl, cycloalkyl, heterocyclyl, aryl, heteroalkyl or heteroaryl; each of which may be optionally substituted, as defined herein.

"Amino" refers to the group —NR$^y$R$^z$ wherein R$^y$ and R$^z$ are independently hydrogen, alkyl, alkenyl, alkynyl, cycloalkyl, heterocyclyl, aryl, heteroalkyl or heteroaryl; each of which may be optionally substituted, as defined herein.

"Amidino" refers to —C(NR)(NR$_2$), wherein each R is independently hydrogen, alkyl, alkenyl, alkynyl, cycloalkyl, heterocyclyl, aryl, heteroalkyl or heteroaryl; each of which may be optionally substituted, as defined herein.

"Aryl" refers to an aromatic carbocyclic group having a single ring (e.g. monocyclic) or multiple rings (e.g. bicyclic or tricyclic) including fused systems. As used herein, aryl has 6 to 20 ring carbon atoms (i.e., $C_{6-20}$ aryl), 6 to 18 carbon ring atoms (i.e., $C_{6-18}$ aryl), 6 to 12 carbon ring atoms (i.e., $C_{6-12}$ aryl) or 6 to 10 carbon ring atoms (i.e., $C_{6-10}$ aryl). Examples of aryl groups include phenyl, naphthyl, fluorenyl and anthryl. Aryl, however, does not encompass or overlap in any way with heteroaryl defined below. If one or more aryl groups are fused with a heteroaryl, the resulting ring system is heteroaryl. If one or more aryl groups are fused with a heterocyclyl, the resulting ring system is heterocyclyl.

"Arylalkyl" or "Aralkyl" refers to the group "aryl-alkyl-".

"Carbamoyl" refers to both an "O-carbamoyl" group which refers to the group —O—C(O)NR$^y$R$^z$ and an "N-carbamoyl" group which refers to the group —NR$^y$C(O)OR$^z$, wherein R$^y$ and R$^z$ are independently hydrogen, alkyl, alkenyl, alkynyl, cycloalkyl, heterocyclyl, aryl, heteroalkyl or heteroaryl; each of which may be optionally substituted, as defined herein.

"Carboxyl ester" or "ester" refer to both —OC(O)R and —C(O)OR, wherein R is alkyl, alkenyl, alkynyl, cycloalkyl, heterocyclyl, aryl, heteroalkyl or heteroaryl; each of which may be optionally substituted, as defined herein.

"Cycloalkyl" refers to a saturated or partially unsaturated cyclic alkyl group having a single ring or multiple rings including fused, bridged and spiro ring systems. The term "cycloalkyl" includes cycloalkenyl groups (i.e., the cyclic group having at least one double bond). As used herein, cycloalkyl has from 3 to 20 ring carbon atoms (i.e., $C_{3-20}$ cycloalkyl), 3 to 15 ring carbon atoms (i.e., $C_{3-15}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl) or 3 to 6 ring carbon atoms (i.e., $C_{3-6}$ cycloalkyl). Cycloalkyl also includes "spiro cycloalkyl" when there are two positions for substitution on the same carbon atom. Monocyclic radicals include, for example, cyclopropyl, cyclobutyl, cyclopentyl, cyclohexyl, cycloheptyl and cyclooctyl. Polycyclic radicals include, for example, adamantyl, norbornyl, decalinyl, 7,7-dimethylbicyclo[2.2.1]heptanyl and the like. Further, the term cycloalkyl is intended to encompass any non-aromatic ring which may be fused to an aryl ring, regardless of the attachment to the remainder of the molecule.

"Cycloalkylalkyl" refers to the group "cycloalkyl-alkyl-".

"Guanidino" refers to —NRC(NR)(NR$_2$), wherein each R is hydrogen, alkyl, alkenyl, alkynyl, cycloalkyl, heterocyclyl, aryl, heteroalkyl or heteroaryl; each of which may be optionally substituted, as defined herein.

"Imino" refers to a group —C(NR)R, wherein each R is independently hydrogen, alkyl, alkenyl, alkynyl, cycloalkyl, heterocyclyl, aryl, heteroalkyl or heteroaryl; each of which may be optionally substituted, as defined herein.

"Imido" refers to a group —C(O)NRC(O)R, wherein each R is independently hydrogen, alkyl, alkenyl, alkynyl, cycloalkyl, heterocyclyl, aryl, heteroalkyl or heteroaryl; each of which may be optionally substituted, as defined herein.

"Halogen" or "halo" includes fluoro, chloro, bromo and iodo.

"Haloalkyl" refers to an unbranched or branched alkyl group as defined above, wherein one or more hydrogen atoms (e.g., one to five or one to three) are replaced by a halogen. For example, where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. Examples of haloalkyl include trifluoromethyl, difluoromethyl, trichloromethyl, 2,2,2-trifluoroethyl, 1,2-difluoroethyl, 3-bromo-2-fluoropropyl, 1,2-dibromoethyl and the like.

"Haloalkoxy" refers to an alkoxy group as defined above, wherein one or more hydrogen atoms (e.g., one to five or one to three) are replaced by a halogen.

"Hydroxyalkyl" refers to an alkyl group as defined above, wherein one or more hydrogen atoms (e.g., one to five or one to three) are replaced by a hydroxy group.

"Heteroalkyl" refers to an alkyl group in which one or more of the carbon atoms (and any associated hydrogen atoms) are each independently replaced with the same or different heteroatomic group, provided the point of attachment to the remainder of the molecule is through a carbon atom. The term "heteroalkyl" includes unbranched or branched saturated chain having carbon and heteroatoms. By way of example, 1, 2 or 3 carbon atoms may be independently replaced with the same or different heteroatomic group. Heteroatomic groups include, but are not limited to, —NR—, —O—, —S—, —S(O)—, —S(O)$_2$—, and the like, where R is hydrogen, alkyl, alkenyl, alkynyl, cycloalkyl, heterocyclyl, aryl, heteroalkyl, or heteroaryl; each of which may be optionally substituted, as defined herein. Examples of heteroalkyl groups include —CH$_2$OCH$_3$, —CH$_2$SCH$_3$, and —CH$_2$NRCH$_3$, where R is hydrogen, alkyl, alkenyl, alkynyl, cycloalkyl, heterocyclyl, aryl, heteroalkyl, or heteroaryl; each of which may be optionally substituted, as defined herein. As used herein, heteroalkyl includes 1 to 10 carbon atoms, 1 to 8 carbon atoms, or 1 to 4 carbon atoms; and 1 to 3 heteroatoms, 1 to 2 heteroatoms, or 1 heteroatom.

"Heteroaryl" refers to an aromatic group (e.g., a 5-14 membered ring system) having a single ring, multiple rings or multiple fused rings, with one or more ring heteroatoms independently selected from nitrogen, oxygen and sulfur. As used herein, heteroaryl includes 1 to 20 ring carbon atoms (i.e., $C_{1-20}$ heteroaryl), 1 to 13 ring carbon atoms (i.e., $C_{3-12}$ heteroaryl), 3 to 12 ring carbon atoms (i.e., $C_{3-12}$ heteroaryl) or 3 to 8 carbon ring atoms (i.e., $C_{3-8}$ heteroaryl); and 1 to 6 heteroatoms, 1 to 5 heteroatoms, 1 to 4 heteroatoms, 1 to 3 ring heteroatoms, 1 to 2 ring heteroatoms or 1 ring heteroatom independently selected from nitrogen, oxygen and sulfur. Examples of heteroaryl groups include azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl and thiophenyl (i.e., thienyl). Examples of the fused-heteroaryl rings include, but are not limited to, benzo[d]thiazolyl, quinolinyl, isoquinolinyl, benzo[b]thiophenyl, indazolyl, benzo[d]imidazolyl, pyrazolo[1,5-a]pyridinyl and imidazo[1,5-a]pyridinyl, where the heteroaryl can be bound via either ring of the fused system. Any aromatic ring, having a single or multiple fused rings, containing at least one heteroatom, is considered a heteroaryl regardless of the attachment to the remainder of the molecule (i.e., through any one of the fused rings). Heteroaryl does not encompass or overlap with aryl as defined above.

"Heteroarylalkyl" refers to the group "heteroaryl-alkyl-".

"Heterocyclyl" refers to a saturated or unsaturated cyclic alkyl group, with one or more ring heteroatoms independently selected from nitrogen, oxygen and sulfur. The term "heterocyclyl" includes heterocycloalkenyl groups (i.e., the heterocyclyl group having at least one double bond), bridged-heterocyclyl groups, fused-heterocyclyl groups and spiro-heterocyclyl groups. A heterocyclyl may be a single ring or multiple rings wherein the multiple rings may be fused, bridged or spiro, and may comprise one or more oxo (C=O) or N-oxide (N—O—) moieties. Any non-aromatic ring containing at least one heteroatom is considered a heterocyclyl, regardless of the attachment (i.e., can be bound through a carbon atom or a heteroatom). Further, the term heterocyclyl is intended to encompass any non-aromatic ring containing at least one heteroatom, which ring may be fused to an aryl or heteroaryl ring, regardless of the attachment to the remainder of the molecule. As used herein, heterocyclyl has 2 to 20 ring carbon atoms (i.e., $C_{2-20}$ heterocyclyl), 2 to 12 ring carbon atoms (i.e., $C_{2-12}$ heterocyclyl), 2 to 10 ring carbon atoms (i.e., $C_{2-10}$ heterocyclyl), 2 to 8 ring carbon atoms (i.e., $C_{2-8}$ heterocyclyl), 3 to 12 ring carbon atoms (i.e., $C_{3-12}$ heterocyclyl), 3 to 8 ring carbon atoms (i.e., $C_{3-8}$ heterocyclyl) or 3 to 6 ring carbon atoms (i.e., $C_{3-6}$ heterocyclyl); having 1 to 5 ring heteroatoms, 1 to 4 ring heteroatoms, 1 to 3 ring heteroatoms, 1 to 2 ring heteroatoms or 1 ring heteroatom independently selected from nitrogen, sulfur or oxygen. Examples of heterocyclyl groups include dioxolanyl, thienyl [1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl and 1,1-dioxo-thiomorpholinyl. Examples of the spiro-heterocyclyl rings include bicyclic and tricyclic ring systems, such as 2-oxa-7-azaspiro[3.5]nonanyl, 2-oxa-6-azaspiro[3.4]octanyl and 6-oxa-1-azaspiro[3.3]heptanyl. Examples of the fused-heterocyclyl rings include, but are not limited to, 1,2,3,4-tetrahydroisoquinolinyl, 4,5,6,7-tetrahydrothieno[2,3-c]pyridinyl, indolinyl and isoindolinyl, where the heterocyclyl can be bound via either ring of the fused system.

"Heterocyclylalkyl" refers to the group "heterocyclyl-alkyl-".

"Oxime" refers to the group —CR(=NOH) wherein R is hydrogen, alkyl, alkenyl, alkynyl, cycloalkyl, heterocyclyl, aryl, heteroalkyl or heteroaryl; each of which may be optionally substituted, as defined herein.

"Sulfonyl" refers to the group —S(O)$_2$R, where R is hydrogen, alkyl, alkenyl, alkynyl, cycloalkyl, heterocyclyl, aryl, heteroalkyl or heteroaryl; each of which may be optionally substituted, as defined herein. Examples of sulfonyl are methylsulfonyl, ethylsulfonyl, phenylsulfonyl and toluenesulfonyl.

"Sulfinyl" refers to the group —S(O)R, where R is hydrogen, alkyl, alkenyl, alkynyl, cycloalkyl, heterocyclyl, aryl, heteroalkyl or heteroaryl; each of which may be optionally substituted, as defined herein. Examples of sulfinyl are methylsulfinyl, ethylsulfinyl, phenylsulfinyl and toluenesulfinyl.

"Sulfonamido" refers to the groups —SO$_2$NRR and —NRSO$_2$R, where each R is independently hydrogen, alkyl, alkenyl, alkynyl, cycloalkyl, aryl, heteroalkyl or heteroaryl; each of which may be optionally substituted, as defined herein.

"Alkylsulfonyl" refers to the group —S(O)$_2$R, where R is alkyl.

"Alkylsulfinyl" refers to the group —S(O)R, where R is alkyl.

The terms "optional" or "optionally" means that the subsequently described event or circumstance may or may not occur and that the description includes instances where said event or circumstance occurs and instances in which it does not. Also, the term "optionally substituted" refers to any one or more hydrogen atoms (e.g., one to five or one to three) on the designated atom or group may or may not be replaced by a moiety other than hydrogen.

The term "substituted" used herein means any of the above groups (i.e., alkyl, alkenyl, alkynyl, alkylene, alkoxy, haloalkyl, haloalkoxy, cycloalkyl, aryl, heterocyclyl, heteroaryl, and/or heteroalkyl) wherein at least one hydrogen atom is replaced by a bond to a non-hydrogen atom such as, but not limited to: alkyl, alkenyl, alkynyl, alkoxy, alkylthio, acyl, amido, amino, amidino, aryl, aralkyl, azido, carbamoyl, carboxyl, carboxyl ester, cyano, cycloalkyl, cycloalkylalkyl, guanadino, halo, haloalkyl, haloalkoxy, hydroxyalkyl, heteroalkyl, heteroaryl, heteroarylalkyl, heterocyclyl, heterocyclylalkyl, hydrazine, hydrazone, imino, imido, hydroxy, oxo, oxime, nitro, sulfonyl, sulfinyl, alkylsulfonyl, alkylsulfinyl, thiocyanate, sulfinic acid, sulfonic acid, sulfonamido, thiol, thioxo, N-oxide, or —Si(R$^{100}$)$_3$ wherein each R$^{100}$ is independently hydrogen, alkyl, alkenyl, alkynyl, heteroalkyl, cycloalkyl, aryl, heteroaryl or heterocyclyl.

The term "substituted" used herein means any of the above groups (i.e., alkyl, alkylene, alkoxy, haloalkoxy, aryl, cycloalkyl, haloalkyl, heterocyclyl, heteroaryl, hydroxylalkyl and/or alkoxyalkyl) wherein at least one hydrogen atom is replaced by a bond to a non-hydrogen atom such as, but not limited to: an alkyl group, a haloalkyl group, a halogen atom such as F, Cl, Br, and I; an alkenyl, a haloalkenyl group, an alkynyl group, a haloalkynyl group, a cyclic group such as an aryl, heteroaryl, cycloalkyl, or heterocyclyl group, an oxygen atom in groups such as hydroxyl groups, alkoxy groups, and ester groups; a sulfur atom in groups such as thiol groups, thioalkyl groups, thiohaloalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms (e.g., one to five or one to three) are replaced by a higher-order bond (e.g., a double- or triple-bond) to a heteroatom such as oxygen in oxo, carbonyl, formyl, carboxyl, carbonate, and ester groups; and nitrogen in groups such as imines, oximes, hydrazones, and nitriles.

In certain embodiments, "substituted" includes any of the above alkyl, alkenyl, alkynyl, cycloalkyl, heterocyclyl, aryl or heteroaryl groups in which one or more hydrogen atoms (e.g., one to five or one to three) are independently replaced with deuterium, halo, cyano, nitro, azido, oxo, alkyl, alkenyl, alkynyl, haloalkyl, cycloalkyl, heterocyclyl, aryl, heteroaryl, —NR$^g$R$^h$, —NR$^g$C(=O)R$^h$, —NR$^g$C(=O)NR$^g$R$^h$, —NR$^g$C(=O)OR$^h$, —NR$^g$S(=O)$_{1-2}$R$^h$, —C(=O)R$^g$, —C(=O)OR$^g$, —OC(=O)OR$^g$, —OC(=O)R$^g$, —C(=O)NR$^g$R$^h$, —OC(=O)NR$^g$R$^h$, —OR$^g$, —SR$^g$, —S(=O)R$^g$, —S(=O)$_2$R$^g$, —OS(=O)$_{1-2}$R$^g$, —S(=O)$_{1-2}$OR$^g$, —NR$^g$S(=O)$_{1-2}$NR$^g$R$^h$, =NSO$_2$R$^g$, =NOR$^g$, —S(=O)$_{1-2}$NR$^g$R$^h$, —SF$_5$, —SCF$_3$ or —OCF$_3$. "Substituted" also means any of the above groups in which one or more hydrogen atoms (e.g., one to five or one to three) are replaced with —C(=O)R$^g$, —C(=O)OR$^g$, —C(=O)NR$^g$R$^h$, —CH$_2$SO$_2$R$^g$, —CH$_2$SO$_2$NR$^g$R$^h$. "Substituted" further means any of the above groups in which one or more hydrogen atoms (e.g., one to five or one to three) are replaced by —NR$^g$S(O)$_{1-2}$NR$^g$R$^h$, —CH$_2$S(O)R$^g$, —CH$_2$S(O)NR$^g$R$^h$, —OC(=O)OR$^g$, —SF$_5$, —SCF$_3$ or —OCF$_3$. "Substituted" further means any of the above groups in which one or more hydrogen atoms (e.g., one to five or one to three) are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocylylalkyl, heteroaryl, and/or heteroarylalkyl group. In the foregoing, R$^g$ and R$^h$ and R$^i$ are the same or different and independently hydrogen, halo, alkyl, alkenyl, alkynyl, alkoxy, thioalkyl, aryl, aralkyl, cycloalkyl, cycloalkylalkyl, haloalkyl, heterocyclyl, heterocyclylalkyl, heteroaryl, and/or heteroarylalkyl, or two of R$^g$ and R$^h$ and R$^i$ are taken together with the atoms to which they are attached to form a heterocyclyl ring optionally substituted with oxo, halo or alkyl optionally substituted with oxo, halo, amino, hydroxyl or alkoxy. In an embodiment, each of said hydrogen, alkyl, alkenyl, alkynyl, alkoxy, thioalkyl, aryl, aralkyl, cycloalkyl, cycloalkylalkyl, haloalkyl, heterocyclyl, heterocyclylalkyl, heteroaryl, and/or heteroarylalkyl are independently optionally substituted with one or more (e.g., one to five or one to three) oxo, alkyl, halo, amino, hydroxyl or alkoxyl. In addition, each of the foregoing substituents may also be optionally substituted with one or more (e.g., one to five or one to three) of the above substituents.

Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl) substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein. Unless specified otherwise, where a group is described as optionally substituted, any substituents of the group are themselves unsubstituted. For example, in certain embodiments, the term "substituted alkyl" refers to an alkyl group having one or more substituents (e.g., one to five or one to three) including hydroxy, halo, alkoxy, acyl, oxo, amino, cycloalkyl, heterocyclyl, aryl and heteroaryl. In certain embodiments, the one or more substituents (e.g., one to five or one to three) may be further substituted with halo, alkyl, haloalkyl, hydroxy, alkoxy, cycloalkyl, heterocyclyl, aryl or heteroaryl, each of which is substituted. In certain embodiments, the substituents may be further substituted with halo, alkyl, haloalkyl, alkoxy, hydroxy, cycloalkyl, heterocyclyl, aryl or heteroaryl, each of which is unsubstituted.

Any compound or Formula given herein, is also intended to represent unlabeled forms as well as isotopically labeled forms of the compounds. Isotopically labeled compounds have structures depicted by the formulas given herein except that one or more atoms (e.g., one to five or one to three) are replaced by an atom having a selected atomic mass or mass number. Examples of isotopes that can be incorporated into the disclosed compounds include isotopes of hydrogen, carbon, nitrogen, oxygen, phosphorous, fluorine, chlorine and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$ and $^{125}I$, respectively. Various isotopically labeled compounds of the present disclosure, for example those into which radioactive isotopes such as $^{3}H$, $^{13}C$ and $^{14}C$ are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also includes "deuterated analogs" of compounds described herein in which from 1 to n hydrogens attached to a carbon atom is/are replaced by deuterium, in which n is the number of hydrogens in the molecule. Such compounds exhibit increased resistance to metabolism and are thus useful for increasing the half-life of any compound when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens (e.g., one to five or one to three) have been replaced by deuterium.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}F$, $^{3}H$, $^{11}C$ labeled compound may be useful for PET or SPECT or other imaging studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in a compound described herein.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

In many cases, the compounds of this disclosure are capable of forming acid and/or base salts by virtue of the presence of amino and/or carboxyl groups or groups similar thereto.

Provided are also pharmaceutically acceptable salts, hydrates, solvates, tautomeric forms, stereoisomers and prodrugs of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use.

The term "pharmaceutically acceptable salt" of a given compound refers to salts that retain the biological effectiveness and properties of the given compound and which are not biologically or otherwise undesirable. "Pharmaceutically acceptable salts" or "physiologically acceptable salts" include, for example, salts with inorganic acids and salts with an organic acid. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts. Pharmaceutically acceptable acid addition salts may be prepared from inorganic and organic acids. Salts derived from inorganic acids include hydrochloric acid, hydrobromic acid, sulfuric acid, nitric acid, phosphoric acid and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid and the like. Likewise, pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines (i.e., $NH_2$(alkyl)), dialkyl amines (i.e., HN(alkyl)$_2$), trialkyl amines (i.e., N(alkyl)$_3$), substituted alkyl amines (i.e., $NH_2$(substituted alkyl)), di(substituted alkyl) amines (i.e., HN(substituted alkyl)$_2$), tri(substituted alkyl) amines (i.e., N(substituted alkyl)$_3$), alkenyl amines (i.e., $NH_2$(alkenyl)), dialkenyl amines (i.e., HN(alkenyl)$_2$), trialkenyl amines (i.e., N(alkenyl)$_3$), substituted alkenyl amines (i.e., $NH_2$(substituted alkenyl)), di(substituted alkenyl) amines (i.e., HN(substituted alkenyl)$_2$), tri(substituted alkenyl) amines (i.e., N(substituted alkenyl)$_3$, mono-, di- or tri-cycloalkyl amines (i.e., $NH_2$(cycloalkyl), HN(cycloalkyl)$_2$, N(cycloalkyl)$_3$), mono-, di- or tri-arylamines (i.e., $NH_2$(aryl), HN(aryl)$_2$, N(aryl)$_3$) or mixed amines, etc. Specific examples of suitable amines include, by way of example only, isopropylamine, trimethyl amine, diethyl amine, tri(iso-propyl) amine, tri(n-propyl) amine, ethanolamine, 2-dimethylaminoethanol, piperazine, piperidine, morpholine, N-ethylpiperidine and the like.

The term "hydrate" refers to the complex formed by the combining of a compound described herein and water.

A "solvate" refers to an association or complex of one or more solvent molecules and a compound of the disclosure. Examples of solvents that form solvates include, but are not limited to, water, isopropanol, ethanol, methanol, dimethylsulfoxide, ethylacetate, acetic acid and ethanolamine.

Some of the compounds exist as tautomers. Tautomers are in equilibrium with one another. For example, amide containing compounds may exist in equilibrium with imidic acid tautomers. Regardless of which tautomer is shown and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

The compounds disclosed herein, or their pharmaceutically acceptable salts include an asymmetric center and may thus give rise to enantiomers, diastereomers, and other stereoisomeric forms that may be defined, in terms of absolute stereochemistry, as (R)- or (S)- or, as (D)- or (L)- for amino acids. The disclosure is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centres of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present disclosure contemplates various stereoisomers and mixtures thereof and includes "enantiomers", which refers to two stereoisomers whose molecules are nonsuperimposeable mirror images of one another.

"Diastereoisomers" are stereoisomers that have at least two asymmetric atoms, but which are not mirror-images of each other.

"Prodrugs" means any compound which releases an active parent drug according to a Formula described herein in vivo when such prodrug is administered to a mammalian subject. Prodrugs of a compound described herein are prepared by modifying functional groups present in the compound described herein in such a way that the modifications may be cleaved in vivo to release the parent compound. Prodrugs may be prepared by modifying functional groups present in the compounds in such a way that the modifications are cleaved, either in routine manipulation or in vivo, to the parent compounds. Prodrugs include compounds described herein wherein a hydroxy, amino, carboxyl or sulfhydryl group in a compound described herein is bonded to any group that may be cleaved in vivo to regenerate the free hydroxy, amino or sulfhydryl group, respectively. Examples of prodrugs include, but are not limited to esters (e.g., acetate, formate and benzoate derivatives), amides, guanidines, carbamates (e.g., N,N-dimethylaminocarbonyl) of hydroxy functional groups in compounds described herein and the like. Preparation, selection and use of prodrugs is discussed in T. Higuchi and V. Stella, "Pro-drugs as Novel Delivery Systems," Vol. 14 of the A.C.S. Symposium Series; "Design of Prodrugs," ed. H. Bundgaard, Elsevier, 1985; and in Bioreversible Carriers in Drug Design, ed. Edward B. Roche, American Pharmaceutical Association and Pergamon Press, 1987, each of which are hereby incorporated by reference in their entirety.

As used herein, "pharmaceutically acceptable carrier" or "pharmaceutically acceptable excipient" or "excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The term "necrotic cell disease" refers to diseases associated with or caused by cellular necrosis. Exemplary necrotic cell diseases include, but are not limited to, acute diseases such as trauma, ischemia, stroke, cardiac infarction, anthrax lethal toxin induced septic shock, sepsis, cell death induced by LPS and HIV induced T-cell death leading to immunodeficiency. The term "necrotic cell disease" also includes but is not limited to chronic neurodegenerative diseases, such as Parkinson's disease, Huntington's disease, amyotrophic lateral sclerosis, Alzheimer's disease, infectious encelopathies, dementia such as HIV associated dementia. The term "necrotic cell disease" also includes but is not limited to diseases such as inflammatory bowel disease and acute and chronic kidney disease which are characterized by inflammation and cell death.

The chemical names used herein are generated using the MarvinSketch Version 6.1.6 (ChemAxon) or the ChemDraw Ultra Version 13.0 software naming programs.

2. Compounds

Provided are compounds of Formula I:

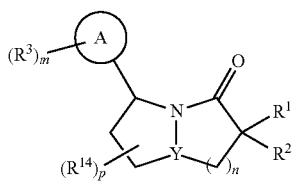

I or a pharmaceutically acceptable salt, prodrug, stereoisomer or a mixture of stereoisomers thereof, wherein:
Y is N or CH;
n is 1 or 2;
m is 0, 1, 2, 3, 4 or 5;
p is 0, 1, 2 or 3;
A is aryl, heteroaryl, $C_{3-10}$ cycloalkyl or heterocyclyl;
each of $R^1$ and $R^2$ are independently hydrogen, deuterium, halo, $C_{1-12}$ alkyl, $C_{1-12}$ alkenyl, $C_{1-12}$ alkynyl, $C_{1-12}$ alkoxy, $C_{1-12}$ haloalkyl, $C_{1-12}$ haloalkoxy, $C_{3-10}$ cycloalkyl, heterocyclyl, heteroaryl or aryl;
wherein each $C_{1-12}$ alkyl, $C_{1-12}$ alkenyl, $C_{1-12}$ alkynyl, $C_{1-12}$ alkoxy, $C_{1-12}$ haloalkyl, $C_{1-12}$ haloalkoxy, $C_{3-10}$ cycloalkyl, heterocyclyl, heteroaryl and aryl are optionally substituted with one, two, three, four or five $Z^1$; or
$R^1$ and $R^2$ taken together with the atom to which they are attached to form a $C_{3-10}$ cycloalkyl; wherein the $C_{3-10}$ cycloalkyl is optionally substituted with one, two, three, four or five $Z^2$;
$R^3$ in each instance is independently deuterium, halo, hydroxy, cyano, nitro, azido, oxo, $C_{1-12}$ alkyl, —$OR^5$, $C_{1-12}$ alkoxy, $C_{2-12}$ alkenyl, $C_{2-12}$ alkynyl, $C_{1-12}$ haloalkyl, $C_{1-12}$ haloalkoxy, $C_{3-10}$ cycloalkyl, heterocyclyl, aryl, heteroaryl, —C(=O)$R^4$, —C(=O)$OR^4$, —OC(=O)$OR^4$, —OC(=O)$R^4$, —C(=O)$NR^4R^5$, —OC(=O)$NR^4R^5$, —$NR^4C$(=O)$NR^5R^6$, —$S$(=O)$_{1-2}R^4$, —$S$(=O)$_{1-2}OR^4$, —$OS$(=O)$_{1-2}R^4$, —$S$(=O)$_{1-2}NR^4$, —$NR^4S$(=O)$_{1-2}R^5$, —$NR^4S$(=O)$_{1-2}NR^4R^5$, —$NR^4R^5$, —$NR^4C$(=O)$R^5$ or —$NR^4C$(=O)$OR^5$; wherein each $C_{1-12}$ alkyl, $C_{1-12}$ alkoxy, $C_{2-12}$ alkenyl, $C_{2-12}$ alkynyl, $C_{1-12}$ haloalkyl, $C_{1-12}$ haloalkoxy, $C_{3-10}$ cycloalkyl, heterocyclyl, aryl and heteroaryl are optionally substituted with one, two, three, four or five $Z^3$;
$R^4$, $R^5$, and $R^6$ in each instance are independently $C_{1-12}$ alkyl, $C_{1-12}$ alkenyl, $C_{1-12}$ alkynyl, $C_{1-12}$ haloalkyl, $C_{3-10}$ cycloalkyl, heterocyclyl, heteroaryl or aryl; wherein each $C_{1-12}$ alkyl, $C_{1-12}$ alkenyl, $C_{1-12}$ alkynyl, $C_{1-12}$ haloalkyl, $C_{3-10}$ cycloalkyl, heterocyclyl, heteroaryl and aryl are optionally substituted with one, two, three, four or five $Z^4$; or
two of $R^4$, $R^5$, and $R^6$ taken together with the atoms to which they are attached to form a heterocyclyl; wherein the heterocyclyl is optionally substituted with one, two, three, four or five $Z^5$;
$R^{14}$ can be bonded to either ring of the fused bicyclic ring and, in each instance, is independently halo, haloalkyl, or two $R^{14}$ bonded to the same carbon atom may be taken together with the atom to which they are attached to form a $C_{3-10}$ cycloalkyl or heterocyclyl; wherein the $C_{3-10}$ cycloalkyl or heterocyclyl is optionally substituted with one, two, three, four or five $Z^6$;
each of $Z^1$, $Z^2$, $Z^3$, $Z^4$, $Z^5$ and $Z^6$ are independently deuterium, halo, hydroxy, cyano, nitro, azido, $C_{1-12}$ alkyl, $C_{1-12}$ alkenyl, $C_{1-12}$ alkynyl, $C_{1-12}$ alkoxy, $C_{1-12}$ haloalkyl, $C_{1-12}$ haloalkoxy, $C_{3-10}$ cycloalkyl, heterocyclyl, aryl, heteroaryl, —C(=O)$R^{11}$, —C(=O)$OR^{11}$, —OC(=O)$OR^{11}$, —OC(=O)$R^{11}$, —C(=O)$NR^{11}R^{12}$, —OC(=O)$NR^{11}R^{12}$, —$NR^{11}C$(=O)$NR^{12}R^{13}$, —$S$(=O)$_{1-2}R^{11}$, —$S$(=O)$_{1-2}OR^{11}$, —$S$(=O)$_{1-2}NR^{11}$, —$NR^{11}S$(=O)$_{1-2}R^{12}$, —$NR^{11}S$(=O)$_{1-2}NR^{12}R^{13}$, —$NR^{11}R^{12}$, —$NR^{11}C$(=O)$R^{12}$ or —$NR^{11}C$(=O)$OR^{12}$;
wherein each $C_{1-12}$ alkyl, $C_{1-12}$ alkenyl, $C_{1-12}$ alkynyl, $C_{1-12}$ alkoxy, $C_{1-12}$ haloalkyl, $C_{1-12}$ haloalkoxy, $C_{3-10}$ cycloalkyl, heterocyclyl, aryl and heteroaryl, are optionally substituted with one, two or three substituents independently selected from deuterium, halo, hydroxy, cyano, amino, nitro, azido, oxo, $C_{1-12}$ alkyl, $C_{1-12}$ alkoxy, $C_{1-12}$ haloalkyl, $C_{1-12}$ haloalkoxy, $C_{2-12}$ alkenyl, $C_{2-12}$ alkynyl, $C_{3-10}$ cycloalkyl, heterocyclyl, aryl and heteroaryl; and
$R^{11}$, $R^{12}$, and $R^{13}$ in each instance are independently $C_{1-12}$ alkyl, $C_{1-12}$ alkenyl, $C_{1-12}$ alkynyl, $C_{1-12}$ alkoxy, $C_{3-10}$ cycloalkyl, heterocyclyl, heteroaryl or aryl; wherein each $C_{1-12}$ alkyl, $C_{1-12}$ alkenyl, $C_{1-12}$ alkynyl, $C_{1-12}$ alkoxy, $C_{3-10}$ cycloalkyl, heterocyclyl, heteroaryl and aryl are optionally substituted with one, two, three, four or five $Z^{11}$; or
two of $R^{11}$, $R^{12}$, and $R^{13}$ are taken together with the atoms to which they are attached to form a heterocyclyl; wherein the heterocyclyl is optionally substituted with one, two, three, four or five $Z^{12}$;
each of $Z^{11}$ and $Z^{12}$ is independently deuterium, halo, hydroxy, cyano, oxo, amino or $C_{1-12}$ alkyl; wherein the $C_{1-12}$ alkyl is optionally substituted with one, two or three halo, hydroxyl, amino or oxo. In certain embodiments, at least one of $R^1$ and $R^2$ is $C_{1-12}$ alkyl, $C_{1-12}$ alkenyl, $C_{1-12}$ alkynyl, $C_{1-12}$ haloalkyl, $C_{3-10}$ cycloalkyl, heterocyclyl, heteroaryl or aryl; wherein each $C_{1-12}$ alkyl, $C_{1-12}$ alkenyl, $C_{1-12}$ alkynyl, $C_{1-12}$ haloalkyl, $C_{3-10}$ cycloalkyl, heterocyclyl, heteroaryl and aryl are optionally substituted with one, two, three, four or five $Z^1$; or
$R^1$ and $R^2$ taken together with the atoms to which they are attached to form a $C_{3-10}$ cycloalkyl; wherein the $C_{3-10}$ cycloalkyl is optionally substituted with one, two, three, four or five $Z^2$.

In certain embodiments, the compound is not hexahydro-6-methyl-3-phenyl-5(1H)-indolizinone, 6-[(2-bromo-1H-indol-3-yl)methyl]hexahydro-3-(4-hydroxyphenyl)-5(1H)-indolizinone, or a stereoisomer thereof.

In certain embodiments, the compound is not hexahydro-6-[hydroxy[3-methoxy-4-(4-methyl-1H-imidazol-1-yl)phenyl]methyl]-3-(3,4,5-trifluorophenyl)-5 (1H)-indolizinone, 3-(3,4-difluorophenyl)hexahydro-6-[hydroxy[3-methoxy-4-(4-methyl-1H-imidazol-1-yl)phenyl]methyl]-5(1H)-indolizinone, or a stereoisomer thereof.

In certain embodiments, the compound is not

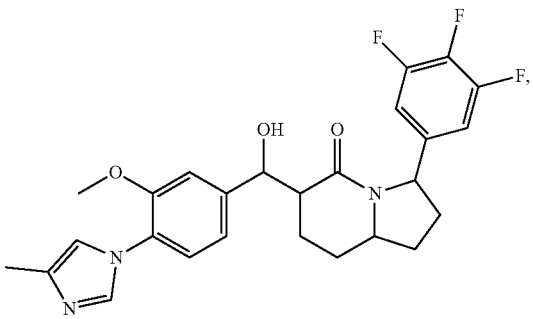

-continued

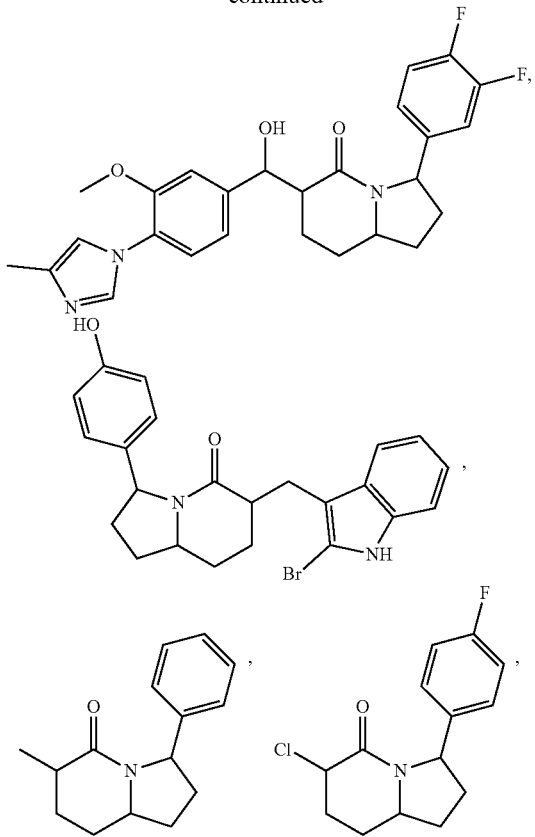

or a stereoisomer, mixture of stereoisomers or tautomer thereof.

In certain embodiments, $R^1$ is —C($R^{1a}$)($R^{1b}$)($R^{1c}$), wherein each of $R^{1a}$, $R^{1b}$ and $R^{1c}$ is independently deuterium, halo, hydroxy, cyano, nitro, azido, $C_{1-12}$ alkyl, $C_{2-12}$ alkenyl, $C_{2-12}$ alkynyl, $C_{1-12}$ alkoxy, $C_{1-12}$ haloalkyl, $C_{1-12}$ haloalkoxy, $C_{3-10}$ cycloalkyl, heterocyclyl, aryl, heteroaryl, —C(=O)$R^{11}$, —C(=O)O$R^{11}$, —OC(=O)O$R^{11}$, —OC(=O)$R^{11}$, —C(=O)N$R^{11}R^{12}$, —OC(=O)N$R^{11}R^{12}$, —N$R^{11}$C(=O)N$R^{12}R^{13}$, —S(=O)$_{1-2}R^{11}$, —S(=O)$_{1-2}$O$R^{11}$, —S(=O)$_{1-2}$N$R^{11}$, —N$R^{11}$S(=O)$_{1-2}R^{12}$, —N$R^{11}$S(=O)$_{1-2}$N$R^{12}R^{13}$, —N$R^{11}R^{12}$, —N$R^{11}$C(=O)$R^{12}$ or —N$R^{11}$C(=O)O$R^{12}$; wherein each $C_{1-12}$ alkyl, $C_{2-12}$ alkenyl, $C_{2-12}$ alkynyl, $C_{1-12}$ alkoxy, $C_{1-12}$ haloalkyl, $C_{1-12}$ haloalkoxy, $C_{3-10}$ cycloalkyl, heterocyclyl, aryl and heteroaryl are optionally substituted with one, two or three $Z^7$;

$Z^7$ is deuterium, halo, hydroxy, cyano, amino, nitro, azido, oxo, $C_{1-12}$ alkyl, $C_{1-12}$ alkoxy, $C_{1-12}$ haloalkyl, $C_{1-12}$ haloalkoxy, $C_{2-12}$ alkenyl, $C_{2-12}$ alkynyl, $C_{3-10}$ cycloalkyl, heterocyclyl, aryl or heteroaryl; and $R^{11}$, $R^{12}$ and $R^{13}$ are as defined herein.

In certain embodiments, provided are compounds of Formula Ia:

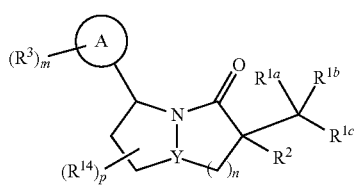

Ia or a pharmaceutically acceptable salt, prodrug, stereoisomer or a mixture of stereoisomers thereof, wherein:

Y is N or CH;
n is 1 or 2;
m is 0, 1, 2, 3, 4 or 5;
p is 0, 1, 2 or 3;
A is aryl, heteroaryl, $C_{3-10}$ cycloalkyl or heterocyclyl;
each of $R^{1a}$, $R^{1b}$ and $R^{1c}$ is independently deuterium, halo, hydroxy, cyano, nitro, azido, $C_{1-12}$ alkyl, $C_{2-12}$ alkenyl, $C_{2-12}$ alkynyl, $C_{1-12}$ alkoxy, $C_{1-12}$ haloalkyl, $C_{1-12}$ haloalkoxy, $C_{3-10}$ cycloalkyl, heterocyclyl, aryl, heteroaryl, —C(=O)$R^{11}$, —C(=O)O$R^{11}$, —OC(=O)O$R^{11}$, —OC(=O)$R^{11}$, —C(=O)N$R^{11}R^{12}$, —OC(=O)N$R^{11}R^{12}$, —N$R^{11}$C(=O)N$R^{12}R^{13}$, —S(=O)$_{1-2}R^{11}$, —S(=O)$_{1-2}$O$R^{11}$, —S(=O)$_{1-2}$N$R^{11}$, —N$R^{11}$S(=O)$_{1-2}R^{12}$, —N$R^{11}$S(=O)$_{1-2}$N$R^{12}R^{13}$, —N$R^{11}R^{12}$, —N$R^{11}$C(=O)$R^{12}$ or —N$R^{11}$C(=O)O$R^{12}$; wherein each $C_{1-12}$ alkyl, $C_{2-12}$ alkenyl, $C_{2-12}$ alkynyl, $C_{1-12}$ alkoxy, $C_{1-12}$ haloalkyl, $C_{1-12}$ haloalkoxy, $C_{3-10}$ cycloalkyl, heterocyclyl, aryl and heteroaryl are optionally substituted with one, two or three $Z^7$;

$R^2$ is hydrogen, deuterium, halo, $C_{1-12}$ alkyl, $C_{2-12}$ alkenyl, $C_{2-12}$ alkynyl, $C_{1-12}$ alkoxy, $C_{1-12}$ haloalkyl, $C_{1-12}$ haloalkoxy, $C_{3-10}$ cycloalkyl, heterocyclyl, heteroaryl or aryl; wherein each $C_{1-12}$ alkyl, $C_{2-12}$ alkenyl, $C_{2-12}$ alkynyl, $C_{1-12}$ alkoxy, $C_{1-12}$ haloalkyl, $C_{1-12}$ haloalkoxy, $C_{3-10}$ cycloalkyl, heterocyclyl, heteroaryl and aryl are optionally substituted with one, two, three, four or five $Z^1$; or any two of $R^{1a}$, $R^{1b}$ or $R^{1c}$ and $R^2$ are taken together with the atom to which they are attached to form a $C_{3-10}$ cycloalkyl or heterocyclyl; wherein the $C_{3-10}$ cycloalkyl or heterocyclyl is optionally substituted with one, two, three, four or five $Z^2$;

$R^3$ in each instance is independently deuterium, halo, hydroxy, cyano, nitro, azido, oxo, $C_{1-12}$ alkyl, —O$R^5$, $C_{1-12}$ alkoxy, $C_{2-12}$ alkenyl, $C_{2-12}$ alkynyl, $C_{1-12}$ haloalkyl, $C_{1-12}$ haloalkoxy, $C_{3-10}$ cycloalkyl, heterocyclyl, aryl, heteroaryl, —C(=O)$R^4$, —C(=O)O$R^4$, —OC(=O)O$R^4$, —OC(=O)$R^4$, —C(=O)N$R^4R^5$, —OC(=O)N$R^4R^5$, —N$R^4$C(=O)N$R^5R^6$, —S(=O)$_{1-2}R^4$, —S(=O)$_{1-2}$O$R^4$, —OS(=O)$_{1-2}R^4$, —S(=O)$_{1-2}$N$R^4$, —N$R^4$S(=O)$_{1-2}R^5$, —N$R^4$S(=O)$_{1-2}$N$R^4R^5$, —N$R^4R^5$, —N$R^4$C(=O)$R^5$ or —N$R^4$C(=O)O$R^5$; wherein each $C_{1-12}$ alkyl, $C_{1-12}$ alkoxy, $C_{2-12}$ alkenyl, $C_{2-12}$ alkynyl, $C_{1-12}$ haloalkyl, $C_{1-12}$ haloalkoxy, $C_{3-10}$ cycloalkyl, heterocyclyl, aryl and heteroaryl are optionally substituted with one, two, three, four or five $Z^3$;

$R^4$, $R^5$, and $R^6$ in each instance are independently $C_{1-12}$ alkyl, $C_{1-12}$ alkenyl, $C_{1-12}$ alkynyl, $C_{1-12}$ haloalkyl, $C_{3-10}$ cycloalkyl, heterocyclyl, heteroaryl or aryl; wherein each $C_{1-12}$ alkyl, $C_{1-12}$ alkenyl, $C_{1-12}$ alkynyl, $C_{1-12}$ haloalkyl, $C_{3-10}$ cycloalkyl, heterocyclyl, heteroaryl and aryl are optionally substituted with one, two, three, four or five $Z^4$; or two of $R^4$, $R^5$, and $R^6$ taken together with the atoms to which they are attached to form a heterocyclyl; wherein the heterocyclyl is optionally substituted with one, two, three, four or five $Z^5$;

$R^{14}$ can be bonded to either ring of the fused bicyclic ring and, in each instance, is independently halo, haloalkyl, or two $R^{14}$ bonded to the same carbon atom may be taken together with the atom to which they are attached to form a $C_{3-10}$ cycloalkyl or heterocyclyl; wherein the $C_{3-10}$ cycloalkyl or heterocyclyl is optionally substituted with one, two, three, four or five $Z^6$;

each of $Z^1$, $Z^2$, $Z^3$, $Z^4$, $Z^5$ and $Z^6$ are independently deuterium, halo, hydroxy, cyano, nitro, azido, $C_{1-12}$ alkyl, $C_{2-12}$ alkenyl, $C_{2-12}$ alkynyl, $C_{1-12}$ alkoxy, $C_{1-12}$ haloalkyl, $C_{1-12}$ haloalkoxy, $C_{3-10}$ cycloalkyl, heterocyclyl, aryl, heteroaryl, $-C(=O)R^{11}$, $-C(=O)OR^{11}$, $-OC(=O)OR^{11}$, $-OC(=O)R^{11}$, $-C(=O)NR^{11}R^{12}$, $-OC(=O)NR^{11}R^{12}$, $-NR^{11}C(=O)NR^{12}R^{13}$, $-S(=O)_{1-2}R^{11}$, $-S(=O)_{1-2}OR^{11}$, $-S(=O)_{1-2}NR^{11}$, $-NR^{11}S(=O)_{1-2}R^{12}$, $-NR^{11}S(=O)_{1-2}NR^{12}R^{13}$, $-NR^{11}R^{12}$, $-NR^{11}C(=O)R^{12}$ or $-NR^{11}C(=O)OR^{12}$;

wherein each $C_{1-12}$ alkyl, $C_{2-12}$ alkenyl, $C_{2-12}$ alkynyl, $C_{1-12}$ alkoxy, $C_{1-12}$ haloalkyl, $C_{1-12}$ haloalkoxy, $C_{3-10}$ cycloalkyl, heterocyclyl, aryl and heteroaryl, are optionally substituted with one, two or three substituents independently selected from deuterium, halo, hydroxy, cyano, amino, nitro, azido, oxo, $C_{1-12}$ alkyl, $C_{1-12}$ alkoxy, $C_{1-12}$ haloalkyl, $C_{1-12}$ haloalkoxy, $C_{2-12}$ alkenyl, $C_{2-12}$ alkynyl, $C_{3-10}$ cycloalkyl, heterocyclyl, aryl and heteroaryl;

$Z^7$ is deuterium, halo, hydroxy, cyano, amino, nitro, azido, oxo, $C_{1-12}$ alkyl, $C_{1-12}$ alkoxy, $C_{1-12}$ haloalkyl, $C_{1-12}$ haloalkoxy, $C_{2-12}$ alkenyl, $C_{2-12}$ alkynyl, $C_{3-10}$ cycloalkyl, heterocyclyl, aryl or heteroaryl;

$R^{11}$, $R^{12}$, and $R^{13}$ in each instance are independently $C_{1-12}$ alkyl, $C_{1-12}$ alkenyl, $C_{1-12}$ alkynyl, $C_{1-12}$ alkoxy, $C_{3-10}$ cycloalkyl, heterocyclyl, heteroaryl or aryl; wherein each $C_{1-12}$ alkyl, $C_{1-12}$ alkenyl, $C_{1-12}$ alkynyl, $C_{1-12}$ alkoxy, $C_{3-10}$ cycloalkyl, heterocyclyl, heteroaryl and aryl are optionally substituted with one, two, three, four or five $Z^{11}$; or two of $R^{11}$, $R^{12}$, and $R^{13}$ are taken together with the atoms to which they are attached to form a heterocyclyl; wherein the heterocyclyl is optionally substituted with one, two, three, four or five $Z^{12}$; and each of $Z^{11}$ and $Z^{12}$ is independently deuterium, halo, hydroxy, cyano, oxo, amino or $C_{1-12}$ alkyl; wherein the $C_{1-12}$ alkyl is optionally substituted with one, two or three halo, hydroxyl, amino or oxo.

In certain embodiments, the compound is not hexahydro-6-methyl-3-phenyl-5(1H)-indolizinone, 6-[(2-bromo-1H-indol-3-yl)methyl]hexahydro-3-(4-hydroxyphenyl)-5(1H)-indolizinone, or a stereoisomer thereof.

In certain embodiments, provided are compounds of Formula Ib:

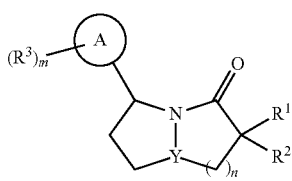

Ib or a pharmaceutically acceptable salt, prodrug, stereoisomer or a mixture of stereoisomers thereof, wherein:
Y is N or CH;
n is 1 or 2;
m is 0, 1, 2, 3, 4 or 5;
A is aryl, heteroaryl, $C_{3-10}$ cycloalkyl or heterocyclyl;
each of $R^1$ and $R^2$ are independently hydrogen, deuterium, halo, $C_{1-12}$ alkyl, $C_{1-12}$ alkenyl, $C_{1-12}$ alkynyl, $C_{1-12}$ alkoxy, $C_{1-12}$ haloalkyl, $C_{1-12}$ haloalkoxy, $C_{3-10}$ cycloalkyl, heterocyclyl, heteroaryl or aryl; wherein each $C_{1-12}$ alkyl, $C_{1-12}$ alkenyl, $C_{1-12}$ alkynyl, $C_{1-12}$ alkoxy, $C_{1-12}$ haloalkyl, $C_{1-12}$ haloalkoxy, $C_{3-10}$ cycloalkyl, heterocyclyl, heteroaryl and aryl are optionally substituted with one, two, three, four or five $Z^1$; or $R^1$ and $R^2$ taken together with the atoms to which they are attached to form a $C_{3-10}$ cycloalkyl; wherein the $C_{3-10}$ cycloalkyl is optionally substituted with one, two, three, four or five $Z^2$;

$R^3$ in each instance is independently deuterium, halo, hydroxy, cyano, nitro, azido, oxo, $C_{1-12}$ alkyl, $-OR^5$, $C_{1-12}$ alkoxy, $C_{2-12}$ alkenyl, $C_{2-12}$ alkynyl, $C_{1-12}$ haloalkyl, $C_{1-12}$ haloalkoxy, $C_{3-10}$ cycloalkyl, heterocyclyl, aryl, heteroaryl, $-C(=O)R^4$, $-C(=O)OR^4$, $-OC(=O)OR^4$, $-OC(=O)R^4$, $-C(=O)NR^4R^5$, $-OC(=O)NR^4R^5$, $-NR^4C(=O)NR^5R^6$, $-S(=O)_{1-2}R^4$, $-S(=O)_{1-2}OR^4$, $-OS(=O)_{1-2}R^4$, $-S(=O)_{1-2}NR^4$, $-NR^4S(=O)_{1-2}R^5$, $-NR^4S(=O)_{1-2}NR^4R^5$, $-NR^4R^5$, $-NR^4C(=O)R^5$ or $-NR^4C(=O)OR^5$; wherein each $C_{1-12}$ alkyl, $C_{1-12}$ alkoxy, $C_{2-12}$ alkenyl, $C_{2-12}$ alkynyl, $C_{1-12}$ haloalkyl, $C_{1-12}$ haloalkoxy, $C_{3-10}$ cycloalkyl, heterocyclyl, aryl and heteroaryl are optionally substituted with one, two, three, four or five $Z^3$;

$R^4$, $R^5$, and $R^6$ in each instance are independently $C_{1-12}$ alkyl, $C_{1-12}$ alkenyl, $C_{1-12}$ alkynyl, $C_{1-12}$ haloalkyl, $C_{3-10}$ cycloalkyl, heterocyclyl, heteroaryl or aryl; wherein each $C_{1-12}$ alkyl, $C_{1-12}$ alkenyl, $C_{1-12}$ alkynyl, $C_{1-12}$ haloalkyl, $C_{3-10}$ cycloalkyl, heterocyclyl, heteroaryl and aryl are optionally substituted with one, two, three, four or five $Z^4$; or two of $R^4$, $R^5$, and $R^6$ taken together with the atoms to which they are attached to form a heterocyclyl; wherein the heterocyclyl is optionally substituted with one, two, three, four or five $Z^5$;

each of $Z^1$, $Z^2$, $Z^3$, $Z^4$ and $Z^5$ are independently deuterium, halo, hydroxy, cyano, nitro, azido, $C_{1-12}$ alkyl, $C_{1-12}$ alkenyl, $C_{1-12}$ alkynyl, $C_{1-12}$ alkoxy, $C_{1-12}$ haloalkyl, $C_{1-12}$ haloalkoxy, $C_{3-10}$ cycloalkyl, heterocyclyl, aryl, heteroaryl, $-C(=O)R^{11}$, $-C(=O)OR^{11}$, $-OC(=O)OR^{11}$, $-OC(=O)R^{11}$, $-C(=O)NR^{11}R^{12}$, $-OC(=O)NR^{11}R^{12}$, $-NR^{11}C(=O)NR^{12}R^{13}$, $-S(=O)_{1-2}R^{11}$, $-S(=O)_{1-2}OR^{11}$, $-S(=O)_{1-2}NR^{11}$, $-NR^{11}S(=O)_{1-2}R^{12}$, $-NR^{11}S(=O)_{1-2}NR^{12}R^{13}$, $-NR^{11}R^{12}$, $-NR^{11}C(=O)R^{12}$ or $-NR^{11}C(=O)OR^{12}$;

wherein each $C_{1-12}$ alkyl, $C_{1-12}$ alkenyl, $C_{1-12}$ alkynyl, $C_{1-12}$ alkoxy, $C_{1-12}$ haloalkyl, $C_{1-12}$ haloalkoxy, $C_{3-10}$ cycloalkyl, heterocyclyl, aryl and heteroaryl, are optionally substituted with one, two or three substituents independently selected from deuterium, halo, hydroxy, cyano, amino, nitro, azido, oxo, $C_{1-12}$ alkyl, $C_{1-12}$ alkoxy, $C_{1-12}$ haloalkyl, $C_{1-12}$ haloalkoxy, $C_{2-12}$ alkenyl, $C_{2-12}$ alkynyl, $C_{3-10}$ cycloalkyl, heterocyclyl, aryl and heteroaryl; and
$R^{11}$, $R^{12}$, and $R^{13}$ in each instance are independently $C_{1-12}$ alkyl, $C_{1-12}$ alkenyl, $C_{1-12}$ alkynyl, $C_{1-12}$ alkoxy, $C_{3-10}$ cycloalkyl, heterocyclyl, heteroaryl or aryl; wherein each $C_{1-12}$ alkyl, $C_{1-12}$ alkenyl, $C_{1-12}$ alkynyl, $C_{1-12}$ alkoxy, $C_{3-10}$ cycloalkyl, heterocyclyl, heteroaryl and aryl are optionally substituted with one, two, three, four or five $Z^{11}$; or two of $R^{11}$, $R^{12}$, and $R^{13}$ are taken together with the atoms to which they are attached to form a heterocyclyl; wherein the heterocyclyl is optionally substituted with one, two, three, four or five $Z^{12}$;

each of $Z^{11}$ and $Z^{12}$ is independently deuterium, halo, hydroxy, cyano, oxo, amino or $C_{1-12}$ alkyl; wherein the $C_{1-12}$ alkyl is optionally substituted with one, two or three halo, hydroxyl, amino or oxo.

In certain embodiments, when n is 1, Y is CH and one of $R^1$ and $R^2$ is iodo, both of $R^1$ and $R^2$ are hydrogen, or one of $R^1$ and $R^2$ is alkenyl, then A is not 3,4-difluorophenyl, and when n is 1, Y is CH, both of $R^1$ and $R^2$ are hydrogen, then A is not heterocyclyl substituted with oxo.

In certain embodiments, when n is 2, Y is CH and one of $R^1$ or $R^2$ is iodo, or both of $R^1$ or $R^2$ are hydrogen, then A is not 4-chlorophenyl, 2,6-difluoropyridin-3-yl, phenyl, or phenyl substituted with 1, 2 or 3 fluoro, and the compound is not (3R,8aR)-6-chloro-3-(4-fluorophenyl)hexahydroindolizin-5(1H)-one; (3R,6S,8aS)-6-methyl-3-phenylhexahydroindolizin-5(1H)-one; or (3R,6R,8aS)-6-((2-bromo-1H-indol-3-yl)methyl)-3-(4-hydroxyphenyl)hexahydroindolizin-5(1H)-one.

In certain embodiments, provided is a compound of formula Ia':

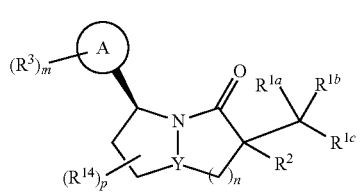

Ia' where A, Y, n, m, p, $R^{1a}$, $R^{1b}$, $R^{1c}$, $R^2$, $R^3$ and $R^{14}$ are as defined herein. In certain embodiments, provided is a compound of formula Ia":

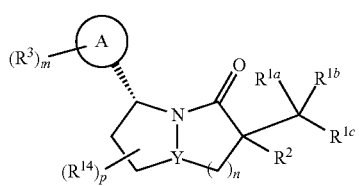

Ia"

where A, Y, n, m, p, $R^{1a}$, $R^{1b}$, $R^{1c}$, $R^2$, $R^3$ and $R^{14}$ are as defined herein. In certain embodiments, provided is a compound of formula Ib':

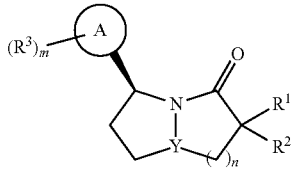

Ib' where A, Y, n, m, $R^1$, $R^2$ and $R^3$ are as defined herein. In certain embodiments, provided is a compound of formula Ib":

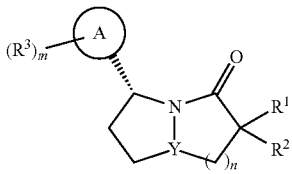

Ib"

where A, Y, n, m, $R^1$, $R^2$ and $R^3$ are as defined herein.

In certain embodiments, provided is a compound of formula Ic:

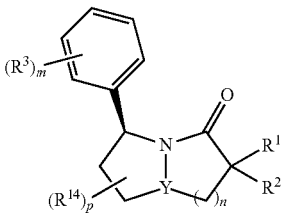

Ic where Y, n, m, p, $R^1$, $R^2$, $R^3$ and $R^{14}$ are as defined herein. In certain embodiments, provided is a compound of formula Id:

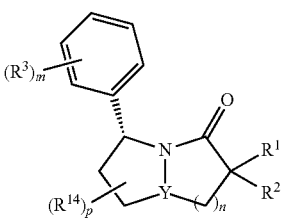

Id where Y, n, m, p, $R^1$, $R^2$, $R^3$ and $R^{14}$ are as defined herein. In certain embodiments, provided is a compound of formula Ie:

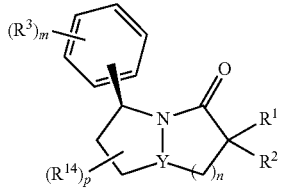

Ie where Y, n, m, p, $R^1$, $R^2$, $R^3$ and $R^{14}$ are as defined herein. In certain embodiments, provided is a compound of formula If:

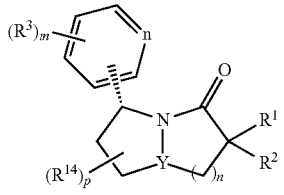

If where Y, n, m, p, $R^1$, $R^2$, $R^3$ and $R^{14}$ are as defined herein. In certain embodiments, provided is a compound of formula Ig:

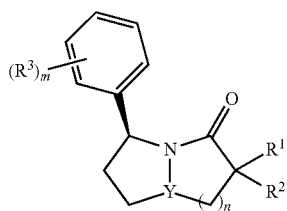

Ig where Y, n, m, $R^1$, $R^2$, and $R^3$ are as defined herein. In certain embodiments, provided is a compound of formula Ih:
($R^3$)

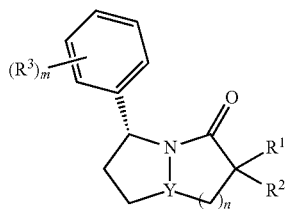

Ih where Y, n, m, $R^1$, $R^2$, and $R^3$ are as defined herein. In certain embodiments, provided is a compound of formula Ii:

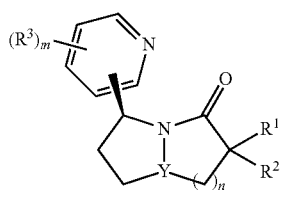

Ii where Y, n, m, $R^1$, $R^2$, and $R^3$ are as defined herein. In certain embodiments, provided is a compound of formula Ij:

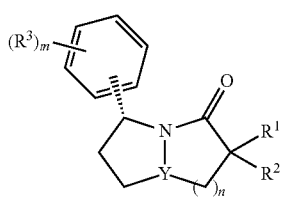

Ij where Y, n, m, $R^1$, $R^2$, and $R^3$ are as defined herein. In certain embodiments, provided is a compound of formula Ik:

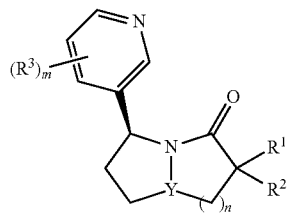

Ik where Y, n, m, $R^1$, $R^2$, $R^3$ and are as defined herein. In certain embodiments, provided is a compound of formula Il:

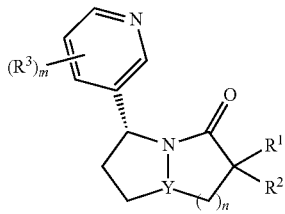

Il where Y, n, m, $R^1$, $R^2$, and $R^3$ are as defined herein.

In certain embodiments, n is 1. In certain embodiments, provided is a compound of formula IIa:

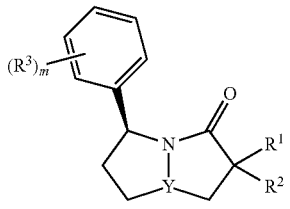

IIa where Y, m, $R^1$, $R^2$, and $R^3$ are as defined herein. In certain embodiments, provided is a compound of formula IIb:

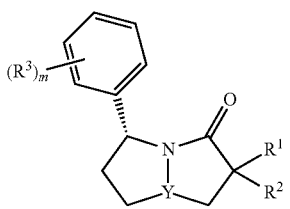

IIb where Y, m, $R^1$, $R^2$, and $R^3$ are as defined herein.

In certain embodiments, n is 2. In certain embodiments, provided is a compound of formula IIc:

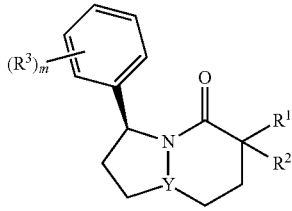

IIc where Y, m, R¹, R², and R³ are as defined herein. In certain embodiments, provided is a compound of formula IId:

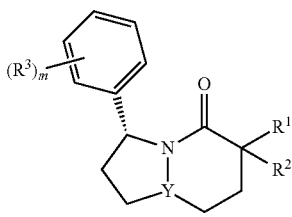

IId where Y, m, R¹, R², and R³ are as defined herein. In certain embodiments, provided is a compound of formula IIe:

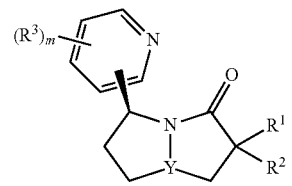

IIe where Y, m, R¹, R², and R³ are as defined herein. In certain embodiments, provided is a compound of formula IIf:

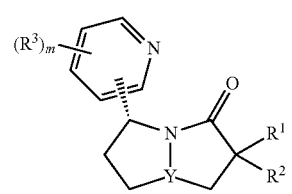

IIf where Y, m, R¹, R², and R³ are as defined herein.

In certain embodiments, n is 2. In certain embodiments, provided is a compound of formula IIg:

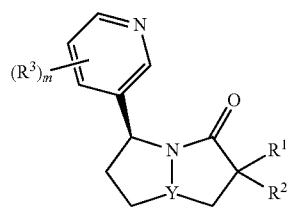

IIg where Y, m, R¹, R², and R³ are as defined herein. In certain embodiments, provided is a compound of formula IIh:

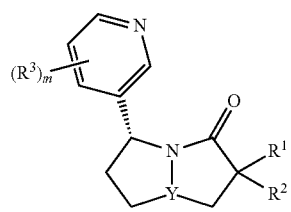

IIh where Y, m, R¹, R², and R³ are as defined herein.

In certain embodiments, n is 2. In certain embodiments, provided is a compound of formula IIi:

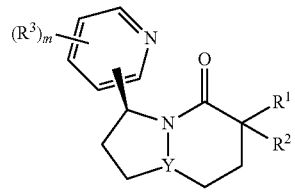

IIi where Y, m, R¹, R², and R³ are as defined herein. In certain embodiments, provided is a compound of formula IIj:

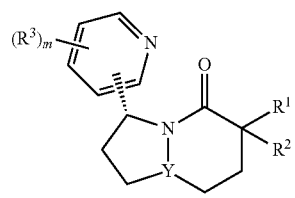

IIj where Y, m, R¹, R², and R³ are as defined herein. In certain embodiments, provided is a compound of formula IIk:

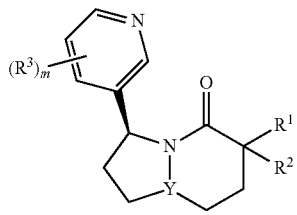

IIk where Y, m, $R^1$, $R^2$, and $R^3$ are as defined herein. In certain embodiments, provided is a compound of formula III:

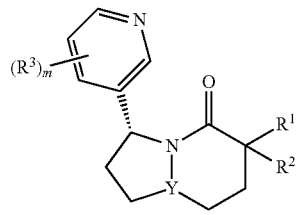

III where Y, m, $R^1$, $R^2$, and $R^3$ are as defined herein.

In certain embodiments, Y is N. In certain embodiments, provided is a compound of formula IIIa:

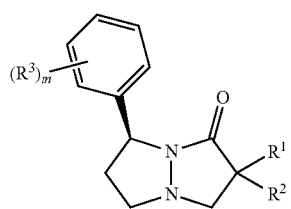

IIIa where m, $R^1$, $R^2$, and $R^3$ are as defined herein. In certain embodiments, provided is a compound of formula IIIb:

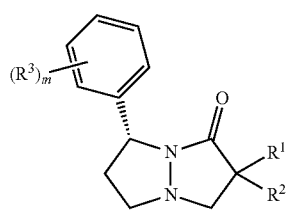

IIIb where m, $R^1$, $R^2$, and $R^3$ are as defined herein. In certain embodiments, provided is a compound of formula IIIc:

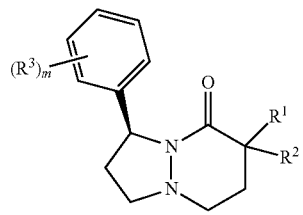

IIIc where m, $R^1$, $R^2$, and $R^3$ are as defined herein. In certain embodiments, provided is a compound of formula IIId:

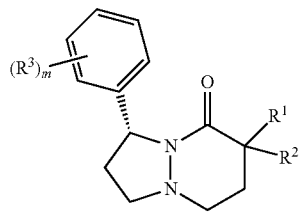

IIId where m, $R^1$, $R^2$, and $R^3$ are as defined herein. In certain embodiments, provided is a compound of formula IIIe:

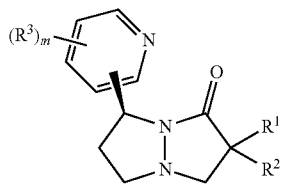

IIIe where m, $R^1$, $R^2$, and $R^3$ are as defined herein. In certain embodiments, provided is a compound of formula IIIf:

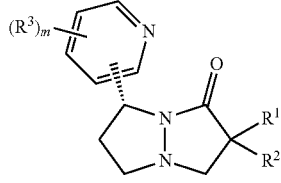

IIIf where m, $R^1$, $R^2$, and $R^3$ are as defined herein. In certain embodiments, provided is a compound of formula IIIg:

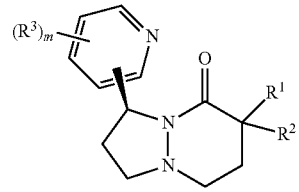

IIIg where m, $R^1$, $R^2$, and $R^3$ are as defined herein. In certain embodiments, provided is a compound of formula IIIh:

IIIh

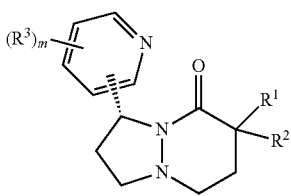

where m, $R^1$, $R^2$, and $R^3$ are as defined herein. In certain embodiments, provided is a compound of formula IIIi:

IIIi

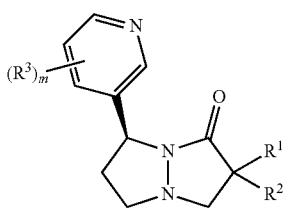

where m, $R^1$, $R^2$, and $R^3$ are as defined herein. In certain embodiments, provided is a compound of formula IIIj:

IIIj

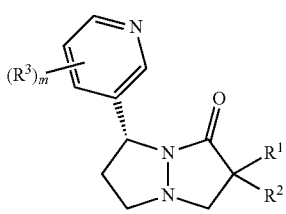

where m, $R^1$, $R^2$, and $R^3$ are as defined herein. In certain embodiments, provided is a compound of formula IIIk:

IIIk

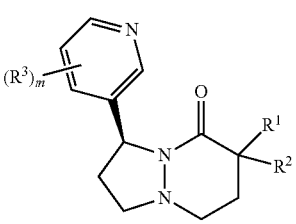

where m, $R^1$, $R^2$, and $R^3$ are as defined herein. In certain embodiments, provided is a compound of formula IIII:

IIII

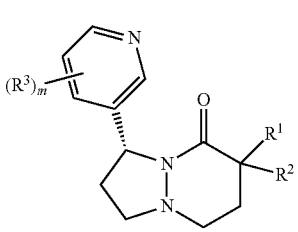

where m, $R^1$, $R^2$, and $R^3$ are as defined herein.

In certain embodiments, Y is CH. In certain embodiments, provided is a compound of formula IVa:

IVa

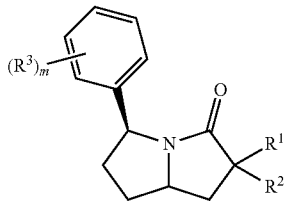

where m, $R^1$, $R^2$, and $R^3$ are as defined herein. In certain embodiments, provided is a compound of formula IVb:

IVb

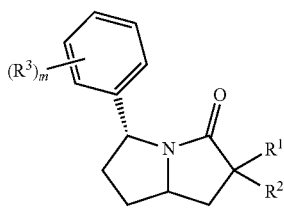

where m, $R^1$, $R^2$, and $R^3$ are as defined herein. In certain embodiments, provided is a compound of formula IVc:

IVc

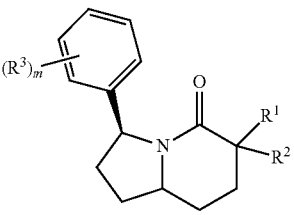

where m, $R^1$, $R^2$, and $R^3$ are as defined herein. In certain embodiments, provided is a compound of formula IVd:

IVd

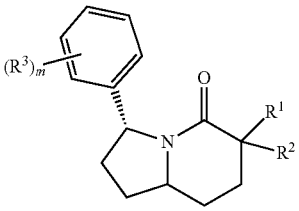

where m, $R^1$, $R^2$, and $R^3$ are as defined herein. In certain embodiments, provided is a compound of formula IVe:

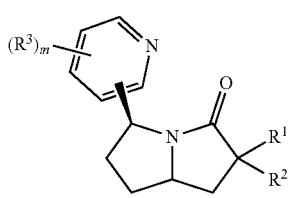
IVe where m, R¹, R², and R³ are as defined herein. In certain embodiments, provided is a compound of formula IVf:

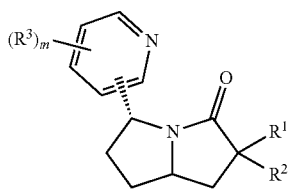
IVf where m, R¹, R², and R³ are as defined herein. In certain embodiments, provided is a compound of formula IVg:

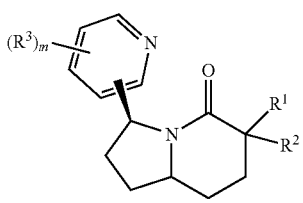
IVg where m, R¹, R², and R³ are as defined herein. In certain embodiments, provided is a compound of formula IVh:

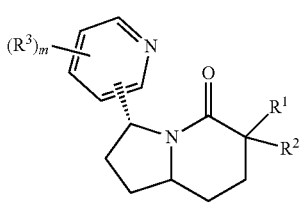
IVh where m, R¹, R², and R³ are as defined herein. In certain embodiments, provided is a compound of formula IVi:

IVi where m, R¹, R², and R³ are as defined herein. In certain embodiments, provided is a compound of formula IVj:

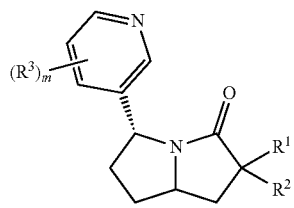
IVj where m, R¹, R², and R³ are as defined herein. In certain embodiments, provided is a compound of formula IVk:

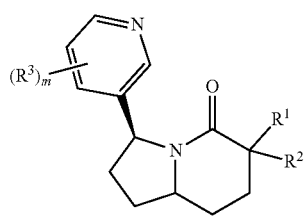
IVk where m, R¹, R², and R³ are as defined herein. In certain embodiments, provided is a compound of formula IVl:

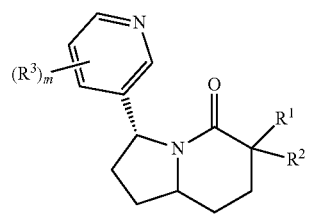
IVl where m, R¹, R², and R³ are as defined herein.

In certain embodiments, m is 0. In certain embodiments, m is 1, 2 or 3. In certain embodiments, m is 1. In certain embodiments, m is 2. In certain embodiments, m is 3.

In certain embodiments, provided is a compound of formula Va, Vb or Vc:

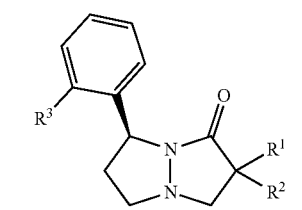
Va

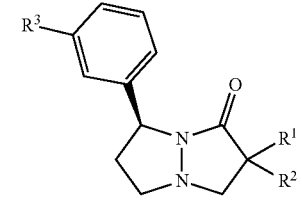
Vb

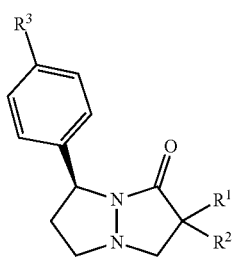

Vc where R¹, R², and R³ are as defined herein. In certain embodiments, provided is a compound of formula VIa, VIb, VIc or VId:

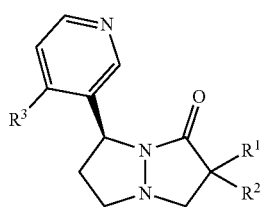

VIa

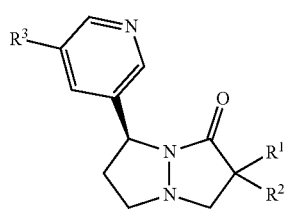

VIb

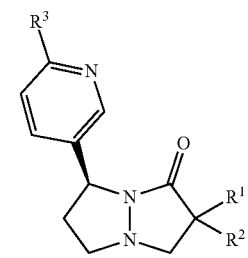

VIc

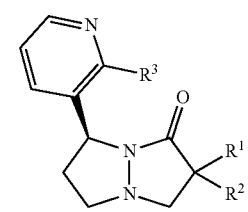

VId where R¹, R², and R³ are as defined herein. In certain embodiments, provided is a compound of formula VIIa, VIIb, VIIc, VIId, VIIe or VIIf:

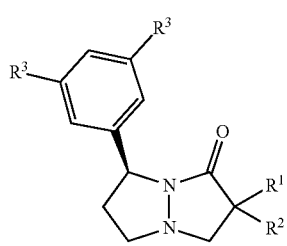

VIIa

VIIb

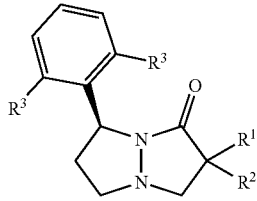

VIIc

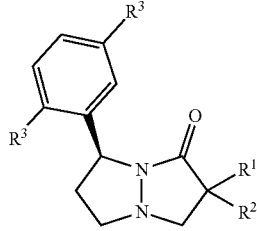

VIId

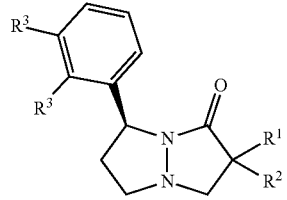

VIIe

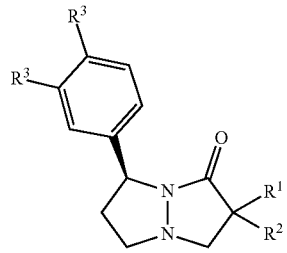

VIIf where R¹, R², and R³ are as defined herein. In certain embodiments, provided is a compound of formula VIIIa, VIIIb, VIIIc, VIIId, VIIIe or VIIIf:

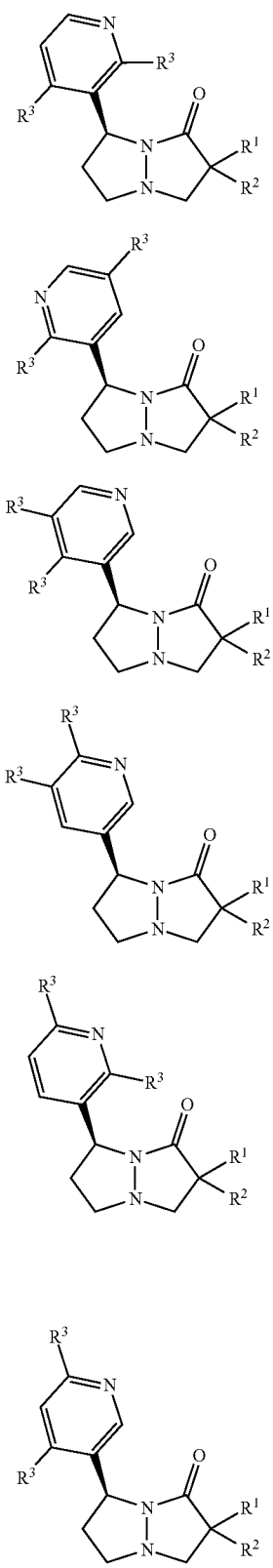
VIIIa
VIIIb
VIIIc
VIIId
VIIIe
VIIIf
where R[1], R[2], and R[3] are as defined herein. In certain embodiments, provided is a compound of formula IXa, IXb or IXc:
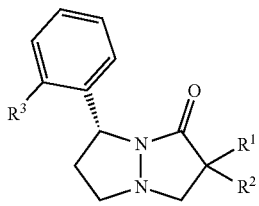 IXa
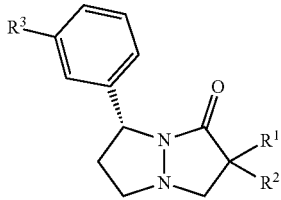 IXb
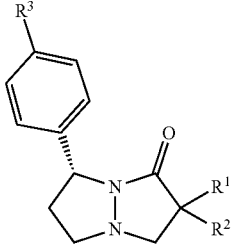 IXc
where R[1], R[2], and R[3] are as defined herein. In certain embodiments, provided is a compound of formula Xa, Xb, Xc or Xd:
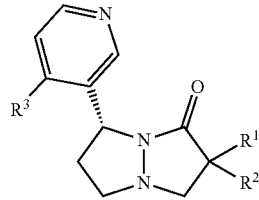 Xa
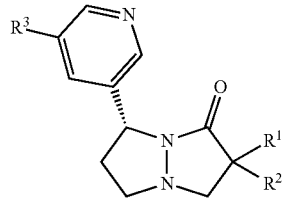 Xb
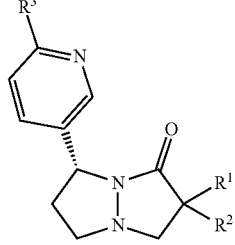 Xc

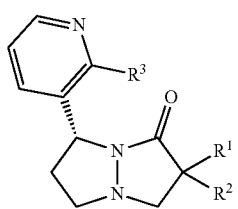
Xd
where R¹, R², and R³ are as defined herein. In certain embodiments, provided is a compound of formula XIa XIb, XIc, XId, XIe or XIf:
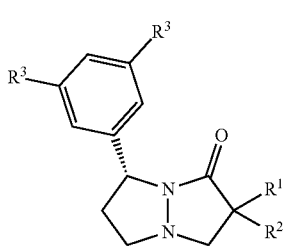
XIa
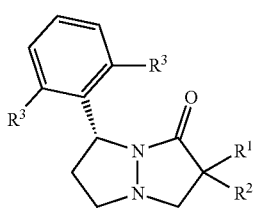
XIb
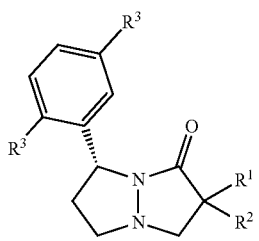
XIc
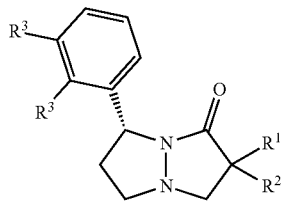
XId
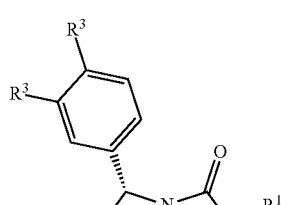
XIe
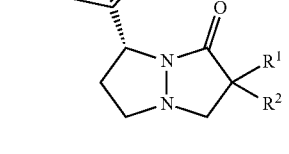
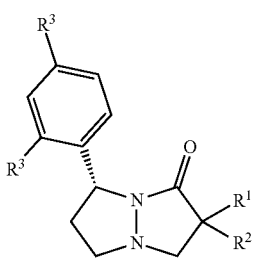
XIf
where R¹, R², and R³ are as defined herein. In certain embodiments, provided is a compound of formula XIIa, XIIb, XIIc, XIId, XIIe or XIIf:
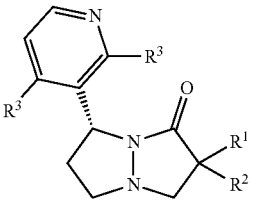
XIIa
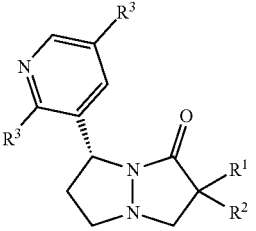
XIIb
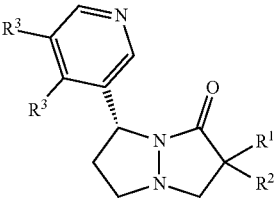
XIIx
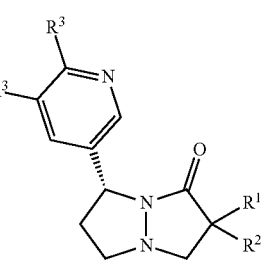
XIId
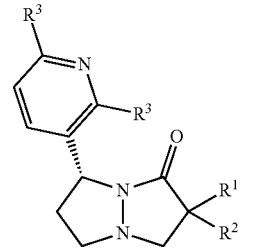
XIIe

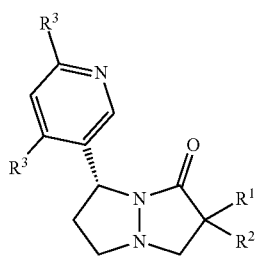

XIIf where R¹, R², and R³ are as defined herein. In certain embodiments, provided is a compound of formula XIIIa, XIIIb or XIIIc:

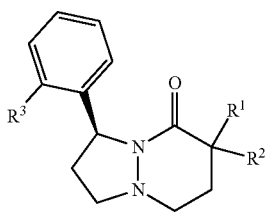

XIIIa

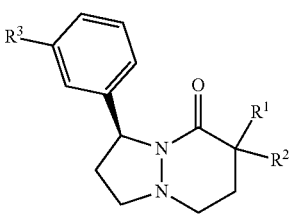

XIIIb

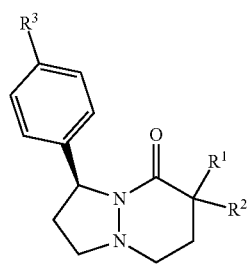

XIIIc where R¹, R², and R³ are as defined herein. In certain embodiments, provided is a compound of formula XIVa, XIVb, XIVc or XIVd:

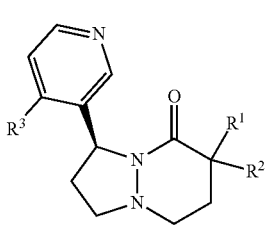

XIVa

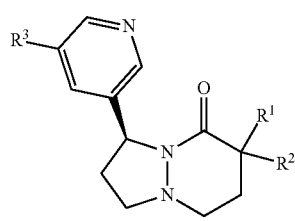

XIVb

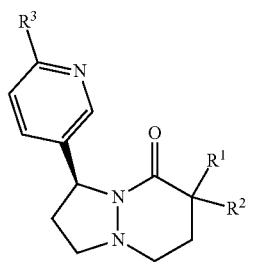

XIVc

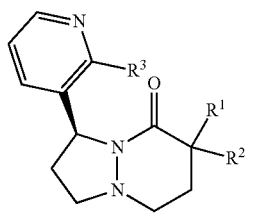

XIVd where R¹, R², and R³ are as defined herein. In certain embodiments, provided is a compound of formula XVa, XVb, XVc, XVd or XVe:

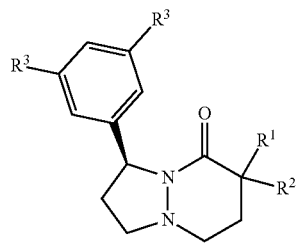

XVa

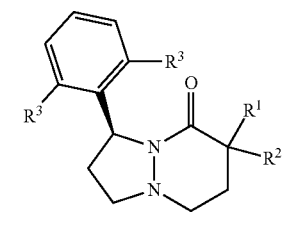

XVb

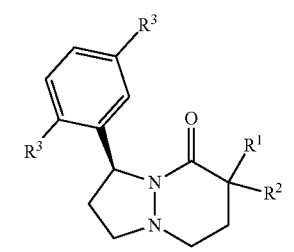

XVc

XVd

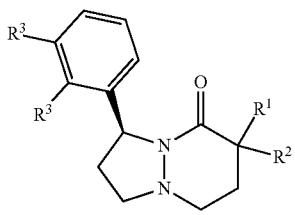

XVe

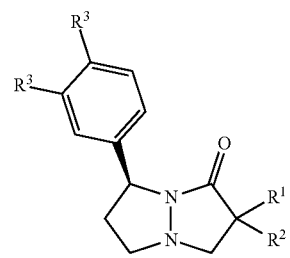

where R¹, R², and R³ are as defined herein. In certain embodiments, provided is a compound of formula XVIa, XVIb, XVIc, XVId, XVIe or XVIf:

XVIa

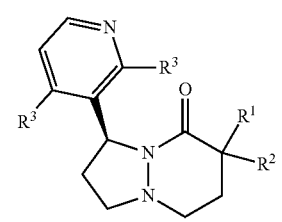

XVIb

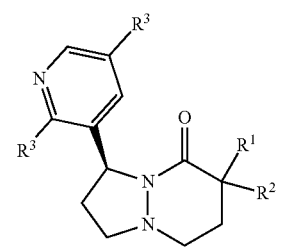

XVIc

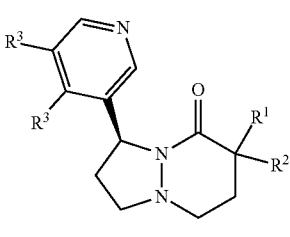

XVId

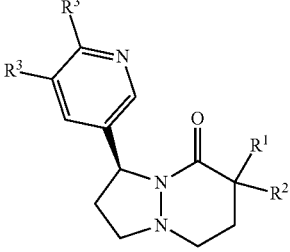

XVIe

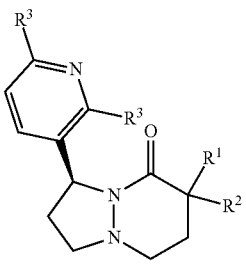

XVIf

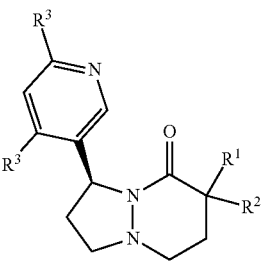

where R¹, R², and R³ are as defined herein. In certain embodiments, provided is a compound of formula XVIIa, XVIIb or XVIIc:

XVIIa

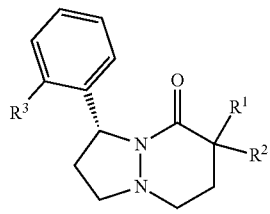

XVIIb

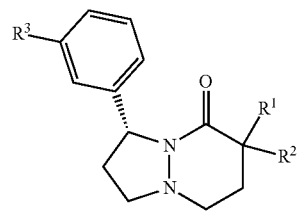

XVIIc

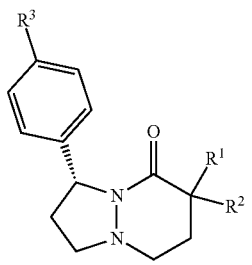

where R¹, R², and R³ are as defined herein. In certain embodiments, provided is a compound of formula XVIIIa, XVIIIb, XVIIIc or XVIIId:

XVIIIa
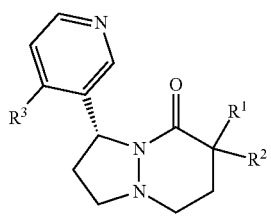
XVIIIb
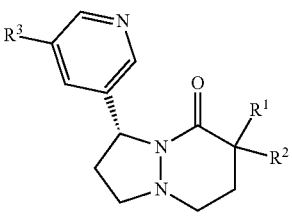
XVIIIc
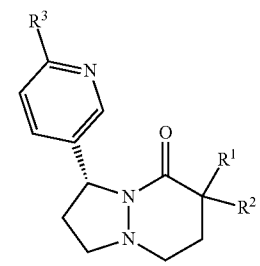
XVIIId
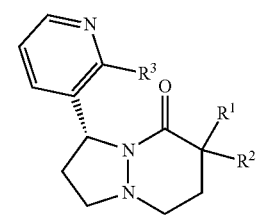
where $R^1$, $R^2$, and $R^3$ are as defined herein. In certain embodiments, provided is a compound of formula XIXa, XIXb, XIXc, XIXd or XIXe:
XIXa
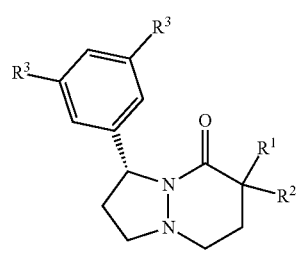
XIXb
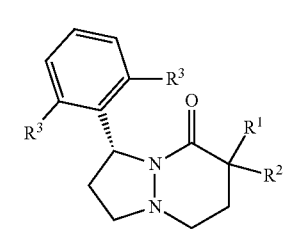
XIXc
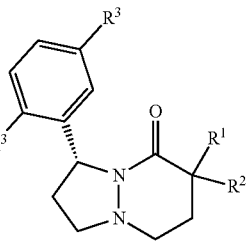
XIXd
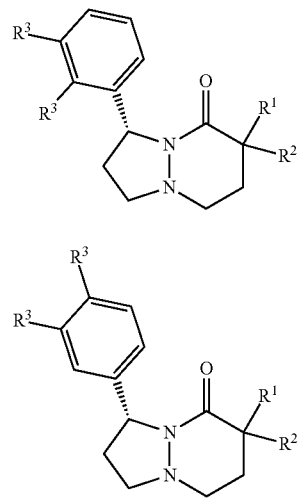
XIXe
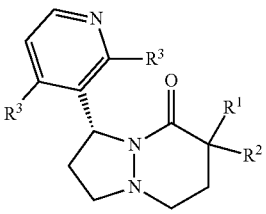
where $R^1$, $R^2$, and $R^3$ are as defined herein. In certain embodiments, provided is a compound of formula XXa, XXb, XXc, XXd, XXe or XXf:
XXa
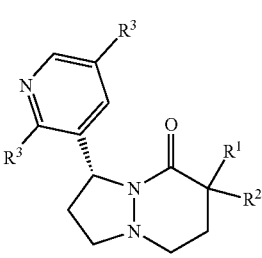
XXb
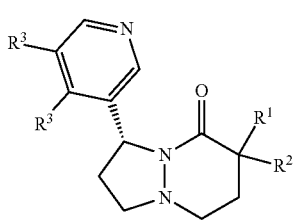
XXc

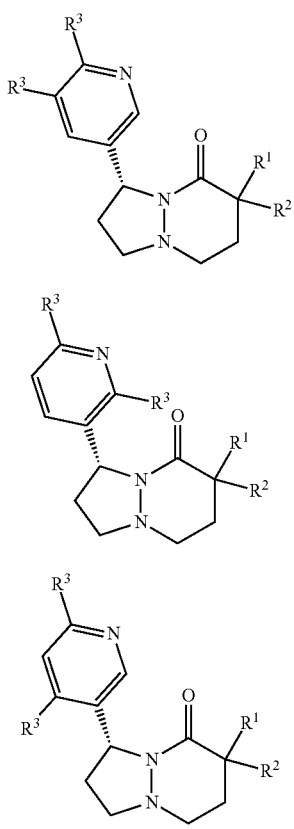

XXd

XXe

XXf where R¹, R², and R³ are as defined herein.

In certain embodiments, in any of the formulas described herein, each of R¹ and R² are independently hydrogen, deuterium, halo, $C_{1-12}$ alkyl, $C_{3-10}$ cycloalkyl, heterocyclyl, heteroaryl or aryl; wherein each $C_{1-12}$ alkyl, $C_{3-10}$ cycloalkyl, heterocyclyl, heteroaryl and aryl group is optionally substituted with one, two, three or four $Z^1$.

In certain embodiments, in any of the formulas described herein, each of R¹ and R² are independently hydrogen, deuterium or $C_{1-12}$ alkyl, which $C_{1-12}$ alkyl is optionally substituted with one, two, three or four $Z^1$. In certain embodiments, in any of the formulas described herein, each of R¹ and R² are independently hydrogen, deuterium, $C_{1-12}$ haloalkyl or $C_{1-12}$ alkyl. In certain embodiments, in any of the formulas described herein, each of R¹ and R² are independently hydrogen, deuterium or $C_{1-12}$ alkyl. In certain embodiments, in any of the formulas described herein, at least one of R¹ and R² is other than hydrogen or deuterium. In certain embodiments, in any of the formulas described herein, each of R¹ and R² are independently $C_{1-12}$ haloalkyl or $C_{1-12}$ alkyl. In certain embodiments, in any of the formulas described herein, each of R¹ and R² are independently $C_{1-12}$ alkyl. In certain embodiments, in any of the formulas described herein, one of R¹ and R² is methyl and the other of R¹ and R² is ethyl. In certain embodiments, in any of the formulas described herein, R¹ and R² are methyl.

In certain embodiments, in any of the formulas described herein, R¹ is —C(R$^{1a}$)(R$^{1b}$)(R$^{1c}$), wherein each of R$^{1a}$, R$^{1b}$ and R$^{1c}$ is independently deuterium, halo, hydroxy, cyano, nitro, azido, $C_{1-12}$ alkyl, $C_{2-12}$ alkenyl, $C_{2-12}$ alkynyl, $C_{1-12}$ alkoxy, $C_{1-12}$ haloalkyl, $C_{1-12}$ haloalkoxy, $C_{3-10}$ cycloalkyl, heterocyclyl, aryl, heteroaryl, —C(=O)R$^{11}$, —C(=O)OR$^{11}$, —OC(=O)OR$^{11}$, —OC(=O)R$^{11}$, —C(=O)NR$^{11}$R$^{12}$, —OC(=O)NR$^{11}$R$^{12}$, —NR$^{11}$C(=O)NR$^{12}$R$^{13}$, —S(=O)$_{1-2}$R$^{11}$, —S(=O)$_{1-2}$OR$^{11}$, —S(=O)$_{1-2}$NR$^{11}$, —NR$^{11}$S(=O)$_{2}$R$^{12}$, —NR$^{11}$S(=O)$_{1-2}$NR$^{12}$R$^{13}$, —NR$^{11}$R$^{12}$, —NRC(=O)R$^{12}$ or —NRC(=O)OR$^{12}$;
wherein each $C_{1-12}$ alkyl, $C_{2-12}$ alkenyl, $C_{2-12}$ alkynyl, $C_{1-12}$ alkoxy, $C_{1-12}$ haloalkyl, $C_{1-12}$ haloalkoxy, $C_{3-10}$ cycloalkyl, heterocyclyl, aryl and heteroaryl are optionally substituted with one, two or three $Z^7$;

$Z^1$ is deuterium, halo, hydroxy, cyano, amino, nitro, azido, oxo, $C_{1-12}$ alkyl, $C_{1-12}$ alkoxy, $C_{1-12}$ haloalkyl, $C_{1-2}$ haloalkoxy, $C_{2-12}$ alkenyl, $C_{2-12}$ alkynyl, $C_{3-10}$ cycloalkyl, heterocyclyl, aryl or heteroaryl; and R$^{11}$, R$^{12}$ and R³ are as defined herein.

In certain embodiments, in any of the formulas described herein, m is 1 or 3. In certain embodiments, in any of the formulas described herein, m is 1 or 2. In certain embodiments, in any of the formulas described herein, R³ in each instance is independently deuterium, halo, hydroxy, cyano, nitro or $C_{1-12}$ alkyl, which $C_{1-12}$ alkyl is optionally substituted with one, two, three or four $Z^3$. In certain embodiments, in any of the formulas described herein, m is 1 or 2, and R³ in each instance is independently deuterium, halo, hydroxy, cyano, nitro or $C_{1-12}$ alkyl.

In certain embodiments, in any of the formulas described herein, R³ in each instance is independently halo, hydroxy or cyano. In certain embodiments, in any of the formulas described herein, R³ in each instance is independently halo or cyano. In certain embodiments, in any of the formulas described herein, R³ in each instance is independently fluoro or cyano.

In certain embodiments, in any of the formulas described herein, each of R¹ and R² are independently hydrogen, deuterium or $C_{1-12}$ alkyl, which $C_{1-12}$ alkyl is optionally substituted with one, two, three or four $Z^1$; and R³ in each instance is independently halo or cyano.

In certain embodiments, in any of the formulas described herein, each of R¹ and R² are independently $C_{1-12}$ alkyl; and R³ in each instance is independently halo or cyano.

In certain embodiments, in any of the formulas described herein, one of R¹ and R² is methyl and the other of R¹ and R² is ethyl; and R³ in each instance is independently halo or cyano. In certain embodiments, in any of the formulas described herein, one of R¹ and R² is methyl and the other of R¹ and R² is ethyl; and R³ in each instance is independently fluoro or cyano.

In certain embodiments, in any of the formulas described herein, R¹ and R² are methyl; and R³ in each instance is independently halo or cyano. In certain embodiments, in any of the formulas described herein, R¹ and R² are methyl; and R³ in each instance is independently fluoro or cyano.

In certain embodiments, the compound is selected from Table 1. Also included within the disclosure are stereoisomers and mixtures of stereoisomers thereof.

TABLE 1

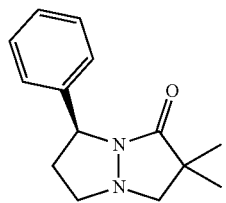 [SMILES: CC1(C)CN2CC[C@@H](c3ccccc3)N2C1=O]

1

TABLE 1-continued
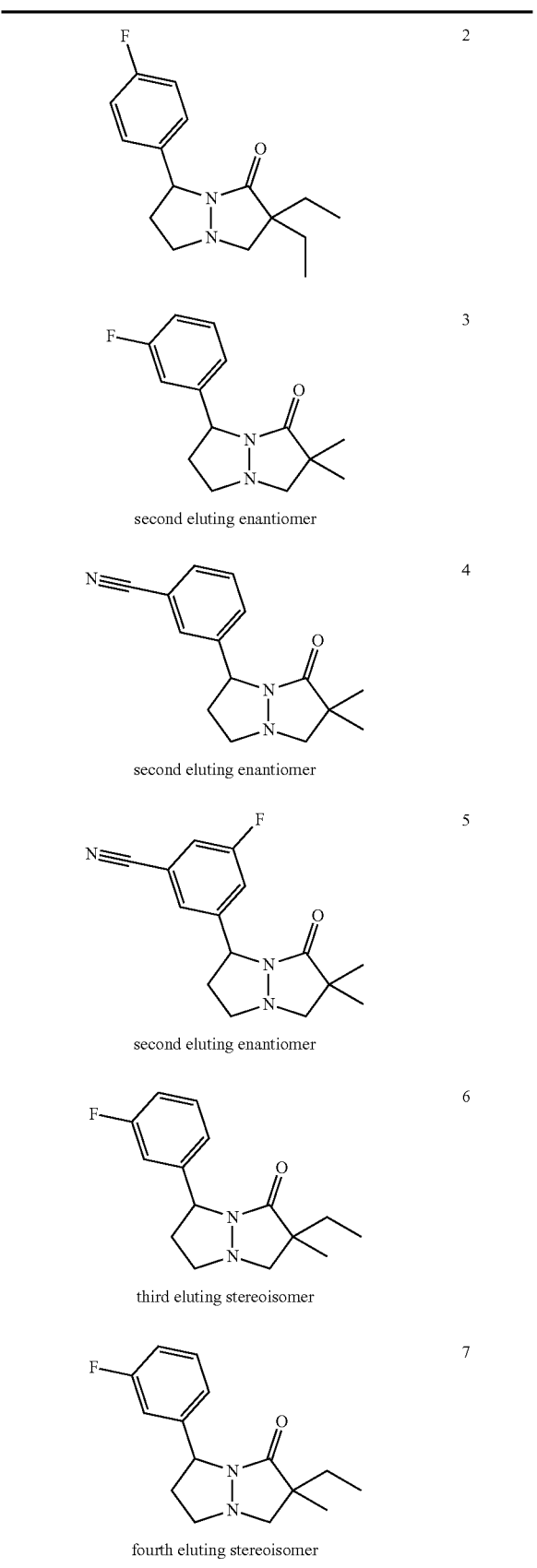
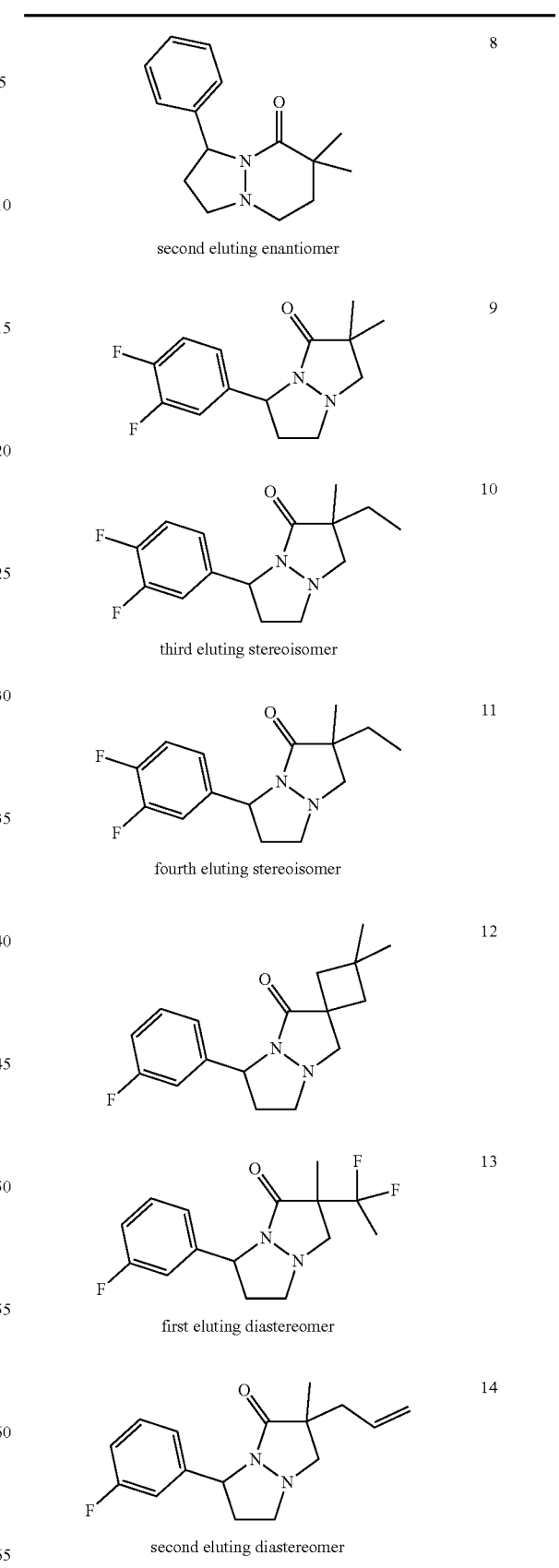

TABLE 1-continued
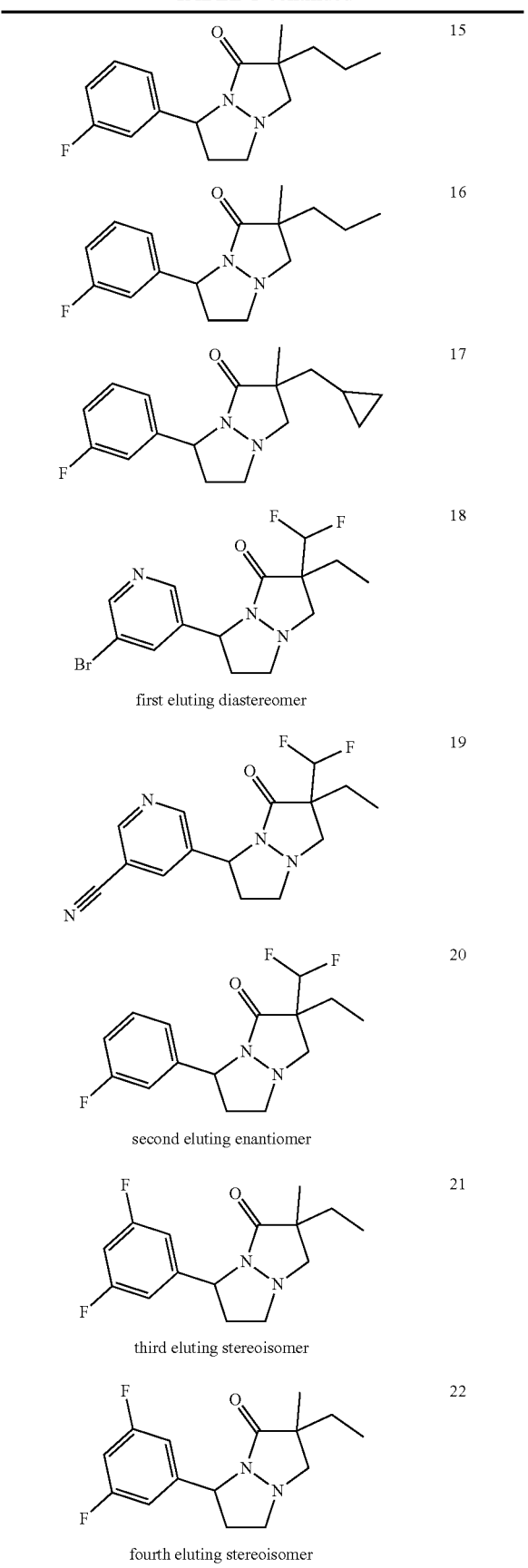
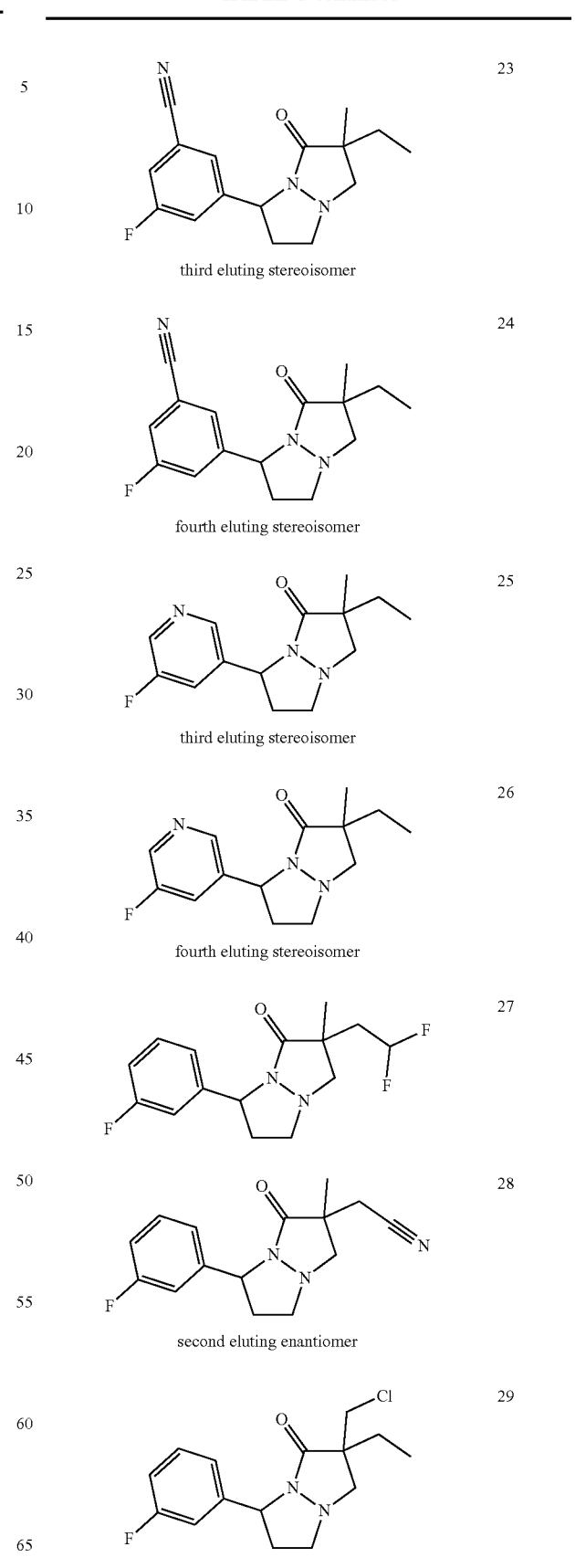

TABLE 1-continued
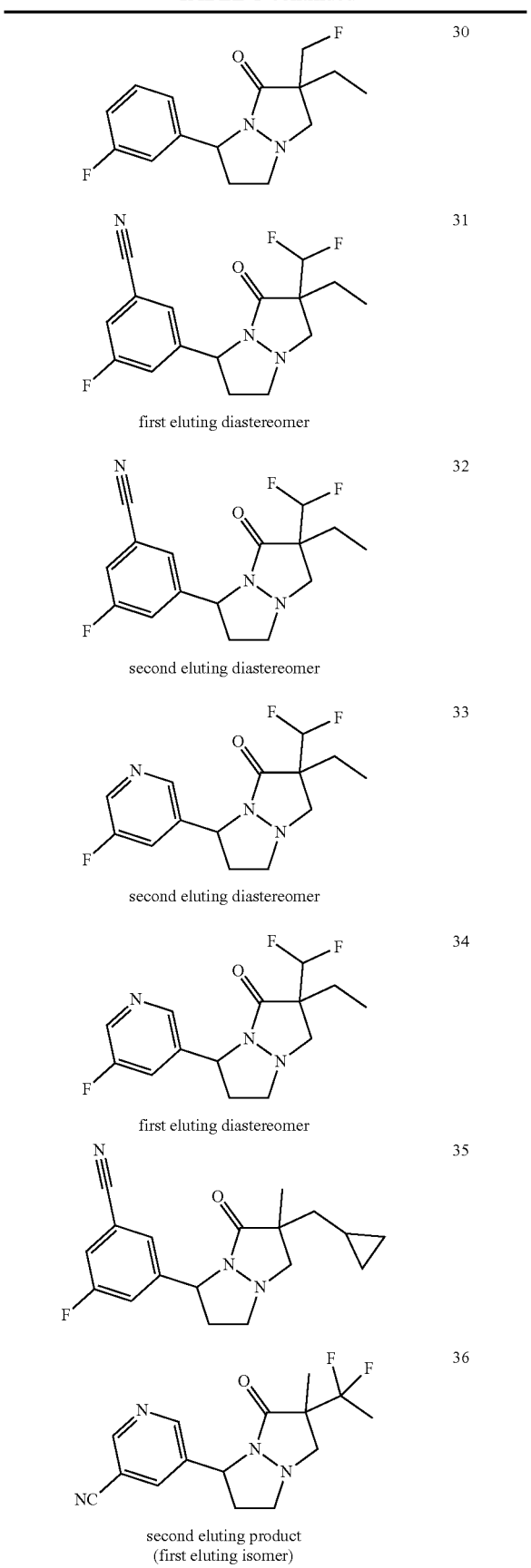
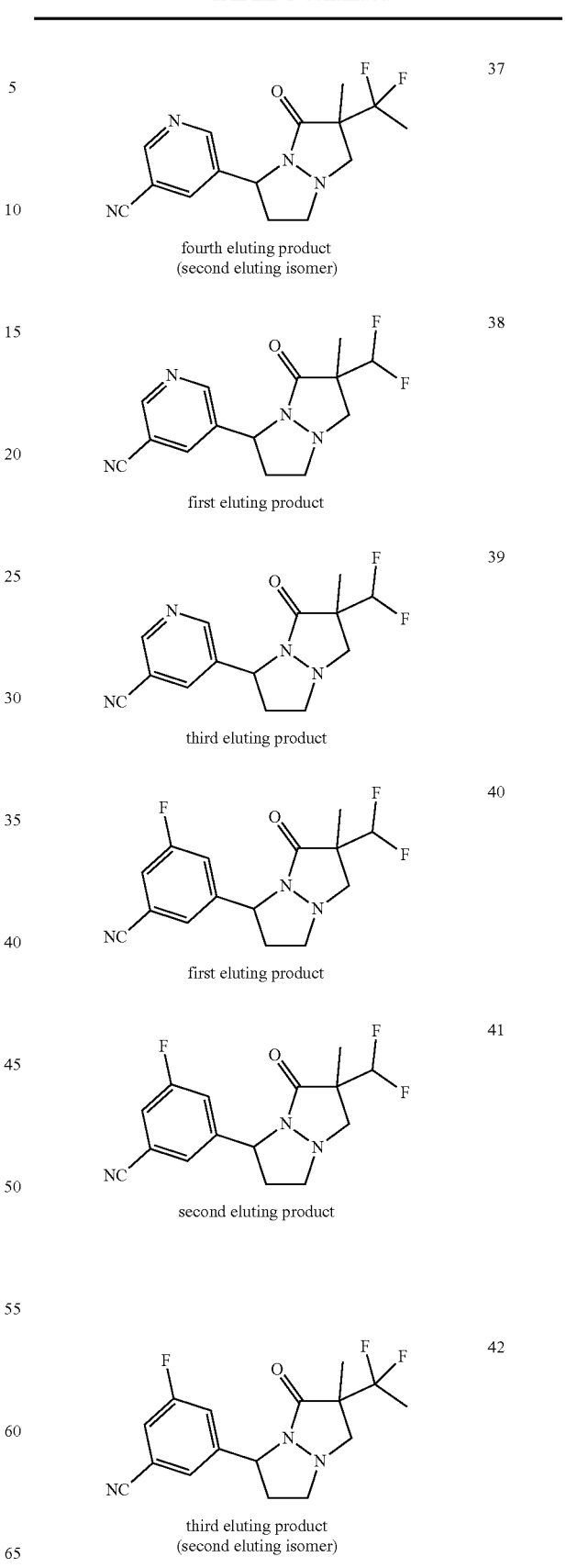

TABLE 1-continued
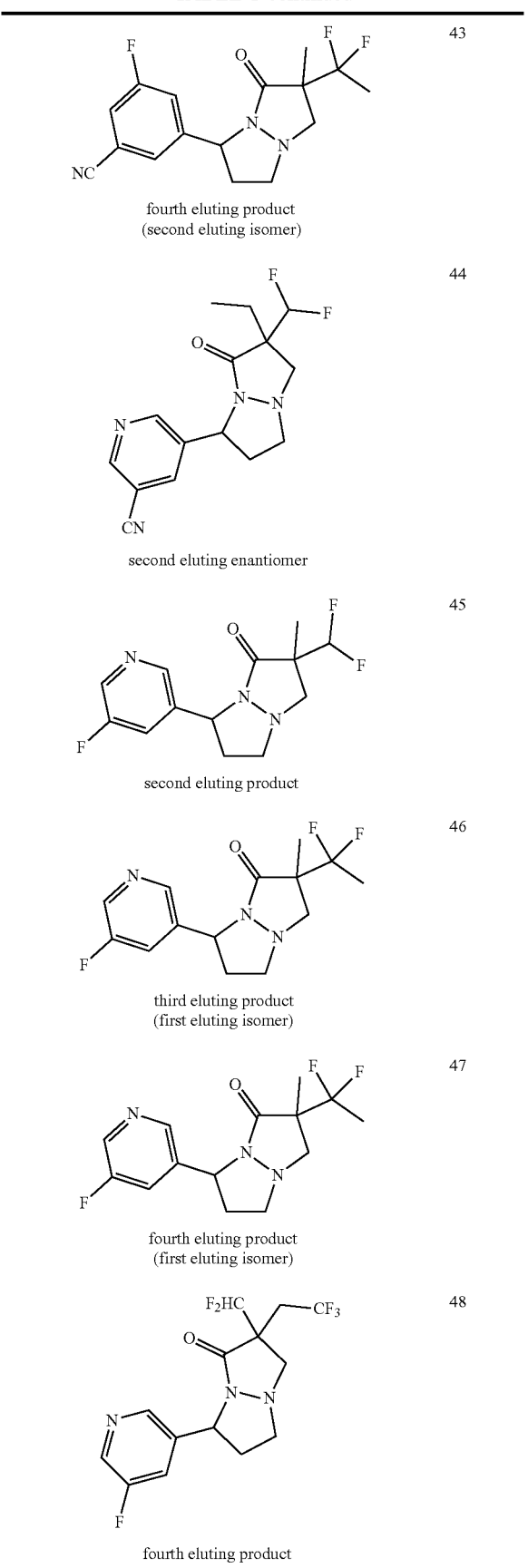
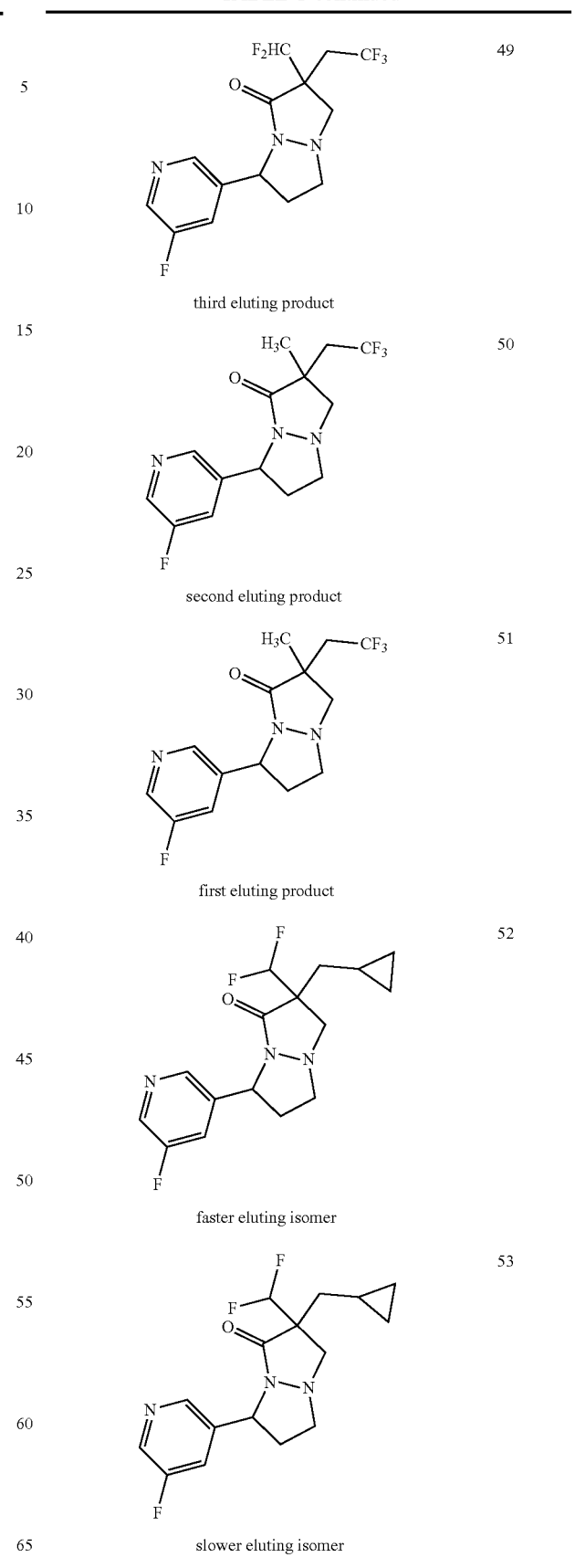

TABLE 1-continued
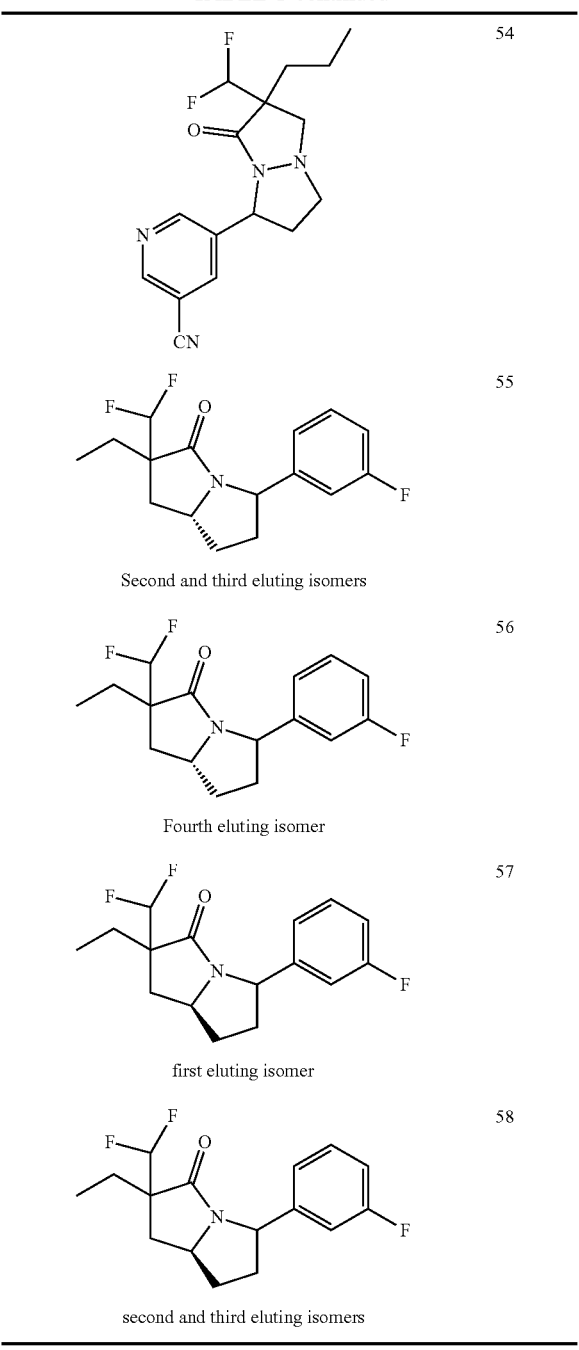
Second and third eluting isomers (55)
Fourth eluting isomer (56)
first eluting isomer (57)
second and third eluting isomers (58)
In certain embodiments, the compound is a compound selected from Table 2.
TABLE 2
TABLE 2-continued
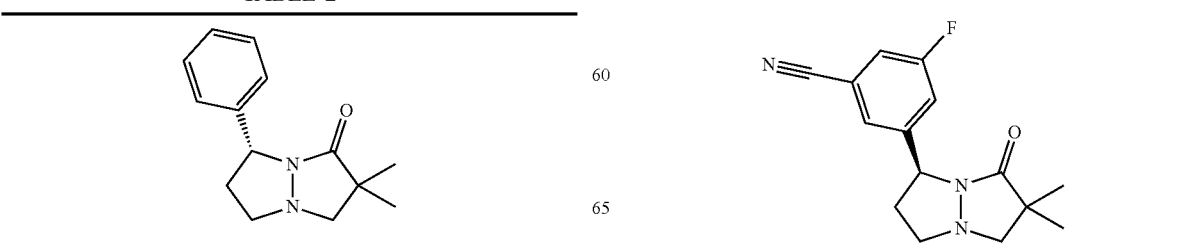

TABLE 2-continued
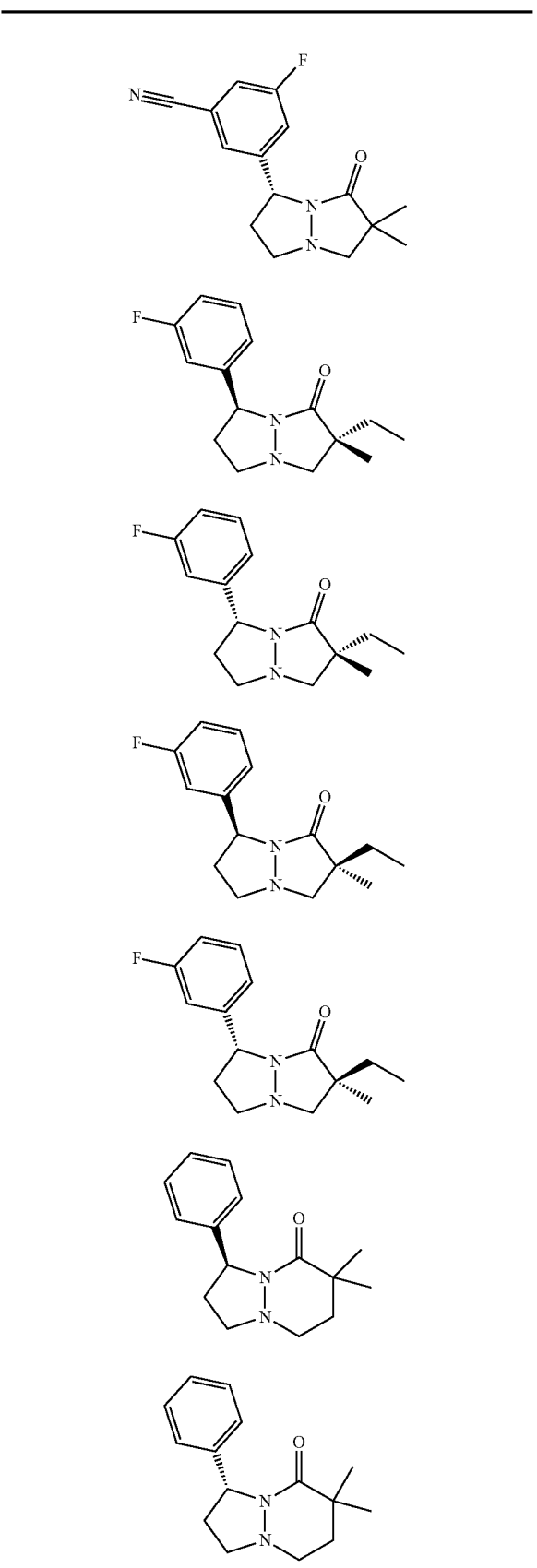
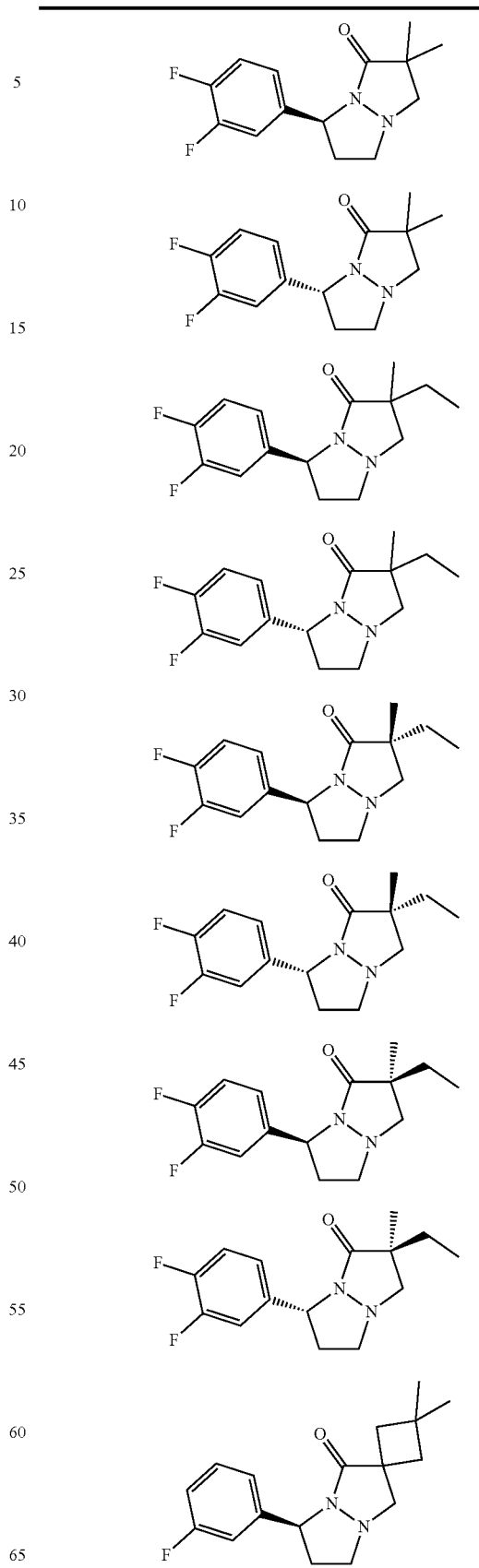

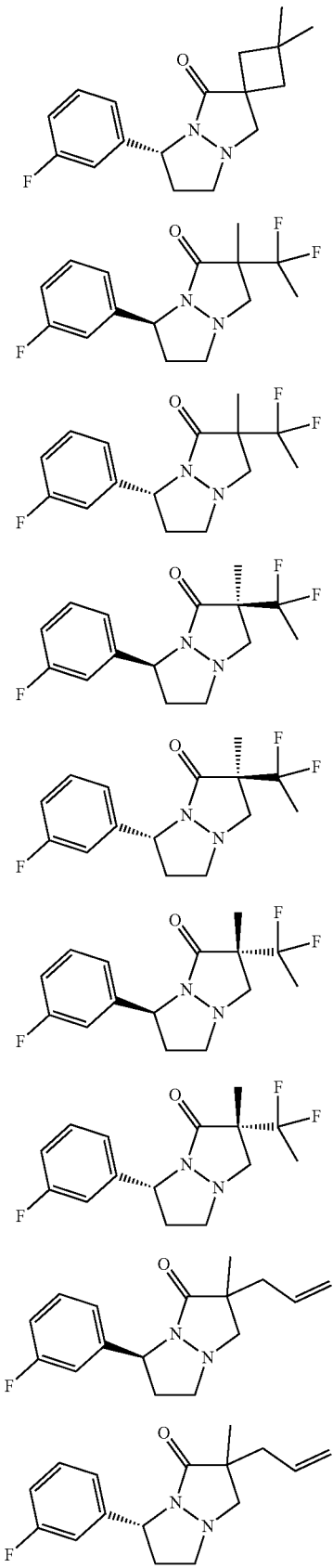
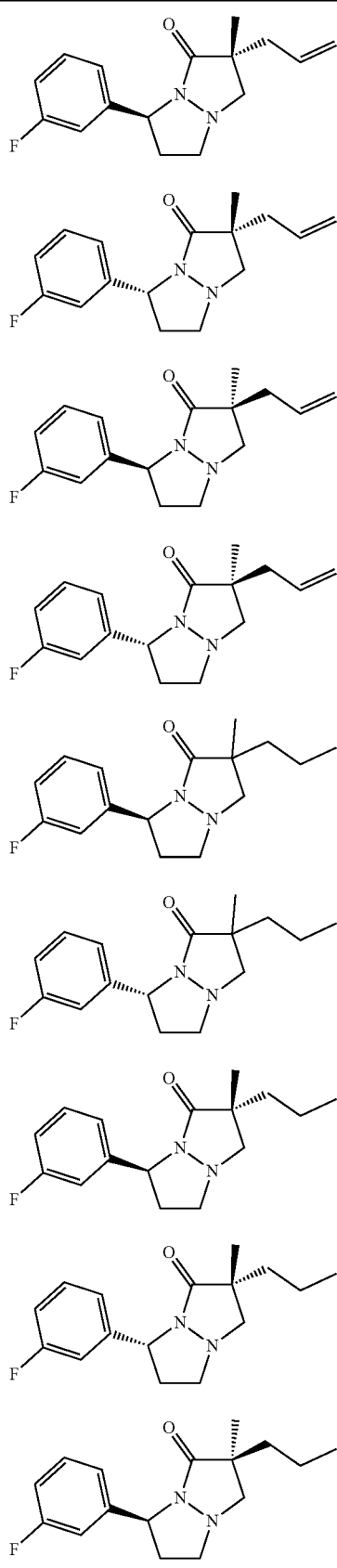

TABLE 2-continued
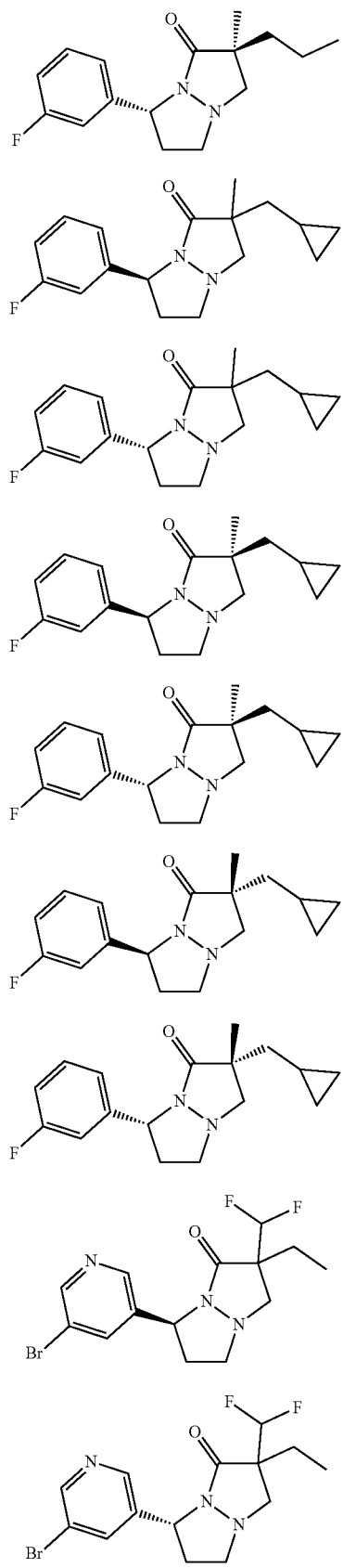
TABLE 2-continued
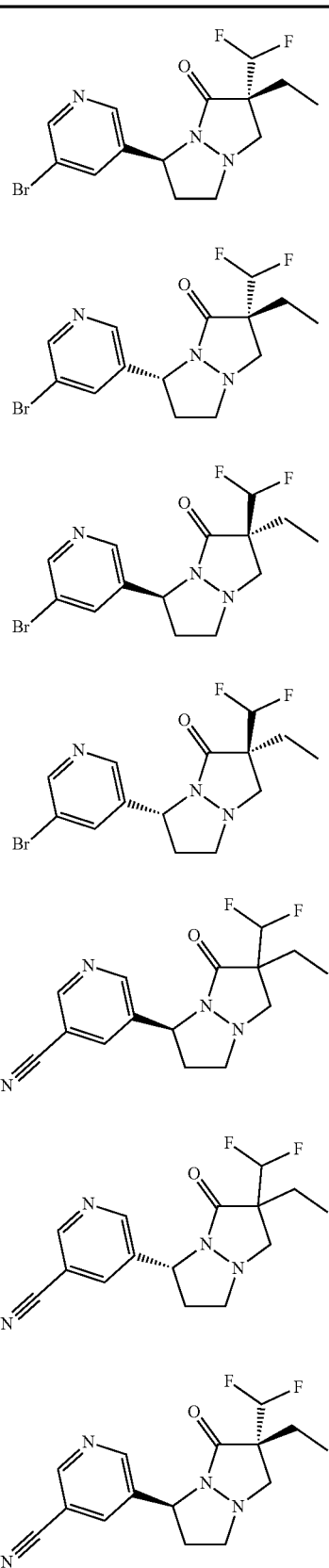

TABLE 2-continued
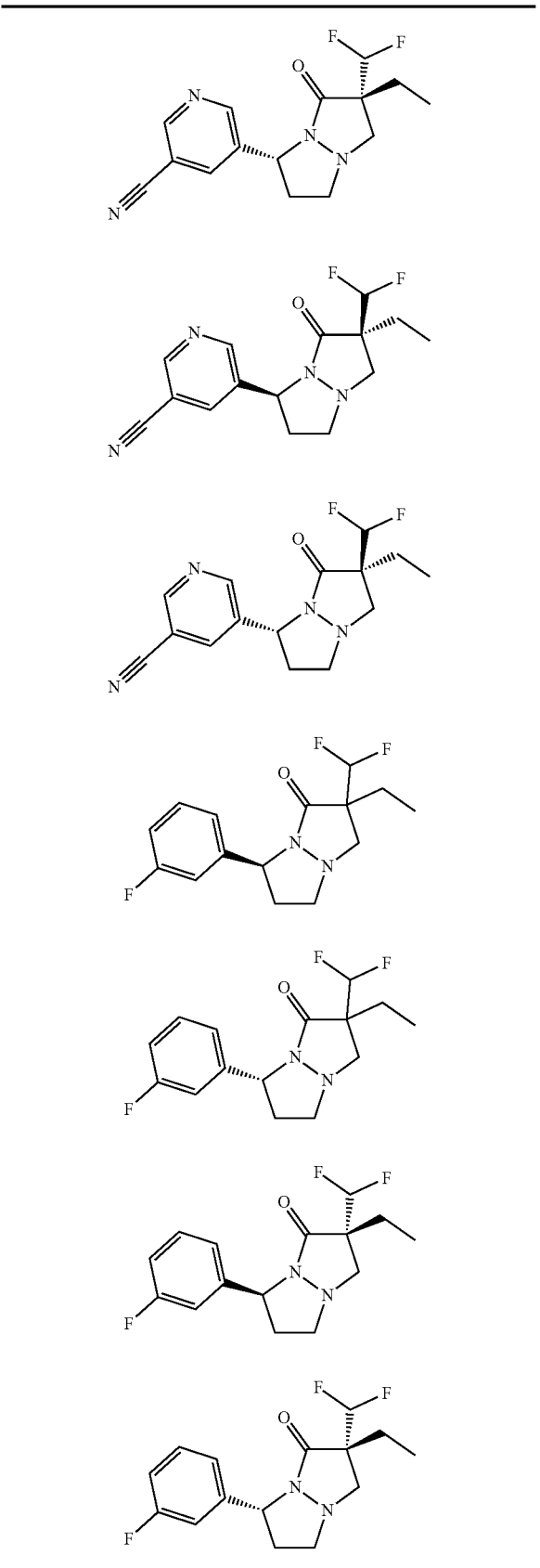
TABLE 2-continued
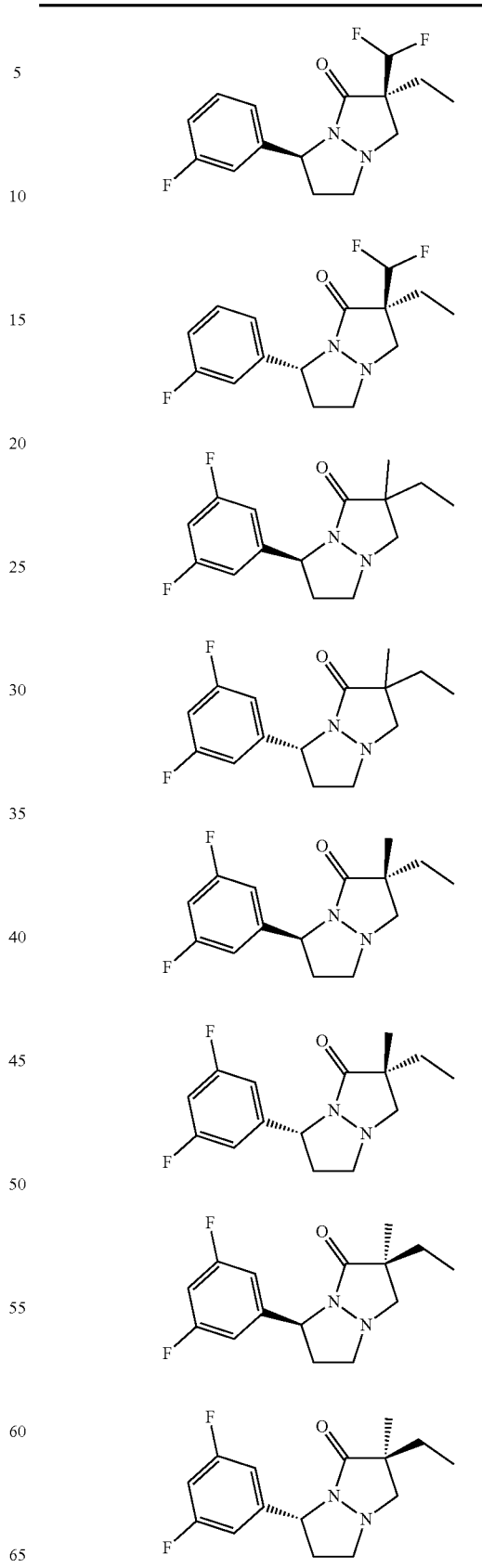

TABLE 2-continued
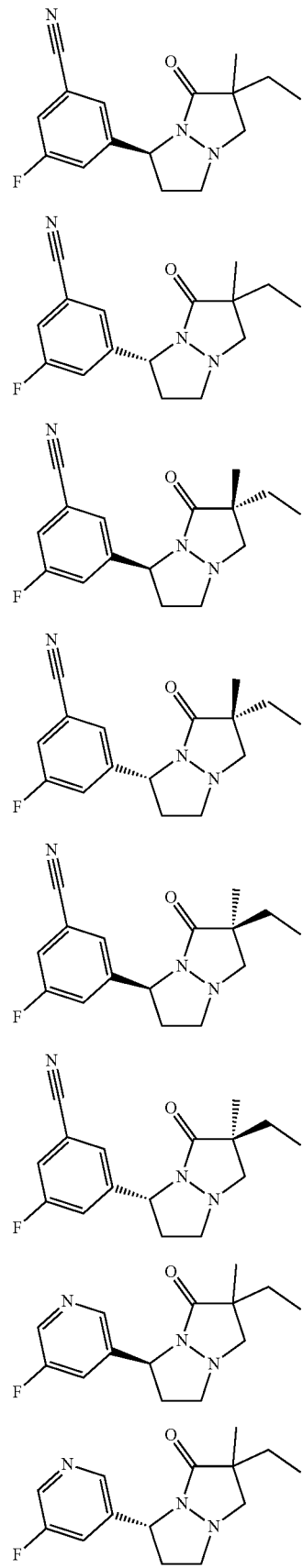
TABLE 2-continued
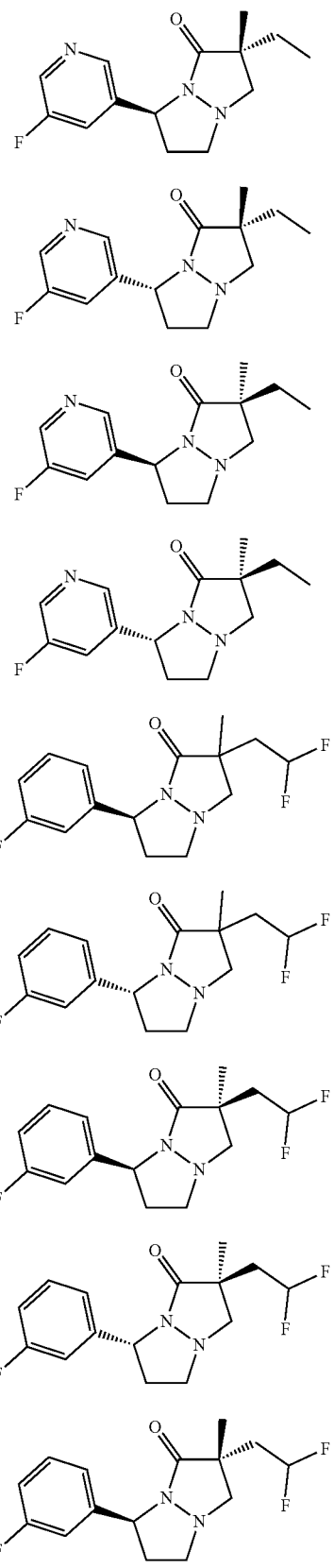

TABLE 2-continued
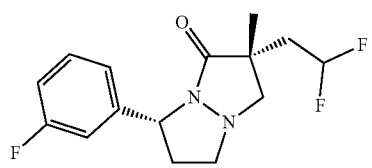 [SMILES: C[C@@]1(CC(F)F)CN2CC[C@H](c3cccc(F)c3)N2C1=O]
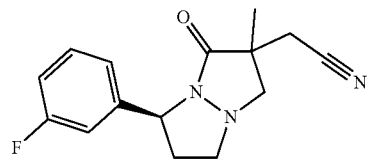 [SMILES: CC1(CC#N)CN2CC[C@@H](c3cccc(F)c3)N2C1=O]
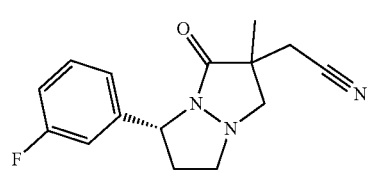 [SMILES: CC1(CC#N)CN2CC[C@H](c3cccc(F)c3)N2C1=O]
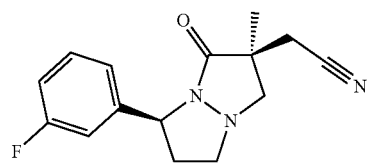 [SMILES: C[C@]1(CC#N)CN2CC[C@@H](c3cccc(F)c3)N2C1=O]
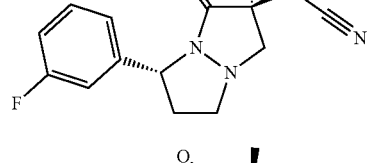
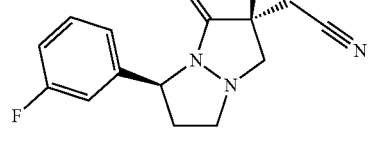
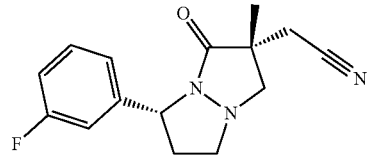 [SMILES: C[C@@]1(CC#N)CN2CC[C@H](c3cccc(F)c3)N2C1=O]
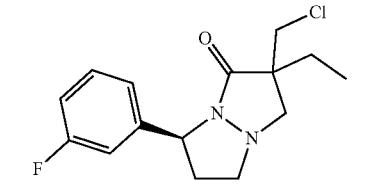 [SMILES: CCC1(CCl)CN2CC[C@@H](c3cccc(F)c3)N2C1=O]
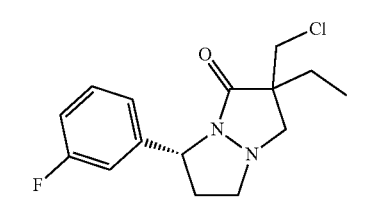 [SMILES: CCC1(CCl)CN2CC[C@H](c3cccc(F)c3)N2C1=O]
TABLE 2-continued
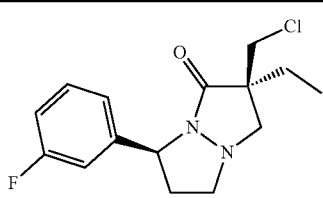
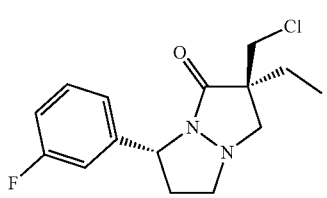
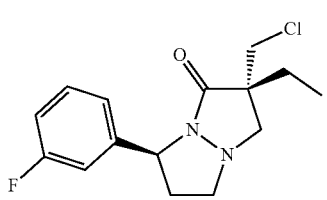
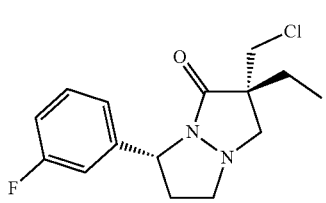 [SMILES: CC[C@@]1(CCl)CN2CC[C@H](c3cccc(F)c3)N2C1=O]
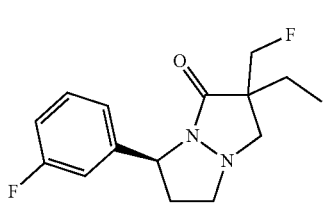
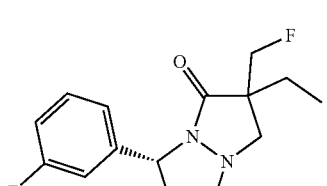
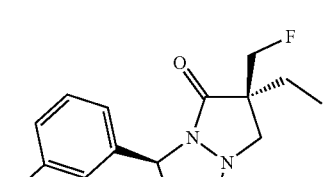
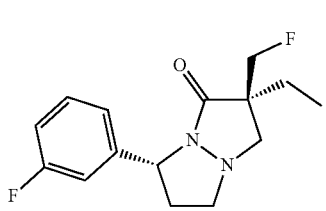 [SMILES: CC[C@]1(CF)CN2CC[C@H](c3cccc(F)c3)N2C1=O]

TABLE 2-continued
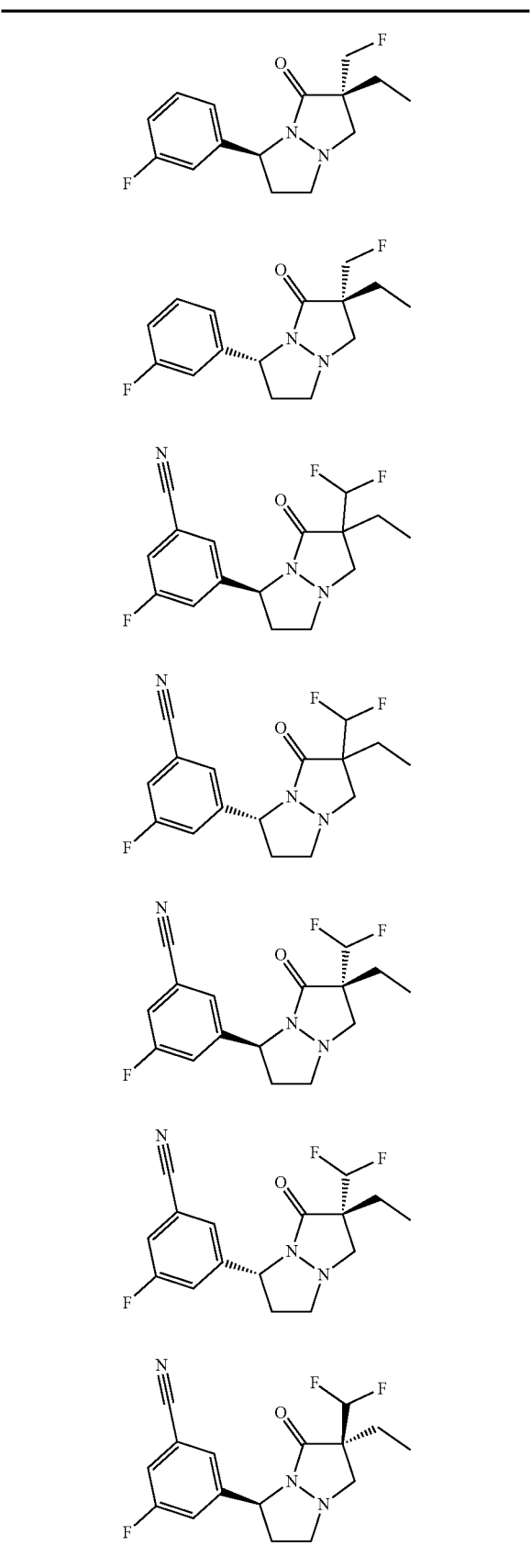
TABLE 2-continued
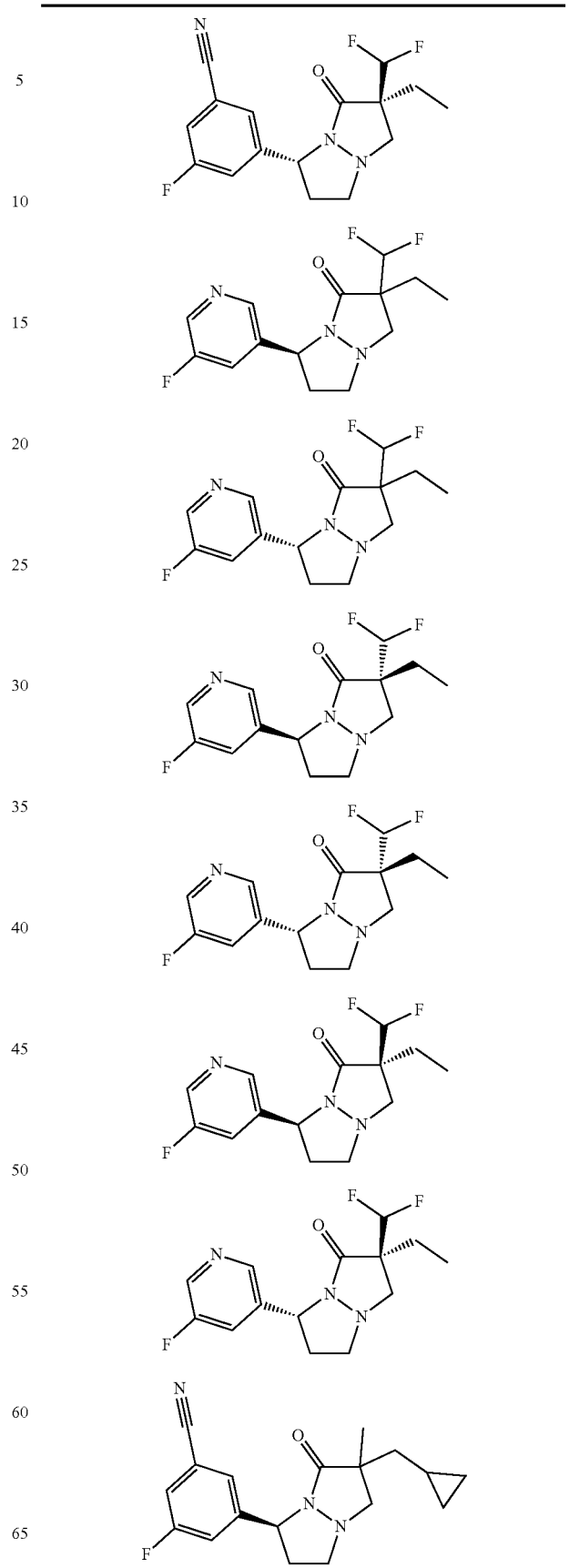

TABLE 2-continued
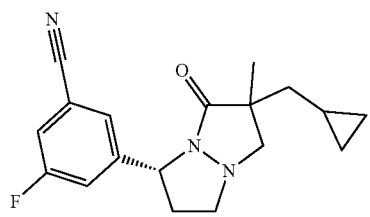 [SMILES: CC1(CC2CC2)CN2CC[C@H](c3cc(F)cc(C#N)c3)N2C1=O]
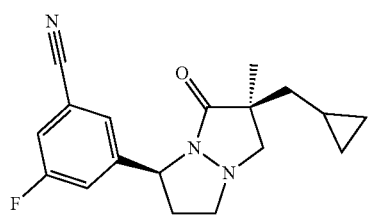 [SMILES: C[C@]1(CC2CC2)CN2CC[C@@H](c3cc(F)cc(C#N)c3)N2C1=O]
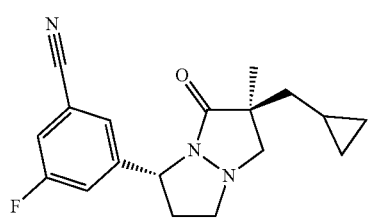 [SMILES: C[C@]1(CC2CC2)CN2CC[C@H](c3cc(F)cc(C#N)c3)N2C1=O]
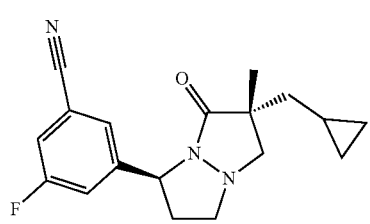 [SMILES: C[C@@]1(CC2CC2)CN2CC[C@@H](c3cc(F)cc(C#N)c3)N2C1=O]
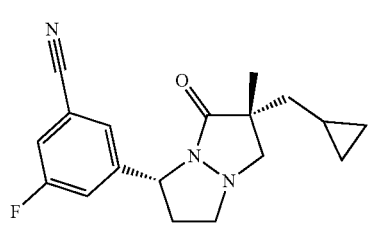 [SMILES: C[C@@]1(CC2CC2)CN2CC[C@H](c3cc(F)cc(C#N)c3)N2C1=O]
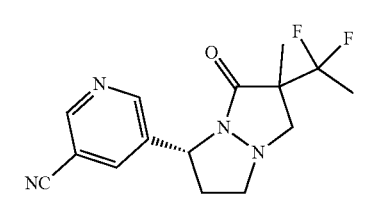 [SMILES: CC(F)(F)C1(C)CN2CC[C@H](c3cncc(C#N)c3)N2C1=O]
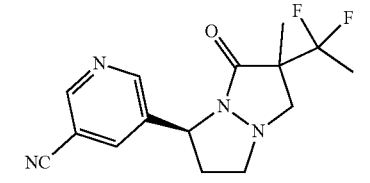 [SMILES: CC(F)(F)C1(C)CN2CC[C@@H](c3cncc(C#N)c3)N2C1=O]
TABLE 2-continued
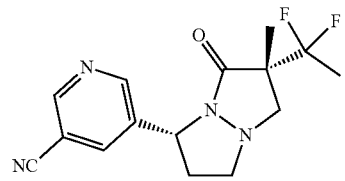 [SMILES: CC(F)(F)[C@]1(C)CN2CC[C@H](c3cncc(C#N)c3)N2C1=O]
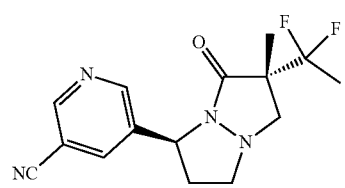 [SMILES: CC(F)(F)[C@]1(C)CN2CC[C@@H](c3cncc(C#N)c3)N2C1=O]
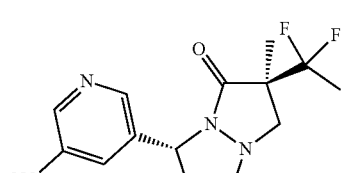
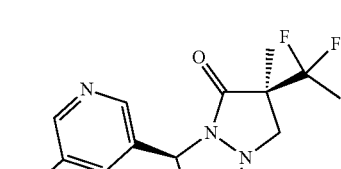
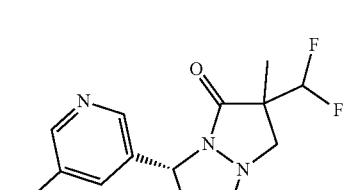
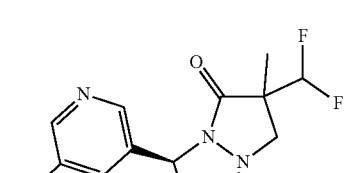
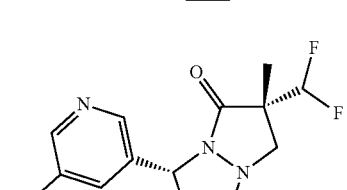

TABLE 2-continued
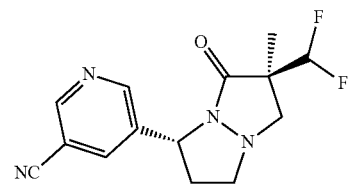 [SMILES: C[C@]1(C(F)F)CN2CC[C@H](c3cncc(C#N)c3)N2C1=O]
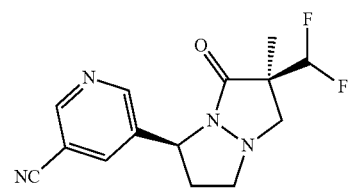 [SMILES: C[C@]1(C(F)F)CN2CC[C@@H](c3cncc(C#N)c3)N2C1=O]
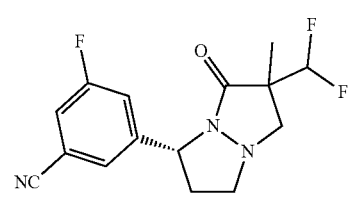 [SMILES: CC1(C(F)F)CN2CC[C@H](c3cc(F)cc(C#N)c3)N2C1=O]
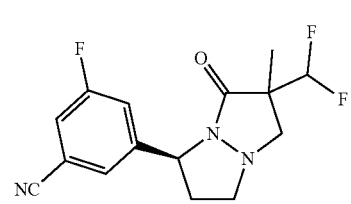 [SMILES: CC1(C(F)F)CN2CC[C@@H](c3cc(F)cc(C#N)c3)N2C1=O]
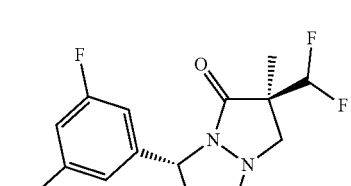
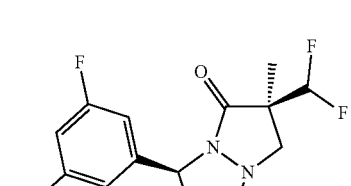
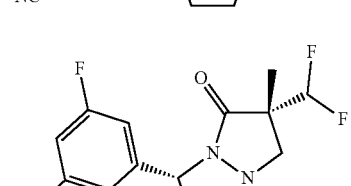
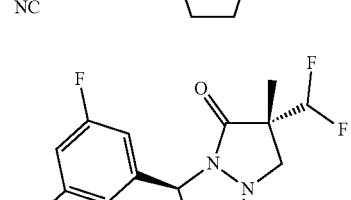
TABLE 2-continued
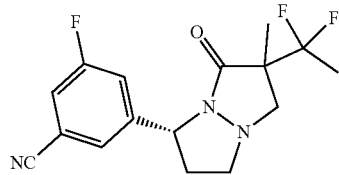 [SMILES: CC(F)(F)C1(C)CN2CC[C@H](c3cc(F)cc(C#N)c3)N2C1=O]
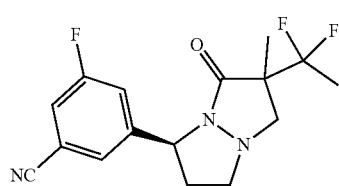 [SMILES: CC(F)(F)C1(C)CN2CC[C@@H](c3cc(F)cc(C#N)c3)N2C1=O]
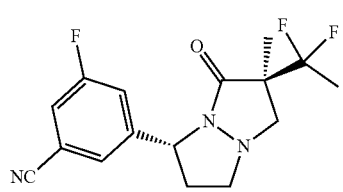 [SMILES: CC(F)(F)[C@@]1(C)CN2CC[C@H](c3cc(F)cc(C#N)c3)N2C1=O]
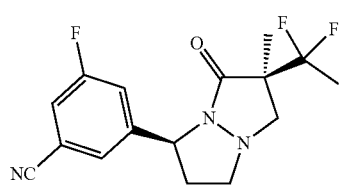 [SMILES: CC(F)(F)[C@@]1(C)CN2CC[C@@H](c3cc(F)cc(C#N)c3)N2C1=O]
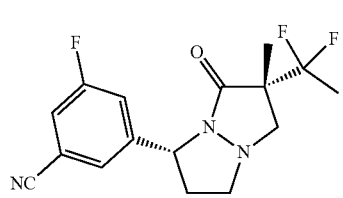 [SMILES: CC(F)(F)[C@]1(C)CN2CC[C@H](c3cc(F)cc(C#N)c3)N2C1=O]
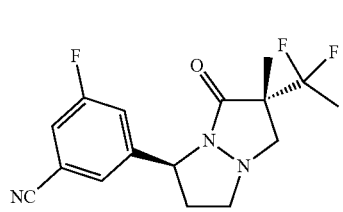 [SMILES: CC(F)(F)[C@]1(C)CN2CC[C@@H](c3cc(F)cc(C#N)c3)N2C1=O]
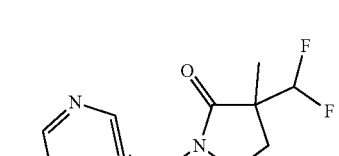
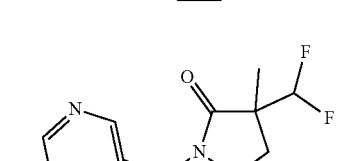

TABLE 2-continued
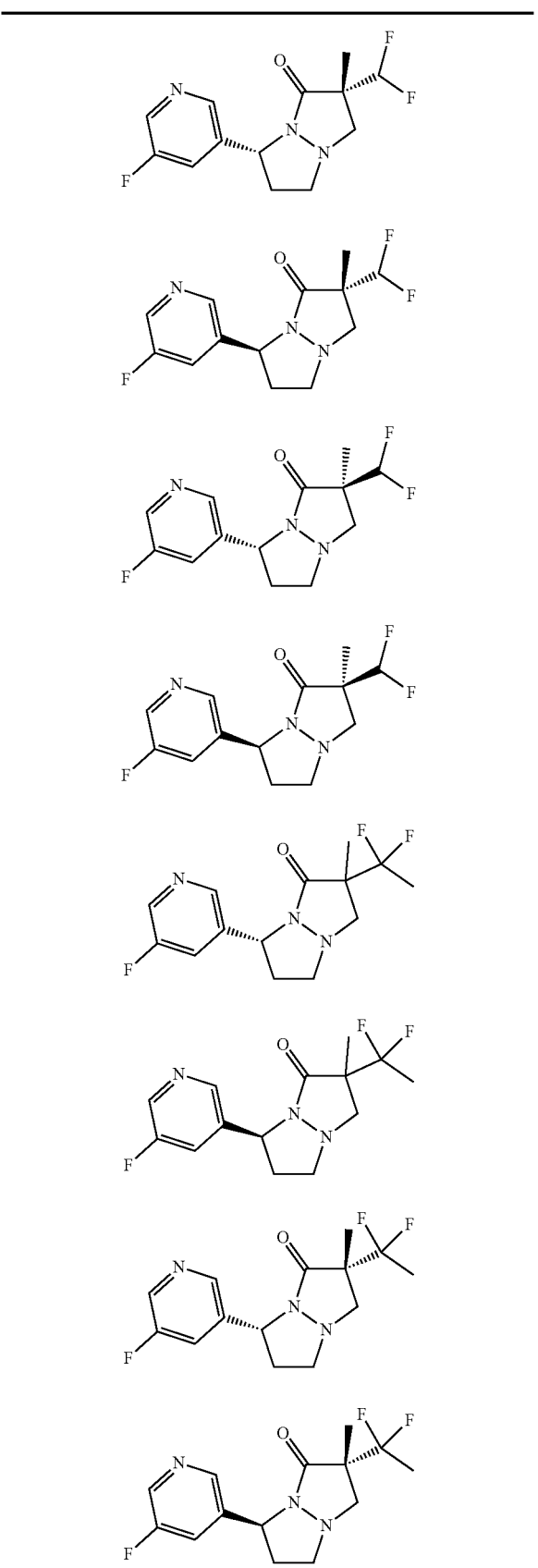
TABLE 2-continued
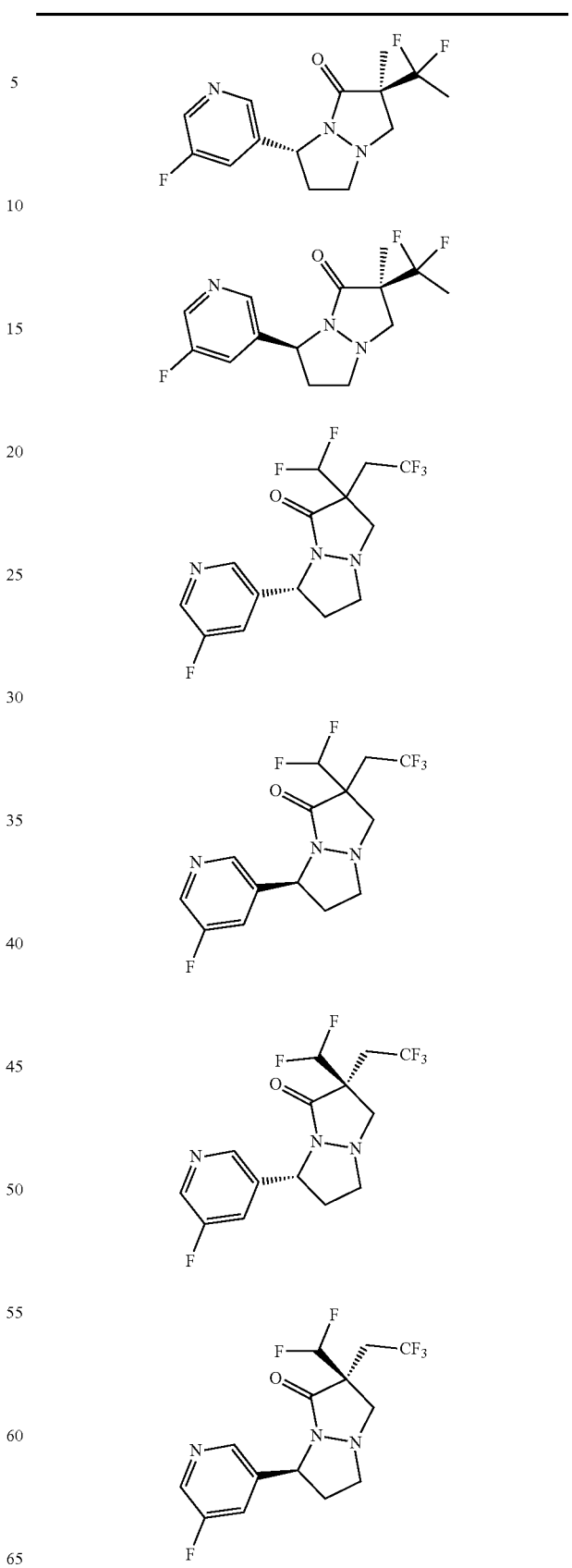

TABLE 2-continued
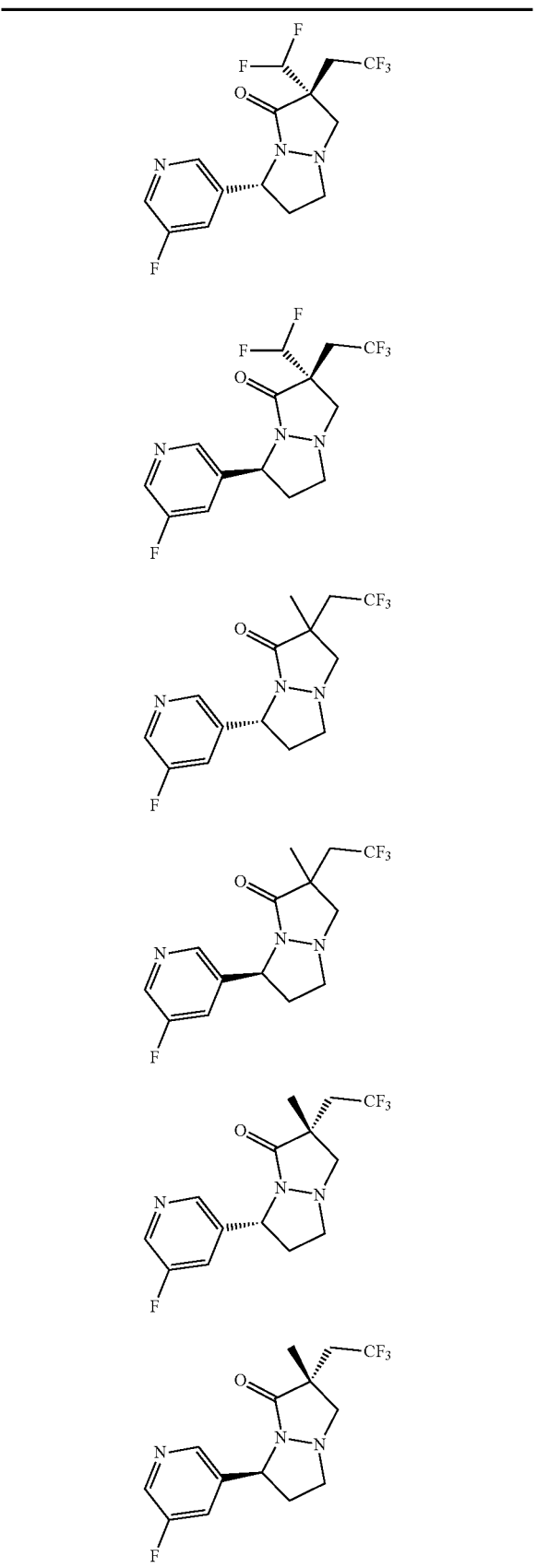
TABLE 2-continued
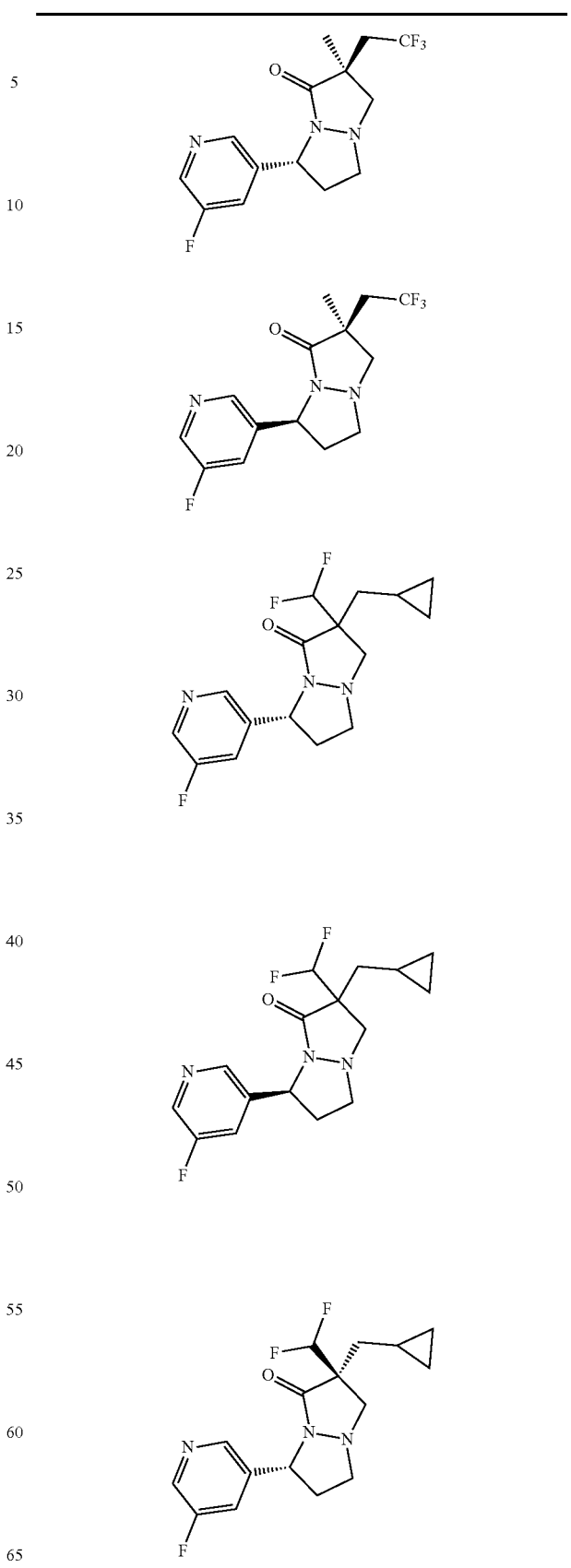

TABLE 2-continued
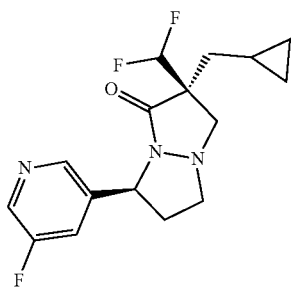 [SMILES: O=C1N2[C@H](c3cncc(F)c3)CCN2C[C@]1(CC1CC1)C(F)F]
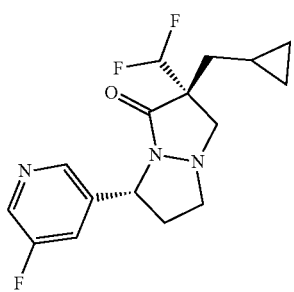 [SMILES: O=C1N2[C@@H](c3cncc(F)c3)CCN2C[C@@]1(CC1CC1)C(F)F]
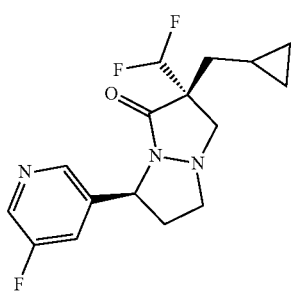 [SMILES: O=C1N2[C@H](c3cncc(F)c3)CCN2C[C@@]1(CC1CC1)C(F)F]
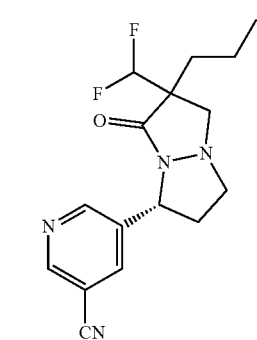 [SMILES: CCCC1(C(F)F)CN2CC[C@H](c3cncc(C#N)c3)N2C1=O]
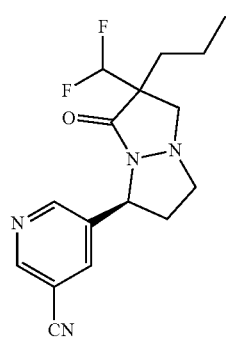 [SMILES: CCCC1(C(F)F)CN2CC[C@@H](c3cncc(C#N)c3)N2C1=O]
TABLE 2-continued
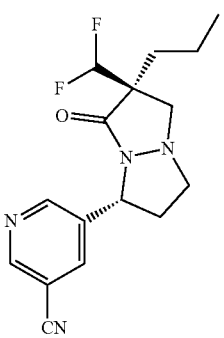 [SMILES: CCC[C@]1(C(F)F)CN2CC[C@H](c3cncc(C#N)c3)N2C1=O]
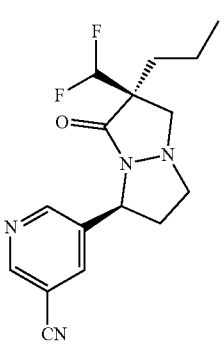 [SMILES: CCC[C@]1(C(F)F)CN2CC[C@@H](c3cncc(C#N)c3)N2C1=O]
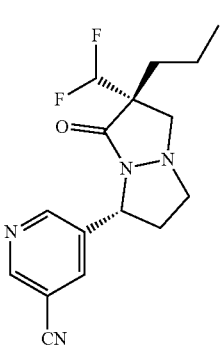 [SMILES: CCC[C@@]1(C(F)F)CN2CC[C@H](c3cncc(C#N)c3)N2C1=O]
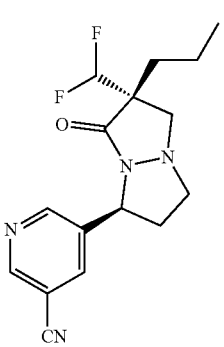 [SMILES: CCC[C@@]1(C(F)F)CN2CC[C@@H](c3cncc(C#N)c3)N2C1=O]
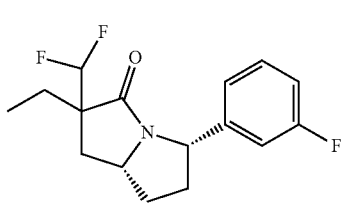 [SMILES: CCC1(C(F)F)C[C@H]2CC[C@@H](c3cccc(F)c3)N2C1=O]

TABLE 2-continued
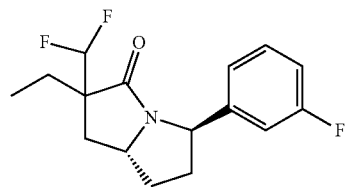 [SMILES: CCC1(C(F)F)C[C@H]2CC[C@H](c3cccc(F)c3)N2C1=O]
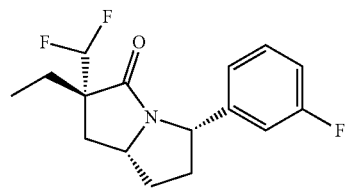 [SMILES: CC[C@]1(C(F)F)C[C@H]2CC[C@@H](c3cccc(F)c3)N2C1=O]
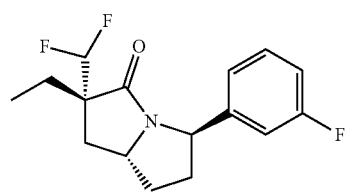 [SMILES: CC[C@]1(C(F)F)C[C@H]2CC[C@H](c3cccc(F)c3)N2C1=O]
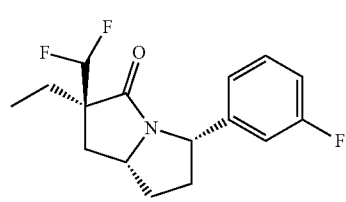 [SMILES: CC[C@@]1(C(F)F)C[C@H]2CC[C@@H](c3cccc(F)c3)N2C1=O]
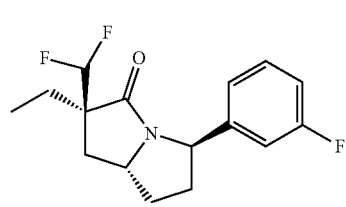 [SMILES: CC[C@@]1(C(F)F)C[C@H]2CC[C@H](c3cccc(F)c3)N2C1=O]
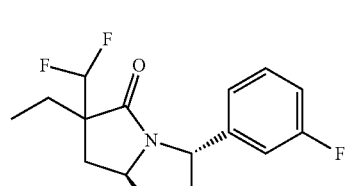
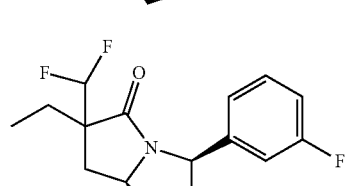
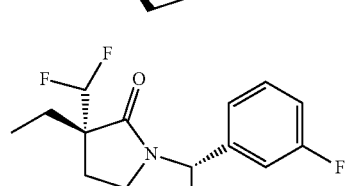
TABLE 2-continued
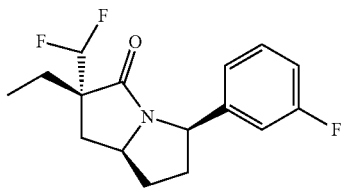 [SMILES: CC[C@]1(C(F)F)C[C@@H]2CC[C@H](c3cccc(F)c3)N2C1=O]
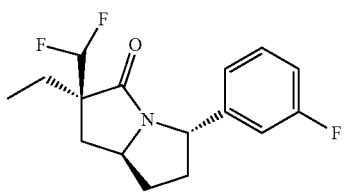 [SMILES: CC[C@@]1(C(F)F)C[C@@H]2CC[C@@H](c3cccc(F)c3)N2C1=O]
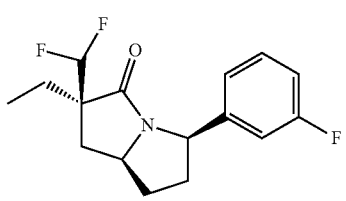 [SMILES: CC[C@@]1(C(F)F)C[C@@H]2CC[C@H](c3cccc(F)c3)N2C1=O]
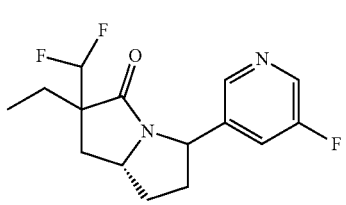
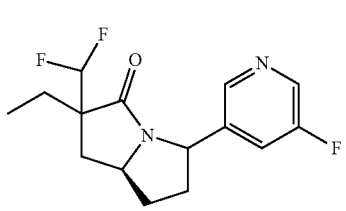
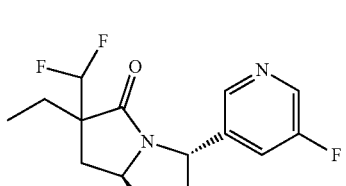
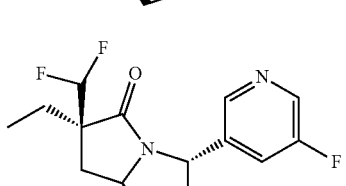
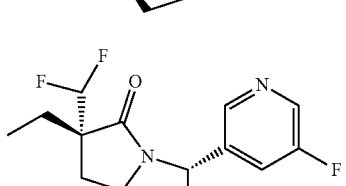

TABLE 2-continued

TABLE 2-continued
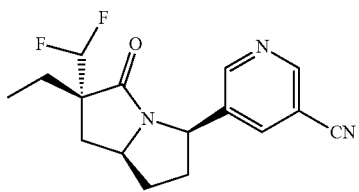 [SMILES: CC[C@]1(C(F)F)C[C@@H]2CC[C@H](c3cncc(C#N)c3)N2C1=O]
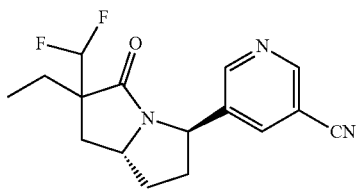 [SMILES: CCC1(C(F)F)C[C@H]2CC[C@H](c3cncc(C#N)c3)N2C1=O]
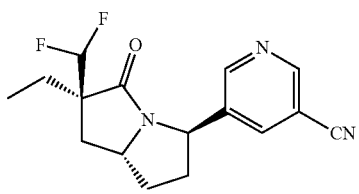 [SMILES: CC[C@@]1(C(F)F)C[C@H]2CC[C@H](c3cncc(C#N)c3)N2C1=O]
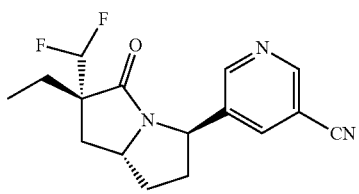 [SMILES: CC[C@]1(C(F)F)C[C@H]2CC[C@H](c3cncc(C#N)c3)N2C1=O]
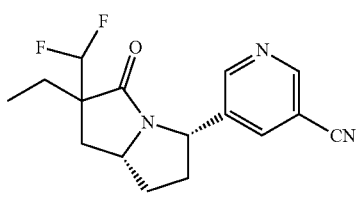 [SMILES: CCC1(C(F)F)C[C@H]2CC[C@@H](c3cncc(C#N)c3)N2C1=O]
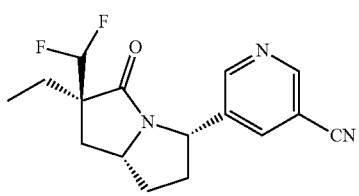 [SMILES: CC[C@@]1(C(F)F)C[C@H]2CC[C@@H](c3cncc(C#N)c3)N2C1=O]
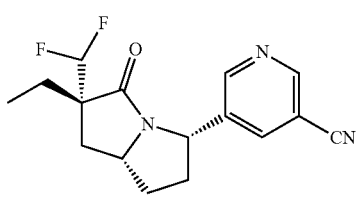 [SMILES: CC[C@]1(C(F)F)C[C@H]2CC[C@@H](c3cncc(C#N)c3)N2C1=O]
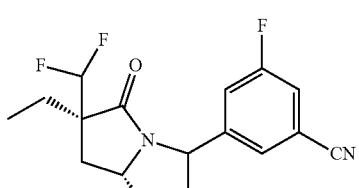
TABLE 2-continued
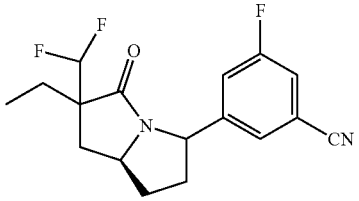
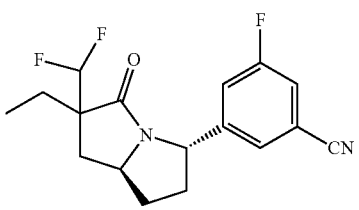 [SMILES: CCC1(C(F)F)C[C@@H]2CC[C@@H](c3cc(F)cc(C#N)c3)N2C1=O]
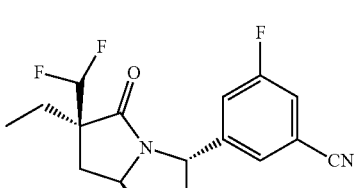
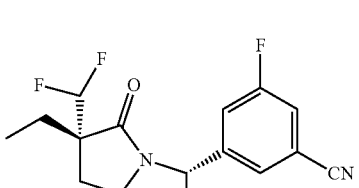
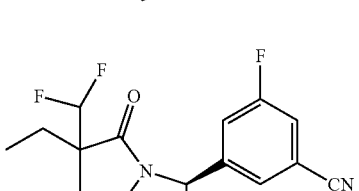
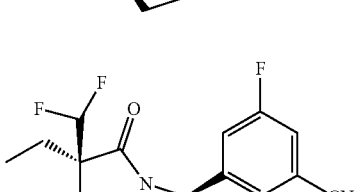
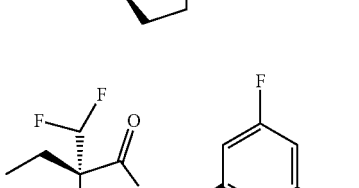

TABLE 2-continued
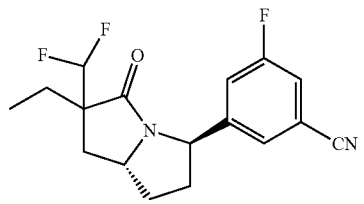 [SMILES: CCC1(C(F)F)C[C@H]2CC[C@H](c3cc(F)cc(C#N)c3)N2C1=O]
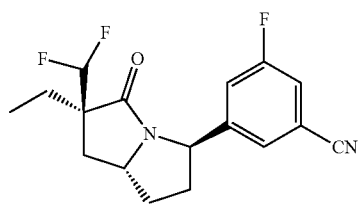 [SMILES: CC[C@@]1(C(F)F)C[C@H]2CC[C@H](c3cc(F)cc(C#N)c3)N2C1=O]
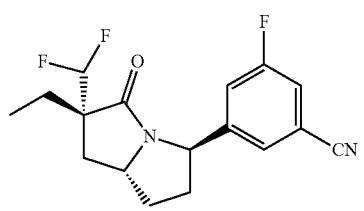 [SMILES: CC[C@]1(C(F)F)C[C@H]2CC[C@H](c3cc(F)cc(C#N)c3)N2C1=O]
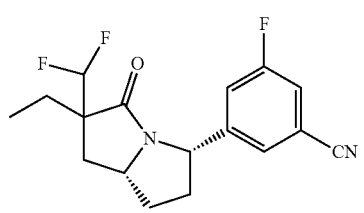 [SMILES: CCC1(C(F)F)C[C@H]2CC[C@@H](c3cc(F)cc(C#N)c3)N2C1=O]
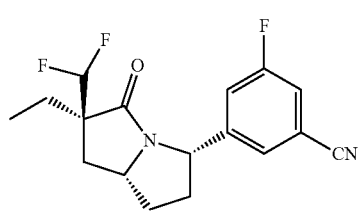 [SMILES: CC[C@@]1(C(F)F)C[C@H]2CC[C@@H](c3cc(F)cc(C#N)c3)N2C1=O]
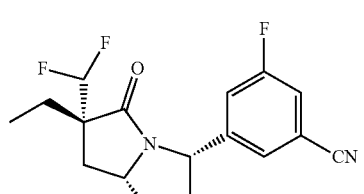
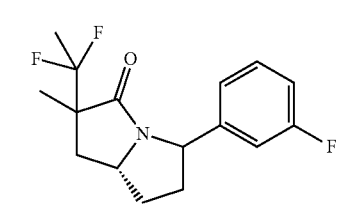
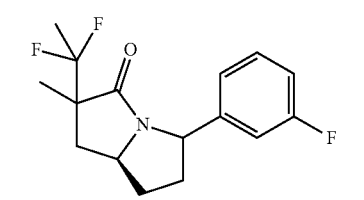
TABLE 2-continued
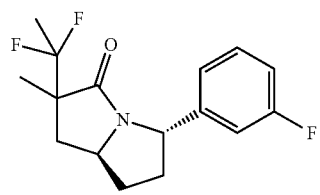 [SMILES: CC(F)(F)C1(C)C[C@@H]2CC[C@@H](c3cccc(F)c3)N2C1=O]
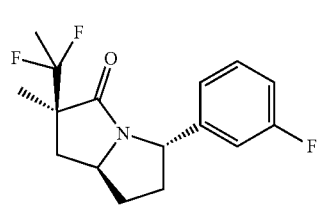 [SMILES: CC(F)(F)[C@]1(C)C[C@@H]2CC[C@@H](c3cccc(F)c3)N2C1=O]
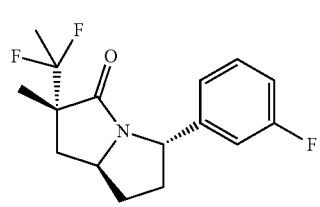 [SMILES: CC(F)(F)[C@@]1(C)C[C@@H]2CC[C@@H](c3cccc(F)c3)N2C1=O]
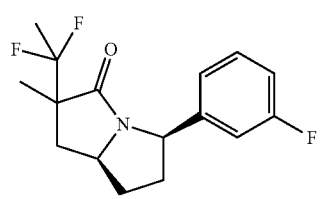 [SMILES: CC(F)(F)C1(C)C[C@@H]2CC[C@H](c3cccc(F)c3)N2C1=O]
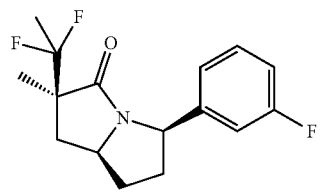 [SMILES: CC(F)(F)[C@]1(C)C[C@@H]2CC[C@H](c3cccc(F)c3)N2C1=O]
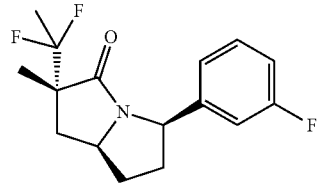 [SMILES: CC(F)(F)[C@@]1(C)C[C@@H]2CC[C@H](c3cccc(F)c3)N2C1=O]
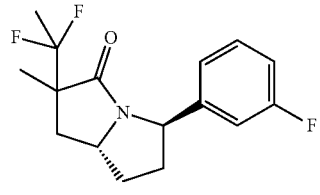 [SMILES: CC(F)(F)C1(C)C[C@H]2CC[C@H](c3cccc(F)c3)N2C1=O]
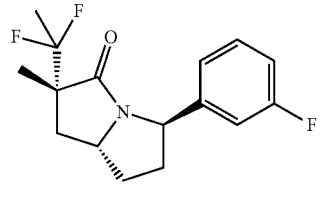 [SMILES: CC(F)(F)[C@@]1(C)C[C@H]2CC[C@H](c3cccc(F)c3)N2C1=O]

TABLE 2-continued
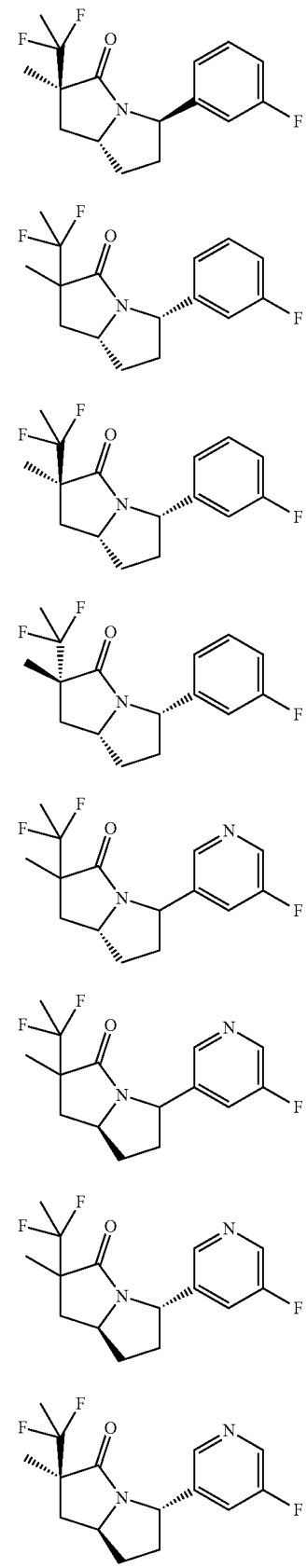
TABLE 2-continued
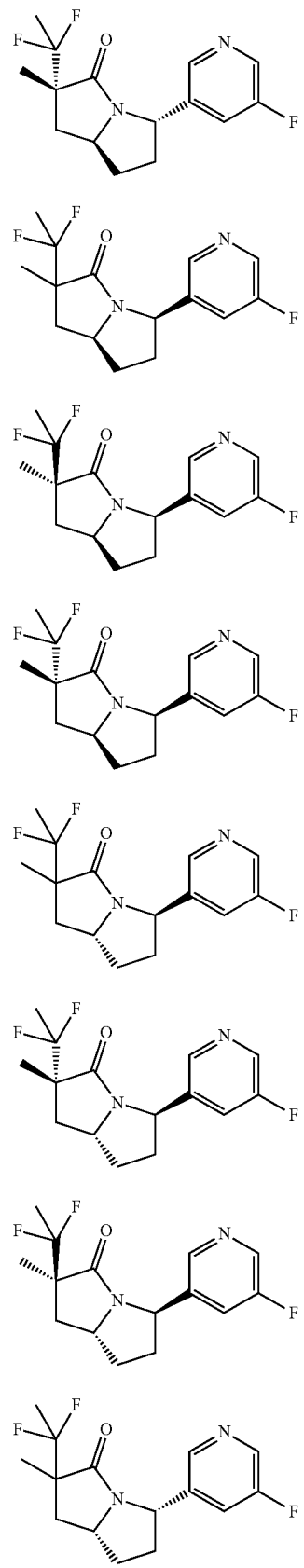

TABLE 2-continued
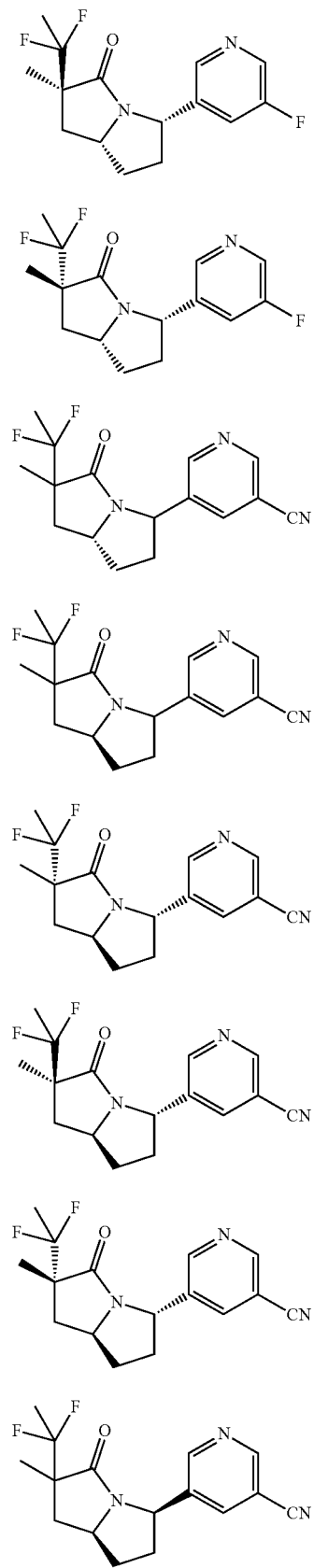
TABLE 2-continued
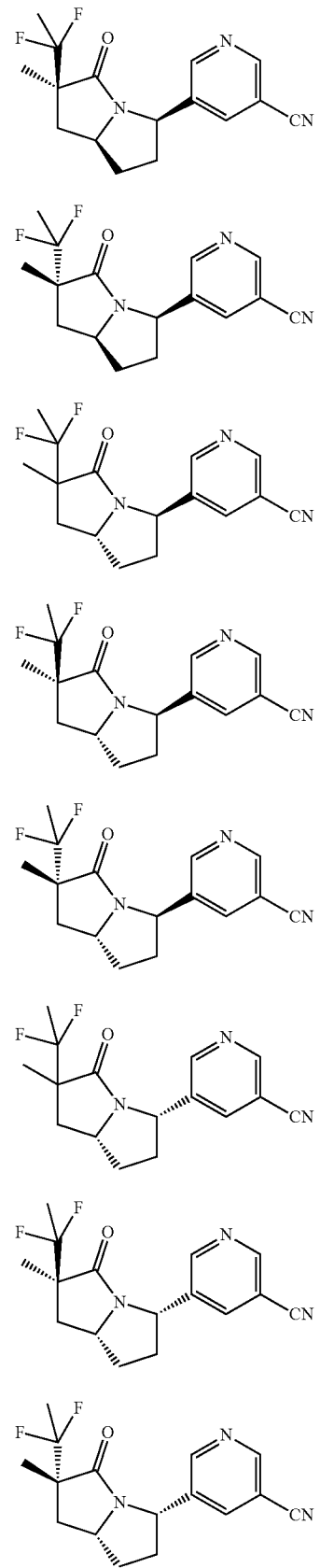

TABLE 2-continued
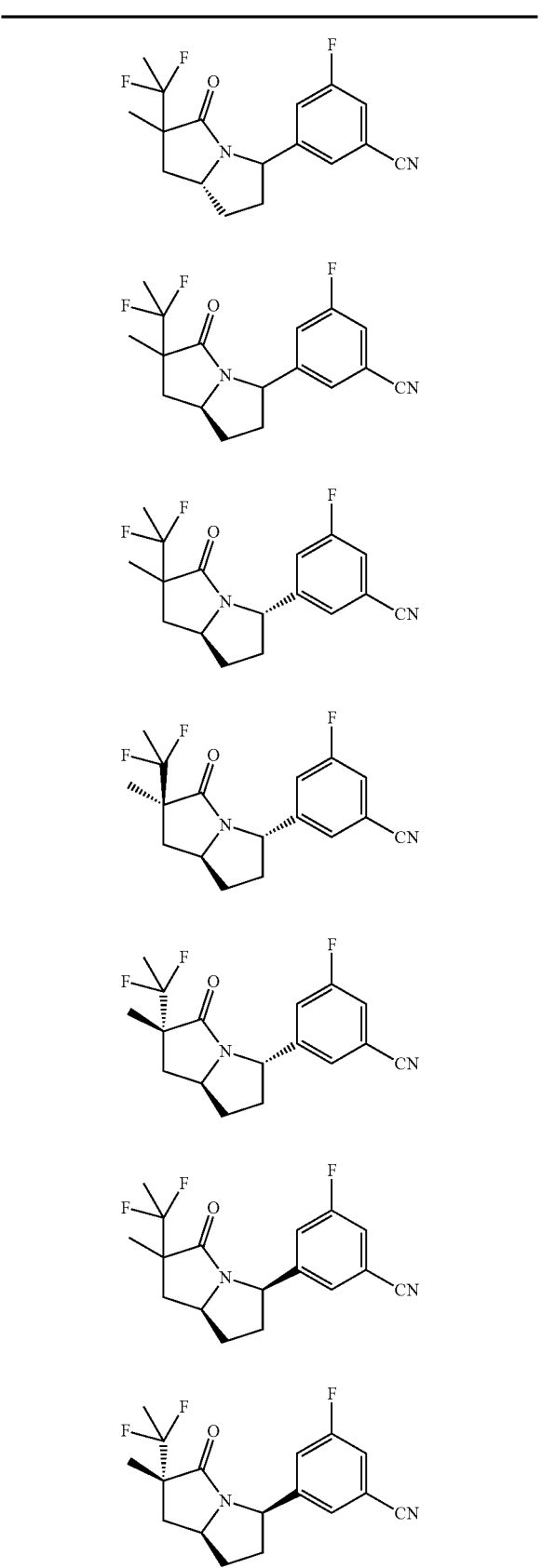
TABLE 2-continued
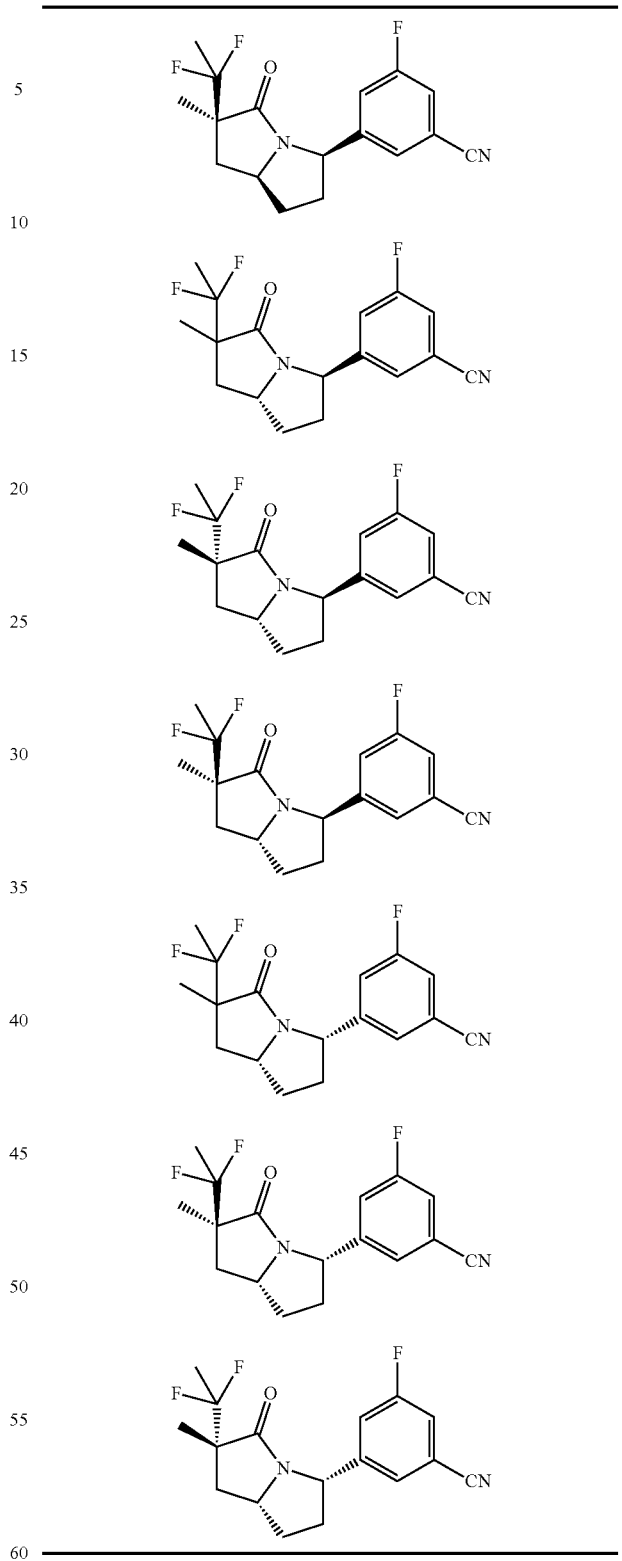
In certain embodiments, the compound of any Formula provided herein is provided in the form of a pharmaceutically acceptable salt. Exemplary salts for this purpose are described herein.
In certain embodiments, the disclosure provides a prodrug which converts to a compound of any Formula provided herein in vivo. Exemplary prodrugs for this purpose are known in the art and described herein.

Enantiomerically enriched compositions of the compounds disclosed herein are also provided. In certain embodiments, the enantiomeric ratio of the composition is greater than 50:50. In certain embodiments, the enantiomeric ratio is calculated only with respect to a single stereocenter (e.g., the optionally substituted phenyl moiety) without regard to other stereocenters which may be present on the molecule. In certain embodiments, the composition comprises a single enantiomer of the compound and is substantially free (i.e., having less than or about 40%, 30%, 25%, 20%, 15%, 10%, 5%, 1%, 0.05%, or 0.01%) of the other enantiomer (or diastereomers).

3. General Synthesis

Also provided herein are methods for preparing a compound any of Formulas I-XX, or subformula thereof. In certain embodiments, provided is a method of preparing a compound of Formula I, comprising contacting a compound of Formula C:

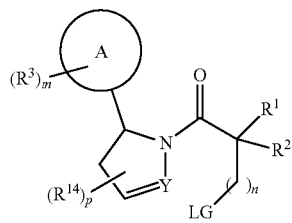

C with a suitable hydride reagent, under conditions to provide the compound of Formula I, wherein A, Y, n, m, p, $R^1$, $R^2$, $R^3$ and $R^{14}$ are as defined herein and LG is a leaving group.

In certain embodiments, the compound of Formula C is represented by Formula C-1:

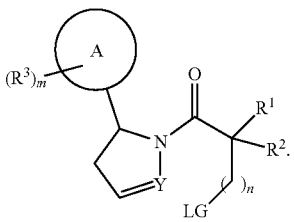

C-1

The following General Reaction Scheme I further illustrates a method of making compounds of Formula I. Other methods for preparing compounds of Formula I and related intermediates are provided in the Examples and/or known in the art. It is understood that one skilled in the art may be able to make these compounds by similar methods or by combining other methods known to one skilled in the art. In general, starting components and reagents may be obtained from sources such as Sigma Aldrich, Lancaster Synthesis, Inc., Maybridge, Matrix Scientific, TCI and Fluorochem USA, etc. or synthesized according to sources known to those skilled in the art (see, for example, Advanced Organic Chemistry: Reactions, Mechanisms and Structure, 5th edition (Wiley, December 2000)) or prepared as described in this disclosure.

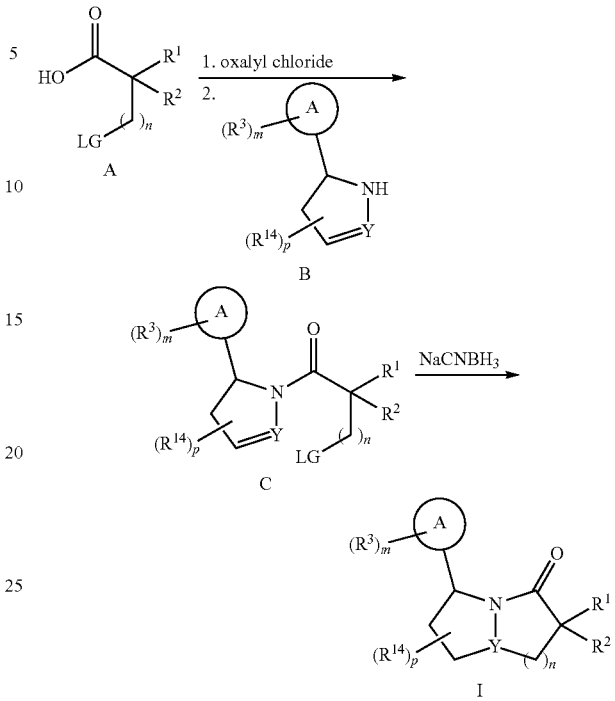

Referring to Scheme I, compounds of Formula I, wherein A, Y, n, m, p, $R^1$, $R^2$, $R^3$ and $R^{14}$ are as defined herein and LG is a leaving group (e.g., halo), may be prepared by contacting compound C with a suitable hydride reagent (e.g., sodium cyanoborohydride, lithium triethylborohydride, etc.). Compound C can be prepared by first reacting compound A with oxalyl chloride, and then adding the resulting solution to compound B.

Appropriate compounds A or B can be prepared according to the more specific methods described in the Examples which follow or by methods known to one of skill in the art.

When enantiomerically pure or enriched compounds are desired, chiral chromatography and/or enantiomerically pure or enriched starting materials (e.g., compound B) may be used as described in the Examples. It will also be appreciated by those skilled in the art that in the process described herein the functional groups of intermediate compounds may need to be protected by suitable protecting groups.

Such functional groups include hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl and the like. Suitable protecting groups for amino, amidino and guanidino include t-butoxycarbonyl, benzyloxycarbonyl and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

It will also be appreciated by those skilled in the art, although such protected derivatives of compounds of this disclosure may not possess pharmacological activity as such, they may be administered to a mammal and thereafter metabolized in the body to form compounds of the disclosure which are pharmacologically active. Such derivatives may therefore be described as "prodrugs." All prodrugs of compounds of this disclosure are included within the scope of the disclosure. Further, the above general scheme can be applied to any other Formula or compound as described herein.

Furthermore, all compounds of Formula I or any other Formula or compound as described herein (e.g., any of Formulas I-XX, or subformula thereof) which exist in free base or acid form can be converted to their pharmaceutically acceptable salts by treatment with the appropriate inorganic or organic base or acid by methods known to one skilled in the art. Salts of the compounds of the disclosure can be converted to their free base or acid form by standard techniques.

4. Methods of Treatment

"Treatment" or "treating" is an approach for obtaining beneficial or desired results including clinical results. Beneficial or desired clinical results may include one or more of the following: a) inhibiting the disease or condition (e.g., decreasing one or more symptoms resulting from the disease or condition and/or diminishing the extent of the disease or condition); b) slowing or arresting the development of one or more clinical symptoms associated with the disease or condition (e.g., stabilizing the disease or condition, preventing or delaying the worsening or progression of the disease or condition and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life and/or prolonging survival).

"Prevention" or "preventing" means any treatment of a disease or condition that causes the clinical symptoms of the disease or condition not to develop. Compounds may, in certain embodiments, be administered to a subject (including a human) who is at risk or has a family history of the disease or condition.

"Subject" refers to an animal, such as a mammal (including a human), that has been or will be the object of treatment, observation or experiment. The methods described herein may be useful in human therapy and/or veterinary applications. In certain embodiments, the subject is a mammal. In certain embodiments, the subject is a human.

The term "therapeutically effective amount" or "effective amount" of a compound described herein or a pharmaceutically acceptable salt, prodrug, stereoisomer or a mixture of stereoisomers thereof means an amount sufficient to effect treatment when administered to a subject, to provide a therapeutic benefit such as amelioration of symptoms or slowing of disease progression. For example, a therapeutically effective amount may be an amount sufficient to decrease a symptom of a disease or condition of as described herein. The therapeutically effective amount may vary depending on the subject and disease or condition being treated, the weight and age of the subject, the severity of the disease or condition and the manner of administering, which can readily be determined by one of ordinary skill in the art.

The term "trauma" as used herein refers to any physical damage to the body caused by violence, accident, fracture etc. The term "ischemia" refers to a cardiovascular disorder characterized by a low oxygen state usually due to the obstruction of the arterial blood supply or inadequate blood flow leading to hypoxia in the tissue. The term "stroke" refers to cardiovascular disorders caused by a blood clot or bleeding in the brain, most commonly caused by an interruption in the flow of blood in the brain as from clot blocking a blood vessel and in certain embodiments of the disclosure the term stroke refers to ischemic stroke or hemorrhagic stroke. The term "myocardial infarction" refers to a cardiovascular disorder characterized by localized necrosis resulting from obstruction of the blood supply.

The methods described herein may be applied to cell populations in vivo or ex vivo. "In vivo" means within a living individual, as within an animal or human. In this context, the methods described herein may be used therapeutically in an individual. "Ex vivo" means outside of a living individual. Examples of ex vivo cell populations include in vitro cell cultures and biological samples including fluid or tissue samples obtained from individuals. Such samples may be obtained by methods well known in the art. Exemplary biological fluid samples include blood, cerebrospinal fluid, urine and saliva. In this context, the compounds and compositions described herein may be used for a variety of purposes, including therapeutic and experimental purposes. For example, the compounds and compositions described herein may be used ex vivo to determine the optimal schedule and/or dosing of administration of a compound of the present disclosure for a given indication, cell type, individual and other parameters. Information gleaned from such use may be used for experimental purposes or in the clinic to set protocols for in vivo treatment. Other ex vivo uses for which the compounds and compositions described herein may be suited are described below or will become apparent to those skilled in the art. The selected compounds may be further characterized to examine the safety or tolerance dosage in human or non-human subjects. Such properties may be examined using commonly known methods to those skilled in the art.

Experiments with knockout animal models and Necrostatin 1, a receptor interacting protein kinase 1 inhibitor, have demonstrated the effectiveness of receptor interacting protein kinase 1 inhibition in protecting tissues from inflammatory bowel diseases (e.g., ulcerative colitis and Crohn's disease), psoriasis, retinal-detachment-induced photoreceptor necrosis, retinitis pigmentosa, cerulein-induced acute pancreatits and sepsis/systemic inflammatory response syndrome (SIRS) and alleviating ischemic brain injury, retinal ischemia/reperfusion injury, Huntington's disease, renal ischemia reperfusion injury, cisplatin induced kidney injury, traumatic brain injury, hematological and solid organ malignancies, bacterial infections and viral infections (e.g., tuberculosis and influenza) and lysosomal storage diseases.

The receptor interacting protein kinase 1 inhibitors of the present disclosure are therefore useful for treating diseases and conditions mediated by receptor interacting protein kinase 1, including but not limited to inflammatory diseases or disorders, necrotic cell diseases, neurodegenerative diseases, central nerve system (CNS) diseases, ocular diseases, infections and malignancies. In certain embodiments, the receptor interacting protein kinase 1 inhibitors described herein can inhibit inflammation, protect tissue or cell from damage or undesired cell death (e.g., necrosis or apoptosis), ameliorate symptoms and improve immune response in a patient suffering from any of the prescribed diseases or conditions. Moreover, the compounds may be suitable for treatment of immune-mediated disease, such as but not limited to, allergic diseases, autoimmune diseases and prevention of transplant rejection.

Necrotic Cell Diseases

The compounds described herein may be used for the treatment of diseases/disorders caused or otherwise associated with cellular necrosis. In particular, the disclosure provides methods for preventing or treating a disorder associated with cellular necrosis in a mammal, comprising the step of administering to said mammal a therapeutically effective amount of a compound or composition described herein. The term "necrotic cell disease" refers to diseases associated with or caused by cellular necrosis, for example trauma, ischemia, stroke, cardiac infarction, infection, Gaucher's disease, Krabbe disease, sepsis, Parkinson's disease, Alzheimer's disease, amyotrophic lateral sclerosis, Huntington's disease, HIV-associated dementia, retinal degenerative disease, glaucoma, age-related macular degeneration, rheumatoid arthritis, psoriasis, psoriatic arthritis or inflammatory bowel disease.

The necrotic cell diseases can be acute diseases such as trauma, ischemia, stroke, cardiac infarction, anthrax lethal toxin induced septic shock, sepsis, cell death induced by LPS and HIV induced T-cell death leading to immunodeficiency. In certain embodiments the disorder is an ischemic disease of organs including but not limited to brain, heart, kidney and liver.

The necrotic cell diseases also include chronic neurodegenerative diseases, such as Parkinson's disease, Huntington's disease, amyotrophic lateral sclerosis, Alzheimer's disease, infectious encephalopathy, dementia such as HIV associated dementia.

In some different embodiments, the disorder is an ocular disorder such as retinal degenerative disease, glaucoma or age-related macular degeneration. In some different embodiments, the disorder is a central nervous system (CNS) disorder.

Inflammatory Diseases or Disorders

The receptor interacting protein kinase 1 inhibitors described herein may be used to treat inflammatory diseases and disorders. Inflammatory diseases and disorders typically exhibit high levels of inflammation in the connective tissues or degeneration of these tissues.

Non-limiting examples of inflammatory diseases and disorders include Alzheimer's disease, ankylosing spondylitis, arthritis including osteoarthritis, rheumatoid arthritis (RA), psoriasis, asthma, atherosclerosis, Crohn's disease, colitis, dermatitis, diverticulitis, fibromyalgia, hepatitis, irritable bowel syndrome (IBS), inflammatory bowel disease (IBD), systemic lupus erythematous (SLE), nephritis, Parkinson's disease and ulcerative colitis. In certain embodiments, the compounds and compositions of the present disclosure are useful for treating an autoimmune disorder, such as rheumatoid arthritis, psoriasis, psoriatic arthritis, encephalitis, allograft rejection, autoimmune thyroid diseases (such as Graves' disease and Hashimoto's thyroiditis), autoimmune uveoretinitis, giant cell arteritis, inflammatory bowel diseases (including Crohn's disease, ulcerative colitis, regional enteritis, granulomatous enteritis, distal ileitis, regional ileitis, and terminal ileitis), insulin-dependent diabetes mellitus, multiple sclerosis, pernicious anemia, sarcoidosis, scleroderma, and systemic lupus erythematosus. In an embodiment, the receptor interacting protein kinase 1 inhibitors described herein are useful for treating autoimmune encephalitis.

In certain embodiments, the compounds and compositions are useful for treating rheumatoid arthritis (RA). In certain embodiments, the compounds and compositions are useful for treating ulcerative colitis. In certain embodiments, the compounds and compositions are useful for treating psoriasis.

In certain embodiments, the disorder is an inflammatory disease of the intestines such as Crohn's disease or ulcerative colitis (both generally known together as inflammatory bowel disease). In certain embodiments, the mammal is a primate, canine or feline subject. In certain embodiments, the mammal is a human subject. While not wishing to be bound by theory, it is believed that inhibition of receptor interacting protein kinase 1 by the presently disclosed compounds is responsible, at least in part, for their anti-inflammatory activity. Accordingly, embodiments of the disclosure also include methods for inhibiting receptor interacting protein kinase 1, either in vitro or in a subject in need thereof, the method comprises contacting a receptor interacting protein kinase 1 with a compound disclosed herein. In some of these embodiments, inhibiting receptor interacting protein kinase 1 is effective to block (partially or fully) the release of inflammatory mediators such as TNF and/or IL6.

Ocular Conditions

The receptor interacting protein kinase 1 inhibitors described herein can also be used to treat ocular conditions, for example to reduce or prevent the loss of photoreceptor and/or retinal pigment epithelial cell viability.

In one aspect, the disclosure provides a method of preserving the visual function of an eye of a subject with an ocular condition, wherein a symptom of the ocular condition is the loss of photoreceptor cell viability in the retina of the eye with the condition. The method comprises administering to the eye of the subject an effective amount of a compound or composition described herein, thereby preserving the viability of the photoreceptor cells disposed within the retina of the eye. After administration, the visual function (e.g., visual acuity) of the eye may be preserved or improved relative to the visual function of the eye prior to administration.

The ocular condition may be a condition selected from the group consisting of age-related macular degeneration (AMD), retinosis pigmentosa (RP), macular edema, diabetic retinopathy, central areolar choroidal dystrophy, BEST disease, adult vitelliform disease, pattern dystrophy, myopic degeneration, central serous retinopathy, Stargardt's disease, Cone-Rod dystrophy, North Carolina dystrophy, infectious retinitis, inflammatory retinitis, uveitis, toxic retinitis and light-induced toxicity. AMD may be the neovascular or the dry form of AMD. Retinal detachment may be a rhegmatogenous, a serous or a tractional retinal detachment.

In another aspect, the disclosure provides a method of preserving the viability of retinal pigment epithelial (RPE) cells within the retina of a subject with an ocular condition, wherein a symptom of the ocular condition is the loss of retinal pigment epithelial cells in the retina of the eye with the condition. The method comprises administering to the eye of the subject an effective amount of a compound or composition described herein, thereby preserving the viability of the retinal pigment epithelial cells. The ocular condition may be selected from the group consisting of AMD, BEST disease, myopic degeneration, Stargardt's disease, uveitis, adult foveomacular dystrophy, fundus falvimaculatus, multiple evanescent white dot syndrome, serpiginous choroidopathy, acute multifocal posterior placoid epitheliopathy (AMPPE) and other uveitis disorders.

The ocular condition may be a condition selected from the group consisting of age-related macular degeneration (AMD), retinosis pigmentosa (RP), macular edema, diabetic retinopathy, central areolar choroidal dystrophy, BEST disease, adult vitelliform disease, pattern dystrophy, myopic degeneration, central serous retinopathy, Stargardt's disease, Cone-Rod dystrophy, North Carolina dystrophy, infectious retinitis, inflammatory retinitis, uveitis, toxic retinitis and light-induced toxicity. Therefore, in certain embodiments, the method comprises administering to the eye an effective amount of a compound or composition described herein, thereby preserving the viability of the photoreceptor cells disposed within the retina of the subject with a condition.

In another aspect, the disclosure provides a method of preserving the viability of photoreceptor cells disposed within a retina of a mammalian eye following retinal detachment. The method comprises administering a compound or composition described herein to the eye in which a region of the retina has been detached in amounts sufficient to preserve the viability of photoreceptor cells disposed within the region of the detached retina.

In certain embodiments, the retinal detachment may be a rhegmatogenous retinal detachment, tractional retinal detachment or serous retinal detachment. In certain embodiments, the retinal detachment may occur as a result of a retinal tear, retinoblastoma, melanoma or other cancers, diabetic retinopathy, uveitis, choroidal neovascularization, retinal ischemia, pathologic myopia or trauma.

In another aspect, the disclosure provides a method of preserving visual function of an eye of a subject with an ocular condition selected from the group consisting of AMD, RP, macular edema, central areolar choroidal dystrophy, retinal detachment, diabetic retinopathy, BEST disease, adult vitelliform disease, pattern dystrophy, myopic degeneration, central serous retinopathy, Stargardt's disease, Cone-Rod dystrophy, North Carolina dystrophy, infectious retinitis, inflammatory retinitis, uveitis, toxic retinitis and light-induced toxicity, wherein a symptom of the ocular condition is the loss of photoreceptor cells viability in the retina of the eye, wherein the method comprises treating the subject with a compound or composition described herein to the subject.

In another aspect, the disclosure provides a method of preserving the visual function of an eye of a subject with an ocular condition, wherein a symptom of the ocular condition is the loss of photoreceptor cell viability and/or RPE viability in the retina of the eye wherein the method comprises treating the subject with a compound or composition described herein to the subject.

In certain embodiments is provided a method of preserving the visual function of an eye of a subject with ocular conditions, wherein a symptom of the ocular condition is the loss of retinal ganglion cell viability in the retina of the eye with the conditions. The method comprises administering to the eye of the subject an effective amount of a compound or composition, thereby preserving the viability of the retinal ganglion cells disposed within the retina of the eye. After administration of the compound or composition, the visual function of the eye may be preserved or improved relative to the visual function of the eye prior to administration. Further, after the administration, the preserved retinal ganglion cell is capable of supporting axonal regeneration.

In each of the foregoing methods, the ocular condition, wherein a symptom of the condition is the loss of retinal ganglion cell viability in the retina of the eye, includes but is not limited to glaucoma, optic nerve injury, optic neuritis, optic neuropathies, diabetic retinopathy, central retinal artery occlusion and central retinal vein occlusion. It is contemplated that the forgoing methods may be used for the treatment of optic neuropathies such as ischemic optic neuropathy (e.g., arteritic or non-arteritic anterior ischemic neuropathy and posterior ischemic optic neuropathy), compressive optic neuropathy, infiltrative optic neuropathy, traumatic optic neuropathy, mitochondrial optic neuropathy (e.g., Leber's optic neuropathy), nutritional optic neuropathy, toxic optic neuropathy and hereditary optic neuropathy (e.g., Leber's optic neuropathy, Dominant Optic Atrophy, Behr's syndrome).

Also disclosed is a method of preserving the visual function of an eye of a subject with an ocular condition selected from the group consisting of glaucoma, optic nerve injury, optic neuropathies, diabetic retinopathy, central retinal artery occlusion and central retinal vein occlusion. The method comprises administering to the eye of the subject an effective amount of a compound or composition described herein, thereby preserving the viability of the retinal ganglion cells disposed within the retina of the eye and the visual function of the eye.

In another aspect, disclosed herein is a method of preserving the viability of retinal ganglion cells disposed within a retina of a mammalian eye affected by, for example, glaucoma, optic nerve injury, optic neuritis, optic neuropathies, diabetic retinopathy, central retinal artery occlusion and central retinal vein occlusion. The method comprises administering a compound or composition described herein to the eye in which a region of the retina has been affected in amounts sufficient to preserve the viability of retinal ganglion cells disposed within the region of the affected retina. The preserved retinal ganglion cell is capable of supporting axonal regeneration.

Also disclosed is a method for promoting axon regeneration in an eye of a subject with an ocular condition, wherein a symptom of the ocular condition is the loss of retinal ganglion cell viability in the retina of the eye with the condition. The method comprises administering to the eye of the subject an effective amount of a compound or composition described herein, thereby promoting axon regeneration of the retinal ganglion cell within the retina of the eye.

In each of the foregoing embodiments, it is understood that the methods and compositions described herein can be used to preserve the viability and/or promote axon regeneration of retinal ganglion cells during treatment of the underlying conditions including, but not limited to, glaucoma, optic nerve injury, optic neuritis, optic neuropathies, diabetic retinopathy, central retinal artery occlusion and central retinal vein occlusion.

Neurodegenerative and CNS Diseases

The receptor interacting protein kinase 1 inhibitors described herein may also be used to treat neurodegenerative diseases. Neurodegenerative diseases can affect many of the body's activities, such as balance, movement, talking, breathing and heart function. Neurodegenerative diseases can be genetic or caused by medical conditions such as alcoholism, tumors, strokes, toxins, chemicals and viruses.

Non-limiting examples of neurodegenerative diseases and CNS diseases include Niemann-Pick disease, type C1 (NPC1), Alzheimer's disease, amyotrophic lateral sclerosis (ALS), Friedreich's ataxia, Huntington's disease, Lewy body disease, Parkinson's disease and spinal muscular atrophy.

In an embodiment, the receptor interacting protein kinase 1 inhibitors described herein may be used to treat NPC1 via inhibiting necroptosis that causes neuronal loss. In certain embodiments, the compounds and compositions of the present disclosure are useful for treating Alzheimer's disease. In certain embodiments, the compounds and compositions of the present disclosure are useful for treating Parkinson's disease. In certain embodiments, the compounds and compositions of the present disclosure are useful for treating amyotrophic lateral sclerosis (ALS).

More generally, the receptor interacting protein kinase 1 inhibitors described herein can be used to preserve neuron viability and promote axon growth and nerve functions within the central nervous system (CNS). Accordingly, the compounds may be used to reduce or even reverse the loss of cognitive, motor and sensory functions associated with a CNS disease or disorder, by preserving neuron viability and/or promoting axon regeneration and/or nerve functions.

The receptor interacting protein kinase 1 inhibitors described herein can be used in a method for promoting axon regeneration in a CNS neuron, such as a CNS sensory neuron, a motor neuron, a cortical neuron, a cerebellar neuron, a hippocampal neuron and a midbrain neuron. The receptor interacting protein kinase 1 inhibitors described herein can be used in a method for promoting nerve function or preserving the viability following injury to a CNS neuron. In certain embodiments, these compounds can be used to promote regeneration of an axon in a CNS neuron that is degenerated in the CNS disease or disorder. The receptor interacting protein kinase 1 inhibitors may be administered by any conventional means, such as locally to the neuron or applied ex vivo before re-implantation.

Accordingly, in one aspect, the disclosure provides a method of treating a CNS disorder in a subject in need thereof, wherein a symptom of the CNS disorder is axon degeneration or injury within a CNS neuron. The method comprises administering to the subject an effective amount of a compound or composition disclosed herein thereby to promote regeneration of an axon in a CNS neuron affected by the CNS disorder. Following administration, neural functions may be measured, for example, as an indication of axon regeneration. It is also contemplated that, following administration of the compound or composition, the neuron function of the CNS neuron is preserved or improved relative to the neuron function prior to administration.

The CNS disorder includes, but is not limited to, brain injury, spinal cord injury, dementia, stroke, Alzheimer's disease, amyotrophic lateral sclerosis (ALS/Lou Gehrig's Disease), Parkinson's disease, Huntington's disease, multiple sclerosis, diabetic neuropathy, polyglutamine (polyQ) diseases, stroke, Fahr disease, Menke's disease, Wilson's disease, cerebral ischemia and a prion disorder. In exemplary embodiments, the CNS disorder is brain injury or spinal cord injury.

Also provided herein are methods for promoting neuron survival and axon regeneration in the CNS. CNS disorders characterized by impaired or failing axon growth or axon degeneration may arise from CNS neuron injury (e.g., trauma, surgery, nerve compression, nerve contusion, nerve transection, neurotoxicity or other physical injury to the brain or spinal cord) or neurodegenerative CNS disease, wherein a symptom of the disorder is axon degeneration (e.g., Alzheimer's disease, amyotrophic lateral sclerosis (ALS/Lou Gehrig's Disease), Parkinson's disease, multiple sclerosis, diabetic neuropathy, polyglutamine (polyQ) diseases, stroke, Fahr disease, Menke's disease, Wilson's disease, cerebral ischemia, prion disorder (e.g., Creutzfeldt-Jakob disease). In certain embodiments, the CNS disorder is brain injury (e.g., traumatic brain injury) or spinal cord injury (e.g., chronic, acute or traumatic spinal cord injury). In certain embodiments, the CNS disorder affects a subject's basic vital life functions such as breathing, heart beat and blood pressure, e.g., an injury to or aneurysm in the brain stem.

In certain embodiments, the CNS disorder affects a subject's cognitive ability, such as, brain injury to the cerebral cortex or a neurodegenerative CNS disorder, such as, Alzheimer's disease, frontotemporal dementia, dementia with Lewy bodies, corticobasal degeneration, progressive supranuclear palsy and prion disorders.

In certain embodiments, the CNS disorder affects a subject's movement and/or strength, such as injury to the brain or spinal cord or a neurodegenerative CNS disorder such as Parkinson's disease, frontotemporal dementia, dementia with Lewy bodies, corticobasal degeneration, progress supranuclear palsy, Huntington's disease, multiple system atrophy, amyotrophic lateral sclerosis and hereditary spastic paresis.

In certain embodiments, the CNS disorder affects a subject's coordination, such as brain injury to the cerebellum or a neurodegenerative CNS disorder such as spinocerebellar atrophies, Friedreich's ataxia and prion disorders.

In each of the foregoing methods, the CNS disorder includes, but is not limited to, brain injury, spinal cord injury, Alzheimer's disease, amyotrophic lateral sclerosis (ALS/Lou Gehrig's Disease), Parkinson's disease, multiple sclerosis, diabetic neuropathy, polyglutamine (polyQ) diseases, stroke, Fahr disease, Menke's disease, Wilson's disease, cerebral ischemia, a prion disorder (e.g., Creutzfeldt-Jakob disease), dementia (e.g., frontotemporal dementia, dementia with Lewy bodies), corticobasal degeneration, progressive supranuclear palsy, multiple system atrophy, hereditary spastic paraparesis and spinocerebellar atrophies.

Tissue Injuries or Damages

The ability of the compounds described herein to inhibit inflammation and cell death makes them suitable for ameliorating tissue injuries or damages. The tissue injuries or damages may be a result of any of the diseases or conditions described above. For example, the compounds may be used for amelioration of brain tissue injury or damage following ischemic brain injury or traumatic brain injury or for amelioration of heart tissue injury or damage following myocardial infarction or for amelioration of brain tissue injury or damage associated with Huntington's disease, Alzheimer's disease or Parkinson's disease or for amelioration of liver tissue injury or damage associated with non-alcohol steatohepatitis, alcohol steatohepatitis, autoimmune hepatitis autoimmune hepatobiliary diseases or primary sclerosing cholangitis or for the amelioration of liver tissue injury or damage associated with overdose of acetaminophen or for amelioration of kidney tissue injury or damage following renal transplant or the administration of nephrotoxic drugs or substances.

Non-limiting examples of brain injury or damage include stroke (e.g., hemorrhagic and non-hemorrhagic), traumatic brain injury (TBI), cerebral hemorrhage, subarachnoid hemorrhage, intracranial hemorrhage secondary to cerebral arterial malformation, cerebral infarction, perinatal brain injury, non-traumatic brain injury, Alzheimer's disease, Parkinson's disease, Huntington's disease, multiple sclerosis, amyotrophic lateral sclerosis, brain hemorrhage, brain infections, brain tumor, subclinical brain injury, spinal cord injury, anoxic-ischemic brain injury, focal cerebral ischemia, global cerebral ischemia, and hypoxic hypoxia.

In an embodiment, the compounds and compositions of the present disclosure may be used to treat peritoneal tissue injury. Non-limiting examples of peritoneal tissue injury include peritoneal deterioration, peritoneal sclerosis, and peritoneal cancer. For example, the receptor interacting protein kinase 1 inhibitors described herein may be used to treat peritoneal damage caused by peritoneal dialysis fluid (PDF) and PD-related side effects.

Liver Injury and Diseases

In an embodiment, the compounds and compositions of the present disclosure may be used to treat liver injury and diseases. Non-limiting examples of liver injury or damage include not only degeneration or necrosis of liver parenchyma cells which results from injury caused by a certain factor, but also undesirable phenomena caused by biological reactions to the injury, such as mobilization, infiltration, activation of Kupffer cells, leukocytes and the like, fibrosis of the liver tissue, etc., which reactions occur alone or in combination. In an embodiment, the receptor interacting protein kinase 1 inhibitors described herein may be used to treat steatohepatitis and hepatocellular carcinoma via inhibiting receptor interacting protein kinase 1 activity-dependent apoptosis of hepatocytes and hepatocarcinogenesis. In an embodiment, the receptor interacting protein kinase 1 inhibitors described herein may be used to treat acute cholestasis and liver injury.

Kidney Injury and Diseases

In an embodiment, the compounds and compositions of the present disclosure may be used to treat kidney injury and diseases. Non-limiting examples of kidney diseases include chronic kidney disease (CKD) (e.g., glomerular diseases, tubulointerstitial diseases, obstruction, polycystic kidney disease), acute kidney injury (AKI), diabetic nephropathy, glomerulonephritis, focal glomerulosclerosis, immune complex nephropathy or lupus nephritis. Kidney disease may be caused by drug-induced renal injury or kidney graft rejection. Kidney disease may be characterized as nephrotic syndrome or renal insufficiency. In an embodiment, the receptor interacting protein kinase 1 inhibitors described herein may be used to treat kidney diseases (e.g., AKI) via inhibiting cell death pathway in kidney diseases. In an embodiment, the receptor interacting protein kinase 1 inhibitors described herein may be used to treat patient with kidney stones and to prevent crystal-induced cytotoxicity and acute kidney injury via inhibiting receptor interacting protein kinase 3-MLKL-mediated necroptosis.

Malignancies

In an embodiment, the compounds and compositions of the present disclosure are useful for treating malignancies/cancers such as carcinoma, sarcoma, melanoma, lymphoma or leukemia. Non-limiting examples of malignancies suitably treated by the receptor interacting protein kinase 1 inhibitors described herein include lung cancer (e.g. non-small cell lung cancer, small-cell lung cancer), hepatocellular cancer, melanoma, pancreatic cancer, urological cancer, bladder cancer, colorectal cancer, colon cancer, breast cancer, prostate cancer, renal cancer, thyroid cancer, gall bladder cancer, peritoneal cancer, ovarian cancer, cervical cancer, gastric cancer, endometrial cancer, esophageal cancer, head and neck cancer, neuroendocrine cancer, CNS cancer, brain tumors (e.g., glioma, anaplastic oligodendroglioma, adult glioblastoma multiforme, and adult anaplastic astrocytoma), bone cancer, soft tissue sarcoma, retinoblastomas, neuroblastomas, peritoneal effusions, malignant pleural effusions, mesotheliomas, Wilms tumors, trophoblastic neoplasms, hemangiopericytomas, Kaposi's sarcomas, myxoid carcinoma, round cell carcinoma, squamous cell carcinomas, esophageal squamous cell carcinomas, oral carcinomas, vulval cancer, cancers of the adrenal cortex, ACTH producing tumors, lymphoma, and leukemia.

Infectious Diseases

In an embodiment, the compounds and compositions of the present disclosure are useful for treating infectious diseases resulting from the presence of pathogenic agents, including pathogenic viruses, pathogenic bacteria, fungi, protozoa, multicellular parasites and aberrant proteins known as prions. Non-limiting examples of infectious diseases suitably treated by the receptor interacting protein kinase 1 inhibitors described herein include virus infectious diseases and bacterial infectious diseases. The virus infectious disease is not particularly limited and includes, for example, infectious diseases with respiratory infectious viruses (e.g., infectious diseases due to respiratory infectious viruses such as influenza virus, rhino virus, corona virus, parainfluenza virus, RS virus, adeno virus, reo virus and the like), herpes zoster caused by herpes virus, diarrhea caused by rotavirus, viral hepatitis, AIDS and the like. The bacterial infectious disease is not particularly limited and includes, for example, infectious diseases caused by *Bacillus cereus*, *Vibrio parahaemolyticus*, Enterohemorrhagic *Escherichia coli*, *Staphylococcus aureus*, MRSA, *Salmonella*, *Botulinus*, *Candida* and the like.

Bone Diseases

In an embodiment, the compounds and compositions of the present disclosure are useful for treating bone diseases that may result from a bone remodeling disorder whereby the balance between bone formation and bone resorption is shifted. Non-limiting examples of bone remodeling disorders include osteoporosis, Paget's disease, osteoarthritis, rheumatoid arthritis, achondroplasia, osteochodrytis, hyperparathyroidism, osteogenesis imperfecta, congenital hypophosphatasia, fribromatous lesions, fibrous displasia, multiple myeloma, abnormal bone turnover, osteolytic bone disease and periodontal disease. Additional examples of bone diseases suitably treated by the receptor interacting protein kinase 1 inhibitors described herein include bone fracture, bone trauma, or a bone deficit condition associated with post-traumatic bone surgery, post-prosthetic joint surgery, post-plastic bone surgery, post-dental surgery, bone chemotherapy treatment or bone radiotherapy treatment. Additional examples of diseases affecting bone or bone joints suitably treated by the receptor interacting protein kinase 1 inhibitors described herein include metastatic bone cancer, rheumatic diseases such as rheumatoid arthritis, osteoarthritis and other inflammatory arthropathies. In an embodiment, the receptor interacting protein kinase 1 inhibitors described herein may be used to treat postmenopausal osteoporosis via inhibiting osteocyte necroptosis and trabecular deterioration.

Cardiovascular Diseases

In an embodiment, the compounds and compositions of the present disclosure are useful for treating cardiovascular diseases that may be relate to the cardiovascular disorders of fragile plaque disorder, occlusive disorder and stenosis. Non-limiting cardiovascular diseases include coronary artery disorders and peripheral arterial disorders, including, among others, atherosclerosis, arterial occlusion, aneurysm formation, thrombosis, post-traumatic aneurysm formation, restenosis, and post-operative graft occlusion. It is believed that atherosclerosis results from maladaptive inflammation driven primarily by macrophages. Thus, the compounds and compositions of the present disclosure may be used to treat atherosclerosis via inhibiting macrophage necroptosis.

Transplantation

In an embodiment, the compounds and compositions of the present disclosure are useful for treating transplant patients. Non-limiting examples of transplant patient suitably treated by the receptor interacting protein kinase 1 inhibitors described herein include patients with solid and non-solid organ and tissue transplantations and transplants, such as liver, heart, kidney, and heterologous and autologous bone marrow transplantations/transplants. Typically, immunosuppressive therapy is used to avoid graft rejection in recipients of solid organ transplants. Recipients of bone marrow transplants are usually subjected to extensive irradiation and chemotherapy prior to transplantation. It is believed that receptor interacting protein kinase 1 and NF-κB signaling in dying cells determines cross-priming of $CD8^+$ T cells. Thus, the receptor interacting protein kinase 1 inhibitors described herein may be used to treat transplant patient and avoid graft rejection by modulating cross-priming of $CD8^+$ T cells.

Other Diseases and Conditions

Additional examples of diseases and disorders suitably treated by the receptor interacting protein kinase 1 inhibitors described herein include Gaucher disease, organ failure, pancreatitis, atopic dermatitis, spondyloarthritis, gout, systemic onset juvenile idiopathic arthritis (SoJIA), systemic lupus erythematosus (SLE), Sjogren's syndrome, systemic scleroderma, anti-phospholipid syndrome (APS), vasculitis, primary sclerosing cholangitis (PSC), acetaminophen toxicity, kidney damage/injury (nephritis, renal transplant, surgery, administration of nephrotoxic drugs e.g. cisplatin, acute kidney injury(AKI)), Celiac disease, autoimmune idiopathic thrombocytopenic purpura (autoimmune ITP), cerebrovascular accident (CVA, stroke), myocardial infarction (MI), allergic diseases (including asthma), diabetes, Wegener's granulomatosis, pulmonary sarcoidosis, Behcet's disease, interleukin-1 converting enzyme (ICE/caspase-1) associated fever syndrome, chronic obstructive pulmonary disease (COPD), tumor necrosis factor receptor-associated periodic syndrome (TRAPS), peridontitis, NEMO-deficiency syndrome (F-kappa-B essential modulator gene (also known as IKK gamma or IKKG) deficiency syndrome), HOIL-1 deficiency ((also known as RBCK1) heme-oxidized IRP2 ubiquitin ligase-1 deficiency), linear ubiquitin chain assembly complex (LUBAC) deficiency syndrome, hematological and solid organ malignancies, bacterial infections and viral infections (e.g., tuberculosis and influenza) and lysosomal storage diseases.

Non-limiting examples of lysosomal storage diseases include Gaucher disease, GM2 Gangliosidosis, alpha-mannosidosis, aspartylglucosaminuria, cholesteryl ester storage disease, chronic hexosaminidase A deficiency, cystinosis, Danon disease, Fabry disease, Farber disease, fucosidosis, galactosialidosis, GM1 gangliosidosis, mucolipidosis, infantile free sialic acid storage disease, juvenile hexosaminidase A deficiency, Krabbe disease, lysosomal acid lipase deficiency, metachromatic leukodystrophy, mucopolysaccharidoses disorders, multiple sulfatase deficiency, Niemann-Pick disease, neuronal ceroid lipofuscinoses, Pompe disease, pycnodysostosis, Sandhoff disease, Schindler disease, sialic acid storage disease, Tay-Sachs and Wolman disease.

In certain embodiments, provided are compounds and compositions for use in medicine. In certain embodiments, the compounds and compositions are for use in the treatment of a receptor interacting protein kinase 1-mediated disease or disorder. Also provided is a method of treating a receptor interacting protein kinase 1-mediated disease or disorder comprising administering a therapeutically effective amount of a compound or pharmaceutical composition disclosed herein to a subject in need thereof.

5. Compositions

For the purposes of administration, the compounds of the present disclosure may be administered as a raw chemical or may be formulated as pharmaceutical compositions. Pharmaceutical compositions of the present disclosure comprise a compound of any of Formulas I-XX, or subformula thereof and a pharmaceutically acceptable carrier, diluent or excipient. Accordingly, different embodiments are directed to pharmaceutical compositions comprising any one or more of the foregoing compounds of any of Formulas I-XX, or subformula thereof or a pharmaceutically acceptable salt, prodrug, stereoisomer or a mixture of stereoisomers thereof and a pharmaceutically acceptable carrier, diluent or excipient are also provided in various embodiments.

The pharmaceutical compositions of the present disclosure may be specially formulated for administration in solid or liquid form, including those adapted for the following: oral administration, for example, drenches (aqueous or non-aqueous solutions or suspensions), tablets, e.g., those targeted for buccal, sublingual and systemic absorption, boluses, powders, granules, pastes for application to the tongue; parenteral administration, for example, by subcutaneous, intramuscular, intravenous or epidural injection as, for example, a sterile solution or suspension or sustained-release formulation; topical application, for example, as a cream, ointment or a controlled-release patch or spray applied to the skin; intravaginally or intrarectally, for example, as a pessary, cream or foam; sublingually; ocularly; transdermally; or nasally, pulmonary and to other mucosal surfaces.

The phrase "pharmaceutically acceptable" is employed herein to refer to those compounds, materials, compositions and/or dosage forms which are, within the scope of sound medical judgment, suitable for use in contact with the tissues of human beings and animals without excessive toxicity, irritation, allergic response or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient or solvent encapsulating material, involved in carrying or transporting the subject compound from one organ or portion of the body, to another organ or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose and its derivatives, such as sodium carboxymethyl cellulose, ethyl cellulose and cellulose acetate; surfactants, such as polysorbate 80 (i.e., Tween 80); powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations. Examples of such formulations include, but are not limited to DMSO, 10 mM DMSO, 8% hydroxypropyl-beta-cyclodextrin in PBS, propylene glycol, etc. For example, in a certain embodiment the compounds of the disclosure can be used as 4 mM solution in 8% hydroxypropyl-beta-cyclodextrin in PBS for parenteral administration. In another certain embodiments, the compounds of the disclosure can be used as a suspension in 0.5% aqueous CMC containing 0.1% TWEEN 80.

As set out herein, certain embodiments of the present compounds may contain a basic functional group, such as amino or methylamino (NCH$_3$) and are, thus, capable of forming pharmaceutically-acceptable salts with pharmaceutically-acceptable acids. The term "pharmaceutically-acceptable salts" in this respect refers to the relatively non-toxic, inorganic and organic acid addition salts of compounds of the present disclosure. These salts can be prepared in situ in the administration vehicle or the dosage form manufacturing process or by separately reacting a purified compound of the disclosure in its free base form with a suitable organic or inorganic acid and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate and laurylsulphonate salts and the like.

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic and the like.

In other cases, the compounds of the present disclosure may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present disclosure. These salts can likewise be prepared in situ in the administration vehicle or the dosage form manufacturing process or by separately reacting the purified compound in its free acid form with a suitable base, such as the hydroxide, carbonate or bicarbonate of a pharmaceutically-acceptable metal cation, with ammonia or with a pharmaceutically-acceptable organic primary, secondary or tertiary amine. Representative alkali or alkaline earth salts include the lithium, sodium, potassium, calcium, magnesium and aluminum salts and the like. Representative organic amines useful for the formation of base addition salts include ethylamine, diethylamine, ethylenediamine, ethanolamine, diethanolamine, piperazine and the like.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol and the like; and metal chelating agents, such as citric acid, ethylenediamine tetraacetic acid (EDTA), sorbitol, tartaric acid, phosphoric acid and the like.

Formulations of the present disclosure include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, this amount will range from about 1% to about 99% of active ingredient, preferably from about 5% to about 70%, most preferably from about 10% to about 30%.

In certain embodiments, a formulation of the present disclosure comprises an excipient selected from the group consisting of cyclodextrins, liposomes, micelle forming agents, e.g., bile acids and polymeric carriers, e.g., polyesters and polyanhydrides; and a compound of the present disclosure. In certain embodiments, an aforementioned formulation renders orally bioavailable a compound of the present disclosure.

Methods of preparing these formulations or compositions include the step of bringing into association a compound of the present disclosure with the carrier and, optionally, one or more accessory ingredients. In general, the formulations are prepared by uniformly and intimately bringing into association a compound of the present disclosure with liquid carriers or finely divided solid carriers or both and then, if necessary, shaping the product.

Formulations of the disclosure suitable for oral administration may be in the form of capsules, cachets, pills, tablets, lozenges (using a flavored basis, usually sucrose and acacia or tragacanth), powders, granules or as a solution or a suspension in an aqueous or non-aqueous liquid or as an oil-in-water or water-in-oil liquid emulsion or as an elixir or syrup or as pastilles (using an inert base, such as gelatin and glycerin or sucrose and acacia) and/or as mouth washes and the like, each containing a predetermined amount of a compound of the present disclosure as an active ingredient. A compound of the present disclosure may also be administered as a bolus, electuary or paste.

In solid dosage forms of the disclosure for oral administration (capsules, tablets, pills, dragees, powders, granules and the like), the active ingredient is mixed with one or more pharmaceutically-acceptable carriers, such as sodium citrate or dicalcium phosphate and/or any of the following: fillers or extenders, such as starches, lactose, sucrose, glucose, mannitol and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates and sodium carbonate; solution retarding agents, such as paraffin; absorption accelerators, such as quaternary ammonium compounds; wetting agents, such as, for example, cetyl alcohol, glycerol monostearate and non-ionic surfactants; absorbents, such as kaolin and bentonite clay; lubricants, such a talc, calcium stearate, magnesium stearate, solid polyethylene glycols, sodium lauryl sulfate and mixtures thereof; and coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made in a suitable machine in which a mixture of the powdered compound is moistened with an inert liquid diluent.

The tablets and other solid dosage forms of the pharmaceutical compositions of the present disclosure, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter or by incorporating sterilizing agents in the form of sterile solid compositions that can be dissolved in sterile water or some other sterile injectable medium immediately before use. These compositions may also optionally contain opacifying agents and may be of a composition that they release the active ingredient(s) only or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the compounds of the disclosure include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth and mixtures thereof.

Formulations of the pharmaceutical compositions of the disclosure for rectal or vaginal administration may be presented as a suppository, which may be prepared by mixing one or more compounds of the disclosure with one or more suitable nonirritating excipients or carriers comprising, for example, cocoa butter, polyethylene glycol, a suppository wax or a salicylate and which is solid at room temperature, but liquid at body temperature and, therefore, will melt in the rectum or vaginal cavity and release the active compound.

Formulations of the present disclosure which are suitable for vaginal administration also include pessaries, tampons, creams, gels, pastes, foams or spray formulations containing such carriers as are known in the art to be appropriate.

Dosage forms for the topical or transdermal administration of a compound of this disclosure include powders, sprays, ointments, pastes, creams, lotions, gels, solutions, patches and inhalants. The active compound may be mixed under sterile conditions with a pharmaceutically-acceptable carrier and with any preservatives, buffers or propellants which may be required.

The ointments, pastes, creams and gels may contain, in addition to an active compound of this disclosure, excipients, such as animal and vegetable fats, oils, waxes, paraffins, starch, tragacanth, cellulose derivatives, polyethylene glycols, silicones, bentonites, silicic acid, talc and zinc oxide or mixtures thereof.

Powders and sprays can contain, in addition to a compound of this disclosure, excipients such as lactose, talc, silicic acid, aluminum hydroxide, calcium silicates and polyamide powder or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present disclosure to the body. Dissolving or dispersing the compound in the proper medium can make such dosage forms. Absorption enhancers can also be used to increase the flux of the compound across the skin. Either providing a rate controlling membrane or dispersing the compound in a polymer matrix or gel can control the rate of such flux.

Ophthalmic formulations, eye ointments, powders, solutions and the like, are also contemplated as being within the scope of this disclosure.

Pharmaceutical compositions of this disclosure suitable for parenteral administration comprise one or more compounds of the disclosure in combination with one or more pharmaceutically-acceptable sterile isotonic aqueous or nonaqueous solutions, dispersions, suspensions or emulsions or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers, which may be employed in the pharmaceutical compositions of the disclosure include water, ethanol, polyols (such as glycerol, propylene glycol, polyethylene glycol and the like) and suitable mixtures thereof, vegetable oils, such as olive oil and injectable organic esters, such as ethyl oleate. Proper fluidity can be maintained, for example, by the use of coating materials, such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenyl sorbic acid and the like. It may also be desirable to include isotonic agents, such as sugars, sodium chloride and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissue.

6. Dosing

The phrases "parenteral administration" and "administered parenterally" as used herein means modes of administration other than enteral and topical administration, usually by injection and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present disclosure, which may be used in a suitable hydrated form and/or the pharmaceutical compositions of the present disclosure, are formulated into pharmaceutically-acceptable dosage forms by conventional methods known to those of skill in the art.

Actual dosage levels of the active ingredients in the pharmaceutical compositions of this disclosure may be varied so as to obtain an amount of the active ingredient that is effective to achieve the desired therapeutic response for a particular patient, composition and mode of administration, without being toxic to the patient.

The selected dosage level will depend upon a variety of factors including the activity of the particular compound of the present disclosure employed or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated and like factors well known in the medical arts. A daily, weekly or monthly dosage (or other time interval) can be used.

A physician or veterinarian having ordinary skill in the art can readily determine and prescribe the effective amount of the pharmaceutical composition required. For example, the physician or veterinarian could start doses of the compounds of the disclosure employed in the pharmaceutical composition at levels lower than that required to achieve the desired therapeutic effect and then gradually increasing the dosage until the desired effect is achieved.

In general, a suitable daily dose of a compound of the disclosure will be that amount of the compound that is the lowest dose effective to produce a therapeutic effect (e.g., inhibit necrosis). Such an effective dose will generally depend upon the factors described above. Generally doses of the compounds of this disclosure for a patient, when used for the indicated effects, will range from about 0.0001 to about 100 mg per kg of body weight per day. Preferably the daily dosage will range from 0.001 to 50 mg of compound per kg of body weight and even more preferably from 0.01 to 10 mg of compound per kg of body weight.

If desired, the effective daily dose of the active compound may be administered as two, three, four, five, six or more sub-doses administered separately at appropriate intervals throughout the day, optionally, in unit dosage forms.

In certain embodiments, the present disclosure relates to compounds for inhibiting cell death, wherein the compounds are represented by structures (I). In certain embodiments, the compounds of the present disclosure are inhibitors of cell death. In any event, the compounds of the present disclosure preferably exert their effect on inhibiting cell death at a concentration less than about 50 micromolar, more preferably at a concentration less than about 10 micromolar and most preferably at a concentration less than 1 micromolar.

The compounds of the disclosure can be tested in standard animal models of stroke and standard protocols such as described by Hara, H., et al. Proc Natl Acad Sci USA, 1997. 94(5): 2007-12.

When the compounds of the present disclosure are administered as pharmaceuticals, to humans and animals, they can be given per se or as a pharmaceutical composition containing, for example, 0.1% to 99.5% (more preferably, 0.5% to 90%) of active ingredient in combination with a pharmaceutically acceptable carrier.

The compounds of the present application or the compositions thereof may be administered once, twice, three or four times daily, using any suitable mode described above. Also, administration or treatment with the compounds may be continued for a number of days; for example, commonly treatment would continue for at least 7 days, 14 days or 28 days, for one cycle of treatment. Treatment cycles are well known and are frequently alternated with resting periods of about 1 to 28 days, commonly about 7 days or about 14 days, between cycles. The treatment cycles, in certain embodiments, may also be continuous.

When administered orally, the total daily dosage for a human subject may be between 1 mg and 1,000 mg, between about 1,000-2,000 mg/day, between about 10-500 mg/day, between about 50-300 mg/day, between about 75-200 mg/day or between about 100-150 mg/day.

The daily dosage may also be described as a total amount of a compound described herein administered per dose or per day. Daily dosage of a compound may be between about 1 mg and 4,000 mg, between about 2,000 to 4,000 mg/day, between about 1 to 2,000 mg/day, between about 1 to 1,000 mg/day, between about 10 to 500 mg/day, between about 20 to 500 mg/day, between about 50 to 300 mg/day, between about 75 to 200 mg/day or between about 15 to 150 mg/day.

In certain embodiments, the method comprises administering to the subject an initial daily dose of about 1 to 800 mg of a compound described herein and increasing the dose by increments until clinical efficacy is achieved. Increments of about 5, 10, 25, 50 or 100 mg can be used to increase the dose. The dosage can be increased daily, every other day, twice per week or once per week.

In certain embodiments, a compound or pharmaceutical preparation is administered orally. In certain embodiments, the compound or pharmaceutical preparation is administered intravenously. Alternative routes of administration include sublingual, intramuscular and transdermal administrations.

The preparations of the present disclosure may be given orally, parenterally, topically or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. In certain embodiments, the administration is oral.

7. Combinations

In another aspect of the disclosure the compounds can be administered in combination with other agents, including (but not limited to) compounds that are apoptosis inhibitors; PARP poly(ADP-ribose) polymerase inhibitors; Src inhibitors; agents for the treatment of cardiovascular disorders; anti-inflammatory agents, anti-thrombotic agents; fibrinolytic agents; anti-platelet agents, lipid reducing agents, direct thrombin inhibitors; glycoprotein IIb/IIIa receptor inhibitors; calcium channel blockers; beta-adrenergic receptor blocking agents; cyclooxygenase (e.g., COX-1 and COX-2) inhibitors; angiotensin system inhibitor (e.g., angiotensin-converting enzyme (ACE) inhibitors); renin inhibitors; and/or agents that bind to cellular adhesion molecules and inhibit the ability of white blood cells to attach to such molecules (e.g., polypeptides, polyclonal and monoclonal antibodies).

Embodiments of the disclosure also provide combinations of two or more compounds that inhibit cellular necrosis (e.g., a compound as disclosed herein and an additional agent for inhibiting necrosis). The disclosure also provides combinations of one or more compounds that inhibit cellular necrosis combined with one or more additional agents or compounds (e.g., other therapeutic compounds for treating a disease, condition or infection such as an apoptosis inhibitor).

8. Kits

Provided herein are also kits that include a compound of the disclosure, combinations, or a pharmaceutically acceptable salt, prodrug, stereoisomer or a mixture of stereoisomers thereof and suitable packaging. In certain embodiments, a kit further includes instructions for use. In one aspect, a kit includes a compound of the disclosure or a pharmaceutically acceptable salt, prodrug, stereoisomer or a mixture of stereoisomers thereof and a label and/or instructions for use of the compounds in the treatment of the indications, including the diseases or conditions, described herein.

Provided herein are also articles of manufacture that include a compound described herein or a pharmaceutically acceptable salt, prodrug, stereoisomer or a mixture of stereoisomers thereof in a suitable container. The container may be a vial, jar, ampoule, preloaded syringe and intravenous bag.

The kit can also contain instructions for using the compounds according to the disclosure. The kit can be compartmentalized to receive the containers in close confinement. As used herein, a kit such as a compartmentalized kit includes any kit in which compounds or agents are contained in separate containers. Illustrative examples of such containers include, but are not limited to, small glass containers, plastic containers or strips of plastic or paper. Particularly preferred types of containers allow the skilled worker to efficiently transfer reagents from one compartment to another compartment such that the samples and reagents are not cross-contaminated and the agents or solutions of each container can be added in a quantitative fashion from one compartment to another. Such containers include, but are not limited to, a container that will accept a compound or combination of compounds and/or other agents of the disclosure. One or more compounds or agents can be provided as a powder (e.g. lyophilized powder) or precipitate. Such compound(s) can be resuspended prior to administration in a solution that may be provided as part of the kit or separately available. A kit can contain compounds or agents in other forms such as liquids, gels, solids, as described herein. Different compounds and/or agents may be provided in different forms in a single kit.

EXAMPLES

The examples and preparations provided below further illustrate and exemplify the compounds of the present disclosure and methods for testing such compounds. It is to be understood that the scope of the present disclosure is not limited in any way by the scope of the following examples. In the following examples and throughout the specification and claims, molecules with a chiral center, unless otherwise noted, exist as a racemic mixture. Single enantiomers may be obtained by methods known to those skilled in the art and described herein. Compounds were named by using either ChemBioDraw Ultra 13.0 or ChemAxon.

General Procedures

All solvents used were commercially available and were used without further purification. Reactions were typically run using anhydrous solvents under an inert atmosphere of nitrogen.

Analytical Methods $^1$H Nuclear magnetic resonance (NMR) spectroscopy was carried out using one of the following instruments: a Bruker Avance 400 instrument equipped with probe DUAL 400 MHz S1, a Bruker Avance 400 instrument equipped with probe 6 S1 400 MHz 5 mm $^1$H-$^{13}$C ID, a Bruker Avance III 400 instrument with nanobay equipped with probe Broadband BBFO 5 mm direct, a 400 MHz Agilent Direct Drive instrument with ID AUTO-X PFG probe, all operating at 400 MHz, or an Agilent VNMRS500 Direct Drive instrument equipped with a 5 mm Triple Resonance $^1H\{^{13}C/^{15}N\}$ cryoprobe operating at 500 MHz. The spectra were acquired in the stated solvent at around room temperature unless otherwise stated. In all cases, NMR data were consistent with the proposed structures. Characteristic chemical shifts (δ) are given in parts-per-million using conventional abbreviations for designation of major peaks: e.g. s, singlet; d, doublet; t, triplet; q, quartet; dd, doublet of doublets; dt, doublet of triplets; br, broad.

Where thin layer chromatography (TLC) has been used it refers to silica gel TLC using silica gel F254 (Merck) plates, Rf is the distance travelled by the compound divided by the distance travelled by the solvent on a TLC plate. Column chromatography was performed using an automatic flash chromatography (Biotage SP1 or Isolera) system over Biotage silica gel cartridges (KP-Sil or KP-NH) or in the case of reverse phase chromatography over Biotage C18 cartridges (KP-C18).

Liquid Chromatography-Mass Spectrometry Method A:
Total ion current (TIC) and DAD UV chromatographic traces together with MS and UV spectra associated with the peaks were taken on a UPLC/MS Acquity™ system equipped with PDA detector and coupled to a Waters single quadrupole mass spectrometer operating in alternated positive and negative electrospray ionization mode. [LC/MS-ES (+/−): analyses performed using an Acquity UPLC™ CSH, C18 column (50×2.1 mm, 1.7 μm particle size), column temperature 40° C., mobile phase: A-water+0.1% HCOOH/B—CH$_3$CN+0.1% HCOOH, flow rate: 1.0 mL/min, runtime=2.0 min, gradient: t=0 min 3% B, t=1.5 min 99.9% B, t=1.9 min 99.9% B, t=2.0 min 3% B, stop time 2.0 min. Positive ES 100-1000, Negative ES 100-1000, UV detection DAD 210-350 nm.

Liquid Chromatography-Mass Spectrometry Method B:
Total ion current (TIC) and DAD UV chromatographic traces together with MS and UV spectra associated with the peaks were taken on a UPLC/MS Acquity™ system equipped with PDA detector and coupled to a Waters single quadrupole mass spectrometer operating in alternated positive and negative electrospray ionization mode. [LC/MS-ES (+/−): analyses performed using an Acquity UPLC™ BEH, C18 column (50×2.1 mm, 1.7 μm particle size), column temperature 40° C., mobile phase: A-0.1% v/v aqueous ammonia solution pH 10/B—CH$_3$CN, flow rate: 1.0 mL/min, runtime=2.0 min, gradient: t=0 min 3% B, t=1.5 min 99.9% B, t=1.9 min 99.9% B, t=2.0 min 3% B, stop time 2.0 min. Positive ES 100-1000, Negative ES 100-1000, UV detection DAD 210-350 nm.

Liquid Chromatography-Mass Spectrometry Method C:
Total ion current (TIC) and DAD UV chromatographic traces together with MS and UV spectra associated with the peaks were taken on a UPLC/MS Acquity™ system equipped with PDA detector and coupled to a Waters single quadrupole mass spectrometer operating in alternated positive and negative electrospray ionization mode. The column used was a Cortecs UPLC C18, 1.6 μm, 2.1×50 mm. A linear gradient was applied, starting at 95% A (A: 0.1% formic acid in water) and ending at 95% B (B: 0.1% formic acid in MeCN) over 2.0 min with a total run time of 2.5 min. The column temperature was at 40° C. with the flow rate of 0.8 mL/min.

Liquid Chromatography-Mass Spectrometry Method D:
LCMS analyses were performed on a SHIMADZU LCMS consisting of an UFLC 20-AD and LCMS 2020 MS detector. The Diode Array Detector was scanned from 190-400 nm. The mass spectrometer was equipped with an electrospray ion source (ESI) operated in a positive or negative mode. The mass spectrometer was scanned between m/z 90-900 with a scan time from 0.5 to 1.0 s. The column used was a Shim-pack XR-ODS, 2.2 μm, 3.0×50 mm. A linear gradient was applied, starting at 95% A (A: 0.05% TFA in water) and ending at 100% B (B: 0.05% TFA in MeCN) over 2.2 min with a total run time of 2.6 min. The column temperature was at 40° C. with a flow rate of 1.0 mL/min.

Liquid Chromatography-Mass Spectrometry Method E:
LCMS analyses were performed on a SHIMADZU LCMS consisting of an UFLC 20-AD and LCMS 2020 MS detector. The Diode Array Detector was scanned from 190-400 nm. The mass spectrometer was equipped with an electrospray ion source (ESI) operated in a positive or negative mode. The mass spectrometer was scanned between m/z 90-900 with a scan time from 0.5 to 1.0 s. The column used was a Shim-pack XR-ODS, 2.2 μm, 3.0×50 mm. A linear gradient was applied, starting at 95% A (A: 0.05% TFA in water) and ending at 100% B (B: 0.05% TFA in MeCN) over 3.2 min with a total run time of 3.6 min. The column temperature was at 40° C. with a flow rate of 1.0 mL/min.

Liquid Chromatography-Mass Spectrometry Method F:
LCMS analyses were performed on a SHIMADZU LCMS consisting of an UFLC 20-AD and LCMS 2020 MS detector. The Diode Array Detector was scanned from 190-400 nm. The mass spectrometer was equipped with an electrospray ion source (ESI) operated in a positive or negative mode. The mass spectrometer was scanned between m/z 90-900 with a scan time from 0.5 to 1.0 s. The column used was an Ascentis Express C18, 2.7 μm, 3.0×50 mm. A linear gradient was applied, starting at 95% A (A: 0.05% TFA in water) and ending at 100% B (B: 0.05% TFA in MeCN) over 1.8 min with a total run time of 2.0 min. The column temperature was at 45° C. with a flow rate of 1.5 mL/min.

Liquid Chromatography-Mass Spectrometry Method G:
LCMS analyses were performed on a SHIMADZU LCMS consisting of an UFLC 20-AD and LCMS 2020 MS detector. The Diode Array Detector was scanned from 190-400 nm. The mass spectrometer was equipped with an electrospray ion source (ESI) operated in a positive or negative mode. The mass spectrometer was scanned between m/z 90-900 with a scan time from 0.5 to 1.0 s. The column used was a Kinetex EVO, 2.6 μm, 3.0×50 mm. A linear gradient was applied, starting at 90% A (A: 0.05% NH$_4$HCO$_3$ in water) and ending at 95% B (B: MeCN) over 1.7 min with a total run time of 2.0 min. The column temperature was at 40° C. with a flow rate of 1.3 mL/min.

Liquid Chromatography-Mass Spectrometry Method H:
LCMS analyses were performed on a SHIMADZU LCMS consisting of an UFLC 20-AD and LCMS 2020 MS detector. The Diode Array Detector was scanned from 190-400 nm. The mass spectrometer was equipped with an electrospray ion source (ESI) operated in a positive or negative mode. The mass spectrometer was scanned between m/z 90-900 with a scan time from 0.5 to 1.0 s. The column used was a Kinetex EVO, 2.6 μm, 3.0×50 mm. A linear gradient was applied, starting at 90% A (A: 0.05% NH$_4$HCO$_3$ in water) and ending at 95% B (B: MeCN) over 2.7 min with a total run time of 3.0 min. The column temperature was at 40° C. with a flow rate of 1.3 mL/min.

Liquid Chromatography-Mass Spectrometry Method I:
The column used was a Poroshell HPH-C18, 2.7 μm, 3.0×50 mm. A linear gradient was applied, starting at 95% A (A: 0.05% NH$_4$HCO$_3$ in water) and ending at 95% B (B: 0.05%

$NH_4HCO_3$ in MeCN) over 1.8 min with a total run time of 2 min. The column temperature was at 45° C. with the flow rate of 1.5 mL/min.

Liquid Chromatography-Mass Spectrometry Method J:

LCMS analyses were performed on a SHIMADZU LCMS consisting of an UFLC 20-AD and LCMS 2020 MS detector. The Diode Array Detector was scanned from 190-400 nm. The mass spectrometer was equipped with an electrospray ion source (ESI) operated in a positive or negative mode. The mass spectrometer was scanned between m/z 90-900 with a scan time from 0.5 to 1.0 s. The column used was an Ascentis Express C18, 2.7 µm, 2.1×50 mm. A linear gradient was applied, starting at 90% A (A: 0.10% formic acid in water) and ending at 95% B (B: 0.10% formic acid in MeCN) over 2.70 min with a total run time of 3.0 min. The column temperature was at 45° C. with a flow rate of 1.0 mL/min.

Liquid Chromatography-Mass Spectrometry Method K:

The column used was an Agilent Poroshell HPH-C18, 2.7 µm, 3.0×50 mm. A linear gradient was applied, starting at 95% A (A: 0.05% $NH_4HCO_3$ in water) and ending at 95% B (B: 0.05% $NH_4HCO_3$ in MeCN) over 1.8 min with a total run time of 2.0 min. The column temperature was at 40° C. with a flow rate of 1.5 mL/min.

Liquid Chromatography-Mass Spectrometry Method L:

The column used was a Shim-pack XR-ODS, 2.2 µm, 3.0×50 mm. A linear gradient was applied, starting at 95% A (A: 0.05% TFA in water) and ending at 100% B (B: 0.05% TFA in MeCN) over 4.2 min with a total run time of 5.3 min. The column temperature was at 40° C. with a flow rate of 1.0 mL/min.

Liquid Chromatography-Mass Spectrometry Method M:

The column used was an Ascentis Express C18, 2.7 µm, 3.0×50 mm. A linear gradient was applied, starting at 95% A (A: 0.05% TFA in water) and ending at 95% B (B: 0.05% TFA in MeCN) over 4.1 min with a total run time of 5.3 min. The column temperature was at 40° C. with the flow rate of 1.5 mL/min.

Liquid Chromatography-Mass Spectrometry Method N:

The column used for chromatography was an Xtimate C18 2.1×30 mm, (3 Cpm particles). Detection methods were diode array (DAD). MS mode was positive electrospray ionization. MS range was 100-1000. Mobile phase A: 0.037% trifluoroacetic acid in water; Mobile phase B: 0.018% trifluoroacetic acid in HPLC grade acetonitrile. The gradient was 5-100% B over 2.00 min. 5% B at 0.00 min, 5-95% B (0.00-1.00 min) 95-100% B (1.00-1.80 min) 100-5% B (1.80-1.81 min) with a hold at 5% B for 0.19 min. The flow rate was 1.0 mL/min.

Liquid Chromatography-Mass Spectrometry Method O:

The column used for chromatography was an Xtimate C18 2.1×30 mm, (3 Cpm particles). Detection methods were diode array (DAD). MS mode was positive electrospray ionization. MS range was 100-1000. Mobile phase A was 0.037% trifluoroacetic acid in water, and mobile phase B was 0.018% trifluoroacetic acid in HPLC grade acetonitrile. The gradient was 5-100% B over 2.00 min. 5% B at 0.00 min, 5-95% B (0.00-0.90 min) 95-100% B (0.90-1.80 min) 100-5% B (1.80-1.81 min) with a hold at 5% B for 0.19 min. The flow rate was 1.0 mL/min.

Liquid Chromatography-Mass Spectrometry Method P:

The column used for chromatography was an Xbridge Shield RP18 2.1×50 mm, (5 Cpm particles). Detection methods were diode array (DAD). MS mode was positive electrospray ionization. MS range was 100-1000. Mobile phase A was 10 mM ammonium bicarbonate in water, and mobile phase B was HPLC grade acetonitrile. The gradient was 0-60% B over 2.20 min. 0% B at 0.00 min, 0-60% B (0.00-0.70 min) with a hold at 60% B for 0.40 min, 60-0% B (1.10-1.11 min) with a hold at 0% B for 1.09 min. The flow rate was 1.0 mL/min.

High Performance Liquid Chromatography Method Q:

HPLC (The gradient was holding 0% B for 0.40 min, and then 0-30% B over 4.40 min with a hold at 30% B for 0.8 min, 30-0% B over 0.02 min, and then held at 0% for 0.68 min (0.01-5.21 min: 0.8 mL/min flow rate; 5.23-5.90 min: 1.2 ml/min flow rate). Mobile phase A was 0.037% trifluoroacetic acid in water, mobile phase B was 0.018% trifluoroacetic acid in acetonitrile. The column used for chromatography was a 2.0×50 mm Luna-C18(2) column (5 µm particles). Detection methods were diode array (DAD).

Liquid Chromatography-Mass Spectrometry Method R:

The column used for chromatography was an Xbridge Shield RP18 2.1×50 mm, (5 µm particles). Detection methods were diode array (DAD) and evaporative light scattering (ELSD). MS mode was negative electrospray ionization. MS range was 100-1000. Mobile phase A was 10 mM ammonium bicarbonate in water, and mobile phase B was HPLC grade acetonitrile. The gradient was 0-60% B over 2.20 min. 0% B at 0.00 min, 0-60% B (0.00-0.70 min) with a hold at 60% B for 0.40 min, 60-0% B (1.10-1.11 min) with a hold at 0% B for 1.09 min. The flow rate was 1.0 mL/min.

Liquid Chromatography-Mass Spectrometry Method S:

The column used for chromatography was an Xbridge Shield RP18 2.1×50 mm, (5 µm particles). Detection methods were diode array (DAD). MS mode was negative electrospray ionization. MS range was 100-1000. Mobile phase A was 10 mM ammonium bicarbonate in water, and mobile phase B was HPLC grade acetonitrile. The gradient was 0-60% B over 2.20 min. 0% B at 0.00 min, 0-60% B (0.00-0.70 min) with a hold at 60% B for 0.40 min, 60-0% B (1.10-1.11 min) with a hold at 0% B for 1.09 min. The flow rate was 1.0 mL/min.

High Performance Liquid Chromatography Method T:

The gradient was 10-80% B over 4.00 min with a hold at 80% B for 0.9 min, 80-10% B over 0.02 min, and then held at 10% B for 0.58 min (0.01-4.90 min: 0.8 mL/min flow rate; 4.93-5.50 min: 1.2 mL/min flow rate). Mobile phase A was 10 mM ammonium bicarbonate aqueous solution, mobile phase B was HPLC grade acetonitrile. The column used for chromatography was a 2.1×50 mm Xbridge Shield RPC18 column (5 µm particles). Detection methods were diode array (DAD).

Compound Preparation

Where the preparation of starting materials is not described, these are commercially available, known in the literature, or readily obtainable by those skilled in the art using standard procedures. Where it is stated that compounds were prepared analogously to earlier examples or intermediates, it will be appreciated by the skilled person that the reaction time, number of equivalents of reagents and temperature can be modified for each specific reaction and that it may be necessary or desirable to employ different work-up or purification techniques. Where reactions are carried out using microwave irradiation, the microwave used is a Biotage Initiator. The actual power supplied varies during the course of the reaction in order to maintain a constant temperature.

Intermediate 1

3-[(1E)-3-oxoprop-1-en-1-yl]benzonitrile

Four different microwave vials were prepared as follows: Palladium(II) acetate (45 mg, 0.2 mmol) and XPHOS (190 mg, 0.4 mmol) were suspended in anhydrous DMF (5 mL) and the suspension was purged with nitrogen at room temperature for 5 min, until a clear solution formed. Then 3-bromobenzonitrile (364 mg, 2 mmol) was added, followed by Et$_3$N (2.23 mL, 16 mmol) and 3,3-diethoxyprop-1-ene (0.38 mL, 2.50 mmol). The resulting mixture was heated under microwave irradiation at 120° C. for 20 min. After cooling, 1N HCl solution (5 mL) was added and the mixture was stirred at room temperature for 30 minutes. The mixtures from all four vials were pooled together, diluted with EtOAc, and then filtered through celite. The organic phase was washed several times with brine, dried over Na$_2$SO$_4$, filtered, and evaporated under reduced pressure to give an orange solid. The crude product was purified by column chromatography (cyclohexane/EtOAc, 90:10 to 70:30) to afford the title compound (518 mg, 41%) as a yellow solid. $^1$H NMR (400 MHz, DMSO-d$_6$) δ 9.71 (d, J=7.5 Hz, 1H), 8.29 (s, 1H), 8.08 (d, J=8.0 Hz, 1H), 7.93 (td, J=1.4, 7.8 Hz, 1H), 7.76 (d, J=16.1 Hz, 1H), 7.68 (t, J=7.9 Hz, 1H), 7.01 (dd, J=16.1, 7.8 Hz, 1H). LC-MS (Method A): m/z=158.0 [M+H]$^+$, 0.78 min.

Intermediate 2 methyl 2-(chloromethyl)-2-methylbutanoate

Prepared following the conditions described by Zhang-Jie Shi et al (Org. Lett., 2016, 18 (9), pp 2040-2043). To a stirred solution of diisopropylamine (1.68 mL, 12 mmol) in THF (15 mL) was added n-butyllithium (2.5 M solution in hexanes, 4.8 mL, 12 mmol) dropwise at −78° C. The mixture was stirred at 0° C. for 30 min, then cooled again to −78° C. A solution of methyl 2-methylbutyrate (1.32 mL, 10 mmol) in THF (5 mL) was added dropwise at −78° C. and the mixture was stirred at this temperature for 1 h. A solution of chloroiodomethane (0.73 mL, 10 mmol) in THF (10 mL) was added dropwise at −78° C. The resulting mixture was then stirred overnight allowing the temperature to reach room temperature. The mixture was quenched with water at 0° C. and extracted with Et$_2$O (3×25 mL). The combined organic layers were washed with brine, dried over Na$_2$SO$_4$, and evaporated under reduced pressure to afford the title compound (1.15 g, crude) as a brown oil. This material was used in the following step without further purification. $^1$H NMR (400 MHz, CDCl$_3$) δ 3.78-3.73 (m, 4H), 3.57 (d, J=10.8 Hz, 1H), 1.82-1.55 (m, 3H), 1.29 (s, 3H), 0.88 (t, J=7.5 Hz, 3H).

Intermediate 3

2-(chloromethyl)-2-methylbutanoic acid

Prepared following the conditions described by Zhang-Jie Shi et al (Org. Lett., 2016, 18 (9), pp 2040-2043). Concentrated HCl (15 mL) was carefully added at 0° C. to methyl 2-(chloromethyl)-2-methylbutanoate (1.15 g, crude, 7.0 mmol considering as 100% pure). The resulting mixture was stirred at 80° C. The reaction was monitored by $^1$H NMR of a reaction aliquot quenched with water and extracted with CH$_2$Cl$_2$. After 5 h a mixture of starting material, presumed desired compound and other unidentified compounds was observed. The mixture was stirred at 80° C. for an additional 2 h, then left overnight at room temperature. At this point an NMR check showed almost complete reversal to the starting material. The mixture was then heated to 100° C. A check after 5 h showed almost complete conversion to the title compound. Water was added to the hot mixture and this was extracted twice with CH$_2$Cl$_2$. The combined organic phases were washed twice with water, dried over Na$_2$SO$_4$, filtered and evaporated under reduced pressure to afford a ~1.75:1 mixture of title compound and methyl 2-(chloromethyl)-2-methylbutanoate (630 mg) as a brown oil. This mixture was used in the following step without further purification. $^1$H NMR (400 MHz, CDCl$_3$) only signals from title compound reported δ 3.76 (d, J=11.0 Hz, 1H), 3.60 (d, J=11.0 Hz, 1H), 1.86-1.57 (m, 2H), 1.32 (s, 3H), 0.95 (t, J=7.5 Hz, 3H). LC-MS (Method A): m/z=149.0 [M−H]$^-$, 0.81 min.

Intermediate 4

4-chloro-2,2-dimethylbutanoyl chloride 3,3-Dimethyloxolan-2-one (1.0 mL, 8.85 mmol) and thionyl chloride (2.58 mL, 35.4 mmol) were added to zinc chloride (0.12 g, 0.88 mmol) in a microwave reaction tube. The tube was capped and the mixture was heated at 65° C. overnight in a PLS reaction station [CAUTION—pressure build up observed]. The tube was carefully vented with a needle. The tube was re-sealed with a fresh cap and heated at 65 DC for a further 6 hours [CAUTION—pressure build up observed]. The tube was carefully vented with a needle. The mixture was evaporated under reduced pressure at room temperature to remove the majority of the excess thionyl chloride then the dark residue was distilled under reduced pressure in a Kugelrohr apparatus. The major fraction, which distilled at ~150° C. at 80 mbar was collected to afford the title compound of ~90% purity (1.12 g, 75%) as a near colorless liquid. This material was used in the following step without further purification. $^1$H NMR (400 MHz, CDCl$_3$) δ 3.59-3.48 (m, 2H), 2.26-2.18 (m, 2H), 1.38 (s, 6H).

Intermediate 5

4-chloro-2,2-dimethyl-1-(5-phenyl-4,5-dihydro-1H-pyrazol-1-yl)butan-1-one

To a solution of 5-phenyl-4,5-dihydro-1H-pyrazole (423 mg, 2.9 mmol) and DIPEA (1.50 mL, 8.7 mmol) in CH$_2$Cl$_2$ (14 mL) at 0° C., was added a solution of 4-chloro-2,2-dimethylbutanoyl chloride (540 mg, 3.19 mmol) in CH$_2$Cl$_2$ (1 mL). The mixture was stirred at 0° C. for 30 min, then concentrated under reduced pressure. The crude product was purified by column chromatography (cyclohexane/EtOAc, 100:0 to 80:20) to afford the title compound (425 mg, 53%) as a pale orange oil. $^1$H NMR (400 MHz, CDCl$_3$)° 7.38-7.30 (m, 2H), 7.29-7.22 (m, 1H), 7.21-7.13 (m, 2H), 6.98 (t, J=1.6 Hz, 1H), 5.38 (dd, J=11.9, 4.9 Hz, 1H), 3.50-3.39 (m, 2H), 3.34 (ddd, J=18.7, 11.9, 1.8 Hz, 1H), 2.74 (ddd, J=18.7, 4.9, 1.8 Hz, 1H), 2.39-2.27 (m, 2H), 1.35 (s, 6H). LC-MS (Method A): m/z=279.1 [M+H]$^+$, 1.15 min.

Intermediate 6

O1-tert-butyl O3-methyl 2-(chloromethyl)-2-ethyl-propanedioate

O3-tert-butyl O1-methyl propanedioate (7.93 g, 39.2 mmol) was slowly added to a suspension of sodium hydride (2.04 g, 60%, 51.0 mmol) in DMF (100 mL). The reaction mixture was stirred at rt for 30 min then chloro(iodo) methane (9.0 g, 51.0 mmol) was added. The reaction mixture was stirred at rt overnight and then added to 300 mL of ice water. The mixture was extracted with 400 mL of ethyl acetate, washed with water (200 mL×2), brine (150 mL) and concentrated under reduced pressure. The residue was purified by flash chromatography to yield the title compound as a colorless oil (8.7 g, 87%). LCMS (Method C): m/z=251.1, 253.1 [M+H]$^+$.

Intermediate 7

2-(chloromethyl)-2-methoxycarbonyl-butanoic acid

TFA (50 mL) was added to a solution of O1-tert-butyl O3-methyl 2-(chloromethyl)-2-ethyl-propanedioate (8.7 g, 34.7 mmol) in DCM (50 mL). The reaction mixture was stirred at rt for 1 h and was then concentrated to dryness under reduced pressure. The resulting residue was taken up in EtOAc (100 mL) and the solution was washed with water (100 mL) and brine (100 mL). The organics were separated and dried over MgSO$_4$ before concentrating to dryness under reduced pressure to yield the title compound as a brown oil (6.4 g, 94.8% yield). LCMS (Method C): m/z=195.1, 197.1 [M+H]$^+$.

Intermediate 8

Methyl 2-chlorocarbonyl-2-(chloromethyl)butanoate 2-(chloromethyl)-2-methoxycarbonyl-butanoic acid (6.4 g, 32.9 mmol) was dissolved in thionyl chloride (50 mL). The reaction mixture was stirred at 75° C. for 2 h and was then concentrated under reduced pressure to yield the title compound as a light brown oil (6.3 g, 90%). $^1$H-NMR (400 MHz, CDCl$_3$): δ 4.11-3.98 (m, 2H), 3.86-3.85 (m, 3H), 2.25 (qd, J=7.6, 1.0 Hz, 2H), 0.93 (t, J=7.6 Hz, 3H).

Intermediate 9

O1-tert-butyl O3-methyl 2-[difluoro(trimethylsilyl)methyl]-2-ethyl-propanedioate LiHMDS (49.4 mL, 1.0 M, 49.4 mmol) was added to a solution of O1-tert-butyl O3-methyl 2-ethylpropanedioate (10 g, 49.4 mmol) in anhydrous THF (100 mL) at −78° C. under argon. The mixture was stirred at −78° C. for 30 min before methyl lithium (30.9 mL, 1.6 M, 49.4 mmol) was added. The mixture was stirred at −78° C. for 10 min before trimethyl(trifluoromethyl)silane (35.2 g, 247 mmol) was added. The reaction mixture was warmed slowly to rt and stirred overnight at rt. The reaction was quenched by adding water (100 mL) and extracted with ethyl acetate (200 mL×2). The organic layers were combined and washed with water and brine before concentrating under reduced pressure. The resulting residue was purified by flash chromatography (20% ethyl acetate in hexanes) to yield the desired product as a colorless oil (12 g, 75%). LCMS (Method C): m/z=325.3, [M+H]$^+$.

Intermediate 10

O1-tert-butyl O3-methyl 2-(difluoromethyl)-2-ethyl-propanedioate

Potassium carbonate (12.8 g, 92.5 mmol) was added to a solution of O1-tert-butyl O3-methyl 2-[difluoro(trimethylsilyl)methyl]-2-ethyl-propanedioate (10 g, 30.8 mmol) in methanol (100 mL). The reaction mixture was stirred at rt for 1 h before concentrating under reduced pressure. The resulting residue was dissolved in ethyl acetate (250 mL) and washed with water (100 mL×2) and brine (100 mL) before concentrating under reduced pressure. The resulting residue was purified by flash chromatography (0-20% ethyl acetate in hexanes) to yield the title compound as a colorless oil (7.1 g, 28.1 mmol, 91% yield). LCMS (Method C): m/z=253.3 [M+H]$^+$.

Intermediate 11 tert-butyl 2-(difluoromethyl)-2-(hydroxymethyl)butanoate

Lithium tri-tert-butoxylaluminohydride (64 mL, 1.7 M, 70.4 mmol) was added to a solution of O1-tert-butyl O3-methyl 2-(difluoromethyl)-2-ethyl-propanedioate (7.1 g, 28.2 mmol) in THF (100 mL) at rt. The reaction mixture was stirred at 75° C. for 5 h under argon. The reaction mixture was cooled to rt and quenched by adding 100 mL of sat. aq. NH4Cl solution. The mixture was extracted with ethyl acetate (200 mL×2) and the organic layers were combined and washed with water and brine before concentrating under reduced pressure. The resulting residue was purified by flash chromatography to provide the title compound (3.9 g, 61.2%). LCMS (Method C): m/z=225.3 [M+H]$^+$.

Intermediate 12 tert-butyl 2-(chloromethyl)-2-(difluoromethyl)butanoate

Triphenylphosphine (5.47 g, 20.9 mmol) was added to a solution of tert-butyl 2-(difluoromethyl)-2-(hydroxymethyl)butanoate (3.9 g, 17.4 mmol) in carbon tetrachloride (60 mL). The reaction mixture was stirred at 76° C. for 12 h. The reaction mixture was concentrated under reduced pressure. Hexanes (50 mL) was added to the resulting residue and the solid was collected by filtration and washed with 50 mL of hexanes. The filtrate was concentrated under reduced pressure and the resulting residue was purified by flash chromatography (0-25% ethyl acetate in hexanes) to yield the desired product as a colorless oil (3.1 g, 73%). $^1$H-NMR (400 MHz; CDCl$_3$): δ 6.12 (t, J=55.2 Hz, 1H), 3.84-3.75 (m, 2H), 1.87 (dtd, J=21.8, 14.4, 7.4 Hz, 2H), 1.53-1.48 (m, 9H), 1.03-0.99 (m, 3H).

Intermediate 13

2-(chloromethyl)-2-(difluoromethyl)butanoic acid

TFA (30 mL) was added to a solution of tert-butyl 2-(chloromethyl)-2-(difluoromethyl)butanoate (5.5 g, 22.7 mmol) in DCM (30 mL). The reaction mixture was stirred at rt for 1 h and then concentrated under reduced pressure to provide the desired product. $^1$H-NMR (400 MHz; CDCl$_3$): δ 6.19 (t, J=54.8 Hz, 1H), 3.91-3.81 (m, 2H), 2.05-1.91 (m, 2H), 1.09-1.05 (m, 3H).

Intermediate 14

2-(chloromethyl)-2-(difluoromethyl)butanoyl chloride 2-(Chloromethyl)-2-(difluoromethyl)butanoic acid (3.9 g, 20.9 mmol) was dissolved in thionyl chloride (50 mL). The mixture was stirred at 68° C. for 2 h. The reaction mixture was concentrated under reduced pressure to yield the desired product as a light brown oil. ¹H-NMR (400 MHz; CDCl₃): δ 6.25 (t, J=54.4 Hz, 1H), 3.94-3.84 (m, 2H), 2.13-1.97 (m, 2H), 1.13-1.09 (m, 3H).

Intermediate 15

3-(3-fluorophenyl)-6-methyl-2,3,6,7-tetrahydro-1H-pyrazolo[1,2-a]pyrazol-5-one

Sodium cyanoborohydride (0.5 g, 8.3 mmol) was added to a solution of 3-bromo-1-[3-(3-fluorophenyl)-3,4-dihydropyrazol-2-yl]-2-methyl-propan-1-one (1.3 g, 4.2 mmol) in acetic acid (50 mL). The reaction mixture was stirred at 90° C. for 18 h before concentrating to dryness. The crude material was purified by flash chromatography eluting with 0-80% EtOAc in hexanes to provide the title compound. ¹H NMR (400 MHz, CDCl₃): δ 7.33-7.29 (m, 1H), 7.10 (ddt, J=7.6, 1.6, 0.8 Hz, 1H), 7.05-7.02 (m, 1H), 6.98-6.93 (m, 1H), 5.06 (t, J=7.8 Hz, 1H), 3.90 (t, J=8.9 Hz, 1H), 3.41-3.37 (m, 1H), 3.20-3.10 (m, 1H), 2.84 (dddd, J=12.6, 8.6, 6.5, 2.2 Hz, 1H), 2.57-2.44 (m, 2H), 2.31 (ddt, J=12.6, 10.4, 7.0 Hz, 1H), 1.28 (d, J=7.1 Hz, 3H).

Intermediate 16

5-(cyclopropylmethyl)-2,2,5-trimethyl-1,3-dioxane-4,6-dione

Bromomethylcyclopropane (5.7 g, 42.2 mmol) was added to a mixture of 2,2,5-trimethyl-1,3-dioxane-4,6-dione (5.2 g, 32.9 mmol) and potassium carbonate (13.6 g, 99 mmol) in DMF (50 mL). The reaction mixture was stirred at rt overnight then concentrated to dryness. The resulting residue was taken up in EtOAc (200 mL) and washed with 2×100 mL water and 1×150 mL saturated brine solution. The organics were separated and dried over MgSO₄ before concentrating to dryness. The crude product was purified by flash column chromatography eluting with 20% EtOAc in hexanes to provide the title compound. ¹H-NMR (400 MHz; CDCl₃): δ 2.02 (d, J=7.2 Hz, 2H), 1.78 (m, 6H), 1.62 (s, 3H), 0.71-0.64 (m, 1H), 0.51-0.46 (m, 2H), 0.22-0.18 (m, 2H).

Intermediate 17

2-(cyclopropylmethyl)-3-methoxy-2-methyl-3-oxo-propanoic acid

Sodium methoxide (1.08 g, 30% in methanol, 6.0 mmol) was added to a solution of 5-(cyclopropylmethyl)-2,2,5-trimethyl-1,3-dioxane-4,6-dione in methanol (30 mL). The reaction mixture was stirred at rt for 1 h then concentrated to dryness. The resulting residue was taken up in EtOAc (100 mL) and washed with 2×100 mL water and 1×150 mL saturated brine solution. The organics were separated and dried over MgSO₄ before concentrating to dryness. The crude product was purified by flash column chromatography eluting with 50% EtOAc in hexanes to provide the title compound as a colorless oil (340 mg, 91%). LCMS (Method C): m/z=187.1 [M+H]⁺.

Intermediate 18

2-(cyclopropylmethyl)-3-hydroxy-2-methyl-propanoic acid

To a solution of 2-(cyclopropylmethyl)-3-methoxy-2-methyl-3-oxo-propanoic acid (343 mg, 1.84 mmol) in THF (10 mL) and Methanol (1 mL) was added Lithium Borohydride (160 mg, 7.4 mmol) in 5 portions. The reaction mixture was stirred at rt for 1 h before quenching by adding water (100 mL). The mixture was extracted with EtOAc (100 mL×3). The organics were combined and washed with saturated brine solution (100 mL) and dried (MgSO₄) before concentration to dryness. The crude product was purified by flash column chromatography eluting with 50% EtOAc in hexanes to provide the title compound as a colorless oil (145 mg, 50%). LCMS (Method C): m/z=159.1 [M+H]⁺.

Intermediate 19

2-(chloromethyl)-3-cyclopropyl-2-methyl-propanoyl chloride

A solution of 2-(cyclopropylmethyl)-3-hydroxy-2-methyl-propanoic acid (159 mg, 1 mmol) in thionyl chloride (3 mL) was heated at 80° C. for 2 h. The reaction mixture was concentrated in vacuo and used directly in the next step without purification. LCMS (Method C): m/z=177.1, 179.1 [M+H]⁺ (corresponds to the carboxylate formed upon hydrolysis).

Intermediate 20

6-(cyclopropylmethyl)-3-(3-fluorophenyl)-2,3,6,7-tetrahydro-1H-pyrazolo[1,2-a]pyrazol-5-one To a solution of 3-(3-fluorophenyl)-2,3,6,7-tetrahydro-1H-pyrazolo[1,2-a]pyrazol-5-one (100 mg, 0.43 mmol) in THF (4.0 mL) and DMPU (55 µL) at −78° C. was added KHMDS (0.5M/PhMe, 0.94 mL, 0.47 mmol) and the resulting yellow solution was stirred at −78° C. for 30 min. Bromomethylcyclopropane (86 mg, 0.64 mmol) was added, and the reaction mixture was allowed to warm to rt and was stirred overnight. The reaction mixture was diluted with NH₄Cl solution (15 mL) and EtOAc (15 mL). The layers were separated and the aqueous layer was extracted with EtOAc (3×15 mL). The combined organic layers were dried over MgSO₄, filtered, and concentrated under reduced pressure. The crude reaction mixture was purified employing silica gel chromatography (0-80% EtOAc/hexanes) to provide the title compound as a mixture of diastereomers.

Intermediates 21 and 22

1-tert-butyl 3-methyl 2-(difluoro(trimethylsilyl)methyl)-2-methylmalonate and 1-tert-butyl 3-methyl 2-(difluoromethyl)-2-methylmalonate To a solution of 1-tert-butyl 3-methyl 2-methylmalonate (20 g, 106.26 mmol) in THF (200 mL) was added LiHMDS (1 M in THF, 106.26 mL) at −78° C. under N₂. The mixture was stirred at −78° C. for 30 min, then MeLi (1 M in THF, 106.26 mL) was added. The mixture was stirred for 10 min then TMSCF₃ (75.55 g, 531.29 mmol) was added. The reaction mixture was stirred for 16 h while slowly warming to 20° C. The mixture was quenched slowly with sat. aqueous NH₄Cl (200 mL). The organic phase was separated and the aqueous phase was extracted with MTBE (2×100 mL). The combined organic phase was washed with brine (100 mL), dried with anhydrous Na₂SO₄, filtered and concentrated under reduced pressure to provide the title compounds (40 g, crude) as a colorless liquid.

Intermediates 23 and 24

1-tert-butyl 3-methyl 2-(1,1-difluoroethyl)-2-methylmalonate and 1-tert-butyl 3-methyl 2-(difluoromethyl)-2-methylmalonate KF (8.98 g, 154.63 mmol) was vacuum dried and added to a mixture of 1-tert-butyl 3-methyl 2-(difluoro(trimethylsilyl)methyl)-2-methylmalonate, 1-tert-butyl 3-methyl 2-(difluoromethyl)-2-methylmalonate (16 g, 51.54 mmol) and CH$_3$I (21.95 g, 154.63 mmol, 9.63 mL) in DMF (150 mL) at 20° C. under N$_2$. The mixture was heated at 80° C. and stirred for 6 h. The mixture was filtered and the filter cake was washed with MTBE (50 mL). The filtrate was poured into water (500 mL) and extracted with MTBE (3×150 mL). The combined organic phase was washed with brine (100 mL), dried over anhydrous Na$_2$SO$_4$, filtered and concentrated under reduced pressure. The residue was purified by silica gel column chromatography (PE:MTBE=1:0 to 6:1) to give a mixture of the title compounds (11.2 g, 86%) as a colorless liquid.

Intermediates 25 and 26 tert-butyl 3,3-difluoro-2-(hydroxymethyl)-2-methylbutanoate and tert-butyl 3,3-difluoro-2-(hydroxymethyl)-2-methylpropanoate To a mixture of 1-tert-butyl 3-methyl 2-(1,1-difluoroethyl)-2-methylmalonate and 1-tert-butyl 3-methyl 2-(difluoromethyl)-2-methylmalonate (11.2 g, 44.4 mmol) in THF (110 mL) was added LiAlH(Ot-Bu)$_3$ (1 M in THF, 111 mL) at 20° C. under N$_2$. The mixture was then heated to 80° C. and stirred for 16 h. The mixture was cooled to 20° C. and quenched with sat. NH$_4$Cl (300 mL). The mixture was filtered and the filter cake was washed with EtOAc (3×70 mL). The combined organic phase was washed with brine (100 mL), dried over anhydrous Na$_2$SO$_4$, filtered and concentrated under reduced pressure. The residue was purified by silica gel column chromatography (PE:EtOAc=1:0 to 6:1) to give a mixture of the title compounds (8.2 g, 82%) as a colorless oil.

Intermediates 27 and 28 tert-butyl 2-(chloromethyl)-3,3-difluoro-2-methylbutanoate and tert-butyl 2-(chloromethyl)-3,3-difluoro-2-methyl-propanoate To a mixture of tert-butyl 3,3-difluoro-2-(hydroxymethyl)-2-methylbutanoate and tert-butyl 3,3-difluoro-2-(hydroxymethyl)-2-methylpropanoate (7 g, 31.22 mmol) in CCl$_4$ (70 mL) was added PPh$_3$ (16.37 g, 62.43 mmol) at 20° C. under N$_2$. The mixture was then heated to 80° C. and stirred for 6 h. The mixture was cooled to 25° C., added to hexane (100 mL) and stirred for 5 min. The mixture was filtered and concentrated under reduced pressure to give a mixture of the title compounds (7.2 g crude) as a colorless oil. The residue was used in the next step directly.

Intermediates 29 and 30

2-(chloromethyl)-3,3-difluoro-2-methyl-butanoic acid and 2-(chloromethyl)-3,3-difluoro-2-methyl-propanoic Acid To a mixture of tert-butyl 2-(chloromethyl)-3,3-difluoro-2-methyl-butanoate and tert-butyl 2-(chloromethyl)-3,3-difluoro-2-methyl-propanoate (7.2 g, 29.67 mmol) in DCM (70 mL) was added TFA (30 mL) at 25° C. under N$_2$. The mixture was stirred at 25° C. for 2 h. The mixture was concentrated under reduced pressure. The resulting residue was added to water (60 mL) and adjusted to pH 9-10. The aqueous phase was extracted with EtOAc (20 mL). The organic phase was separated and the aqueous phase was adjusted to pH 2-3 by the addition of HCl (2 N) and extracted with EtOAc (3×20 mL). The combined organic phase was washed with brine (10 mL), dried over anhydrous Na$_2$SO$_4$, filtered and concentrated under reduced pressure to give a mixture of the title compounds (4 g, 72%) as a colorless oil, which was used in the next step directly.

Intermediates 31 and 32

2-(chloromethyl)-3,3-difluoro-2-methyl-butanoyl chloride and 2-(chloromethyl)-3,3-difluoro-2-methyl-propanoyl Chloride A mixture of 2-(chloromethyl)-3,3-difluoro-2-methyl-butanoic acid and 2-(chloromethyl)-3,3-difluoro-2-methyl-propanoic acid (1 g, 5.36 mmol) in thionyl chloride (10 mL) was heated to 70° C. and stirred for 2 h. The mixture was cooled to 25° C. and concentrated under reduced pressure to give a mixture of the title compounds (0.9 g, 81%) as a light yellow oil, which was used in the next step directly.

Intermediate 33

1-tert-butyl 3-methyl 2-(2,2,2-trifluoroethyl)propanedioate

To a solution of 3-tert-butyl 1-methyl propanedioate (50 g, 287.04 mmol, 48.54 mL) in DMF (250 mL) was added NaH (14.92 g, 373.15 mmol, 60% in mineral oil) at 0° C. under N$_2$. The mixture was stirred at 0° C. for 30 min before 1,1,1-trifluoro-2-iodo-ethane (78.34 g, 373.15 mmol, 36.61 mL) was added at 0° C. The reaction mixture was heated at 50° C. for 12 h. The mixture was poured into ice-water (750 mL) and extracted with EtOAc (3×200 mL). The combined organic phase was washed with brine (150 mL), dried over Na$_2$SO$_4$, filtered and concentrated under reduced pressure. The residue was purified by silica gel column chromatography (PE:EtOAc=10:1 to 1:1) to give the title compound (19.2 g, 26%) as a yellow oil.

Intermediate 34

1-tert-butyl3-methyl2-[difluoro(trimethylsilyl)methyl]-2-(2,2,2-trifluoroethyl)propanedioate To a solution of 1-tert-butyl 3-methyl 2-(2,2,2-trifluoroethyl)propanedioate (10 g, 39.03 mmol) in THF (100 mL) was added LiHMDS (39.03 mL, 1M in THF) at −78° C. under N$_2$. The reaction mixture was stirred at −78° C. for 30 min, and then MeLi (39.03 mL, 1M) was added dropwise at −78° C. under N$_2$. The mixture was stirred at −78° C. for 30 min and TMSCF$_3$ (27.75 g, 195.15 mmol) was added at −78° C. under N$_2$, then the reaction solution was stirred at 25° C. for 12 h. The mixture was poured into water (100 mL), extracted with EtOAc (3×50 mL). The combined organic phase was washed with brine (50 mL), dried over anhydrous Na$_2$SO$_4$, filtered and concentrated under reduced pressure to give the title compound (9.5 g, 64%) as a yellow oil.

Intermediate 35

1-tert-butyl 3-methyl 2-(difluoromethyl)-2-(2,2,2-trifluoroethyl)propanedioate To a mixture of 1-tert-butyl 3-methyl 2-[difluoro(trimethylsilyl)methyl]-2-(2,2,2-trifluoroethyl)propanedioate (9.5 g, 25.11 mmol) in DMF (100 mL) was added KF (4.38 g, 75.32 mmol, 1.76 mL) at 25° C. The mixture was heated to 80° C. and stirred for 2 h. The mixture was poured into water (300 mL) and extracted with EtOAc (3×100 mL). The combined organic phase was washed with brine (50 mL), dried over anhydrous $Na_2SO_4$, filtered and concentrated under reduced pressure. The residue was purified by silica gel column chromatography (PE:EtOAc=20:1 to 5:1) to provide the title compound (5.3 g, 69%) as a yellow oil.

Intermediate 36 tert-butyl 2-(difluoromethyl)-4,4,4-trifluoro-2-(hydroxymethyl)butanoate

To a solution of 1-tert-butyl 3-methyl 2-(difluoromethyl)-2-(2,2,2-trifluoroethyl)propanedioate (4.1 g, 13.39 mmol) in THF (40 mL) was added LiAlH(Ot-Bu)$_3$ (33.47 mL, 1M) at 25° C. The reaction mixture was stirred at 80° C. for 5 h. The residue was poured into sat. aq. $NH_4Cl$ (50 mL) at 0° C., stirred for 5 min and extracted with EtOAc (3×50 mL). The combined organic phase was washed with brine (50 mL), dried over anhydrous $Na_2SO_4$, filtered and concentrated under reduced pressure. The residue was purified by silica gel column chromatography (PE:EtOAc=100:1 to 4:1) to provide the title compound (1.44 g, 39%) as a yellow oil.

Intermediate 37 tert-butyl 2-(chloromethyl)-2-(difluoromethyl)-4,4,4-trifluoro-butanoate

To a solution of tert-butyl 2-(difluoromethyl)-4,4,4-trifluoro-2-(hydroxymethyl)butanoate (1.4 g, 5.03 mmol) in $CCl_4$ (15 mL) was added $PPh_3$ (1.58 g, 6.04 mmol) and the solution was stirred at 80° C. for 12 h. The reaction mixture was concentrated under reduced pressure. The resulting residue was diluted with MTBE (10 mL), filtered and concentrated under reduced pressure to give the title compound (1.1 g, 74%) as a yellow oil.

Intermediate 38

2-(chloromethyl)-2-(difluoromethyl)-4,4,4-trifluoro-butanoic acid

To a solution of tert-butyl 2-(chloromethyl)-2-(difluoromethyl)-4,4,4-trifluoro-butanoate (1.1 g, 3.71 mmol) in DCM (12 mL) was added TFA (11 mL) at 0° C. and the mixture was stirred at 25° C. for 1 h. The reaction mixture was concentrated under reduced pressure to remove TFA. The residue was adjusted to pH=7-8 by the addition of sat. aq. $NaHCO_3$ and extracted with EtOAc (3×10 mL). The combined organic phase was washed with brine (10 mL), dried over anhydrous $Na_2SO_4$, filtered and concentrated under reduced pressure to provide the title compound (0.85 g, 95%) as a yellow oil.

Intermediate 39

2-(chloromethyl)-2-(difluoromethyl)-4,4,4-trifluoro-butanoyl chloride

A solution of 2-(chloromethyl)-2-(difluoromethyl)-4,4,4-trifluoro-butanoic acid (0.65 g, 2.70 mmol) in $SOCl_2$ (13 mL) was stirred at 68° C. for 1 h. The reaction mixture was concentrated under reduced pressure to give the title compound (520 mg, 74%) as a yellow oil.

Intermediate 40

1-tert-butyl 3-methyl 2-(cyclopropylmethyl)malonate

To a solution of NaH (6.89 g, 172.22 mmol, 60% in mineral oil) in DMF (150 mL) was added tert-butyl methyl malonate (30 g, 172.22 mmol, 29.13 mL) and the reaction mixture was stirred at 25° C. for 2 h. Bromomethylcyclopropane (27.9 g, 206.67 mmol, 19.79 mL) was added dropwise slowly and stirred for 16 h. The reaction mixture was quenched by the addition of aq. $NH_4Cl$ (300 mL) at 0° C., extracted with EtOAc (3×300 mL), washed with brine (3×300 mL), dried over anhydrous $Na_2SO_4$, filtered and concentrated under reduced pressure. The residue was purified by silica gel column chromatography (PE:MTBE=100:1 to 4:1) to provide the title compound (29.5 g, 75%) as a white oil.

Intermediate 41

1-tert-butyl 3-methyl 2-(cyclopropylmethyl)-2-[difluoro (trimethylsilyl) methyl] propaedioate To a solution of 1-tert-butyl 3-methyl 2-(cyclopropylmethyl)propanedioate (20 g, 87.61 mmol) in THF (200 mL) was added LiHMDS (87.61 mL, 1 M) at −78° C. The reaction mixture was stirred at −78° C. for 1 h. MeLi (87.61 mL, 1 M) was added at −78° C. and stirred for 10 min and then TMSCF$_3$ (62.29 g, 438.05 mmol, 64.75 mL) was added. The reaction mixture was warmed slowly to 25° C. and stirred for 18 h. The reaction mixture was quenched by the addition of sat. aq. $NH_4Cl$ (200 mL) at 0° C., and then extracted with EtOAc (3×200 mL). The combined organic layers were washed with brine (200 mL), dried over $Na_2SO_4$, filtered and concentrated under reduced pressure. The resulting residue was purified by silica gel column chromatography (PE:MTBE=100:1 to 4:1) to give the title compound (27.3 g, 89%) as a light yellow liquid.

Intermediate 42

1-tert-butyl 3-methyl 2-(cyclopropylmethyl)-2-(difluoromethyl) propanedioate To a solution of 1-tert-butyl 3-methyl 2-(cyclopropylmethyl)-2-[difluoro(trimethylsilyl) methyl]propanedioate (27 g, 77.04 mmol) in DMF (270 mL) was added KF (13.43 g, 231.12 mmol, 5.41 mL) at 25° C. The reaction mixture was heated at 80° C. and stirred for 2 h under $N_2$ atmosphere. The reaction mixture was cooled to 25° C. then quenched by the addition of water (300 mL) and extracted with EtOAc (3×300 mL). The combined organic phase was washed with water (150 mL) and brine (300 mL), dried over anhydrous Na$_2$SO$_4$, filtered and concentrated under reduced pressure to provide the title compound (21 g, 98%) as a yellow oil.

Intermediate 43

2-tert-butoxycarbonyl-2-(cyclopropylmethyl)-3,3-difluoro-propanoic acid

To a solution of 1-tert-butyl 3-methyl 2-(cyclopropylmethyl)-2-(difluoromethyl) propanedioate (21 g, 75.46 mmol) in THF (200 mL) was added LiAlH(Ot—Bu)$_3$ (188.65 mL, 1 M) at 25° C. The reaction mixture was stirred at 84° C. for 5 h before quenching by the addition of sat. aq. NH$_4$Cl (200 mL). The mixture was extracted with EtOAc (3×200 mL), washed with brine (200 mL), dried over anhydrous Na$_2$SO$_4$, filtered and concentrated under reduced pressure. The resulting residue was purified by silica gel column chromatography (PE:EtOAc=100:1 to 4:1) to provide the title compound (8.8 g, 44%) as a yellow oil.

Intermediate 44 tert-butyl 2-(chloromethyl)-2-(cyclopropylmethyl)-3,3-difluoro-propanoate

To a solution of tert-butyl 2-(cyclopropylmethyl)-3,3-difluoro-2-(hydroxymethyl)propanoate (8.8 g, 35.16 mmol) in CCl$_4$ (100 mL) was added PPh$_3$ (11.07 g, 42.19 mmol) and the solution was stirred at 80° C. for 12 h. Hexane (100 mL) was added and the mixture was filtered and the cake was washed with 100 mL of hexane. The filtrate was concentrated to give the title compound (8.7 g, 92%) as a yellow oil.

Intermediate 45

2-(chloromethyl)-2-(cyclopropylmethyl)-3,3-difluoro-propanoic acid

To a solution of tert-butyl 2-(chloromethyl)-2-(cyclopropylmethyl)-3,3-difluoro-propanoate (3 g, 11.16 mmol) in DCM (30 mL) was added TFA (30 mL, 405.19 mmol). The reaction mixture was stirred at 25° C. for 1 h. The solution was concentrated under reduced pressure to provide the title compound (2.3 g, 97%) as a yellow oil.

Intermediate 46

2-(chloromethyl)-2-(cyclopropylmethyl)-3,3-difluoro-propanoyl chloride

A solution of 2-(chloromethyl)-2-(cyclopropylmethyl)-3,3-difluoro-propanoic acid (1.2 g, 5.64 mmol) in SOCl$_2$ (20 mL) was stirred at 70° C. for 2 h. The solution was concentrated under reduced pressure to provide the title compound (1.2 g, 92%) as a yellow oil, which was used in the next step directly.

Intermediate 47

1-tert-butyl 3-methyl 2-allylmalonate

To a mixture of NaH (12.63 g, 315.74 mmol, 60% in mineral oil) in THF (500 mL) was added a solution of tert-butyl methyl malonate (50 g, 287.04 mmol) in THF (500 mL) dropwise at 0° C. under N$_2$. The mixture was warmed to 25° C. and stirred for 1 h. Then a solution of 3-bromoprop-1-ene (38.2 g, 315.74 mmol) in THF (500 mL) was added in one portion at 25° C. under N$_2$. The reaction mixture was stirred for 16 h at 25° C. The mixture was quenched by the addition of sat. NH$_4$Cl solution (200 mL), diluted with water (200 mL) and extracted with EtOAc (3×200 mL). The combined organics were washed with brine (500 mL), dried over anhydrous Na$_2$SO$_4$, filtered and concentrated under vacuum. The residue was purified by silica gel column chromatography (PE:EtOAc=100 to 20:1) to yield the title compound (20 g, 32%) as a colorless oil.

Intermediate 48

1-tert-butyl 3-methyl 2-allyl-2-(difluoro(trimethylsilyl)methyl)malonate

To a solution of 1-tert-butyl 3-methyl 2-allylmalonate (19 g, 88.68 mmol) in THF (200 mL) was added LiHMDS (1 M, 88.68 mL, 88.68 mmol) dropwise at −78° C. under N$_2$. The reaction mixture was stirred for 0.5 h and then MeLi (1 M, 88.68 mL, 88.68 mmol) was added dropwise at −78° C. under N$_2$. The reaction mixture was stirred for 15 min before TMSCF$_3$ (63.05 g, 443.39 mmol) was added dropwise at −78° C. The mixture was warmed to 25° C. and stirred for 16 h under N$_2$. The mixture was quenched by the addition of sat. NH$_4$Cl solution (100 mL) and extracted with EtOAc (2×50 mL). The combined organics were washed with brine (100 mL), dried over anhydrous Na$_2$SO$_4$, filtered and concentrated under vacuum to provide the title compound (39 g, 78%) as a brown oil.

Intermediate 49

1-tert-butyl 3-methyl 2-allyl-2-(difluoromethyl)malonate

To a solution of 1-tert-butyl 3-methyl 2-allyl-2-(difluoro(trimethylsilyl)methyl)malonate (39 g, 69.55 mmol) in THF (400 mL) was added TBAF (1 M/THF, 139.10 mL, 139.10 mmol) in one portion at 25° C. The reaction mixture was stirred for 1 h at 70° C. under N$_2$. The mixture was concentrated under vacuum and the resulting residue was purified by silica gel column chromatography (PE:EtOAc=50:1) to give the title compound (15.7 g, 85%) as a colorless oil.

Intermediate 50 tert-butyl 2-(difluoromethyl)-2-(hydroxymethyl)pent-4-enoate

To a solution of 1-tert-butyl 3-methyl 2-allyl-2-(difluoromethyl)malonate (15.7 g, 59.41 mmol) in THF (200 mL) was added LiAlH(Ot—Bu)$_3$ (1 M, 297.05 mL, 297.05 mmol) in one portion at 25° C. The reaction mixture was heated to 80° C. and stirred for 16 h. The reaction was quenched by the addition of sat. NH$_4$Cl (100 mL) and filtered through a pad of celite. The filtrate was extracted with EtOAc (2×100 mL). The combined organics were washed with brine (200 mL), dried over anhydrous Na$_2$SO$_4$, filtered and concentrated under reduced pressure to provide the title compound (14.3 g, 97%) as a light yellow oil.

Intermediate 51 tert-butyl 2-(chloromethyl)-2-(difluoromethyl)pent-4-enoate

To a solution of tert-butyl 2-(difluoromethyl)-2-(hydroxymethyl)pent-4-enoate (14.3 g, 60.53 mmol) in CCl$_4$ (200 mL) was added triphenylphosphine (39.69 g, 151.32 mmol) in one portion at 25° C. The reaction mixture was heated at 80° C. for 2 h. The mixture was concentrated under vacuum and the resulting residue was purified by silica gel column chromatography (PE:EtOAc=50:1) to yield the title compound (12.1 g, 78%) as a yellow oil.

Intermediate 52

2-(chloromethyl)-2-(difluoromethyl)pent-4-enoic acid

To a solution of tert-butyl 2-(chloromethyl)-2-(difluoromethyl)pent-4-enoate (12.1 g, 47.51 mmol) in anhydrous DCM (200 mL) was added TFA (162.51 g, 1.43 mol) in one portion at 25° C. The reaction mixture was stirred for 16 h at rt. The reaction mixture was diluted with water (50 mL) and concentrated under vacuum to remove TFA. The pH was adjusted to 8 by the addition of saturated aqueous $Na_2CO_3$ and washed with EtOAc (3×50 mL). The aqueous layer was adjusted to pH=3 by the addition of HCl (2 N) and extracted with EtOAc (3×50 mL). The combined organics were washed with brine (100 mL), dried over anhydrous $Na_2SO_4$, filtered and concentrated under vacuum to provide the title compound (9.4 g, 99%) as a light pink oil.

Intermediate 53

2-(chloromethyl)-2-(difluoromethyl)pent-4-enoyl chloride

A solution of 2-(chloromethyl)-2-(difluoromethyl)pent-4-enoic acid (1 g, 5.04 mmol) in $SOCl_2$ (10 mL) was stirred at 70° C. for 2 h. The reaction mixture was concentrated under vacuum to give the title compound (1.06 g, 97%) as a light yellow oil.

Preparation 1

(E)-3-(5-fluoro-3-pyridyl)prop-2-enal

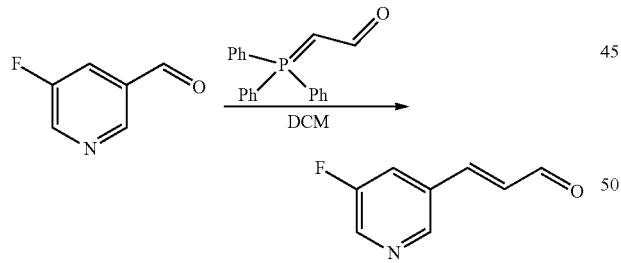

A solution of 5-fluoropyridine-3-carbaldehyde (10 g, 79.94 mmol) and (triphenylphosphoranylidene)acetaldehyde (24.33 g, 79.94 mmol) in DCM (200 mL) was stirred at rt overnight. The reaction mixture was treated with silica, evaporated under reduced pressure and purified by column chromatography eluting with a gradient of ethyl acetate (0 to 100%) in hexanes to provide a light yellow solid. $^1$H-NMR (400 MHz, $CDCl_3$): δ 9.78 (d, J=7.4 Hz, 1H), 8.64 (t, J=1.6 Hz, 1H), 8.56 (d, J=2.7 Hz, 1H), 7.62 (dddd, J=8.9, 2.7, 1.8, 0.5 Hz, 1H), 7.54-7.49 (m, 1H), 6.79 (dd, J=16.1, 7.4 Hz, 1H).

The following intermediates were prepared using methods analogous to the one described above.

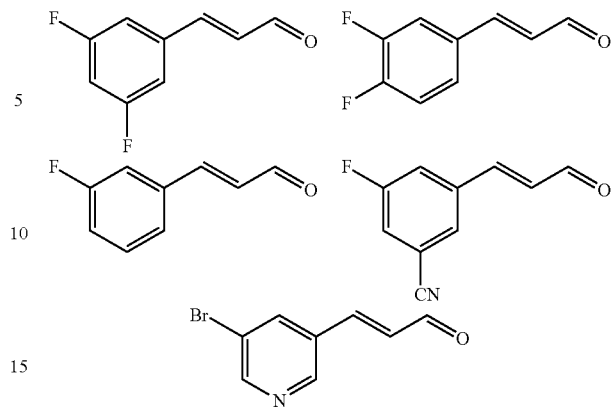

Preparation 2

5-Phenyl-4,5-dihydro-1H-pyrazole

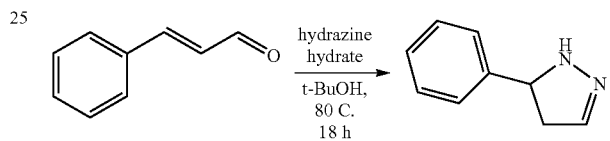

Hydrazine hydrate (65%, 2 mL) was added to a solution of (2E)-3-phenylprop-2-enal (1.0 g, 7.6 mmol) in t-BuOH (12 mL). The resulting mixture was stirred at 80° C. for 18 h then the reaction mixture was concentrated under reduced pressure. The crude product was purified by reverse phase column chromatography (water/MeCN, 100:0 to 50:50) to afford the title compound (396 mg, 36%) as a colorless oil. $^1$H NMR (400 MHz, $CDCl_3$) δ 7.43-7.23 (m, 5H), 6.87-6.82 (m, 1H), 4.75 (dd, J=10.7, 8.7 Hz, 1H), 3.16 (ddd, J=17.1, 10.8, 1.5 Hz, 1H), 2.74 (ddd, J=17.2, 8.7, 1.8 Hz, 1H). LC-MS (Method A): m/z=147.1 [M+H]$^+$, 0.57 min.

The following intermediates were prepared using methods analogous to the one described above.

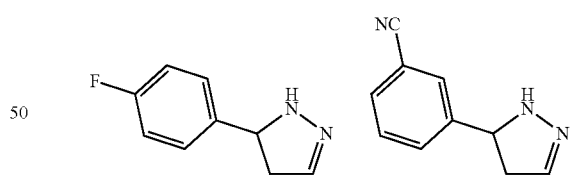

Preparation 3

5-(3-fluorophenyl)-4,5-dihydro-1H-pyrazole

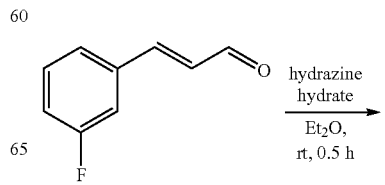

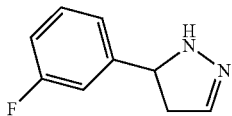

To a vigorously stirring mixture of (2E)-3-(3-fluorophenyl)prop-2-enal (20 g, 0.133 mol) in ether (500 mL) was added hydrazine hydrate (80%, 66 g, 1.33 mol) dropwise. The resulting mixture was stirred at room temperature for 0.5 hour and concentrated under vacuum. The residue was diluted with water (500 mL) and extracted with ethyl acetate (3×500 mL). The combined organic layers were washed with brine, dried over anhydrous sodium sulfate, and filtered. The filtrate was concentrated under vacuum to afford the title compound (15 g crude) as a yellow oil. $^1$H NMR (400 MHz, DMSO-d$_6$) δ 7.37 (td, J=7.9, 6.3 Hz, 1H) 7.26 (d, J=3.5 Hz, 1H) 7.20-7.10 (m, 2H) 7.03-7.10 (m, 1H) 6.72 (s, 1H) 4.62 (td, J=10.7, 3.8 Hz, 1H) 3.06 (ddd, J=16.9, 10.7, 1.8 Hz, 1H) 2.50-2.41 (m, 1H). LC-MS (Method A): m/z=165.0 [M+H]$^+$, 0.68 min.

The following intermediates were prepared using methods analogous to the one described above.

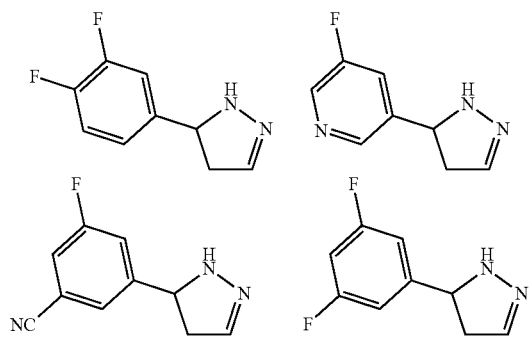

Preparation 4 di-tert-butyl 3-(5-fluoro-3-pyridyl)-5-hydroxy-pyrazolidine-1,2-dicarboxylate

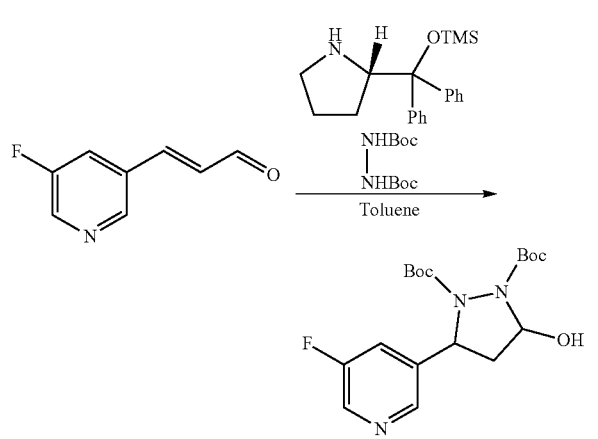

To a solution of (E)-3-(5-fluoro-3-pyridyl)prop-2-enal (5.9 g, 39.04 mmol) in toluene (50 mL) was added (S)-(−)-α,α-Diphenyl-2-pyrrolidinemethanol trimethylsilyl ether (2.92 g, 8.98 mmol) followed by tert-butyl N-(tert-butoxycarbonylamino)carbamate (13.6 g, 58.56 mmol). Toluene (23 mL) was used to wash the reactants off the reaction flask wall and added to the reaction mixture. The reaction vessel was sealed and stirred at rt overnight. The reaction mixture was loaded directly onto silica gel and purified by flash chromatography (0-100% ethyl acetate in hexanes) to yield the desired product as a yellow solid (9.6 g). LCMS (Method B): m/z=384.3 [M+H]$^+$.

The following intermediates were prepared using methods analogous to the one described above.

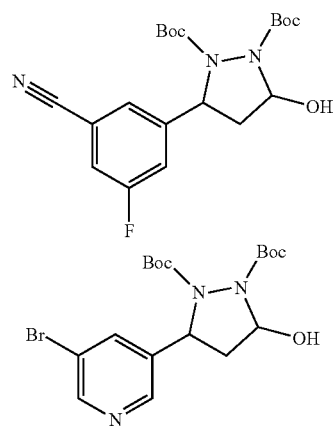

Preparation 5

3-(4,5-dihydro-1H-pyrazol-5-yl)-5-fluoro-pyridine

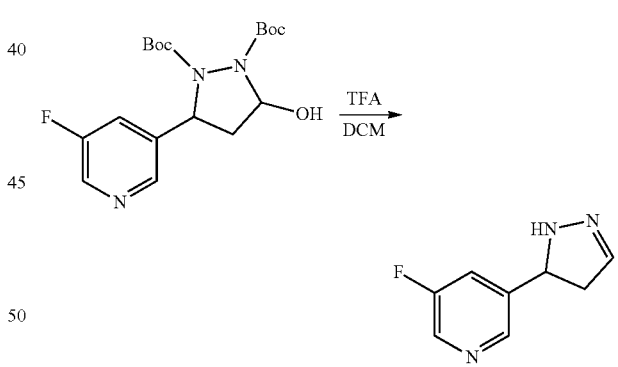

To a solution of di-tert-butyl 3-(5-fluoro-3-pyridyl)-5-hydroxy-pyrazolidine-1,2-dicarboxylate (2.0 g, 5.22 mmol) in DCM (20 mL) was added 2,2,2-trifluoroacetic acid (20 mL). The reaction mixture was stirred at rt for 1 h and was then concentrated under reduced pressure. The resulting residue was dissolved in ethyl acetate (50 mL) and washed with 5% NaHCO$_3$ (20 mL), water (20 mL) and brine (20 mL). The organic layer was collected and dried over MgSO$_4$ before concentrating under reduced pressure to yield the crude product (0.75 g, 4.5 mmol), which was used in the next step without purification. LCMS (Method B): m/z=166.1 [M+H]$^+$.

The following intermediates were prepared using methods analogous to the one described above.

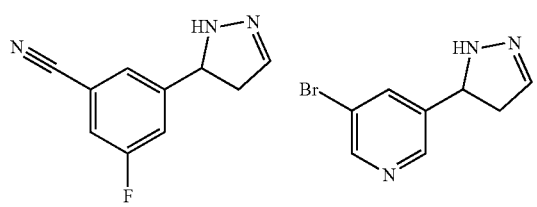

Preparation 6

Preparation of 3-[1-(3-chloro-2,2-dimethylpropanoyl)-4,5-dihydro-1H-pyrazol-5-yl]-5-fluorobenzonitrile

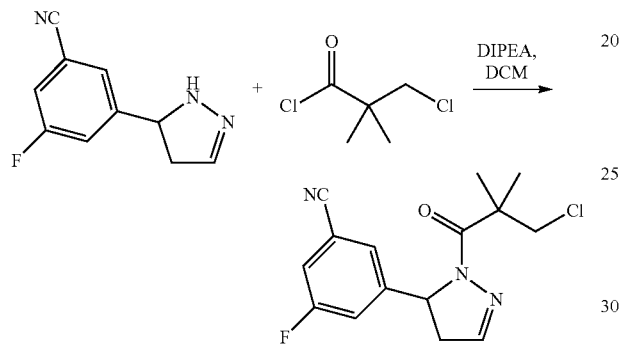

DIPEA (0.39 mL, 2.25 mmol) and 3-chloro-2,2-dimethylpropanoyl chloride (0.16 mL, 1.17 mmol) were added at 0° C. to a solution of 3-(4,5-dihydro-1H-pyrazol-5-yl)-5-fluorobenzonitrile (170 mg, 0.90 mmol) in anhydrous CH$_2$Cl$_2$ (6 mL). The mixture was stirred at room temperature for 1 h then washed with sat. NH$_4$Cl solution, sat. NaHCO$_3$ solution and water. The organic phase was dried over Na$_2$SO$_4$, filtered and concentrated under reduced pressure. The crude product was purified by column chromatography (cyclohexane/EtOAc, 93:7 to 40:60) to give the title compound (187 mg, 67%) as a pale yellow oil. $^1$H NMR (400 MHz, CDCl$_3$) δ 7.33 (t, J=1.4 Hz, 1H), 7.26 (ddd, J=7.8, 2.4, 1.3 Hz, 1H), 7.20 (td, J=2.0, 9.0 Hz, 1H), 7.01 (t, J=1.6 Hz, 1H), 5.42 (dd, J=12.0, 5.3 Hz, 1H), 4.14 (d, J=10.5 Hz, 1H), 3.83 (d, J=10.5 Hz, 1H), 3.43 (ddd, J=18.9, 12.1, 1.6 Hz, 1H), 2.71 (ddd, J=18.8, 5.5, 1.8 Hz, 1H), 1.41 (s, 3H), 1.40 (s, 3H). LC-MS (Method A): m/z=308.2 [M+H]$^+$, 1.07 min.

The following intermediates were prepared using methods analogous to the one described above.

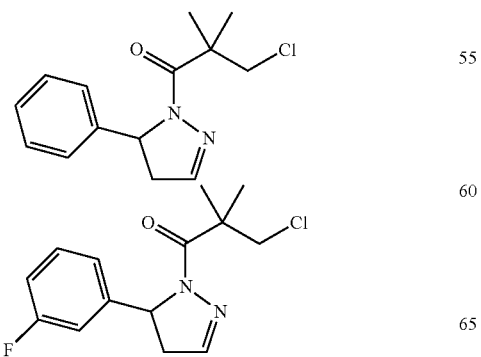

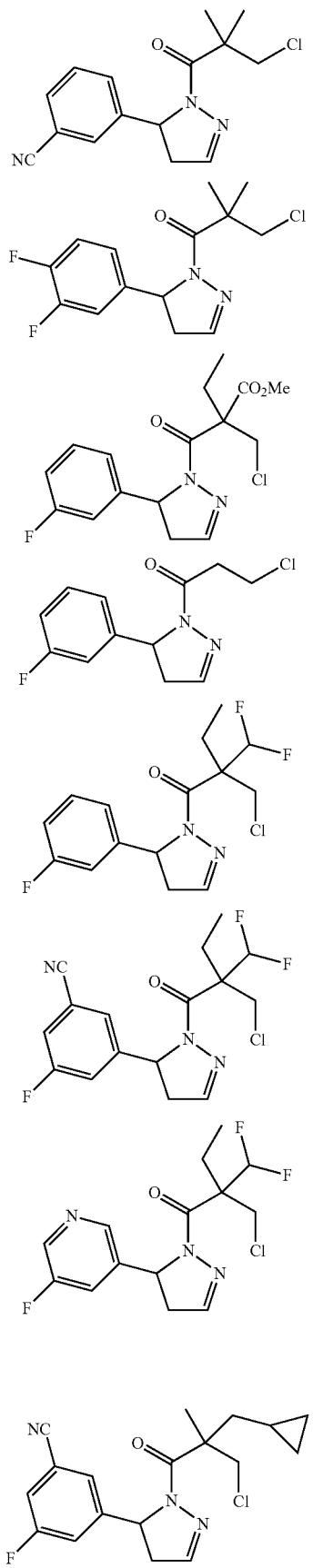

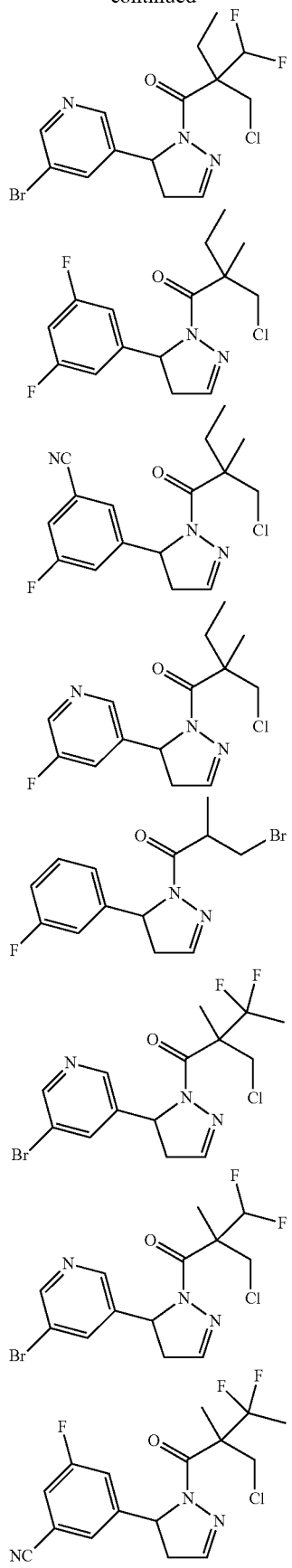
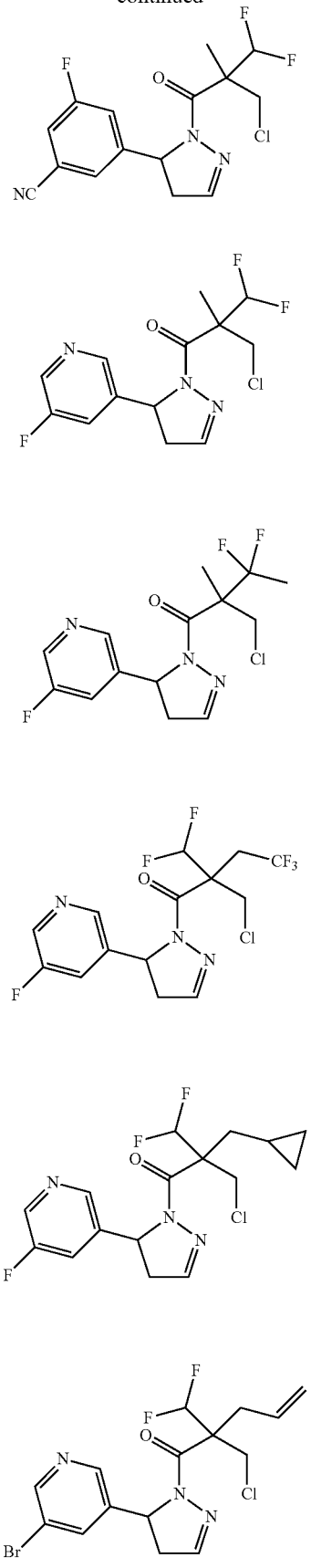

Preparation 7

2-(chloromethyl)-1-[5-(3-fluorophenyl)-4,5-dihydro-1H-pyrazol-1-yl]-2-methylbutan-1-one

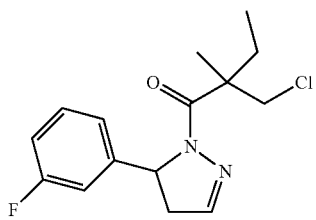 [SMILES: CCC(C)(CCl)C(=O)N1N=CCC1c1cccc(F)c1]

2-(Chloromethyl)-2-methylbutanoic acid (366 mg, ~64 mol %, ~1.5 mmol) was dissolved in CH$_2$Cl$_2$ (3 mL) and oxalyl chloride (0.127 mL, 1.5 mmol) was added at 0° C. followed by one drop of DMF. The mixture was stirred at room temperature for 3.5 h. This mixture was then added dropwise at 0° C. to a stirred solution of 5-(3-fluorophenyl)-4,5-dihydro-1H-pyrazole (164 mg, 1.0 mmol) and DIPEA (0.521 mL, 3 mmol) in CH$_2$Cl$_2$ (4 mL). The mixture was stirred at room temperature for 3 h then diluted with CH$_2$Cl$_2$ and washed with sat. NaHCO$_3$ solution, with sat. NH$_4$Cl solution and with brine. The organic phase was dried over Na$_2$SO$_4$, filtered and concentrated under reduced pressure. The crude product was purified by column chromatography (cyclohexane/EtOAc, 100:0 to 60:40) to afford a yellow oil (72 mg) which contains the title compound as a mixture of diastereoisomers plus unidentified side-products. This mixture was used in the following step without further purification. LC-MS (Method A): m/z=297.2 [M+H]$^+$, 1.18 min.

The following intermediates were prepared using methods analogous to the one described above.

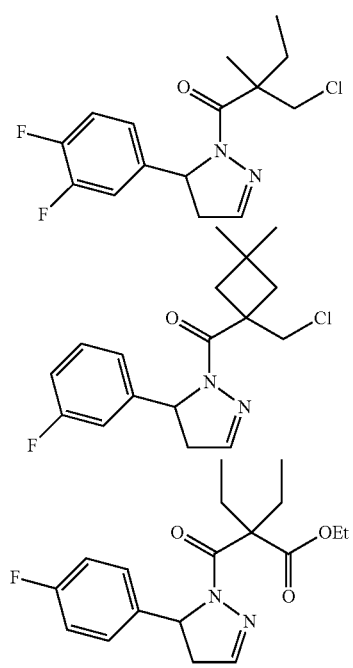

Example 1

Procedure A (7S)-2,2-dimethyl-7-phenyl-hexahydropyrazolo[1,2-a]pyrazolidin-1-one

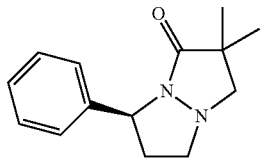 [SMILES: CC1(C)CN2CC[C@@H](c3ccccc3)N2C1=O]

3-Chloro-2,2-dimethyl-1-(5-phenyl-4,5-dihydro-1H-pyrazol-1-yl)propan-1-one (100 mg, 0.37 mmol) was dissolved in MeOH (4 mL). NaCNBH$_3$ (35 mg, 0.568 mmol) was added followed by two drops of 1N HCl solution and the mixture was stirred at room temperature for 1 h, then warmed to 60° C. and stirred at that temperature for 5 hours. The solvent was evaporated under reduced pressure. The residue was dissolved in EtOAc and washed with sat. NaHCO$_3$ solution. The organic phase was dried over Na$_2$SO$_4$ and evaporated under reduced pressure. The crude product was purified by column chromatography (cyclohexane/EtOAc, 50:50) to afford 2,2-dimethyl-7-phenyl-hexahydropyrazolo[1,2-a]pyrazolidin-1-one (62 mg) as a mixture of enantiomers as a white solid. This mixture was resolved by chiral HPLC on a Chiralpak IC (25×2.0 cm), 5 μm column using a mobile phase of n-hexane/(EtOH/MeOH 1/1) 50/50% v/v and a flow rate of 18 mL/min to afford the title compound as the second eluting enantiomer. $^1$H NMR (400 MHz, CDCl$_3$) δ 7.40-7.19 (m, 5H), 5.05 (t, J=7.8 Hz, 1H), 3.48 (br. d, J=9.5 Hz, 1H), 3.35 (br. s, 1H), 2.86 (dddd, J=12.5, 8.7, 6.6, 2.5 Hz, 1H), 2.75 (br. d, J=9.3 Hz, 1H), 2.51 (br. s, 1H), 2.33 (tdd, J=6.8, 12.5, 10.2 Hz, 1H), 1.40 (s, 3H), 1.27 (s, 3H). LC-MS (Method A): m/z=231.3 [M+H]$^+$, 0.69 min. e.e.>99% as determined on a Chiralpak IC (25×0.46 cm), 5 m column using a mobile phase of n-hexane/(EtOH/MeOH 1/1) 50/50% v/v, flow rate: 1 mL/min, retention time: 7.9 min.

Example 2

2,2-diethyl-7-(4-fluorophenyl)-hexahydropyrazolo[1,2-a]pyrazolidin-1-one

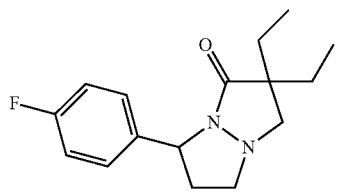 [SMILES: CCC1(CC)CN2CCC(c3ccc(F)cc3)N2C1=O]

To a solution of ethyl 2-ethyl-2-[5-(4-fluorophenyl)-4,5-dihydro-1H-pyrazole-1-carbonyl]butanoate (100 mg, 0.3 mmol) in THF (2.5 mL) at −78° C. was added DIBAL (1M solution in toluene, 0.3 mL, 0.3 mmol) and the mixture was stirred at −78° C. for 1 h and then at room temperature for 20 h. The reaction was cooled again to −78° C. and DIBAL (1M solution in toluene, 0.3 mL, 0.3 mmol) was added, then stirring was continued at room temperature for 5 h. The THF was evaporated under reduced pressure, methanol (3 mL) and NaBH$_3$CN (18 mg, 0.3 mmol) were added. The mixture was stirred at room temperature for 1 h then further NaBH$_3$CN (18 mg, 0.3 mmol) was added together with a drop of 1N HCl solution and the mixture was stirred at 60° C. overnight. The mixture was evaporated under reduced pressure, the residue was diluted with EtOAc and washed with water. The organic phase was dried over Na$_2$SO$_4$ and evaporated under reduced pressure. The crude product was purified by column chromatography (cyclohexane/EtOAc, 50:50) and then by reverse phase column chromatography (water/MeCN, 50:50) to afford the title compound as a racemic mixture. $^1$H NMR (400 MHz, CDCl$_3$) δ 7.35-7.26 (m, 2H), 7.06-6.98 (m, 2H), 5.03 (t, J=7.8 Hz, 1H), 3.48 (d, J=10.3 Hz, 1H), 3.40-3.29 (m, 1H), 2.90-2.77 (m, 2H), 2.54-2.42 (m, 1H), 2.33-2.21 (m, 1H), 1.77-1.69 (m, 2H), 1.65 (q, J=7.5 Hz, 2H), 1.02 (t, J=7.4 Hz, 3H), 0.95 (t, J=7.5 Hz, 3H). LC-MS (Method A): m/z=277.2 [M+H]$^+$, 0.88 min.

Example 3

7-(3-fluorophenyl)-2,2-dimethyl-hexahydropyrazolo [1,2-a]pyrazolidin-1-one

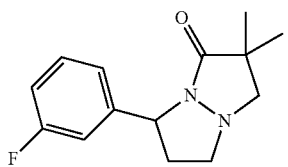 [SMILES: CC1(C)CN2CCC(c3cccc(F)c3)N2C1=O]

The title compound was prepared according to Procedure A and the crude product was purified by column chromatography (cyclohexane/EtOAc, 50:50) to afford the racemate as a colorless oil. This mixture was resolved by chiral HPLC on a Chiralpak AD-H (25×2.0 cm), 5 μm column using a mobile phase of n-hexane/(EtOH+0.1% isopropylamine) 70/30% v/v and a flow rate of 18 mL/min to afford the title compound as the second eluting enantiomer. $^1$H NMR (400 MHz, CDCl$_3$) δ 7.34-7.26 (m, 1H), 7.08 (dd, J=7.8, 0.8 Hz, 1H), 7.01 (td, J=2.1, 9.7 Hz, 1H), 6.98-6.91 (m, 1H), 5.03 (t, J=7.8 Hz, 1H), 3.48 (br. d, J=9.0 Hz, 1H), 3.40-3.28 (m, 1H), 2.86 (dddd, J=12.6, 8.7, 6.7, 2.4 Hz, 1H), 2.74 (d, J=9.3 Hz, 1H), 2.57-2.45 (m, 1H), 2.29 (tdd, J=7.0, 12.6, 10.3 Hz, 1H), 1.39 (s, 3H), 1.26 (s, 3H). LC-MS (Method A): m/z=249.3 [M+H]$^+$, 0.75 min. e.e.>99% as determined on a Chiralpak AD-H (25×0.46 cm), 5 μm column using a mobile phase of n-hexane/(EtOH+0.1% isopropylamine) 70/30% v/v, flow rate: 1 mL/min, retention time: 8.0 min.

Example 4

3-[6,6-dimethyl-7-oxo-hexahydropyrazolo[1,2-a] pyrazolidin-1-yl]benzonitrile

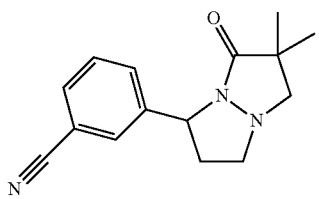 [SMILES: CC1(C)CN2CCC(c3cccc(C#N)c3)N2C1=O]

The title compound was prepared according to Procedure A and the crude product was purified by column chromatography (cyclohexane:EtOAc, 70:30 to 0:100) to afford the racemate. This mixture was resolved by chiral HPLC on a Chiralpak AD-H (25×2.0 cm), 5 μm column using a mobile phase of n-hexane/EtOH 60/40% v/v and a flow rate of 17 mL/min to afford the title compound as the second eluting enantiomer. $^1$H NMR (400 MHz, DMSO-d$_6$) δ 7.75 (td, J=1.8, 7.0 Hz, 1H), 7.71-7.68 (m, 1H), 7.63-7.55 (m, 2H), 5.01 (t, J=7.9 Hz, 1H), 3.45-3.35 (m, 1H), 3.31-3.18 (m, 1H), 2.93-2.82 (m, 1H), 2.81-2.71 (m, 1H), 2.13-1.99 (m, 1H), 1.23 (s, 3H), 1.11 (s, 3H). LC-MS (Method A): m/z=256.3 [M+H]$^+$, 0.69 min. e.e.>99% as determined on a Chiralpak AD-H (25×0.46 cm), 5 μm column using a mobile phase of n-hexane/EtOH 60/40% v/v, flow rate: 1 mL/min, retention time: 9.9 min.

Example 5

3-[6,6-dimethyl-7-oxo-hexahydropyrazolo[1,2-a] pyrazolidin-1-yl]-5-fluorobenzonitrile

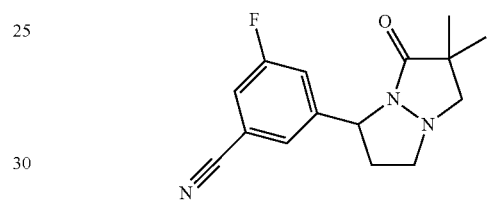

The title compound was prepared according to Procedure A and the crude product was purified by column chromatography (cyclohexane/EtOAc, 50:50 to 0:100) to afford the racemate. This mixture was resolved by chiral HPLC on a Chiralpak IC (25×2.0 cm), 5 μm column using a mobile phase of n-hexane/(EtOH+0.1% isopropylamine) 50/50% v/v and a flow rate of 18 mL/min to afford the title compound as the second eluting enantiomer. $^1$H NMR (400 MHz, CDCl$_3$) δ 7.43-7.41 (m, 1H), 7.32-7.25 (m, 2H), 5.04 (t, J=7.5 Hz, 1H), 3.51 (br. d, J=9.8 Hz, 1H), 3.37 (br. t, J=7.4 Hz, 1H), 2.90 (dddd, J=12.7, 8.7, 6.7, 2.0 Hz, 1H), 2.79 (br. d, J=9.5 Hz, 1H), 2.60-2.49 (m, 1H), 2.26 (tdd, J=7.1, 12.7, 10.3 Hz, 1H), 1.40 (s, 3H), 1.28 (s, 3H). LC-MS (Method A): m/z=274.3 [M+H]$^+$, 0.74 min. e.e.>99% as determined on a Chiralpak IC (25×0.46 cm), 5 μm column using a mobile phase of n-hexane/(EtOH+0.1% isopropylamine) 50/50% v/v, flow rate: 1 mL/min, retention time: 8.3 min.

Examples 6 and 7

2-ethyl-7-(3-fluorophenyl)-2-methyl-hexahydropyrazolo[1,2-a]pyrazolidin-1-ones

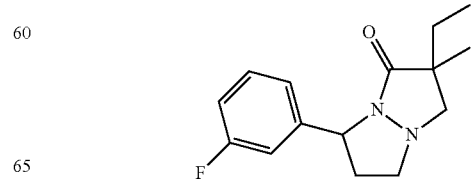

Prepared according to Procedure A and purified by column chromatography (cyclohexane/EtOAc, 83:17 to 0:100) to provide a mixture of the four stereoisomers. This mixture was resolved by chiral HPLC on a Chiralpak AD-H (25×2.0 cm), 5 μm column using a mobile phase of n-hexane/EtOH 80/20% v/v and a flow rate of 18 mL/min to afford the two diastereomeric title compounds as single enantiomers.

2-Ethyl-7-(3-fluorophenyl)-2-methyl-hexahydropyrazolo[1,2-a]pyrazolidin-1-one as the third eluting stereoisomer (Example 6). $^1$H NMR (500 MHz, CDCl$_3$) δ 7.32-7.27 (m, 1H), 7.08 (d, J=7.8 Hz, 1H), 7.01 (dt, J=9.8, 2.0 Hz, 1H), 6.94 (td, J=8.2, 2.2 Hz, 1H), 5.04 (t, J=7.8 Hz, 1H), 3.60 (br. d, J=8.3 Hz, 1H), 3.33 (br. s, 1H), 2.83 (dddd, J=12.7, 8.6, 6.6, 2.5 Hz, 1H), 2.71 (br. d, J=9.8 Hz, 1H), 2.49 (br. s, 1H), 2.26 (ddt, J=12.6, 10.5, 7.0 Hz, 1H), 1.81-1.66 (m, 2H), 1.23 (s, 3H), 1.01 (t, J=7.6 Hz, 3H). LC-MS (Method A): m/z=263.8 [M+H]$^+$, 0.83 min. e.e.>99% as determined on a Chiralpak AD-H (25×0.46 cm), 5 μm column using a mobile phase of n-hexane/EtOH 80/20% v/v, flow rate: 1 mL/min, retention time: 8.6 min. 2-Ethyl-7-(3-fluorophenyl)-2-methyl-hexahydropyrazolo[1,2-a]pyrazolidin-1-one (Example 7) as the fourth eluting stereoisomer. $^1$H NMR (400 MHz, CDCl$_3$) δ 7.34-7.27 (m, 1H), 7.09 (d, J=7.8 Hz, 1H), 7.03 (td, J=2.0, 9.8 Hz, 1H), 6.95 (dt, J=2.0, 8.4 Hz, 1H), 5.03 (t, J=7.6 Hz, 1H), 3.44-3.27 (m, 2H), 2.92-2.77 (m, 2H), 2.55-2.43 (m, 1H), 2.36-2.14 (m, 1H), 1.66 (q, J=7.5 Hz, 2H), 1.38 (s, 3H), 0.96 (t, J=7.5 Hz, 3H). LC-MS (Method A): m/z=263.8 [M+H]$^+$, 0.83 min. e.e.>99% as determined on a Chiralpak AD-H (25×0.46 cm), 5 μm column using a mobile phase of n-hexane/EtOH 80/20% v/v, flow rate: 1 mL/min, retention time: 9.3 min.

Example 8

6,6-dimethyl-3-phenyl-hexahydro-1H-pyrazolidino[1,2-a]pyridazin-5-one

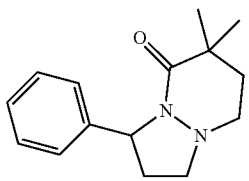 [SMILES: CC1(C)CCN2CCC(c3ccccc3)N2C1=O]

Lithium triethylborohydride (1M solution in THF, 2.92 mL, 2.92 mmol) was added dropwise at 0° C. to a stirred solution of 4-chloro-2,2-dimethyl-1-(5-phenyl-4,5-dihydro-1H-pyrazol-1-yl)butan-1-one (406 mg, 1.46 mmol) in THF (25 mL). The mixture was stirred and allowed to warm to room temperature overnight. Further lithium triethylborohydride (1M solution in THF, 0.8 mL, 0.8 mmol) was added dropwise and the mixture was stirred at room temperature for 1 h. The volatiles were evaporated under reduced pressure to give a yellow oil, which was dissolved in EtOAc and washed with sat. KHCO$_3$ solution and sat. NH$_4$Cl solution. The organic phase was dried over Na$_2$SO$_4$ and evaporated under reduced pressure. The crude product was purified by column chromatography (cyclohexane/EtOAc, 50:50 to 0:100) to afford the 6,6-dimethyl-3-phenyl-hexahydro-1H-pyrazolidino[1,2-a]pyridazin-5-one as a racemic mixture isolated as a white solid. This mixture was resolved by chiral HPLC on a Chiralpak AD-H (25×2.0 cm), 5 μm column using a mobile phase of n-hexane/EtOH 65/35% v/v and a flow rate of 17 mL/min to afford the title compound as the second eluting enantiomer as a yellow oil. $^1$H NMR (400 MHz, CDCl$_3$) δ 7.38-7.17 (m, 5H), 5.20 (dd, J=9.0, 6.0 Hz, 1H), 3.35-3.23 (m, 2H), 2.91-2.75 (m, 2H), 2.60 (dddd, J=12.5, 9.1, 6.7, 4.4 Hz, 1H), 2.10-1.96 (m, 2H), 1.87 (ddd, J=13.8, 6.1, 2.9 Hz, 1H), 1.28 (s, 3H), 1.23 (s, 3H). LC-MS (Method A): m/z=245.3 [M+H]$^+$, 0.78 min. e.e.>99% as determined on a Chiralpak AD-H (25×0.46 cm), 5 μm column using a mobile phase of n-hexane/EtOH 65/35% v/v, flow rate: 1 mL/min, retention time: 7.1 min.

Example 9

3-(3,4-difluorophenyl)-6,6-dimethyl-1,2,3,7-tetrahydropyrazolo[1,2-a]pyrazol-5-one

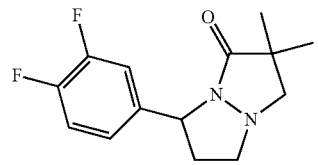 [SMILES: CC1(C)CN2CCC(c3ccc(F)c(F)c3)N2C1=O]

Prepared according to Procedure A and purified by column chromatography (cyclohexane/EtOAc, 50/50 to 0/100) to afford the title compound. $^1$H NMR (400 MHz, CDCl$_3$) δ 7.19-7.08 (m, 2H), 7.07-7.00 (m, 1H), 4.99 (t, J=7.8 Hz, 1H), 3.48 (d, J=9.0 Hz, 1H), 3.40-3.30 (m, 1H), 2.85 (dddd, J=12.6, 8.7, 6.7, 2.1 Hz, 1H), 2.75 (d, J=9.5 Hz, 1H), 2.59-2.47 (m, 1H), 2.35-2.22 (m, 1H), 1.39 (s, 3H), 1.26 (s, 3H). LC-MS (Method A): m/z=267.2 [M+H]$^+$, 0.79 min.

Examples 10 and 11

3-(3,4-difluorophenyl)-6-ethyl-6-methyl-1,2,3,7-tetrahydropyrazolo[1,2-a]pyrazol-5-one

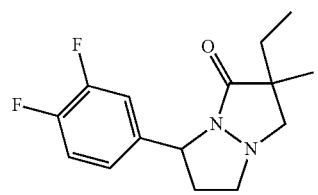 [SMILES: CCC1(C)CN2CCC(c3ccc(F)c(F)c3)N2C1=O]

Prepared according to Procedure A and purified by column chromatography (cyclohexane/EtOAc, 80:20 to 0:100) to give the title compounds as a mixture of the four stereoisomers isolated as a yellow oil. This mixture was resolved by chiral HPLC on a Chiralpak AD-H (25×2.0 cm), 5 μm column using a mobile phase of n-hexane/2-propanol 60/40% v/v and a flow rate of 18 mL/min to afford the two diastereomeric title compounds as single enantiomers.

3-(3,4-Difluorophenyl)-6-ethyl-6-methyl-1,2,3,7-tetrahydropyrazolo[1,2-a]pyrazol-5-one as the third eluting stereoisomer (Example 10). $^1$H NMR (400 MHz, CDCl$_3$) δ 7.18-7.08 (m, 2H), 7.07-7.01 (m, 1H), 5.00 (t, J=7.8 Hz, 1H), 3.60 (d, J=9.8 Hz, 1H), 3.34 (t, J=6.8 Hz, 1H), 2.83 (dddd, J=12.7, 8.6, 6.7, 2.1 Hz, 1H), 2.73 (d, J=10.0 Hz, 1H), 2.57-2.45 (m, 1H), 2.25 (tdd, J=7.0, 12.6, 10.5 Hz, 1H), 1.82-1.65 (m, 2H), 1.24 (s, 3H), 1.02 (t, J=7.5 Hz, 3H). LC-MS (Method A): m/z=281.2 [M+H]$^+$, 0.88 min. e.e.>99% as determined on a Chiralpak AD-H (25×0.46 cm), 5 μm column using a mobile phase of n-hexane/EtOH 80/20% v/v, flow rate: 1 mL/min, retention time: 9.7 min.

3-(3,4-Difluorophenyl)-6-ethyl-6-methyl-1,2,3,7-tetrahydropyrazolo[1,2-a]pyrazol-5-one as the fourth eluting stereoisomer (Example 11). ¹H NMR (400 MHz, CDCl₃) δ 7.18-7.08 (m, 2H), 7.07-7.01 (m, 1H), 4.98 (t, J=7.8 Hz, 1H), 3.43-3.30 (m, 2H), 2.91-2.76 (m, 2H), 2.55-2.43 (m, 1H), 2.28 (tdd, J=7.0, 12.7, 10.3 Hz, 1H), 1.65 (q, J=7.5 Hz, 2H), 1.36 (s, 3H), 0.95 (t, J=7.5 Hz, 3H). LC-MS (Method A): m/z=281.2 [M+H]⁺, 0.88 min. e.e.>99% as determined on a Chiralpak AD-H (25×0.46 cm), 5 μm column using a mobile phase of n-hexane/EtOH 80/20% v/v, flow rate: 1 mL/min, retention time: 11.8 min.

Example 12

3-(3-fluorophenyl)-3',3'-dimethyl-spiro[1,2,3,7-tetrahydropyrazolo[1,2-a]pyrazole-6,1'-cyclobutane]-5-one

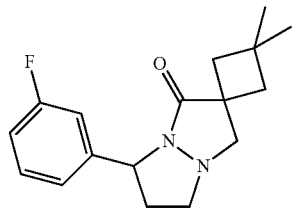 [SMILES: CC1(C)CC2(CN3CCC(c4cccc(F)c4)N3C2=O)C1]

1-[1-(Chloromethyl)-3,3-dimethylcyclobutanecarbonyl]-5-(3-fluorophenyl)-4,5-dihydro-1H-pyrazole (65 mg, 0.20 mmol) was dissolved in anhydrous THF (6 mL) and the resulting solution was cooled to 0° C. Super hydride (1M solution in THF, 0.6 mL, 0.6 mmol) was added dropwise and the mixture was then stirred at room temperature for 4 h. Another equivalent of Super hydride solution was added and the mixture was stirred at room temperature for 1 h. Sat. NH₄Cl solution was added and the mixture was extracted with EtOAc. The combined organic phases were washed with brine, dried over Na₂SO₄, filtered and evaporated under reduced pressure. The crude product was purified by column chromatography (cyclohexane/EtOAc, 85:15 to 20:80) to afford the title compound as a racemic mixture. ¹H NMR (400 MHz, CDCl₃) δ 7.35-7.29 (m, 1H), 7.15-7.01 (m, 2H), 6.99-6.88 (m, 1H), 5.10-4.99 (m, 1H), 3.78 (d, J=10.3 Hz, 1H), 3.33-3.20 (m, 2H), 2.80-2.67 (m, 1H), 2.49-2.33 (m, 3H), 2.27-2.15 (m, 1H), 1.95 (d, J=12.0 Hz, 1H), 1.74 (d, J=11.8 Hz, 1H), 1.25-1.17 (m, 6H). LC-MS (Method A): m/z=289.2 [M+H]⁺, 1.01 min.

Example 13

6-(1,1-difluoroethyl)-3-(3-fluorophenyl)-6-methyl-1,2,3,7-tetrahydropyrazolo[1,2-a]pyrazol-5-one

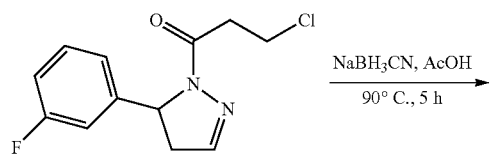

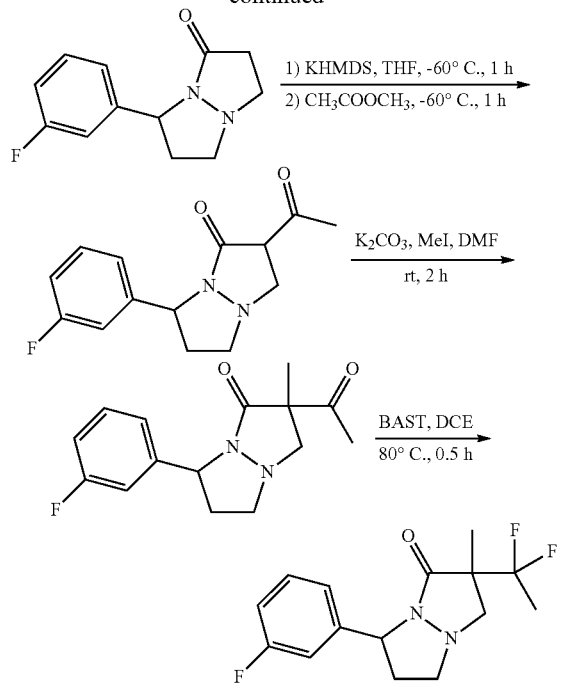

3-(3-fluorophenyl)-2,3,6,7-tetrahydro-1H-pyrazolo[1,2-a]pyrazol-5-one (Procedure B): To a stirring mixture of 3-chloro-1-(5-(3-fluorophenyl)-4,5-dihydropyrazol-1-yl)propan-1-one (2 g, 7.85 mmol) in acetic acid (50 mL) was added sodium cyanborohydride (1.2 g, 19.1 mmol). The resulting mixture was heated at 90° C., and stirred for 5 hours. After cooling to room temperature, the reaction mixture was concentrated under vacuum, diluted with water (50 mL), the pH value was adjusted to 9 by the addition of aqueous hydrochloric acid (1 N, 50 mL), and extracted with ethyl acetate (3×100 mL). The combined organic layers were washed with brine, dried over anhydrous sodium sulfate, filtered and concentrated under vacuum. The residue was purified by column chromatography (methane/dichloromethane, 1/10) to afford the title compound (1.5 g, 87%) as a yellow oil. LCMS (Method E): m/z=221.0 [M+H]⁺, 0.577 min.

6-acetyl-3-(3-fluorophenyl)-2,3,6,7-tetrahydro-1H-pyrazolo[1,2-a]pyrazol-5-one: A solution of potassium bis(trimethylsilyl)amide in tetrahydrofuran (1 M, 17 mL, 17 mmol) was added to a stirring mixture of 3-(3-fluorophenyl)-2,3,6,7-tetrahydro-1H-pyrazolo[1,2-a]pyrazol-5-one (3.0 g, 13.6 mmol) in tetrahydrofuran (70 mL) dropwise at −60° C. The resulting mixture was stirred at −60° C. for 1 hour followed by the addition of a solution of methyl acetate (1.2 g, 16.4 mmol) in tetrahydrofuran (10 mL) dropwise. After stirring for 1 hour at −60° C., the reaction mixture was quenched by the addition of saturated aqueous ammonium chloride (20 mL) and extracted with ethyl acetate (3×50 mL). The combined organic layers were washed with brine, dried over anhydrous sodium sulfate, filtered and concentrated under vacuum. The residue was purified by column chromatography (ethyl acetate/petroleum ether, 1/3) to afford the title compound as the first eluting racemic diastereomer (1.40 g, 39%) isolated as a yellow oil. LCMS (Method M): m/z=263.0 [M+H]⁺, 1.066 min.

6-acetyl-3-(3-fluorophenyl)-6-methyl-1,2,3,7-tetrahydropyrazolo[1,2-a]pyrazol-5-one: To a stirring mixture of 6-acetyl-3-(3-fluorophenyl)-2,3,6,7-tetrahydro-1H-pyrazolo[1,2-a]pyrazol-5-one (600 mg, 2.30 mmol) and potassium carbonate (316 mg, 2.30 mmol) in N,N-dimethylformamide (10 mL) was added iodomethane (325 mg, 2.30 mmol) dropwise. After stirring at room temperature for 2 hours, the reaction mixture was quenched by the addition of water (50 mL) and extracted with ethyl acetate (3×100 mL). The combined organic layers were washed with brine, dried over anhydrous sodium sulfate, filtered and concentrated under vacuum. The residue was purified by column chromatography (ethyl acetate/petroleum ether, 3/2) to afford the title compound (150 mg, 24%) as a colorless oil. LC-MS (Method M): m/z=277.1 [M+H]$^+$, 1.387 min.

6-(1,1-difluoroethyl)-3-(3-fluorophenyl)-6-methyl-1,2,3,7-tetrahydropyrazolo[1,2-a]pyrazol-5-one: To a stirring mixture of 6-acetyl-3-(3-fluorophenyl)-6-methyl-1,2,3,7-tetrahydropyrazolo[1,2-a]pyrazol-5-one (14 mg, 0.05 mmol) in 1,2-dichloroethane (1.0 mL) was added bis(2-methoxyethyl)aminosulphur trifluoride (23 mg, 0.10 mmol). The resulting mixture was stirred at 80° C. for 0.5 hour. After cooling to room temperature, the reaction mixture was quenched by the addition of water (20 mL) and extracted with ethyl acetate (3×50 mL). The combined organic layers were washed with brine, dried over anhydrous sodium sulfate, filtered and concentrated under vacuum. The residue was purified by Prep-HPLC with the following conditions: Column: XBridge Prep C18, 5 mm, 30×100 mm; Mobile Phase A: water (0.1% NH$_4$HCO$_3$), Mobile Phase B: ACN; Flow rate: 20 mL/min; Gradient: 20% B to 50% B over 8.5 min; UV 254 & 220 nm Rt: 8.00 min to afford the title compound as the first eluting racemic diastereomer. $^1$H NMR (400 MHz, CD$_3$OD) δ 7.39-7.33 (m, 1H), 7.14-7.11 (m, 1H), 7.06-6.97 (m, 2H), 5.02 (t, J=8.0 Hz, 1H), 3.50-3.47 (m, 1H), 3.42-3.37 (m, 1H), 3.33-3.20 (m, 1H), 3.00-2.91 (m, 1H), 2.64-2.56 (m, 1H), 2.30-2.20 (m, 1H), 1.79 (t, J=20.0 Hz, 3H), 1.51 (s, 3H). LC-MS (Method E): m/z=299.0 [M+H]$^+$, 1.711 min.

Example 14

6-allyl-3-(3-fluorophenyl)-6-methyl-1,2,3,7-tetrahydropyrazolo[1,2-a]pyrazol-5-one

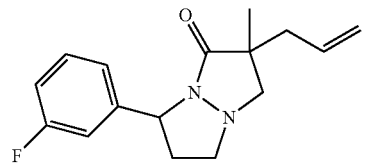 [SMILES: C=CCC1(C)CN2CCC(c3cccc(F)c3)N2C1=O]

To a solution of 3-(3-fluorophenyl)-6-methyl-2,3,6,7-tetrahydro-1H-pyrazolo[1,2-a]pyrazol-5-one (431 mg, 2.2 mmol) in THF at −78° C. was added DMPU (2 mL) followed by KHMDS solution (0.5M/PhMe, 4.31 mL, 2.2 mmol). The resulting reaction mixture was stirred for 20 min before allyl bromide (285 mg, 2.36 mmol) was added. The reaction mixture was stirred at −78° C. for 1 h. The reaction mixture was diluted with NH$_4$Cl solution (15 mL) and EtOAc (15 mL). The layers were separated and the aqueous layer was extracted with EtOAc (3×15 mL). The combined organic layers were dried over MgSO$_4$, filtered, and concentrated under reduced pressure. The crude reaction mixture was purified employing silica gel chromatography (25-90% EtOAc/hexanes) to provide the title compound as the second eluting racemic diastereomer. $^1$H-NMR (400 MHz, CDCl$_3$): δ 7.30 (td, J=8.0, 5.9 Hz, 1H), 7.10-7.07 (m, 1H), 7.03-7.00 (m, 1H), 6.98-6.93 (m, 1H), 5.85-5.74 (m, 1H), 5.17-5.10 (m, 2H), 5.04-5.00 (m, 1H), 3.36-3.32 (m, 2H), 2.89-2.82 (m, 2H), 2.52-2.46 (m, 1H), 2.41 (ddt, J=14.0, 6.7, 1.3 Hz, 1H), 2.34-2.25 (m, 2H), 1.40 (s, 3H). LCMS (Method C): m/z=275.59 [M+H]$^+$.

Example 15

3-(3-fluorophenyl)-6-methyl-6-propyl-1,2,3,7-tetrahydropyrazolo[1,2-a]pyrazol-5-one

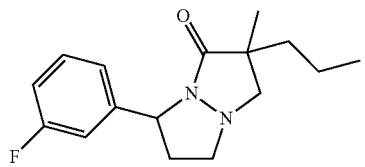 [SMILES: CCCC1(C)CN2CCC(c3cccc(F)c3)N2C1=O]

To a solution of 6-allyl-3-(3-fluorophenyl)-6-methyl-1,2,3,7-tetrahydropyrazolo[1,2-a]pyrazol-5-one (25 mg, 0.091 mmol) (first eluting racemic diastereomer) in EtOH (2 mL) was added Pd(OH)$_2$ (2.5 mg, 20 wt %). The solution was stirred under an atmosphere of hydrogen overnight. The reaction mixture was filtered through a pad of celite and concentrated under reduced pressure to provide the title compound as a racemic mixture. $^1$H-NMR (400 MHz, CDCl$_3$): δ 7.33-7.27 (m, 1H), 7.10-7.07 (m, 1H), 7.04-7.00 (m, 1H), 6.97-6.92 (m, 1H), 5.04 (t, J=7.8 Hz, 1H), 3.62-3.59 (m, 1H), 3.35-3.31 (m, 1H), 2.83 (dddd, J=12.6, 8.7, 6.5, 2.3 Hz, 1H), 2.74-2.71 (m, 1H), 2.53-2.46 (m, 1H), 2.27 (ddt, J=12.6, 10.3, 7.0 Hz, 1H), 1.73-1.61 (m, 2H), 1.57-1.47 (m, 1H), 1.45-1.34 (m, 1H), 1.25 (s, 3H), 0.97 (t, J=7.3 Hz, 3H). LCMS (Method C): m/z=277.50 [M+H]$^+$.

Example 16

3-(3-fluorophenyl)-6-methyl-6-propyl-1,2,3,7-tetrahydropyrazolo[1,2-a]pyrazol-5-one

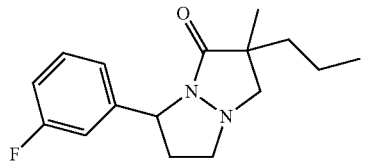 [SMILES: CCCC1(C)CN2CCC(c3cccc(F)c3)N2C1=O]

To a solution of 6-allyl-3-(3-fluorophenyl)-6-methyl-1,2,3,7-tetrahydropyrazolo[1,2-a]pyrazol-5-one (3.3 mg, 0.012 mmol) (second eluting racemic diastereomer) in EtOH (1 mL) was added Pd(OH)$_2$ (1 mg, 20 wt %). The solution was stirred under an atmosphere of hydrogen overnight. The reaction mixture was filtered through a pad of celite and concentrated under reduced pressure to provide the title compound as a racemic mixture. $^1$H-NMR (400 MHz, CDCl$_3$): δ 7.31 (td, J=8.0, 5.9 Hz, 1H), 7.10-7.07 (m, 1H), 7.04-7.00 (m, 1H), 6.98-6.93 (m, 1H), 5.04-5.00 (m, 1H), 3.42-3.32 (m, 2H), 2.90-2.79 (m, 2H), 2.53-2.46 (m, 1H), 2.30 (ddt, J=12.6, 10.2, 6.9 Hz, 1H), 1.67-1.45 (m, 4H), 1.38 (s, 3H), 0.98-0.95 (m, 3H).

Example 17

6-(cyclopropylmethyl)-3-(3-fluorophenyl)-6-methyl-1,2,3,7-tetrahydropyrazolo[1,2-a]pyrazol-5-one

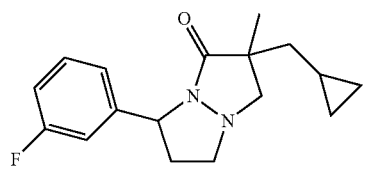 [SMILES: CC1(CC2CC2)CN2CCC(c3cccc(F)c3)N2C1=O]

6-(Cyclopropylmethyl)-3-(3-fluorophenyl)-2,3,6,7-tetrahydro-1H-pyrazolo[1,2-a]pyrazol-5-one (16.0 mg, 0.06 mmol) and DMPU (0.4 mL, 0.06 mmol) were treated with KHMDS solution (0.5M/PhMe, 0.13 mL, 0.06 mmol) in THF at −78° C. The reaction mixture was stirred for 30 min, MeI (60.0 µL, 0.09 mmol) was added and the reaction was warmed to 0° C. The reaction mixture was treated with NH$_4$Cl solution (10 mL) and EtOAc (10 mL) The layers were separated and the aqueous layer was extracted with EtOAc (3×10 mL). The combined organic layers were dried over anhydrous MgSO$_4$, filtered, and concentrated under reduced pressure. The crude reaction mixture was purified employing silica gel column chromatography (0-80% EtOAc/hexanes) to provide the desired product as a racemic mixture. $^1$H-NMR (400 MHz, CDCl$_3$): δ 7.33-7.28 (m, 1H), 7.10-7.07 (m, 1H), 7.04-7.00 (m, 1H), 6.95 (tdd, J=8.5, 2.6, 0.9 Hz, 1H), 5.05-5.01 (m, 1H), 3.49-3.47 (m, 1H), 3.39-3.34 (m, 1H), 3.03-3.01 (m, 1H), 2.86 (dddd, J=12.7, 8.6, 6.5, 2.2 Hz, 1H), 2.55-2.48 (m, 1H), 2.30 (ddt, J=12.6, 10.4, 7.0 Hz, 1H), 1.63-1.48 (m, 2H), 1.44 (s, 3H), 0.74-0.65 (m, 1H), 0.57-0.52 (m, 1H), 0.49-0.44 (m, 1H), 0.15-0.08 (m, 2H). LCMS (Method C): m/z=289.1 [M+H]$^+$.

Example 18

3-(5-bromo-3-pyridyl)-6-(difluoromethyl)-6-ethyl-1,2,3,7-tetrahydropyrazolo[1,2-a]pyrazol-5-one

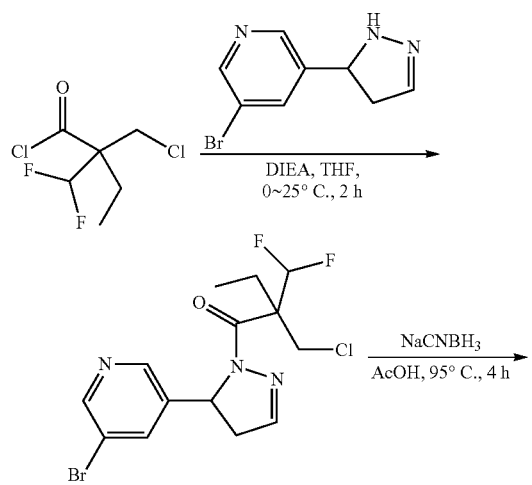

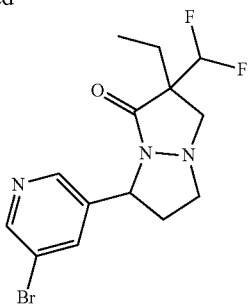

1-(5-(5-bromopyridin-3-yl)-4,5-dihydro-1H-pyrazol-1-yl)-2-(chloromethyl)-2-(difluoromethyl)butan-1-one: Synthesized according to Preparation 6 and purified by silica gel column chromatography (PE:EtOAc=1:1) to provide the title compound (0.33 g, 13.19%) as a light yellow oil.

3-(5-bromo-3-pyridyl)-6-(difluoromethyl)-6-ethyl-1,2,3,7-tetrahydropyrazolo[1,2-a]pyrazol-5-one: Prepared according to Procedure B. The crude reaction mixture was purified employing reverse-phase HPLC to provide the title compound as the first eluting diastereomer isolated as a mixture of enantiomers. $^1$H-NMR (400 MHz CDCl$_3$): δ 8.59 (d, J=2.2 Hz, 1H), 8.50 (d, J=1.9 Hz, 1H), 7.78 (t, J=2.1 Hz, 1H), 5.95 (t, J=56.3 Hz, 1H), 5.06 (t, J=8.0 Hz, 1H), 3.57-3.54 (m, 1H), 3.43-3.34 (m, 2H), 2.85 (dddd, J=12.6, 8.7, 6.8, 1.2 Hz, 1H), 2.62-2.55 (m, 1H), 2.24 (ddt, J=12.6, 11.2, 7.2 Hz, 1H), 1.90 (dq, J=14.2, 7.2 Hz, 1H), 1.78-1.69 (m, 1H), 1.09 (t, J=7.5 Hz, 3H). LCMS (Method C): m/z=360.1, 362.1 [M+H]$^+$.

Example 19

5-(6-(difluoromethyl)-6-ethyl-5-oxo-1,2,3,7-tetrahydropyrazolo[1,2-a]pyrazol-3-yl)pyridine-3-carbonitrile Procedure C

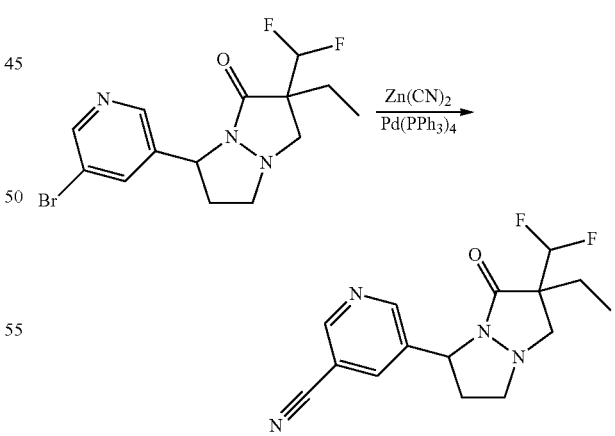

To a flask containing 3-(5-bromo-3-pyridyl)-6-(difluoromethyl)-6-ethyl-1,2,3,7-tetrahydropyrazolo[1,2-a]pyrazol-5-one (38.0 mg, 0.11 mmol) (first eluting diastereomer as a mixture of enantiomers), and Zn(CN)$_2$ (12.4 mg, 0.11 mmol) was added DMF (1.0 mL). The suspension was sparged with argon for 15 min before Pd(PPh$_3$)$_4$(24.4 mg, 0.02 mmol) was added. The resulting reaction mixture was heated at 100° C. overnight. The reaction mixture was diluted with EtOAc (20 mL) and filtered through celite. The filtrate was treated with NH₄Cl solution (10 mL). The layers were separated and the aqueous layer was extracted with EtOAc (3×10 mL). The combined organic layers were dried over anhydrous MgSO₄, filtered, and concentrated under reduced pressure. The crude reaction mixture was purified employing reverse-phase HPLC to provide the title product as a mixture of enantiomers. ¹H-NMR (400 MHz, CDCl₃): δ 8.83-8.80 (m, 2H), 7.94-7.93 (m, 1H), 5.97 (dd, J=56.6, 56.0 Hz, 1H), 5.14 (dd, J=8.3, 7.9 Hz, 1H), 3.59 (dd, J=12.1, 2.1 Hz, 1H), 3.47 (d, J=12.1 Hz, 1H), 3.42-3.38 (m, 1H), 2.91 (dddd, J=12.6, 8.8, 6.7, 1.2 Hz, 1H), 2.68-2.61 (m, 1H), 2.29-2.20 (m, 1H), 1.96-1.87 (m, 1H), 1.81-1.71 (m, 1H), 1.10 (t, J=7.5 Hz, 3H). LCMS (Method C): m/z=307.13 [M+H]⁺.

Example 20

6-(difluoromethyl)-6-ethyl-3-(3-fluorophenyl))-1,2,3,7-tetrahydropyrazolo[1,2-a]pyrazol-5-one

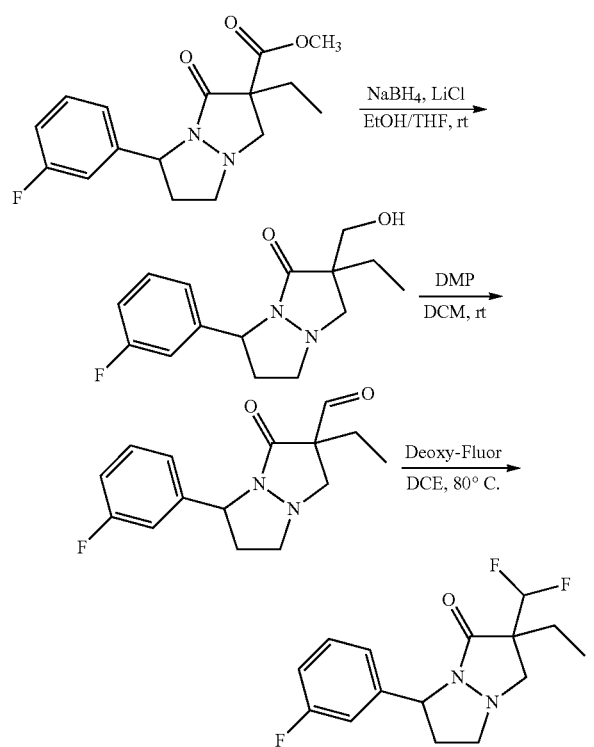

Methyl 6-ethyl-3-(3-fluorophenyl)-5-oxo-1,2,3,7-tetrahydropyrazolo[1,2-a]pyrazole-6-carboxylate: Prepared according to Procedure B to provide the title compound as a colorless oil. LCMS (Method C): m/z=307.3 [M+H]⁺.

6-ethyl-3-(3-fluorophenyl)-6-(hydroxymethyl)-1,2,3,7-tetrahydropyrazolo[1,2-a]pyrazol-5-one: Lithium chloride (21.7 mg, 0.50 mmol) and sodium borohydride (37.8 mg, 1.0 mmol) were added to a solution of methyl 6-ethyl-3-(3-fluorophenyl)-5-oxo-1,2,3,7-tetrahydropyrazolo[1,2-a]pyrazole-6-carboxylate (153 mg, 0.50 mmol) in THF (5 mL) and Ethanol (5 mL) at 0° C. The reaction mixture was stirred at 0° C. for 3 h. The reaction was quenched by adding 10 mL of water then extracted with ethyl acetate (20 mL×3). The organics were collected and dried over MgSO₄ before concentrating under reduced pressure. The resulting residue was purified by flash chromatography (0-100% ethyl acetate in hexanes) to yield the title compound as a colorless oil (49 mg, 0.18 mmol, 35.2%). LCMS (Method C): m/z=279.3 [M+H]⁺.

6-ethyl-3-(3-fluorophenyl)-5-oxo-1,2,3,7-tetrahydropyrazolo[1,2-a]pyrazole-6-carbaldehyde: Dess-Martin periodinane (68.6 mg, 0.16 mmol) was added to a solution of 6-ethyl-3-(3-fluorophenyl)-6-(hydroxymethyl)-1,2,3,7-tetrahydropyrazolo[1,2-a]pyrazol-5-one (30 mg, 0.11 mmol) in DCM (3 mL). The reaction mixture was stirred at rt for 1 h before adding sodium thiosulfate solution (2.0 M, 2 mL). The mixture was extracted with ethyl acetate (10 mL×2) and the organic layers were collected and washed with water (10 mL) and brine (20 mL) before concentrating under reduced pressure to provide the title compound as a colorless oil (5 mg, 30%). LCMS (Method C): m/z=277.3 [M+H]⁺.

6-(difluoromethyl)-6-ethyl-3-(3-fluorophenyl)-1,2,3,7-tetrahydropyrazolo[1,2-a]pyrazol-5-one: Deoxy-fluor (0.07 mL, 0.41 mmol) was added to a solution of 6-ethyl-3-(3-fluorophenyl)-5-oxo-1,2,3,7-tetrahydropyrazolo[1,2-a]pyrazole-6-carbaldehyde (56 mg, 0.20 mmol) in DCE (5 mL). The reaction mixture was sealed and stirred at 80° C. for 1 h. The reaction mixture was diluted with 5% aqueous NaHCO₃ solution (25 mL) and EtOAc (50 mL). The organic layer was collected and washed with water (25 mL) and brine (25 mL), dried over anhydrous MgSO₄, filtered and concentrated under reduced pressure. The crude product was purified using flash chromatography (0-80% ethyl acetate in hexanes) to provide the title compound as a racemic mixture isolated as a yellow oil. This mixture was resolved by chiral HPLC on a Chiralpak IA (25×2.0 cm), 5 μm column using a mobile phase of n-hexane/ethanol 75/25% v/v and a flow rate of 17 mL/min to afford the title compound as the second eluting enantiomer. ¹H NMR (400 MHz, CDCl₃) δ 7.35-7.29 (m, 1H), 7.12-7.08 (m, 1H), 7.07-7.01 (m, 1H), 6.97 (dt, J=2.8, 8.4 Hz, 1H), 5.97 (t, J=56.7 Hz, 1H), 5.07 (t, J=8.0 Hz, 1H), 3.56 (dd, J=11.8, 2.0 Hz, 1H), 3.40 (d, J=11.8 Hz, 1H), 3.35 (t, J=7.7 Hz, 1H), 2.83 (td, J=7.5, 12.6 Hz, 1H), 2.62-2.53 (m, 1H), 2.27 (tt, J=11.8, 7.2 Hz, 1H), 1.98-1.87 (m, 1H), 1.76 (qd, J=7.3, 14.2 Hz, 1H), 1.13 (t, J=7.4 Hz, 3H). LC-MS (Method A): m/z=299.5 [M+H]⁺, 597.4 [2M+H]⁺, 0.99 min. e.e.>99% as determined on a Chiralpak IA (25×0.46 cm), 5 μm column using a mobile phase of n-hexane/ethanol 75/25% v/v, flow rate: 1.0 mL/min, retention time: 10.3 min.

Examples 21 and 22

3-(3,5-difluorophenyl)-6-ethyl-6-methyl-1,2,3,7-tetrahydropyrazolo[1,2-a]pyrazol-5-one

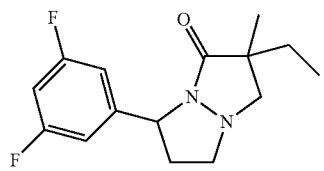 [SMILES: CCC1(C)CN2CCC(c3cc(F)cc(F)c3)N2C1=O]

Prepared according to Procedure A to give the title compounds as a mixture of the four stereoisomers. This mixture was resolved by chiral HPLC on a Chiralpak AD-H (25×2.0 cm), 5 μm column using a mobile phase of n-hexane/ethanol 85/15% v/v and a flow rate of 17 mL/min to afford the two diastereomeric title compounds as single enantiomers.

3-(3,5-difluorophenyl)-6-ethyl-6-methyl-1,2,3,7-tetrahydropyrazolo[1,2-a]pyrazol-5-one as the third eluting stereoisomer (Example 21). $^1$H NMR (400 MHz, CDCl$_3$) δ 6.89-6.81 (m, 2H), 6.70 (tt, J=8.9, 2.3 Hz, 1H), 5.05-4.99 (m, 1H), 3.61 (d, J=10.0 Hz, 1H), 3.38-3.30 (m, 1H), 2.84 (dddd, J=12.7, 8.7, 6.7, 2.1 Hz, 1H), 2.74 (d, J=10.0 Hz, 1H), 2.56-2.45 (m, 1H), 2.25 (tdd, J=7.0, 12.6, 10.4 Hz, 1H), 1.84-1.68 (m, 2H), 1.25 (s, 3H), 1.03 (t, J=7.5 Hz, 3H). LC-MS (Method B): m/z=281.2 [M+H]$^+$, 561.4 [2M+H]$^+$, 0.92 min. e.e.>99% as determined on a Chiralpak AD-H (25×0.46 cm), 5 μm column using a mobile phase of n-hexane/ethanol 85/15% v/v, flow rate: 1.0 mL/min, retention time: 9.9 min.

3-(3,5-difluorophenyl)-6-ethyl-6-methyl-1,2,3,7-tetrahydropyrazolo[1,2-a]pyrazol-5-one as the fourth eluting stereoisomer (Example 22). $^1$H NMR (400 MHz, CDCl$_3$) δ 6.88-6.80 (m, 2H), 6.70 (tt, J=8.9, 2.3 Hz, 1H), 5.03-4.95 (m, 1H), 3.42-3.31 (m, 2H), 2.90-2.78 (m, 2H), 2.54-2.44 (m, 1H), 2.27 (tdd, J=6.9, 12.7, 10.4 Hz, 1H), 1.65 (q, J=7.5 Hz, 2H), 1.38 (s, 3H), 0.96 (t, J=7.5 Hz, 3H). LC-MS (Method B): m/z=281.2 [M+H]$^+$, 561.4 [2M+H]$^+$, 0.91 min. e.e.>99% as determined on a Chiralpak AD-H (25×0.46 cm), 5 μm column using a mobile phase of n-hexane/ethanol 85/15% v/v, flow rate: 1.0 mL/min, retention time: 11.3 min.

Examples 23 and 24

3-fluoro-5-(6-ethyl-6-methyl-5-oxo-1,2,3,7-tetrahydropyrazolo[1,2-a]pyrazol-3-yl)benzonitrile

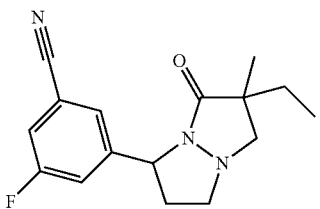 [SMILES: CCC1(C)CN2CCC(c3cc(F)cc(C#N)c3)N2C1=O]

Prepared according to Procedure A to give the title compounds as a mixture of the four stereoisomers. This mixture was resolved by chiral HPLC on a Chiralpak AD-H (25×2.0 cm), 5 μm column using a mobile phase of n-hexane/ethanol 55/45% v/v and a flow rate of 17 mL/min to afford the two diastereomeric title compounds as single enantiomers.

3-fluoro-5-(6-ethyl-6-methyl-5-oxo-1,2,3,7-tetrahydropyrazolo[1,2-a]pyrazol-3-yl)benzonitrile as the third eluting stereoisomer (Example 23). $^1$H NMR (400 MHz, CDCl$_3$) δ 7.43 (s, 1H), 7.33-7.24 (m, 2H), 5.06 (t, J=7.9 Hz, 1H), 3.63 (d, J=10.0 Hz, 1H), 3.42-3.29 (m, 1H), 2.94-2.82 (m, 1H), 2.77 (d, J=10.3 Hz, 1H), 2.61-2.48 (m, 1H), 2.23 (tdd, J=7.0, 12.6, 10.5 Hz, 1H), 1.83-1.66 (m, 2H), 1.26 (s, 3H), 1.03 (t, J=7.5 Hz, 3H). LC-MS (Method A): m/z=288.2 [M+H]$^+$, 0.86 min. e.e.>99% as determined on a Chiralpak AD-H (25×0.46 cm), 5 m column using a mobile phase of n-hexane/ethanol 55/45% v/v, flow rate: 1.0 mL/min, retention time: 8.5 min.

3-fluoro-5-(6-ethyl-6-methyl-5-oxo-1,2,3,7-tetrahydropyrazolo[1,2-a]pyrazol-3-yl)benzonitrile as the fourth eluting stereoisomer (Example 24). $^1$H NMR (400 MHz, CDCl$_3$) δ 7.42 (s, 1H), 7.32-7.24 (m, 2H), 5.07-5.00 (m, 1H), 3.46-3.32 (m, 2H), 2.95-2.80 (m, 2H), 2.58-2.47 (m, 1H), 2.26 (tdd, J=7.0, 12.7, 10.4 Hz, 1H), 1.66 (q, J=7.5 Hz, 2H), 1.38 (s, 3H), 0.96 (t, J=7.5 Hz, 3H). LC-MS (Method A): m/z=288.2 [M+H]$^+$, 0.86 min. e.e.>99% as determined on a Chiralpak AD-H (25×0.46 cm), 5 Cpm column using a mobile phase of n-hexane/ethanol 55/45% v/v, flow rate: 1.0 mL/min, retention time: 9.9 min.

Examples 25 and 26

6-ethyl-3-(5-fluoro-3-pyridyl)-6-methyl-1,2,3,7-tetrahydropyrazolo[1,2-a]pyrazol-5-one

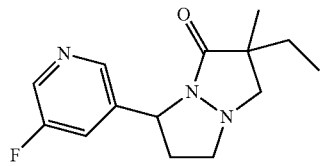 [SMILES: CCC1(C)CN2CCC(c3cncc(F)c3)N2C1=O]

Prepared according to Procedure A to give the title compounds as a mixture of the four stereoisomers. This mixture was resolved by chiral SFC on a Chiralpak AD-H (25×2.0 cm), 5 μm column using a mobile phase of 12% methanol in CO$_2$ and a flow rate of 45 mL/min to afford the two diastereomeric title compounds as single enantiomers.

6-ethyl-3-(5-fluoro-3-pyridyl)-6-methyl-1,2,3,7-tetrahydropyrazolo[1,2-a]pyrazol-5-one as the third eluting stereoisomer (Example 25). $^1$H NMR (400 MHz, CDCl$_3$) δ 8.44-8.41 (m, 1H), 8.40 (d, J=2.8 Hz, 1H), 7.39 (td, J=2.1, 9.1 Hz, 1H), 5.11 (t, J=7.9 Hz, 1H), 3.62 (d, J=9.8 Hz, 1H), 3.42-3.33 (m, 1H), 2.90 (dddd, J=12.7, 8.8, 6.7, 2.0 Hz, 1H), 2.77 (d, J=10.3 Hz, 1H), 2.60-2.47 (m, 1H), 2.29 (tdd, J=7.0, 12.7, 10.4 Hz, 1H), 1.83-1.65 (m, 2H), 1.26 (s, 3H), 1.02 (t, J=7.5 Hz, 3H). LC-MS (Method A): m/z=264.2 [M+H]$^+$, 0.63 min. e.e.>99% as determined on a Chiralpak AD-H (25×0.46 cm), 5 μm column using a mobile phase of n-hexane/ethanol 75/25% v/v, flow rate: 1.0 mL/min, retention time: 22.6 min.

6-ethyl-3-(5-fluoro-3-pyridyl)-6-methyl-1,2,3,7-tetrahydropyrazolo[1,2-a]pyrazol-5-one as the fourth eluting stereoisomer (Example 26). $^1$H NMR (400 MHz, CDCl$_3$) δ 8.42 (t, J=1.6 Hz, 1H), 8.40 (d, J=2.8 Hz, 1H), 7.38 (td, J=2.0, 9.0 Hz, 1H), 5.13-5.04 (m, 1H), 3.40 (d, J=10.0 Hz, 2H), 2.92 (dddd, J=12.7, 8.7, 6.6, 2.1 Hz, 1H), 2.84 (d, J=9.8 Hz, 1H), 2.59-2.48 (m, 1H), 2.32 (tdd, J=7.0, 12.8, 10.3 Hz, 1H), 1.66 (q, J=7.5 Hz, 2H), 1.37 (s, 3H), 0.96 (t, J=7.5 Hz, 3H). LC-MS (Method A): m/z=264.2 [M+H]$^+$, 0.63 min. e.e.>99% as determined on a Chiralpak AD-H (25×0.46 cm), 5 μm column using a mobile phase of n-hexane/ethanol 75/25% v/v, flow rate: 1.0 mL/min, retention time: 31.3 min.

Example 27

6-(2,2-difluoroethyl)-3-(3-fluorophenyl)-6-methyl-1,2,3,7-tetrahydropyrazolo[1,2-a]pyrazol-5-one

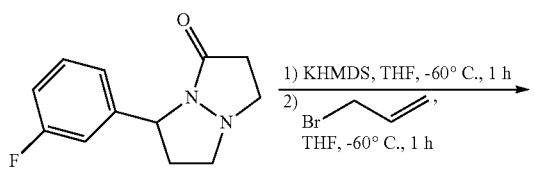

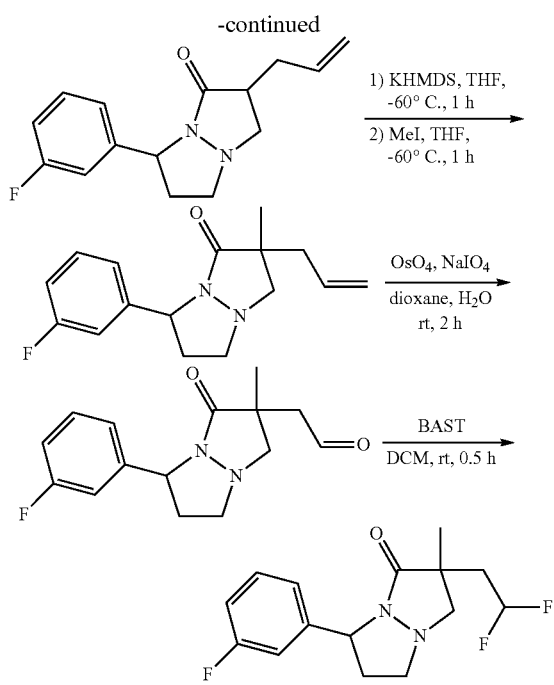

6-allyl-3-(3-fluorophenyl)-2,3,6,7-tetrahydro-1H-pyrazolo[1,2-a]pyrazol-5-one: To a stirring mixture of 3-(3-fluorophenyl)-2,3,6,7-tetrahydro-1H-pyrazolo[1,2-a]pyrazol-5-one (9.3 g, 42.3 mmol) in tetrahydrofuran (150 mL) was added a solution of potassium bis(trimethylsilyl)amide in tetrahydrofuran (1 M, 42.3 mL, 42.3 mmol) dropwise at −60° C. The resulting mixture was stirred for 1 hour at −60° C. followed by the addition of a solution of allyl bromide (5.12 g, 42.3 mmol) in tetrahydrofuran (20 mL) dropwise. After stirring for 1 hour at −60° C., the reaction mixture was quenched by the addition of saturated aqueous ammonium chloride (50 mL) and extracted with ethyl acetate (3×50 mL). The combined organic layers were washed with brine, dried over anhydrous sodium sulfate, filtered and concentrated under vacuum. The residue was purified by column chromatography (ethyl acetate/petroleum ether, 1/3) to afford the title compound (2.3 g, 21%) as a yellow oil. LCMS (Method D): m/z=261.2 [M+H]$^+$, 0.886 min.

6-allyl-3-(3-fluorophenyl)-6-methyl-1,2,3,7-tetrahydropyrazolo[1,2-a]pyrazol-5-one: To a stirring mixture of 6-allyl-3-(3-fluorophenyl)-2,3,6,7-tetrahydro-1H-pyrazolo[1,2-a]pyrazol-5-one (2.3 g, 8.85 mmol) in tetrahydrofuran (50 mL) at −60° C. was added a solution of potassium bis(trimethylsilyl)amide in tetrahydrofuran (1 M, 8.85 mL, 8.85 mmol) dropwise. The resulting mixture was stirred for 1 hour at −60° C., and followed by the addition of a solution of iodomethane (1.26 g, 8.85 mmol) in tetrahydrofuran (5 mL) dropwise. After stirring for 1 hour at −60° C., the reaction mixture was quenched by the addition of saturated aqueous ammonium chloride (20 mL) and extracted with ethyl acetate (3×30 mL). The combined organic layers were washed with brine, dried over anhydrous sodium sulfate, filtered and concentrated under vacuum. The residue was purified by column chromatography (ethyl acetate/petroleum ether, 1/3) to afford the title compound (1.65 g, 68%) as a racemic mixture isolated as a yellow oil. LCMS (Method D): m/z=275.2 [M+H]$^+$, 0.955 min.

2-[3-(3-fluorophenyl)-6-methyl-5-oxo-1,2,3,7-tetrahydropyrazolo[1,2-a]pyrazol-6-yl]acetaldehyde: To a stirring mixture of 6-allyl-3-(3-fluorophenyl)-6-methyl-1,2,3,7-tetrahydropyrazolo[1,2-a]pyrazol-5-one (1.70 g, 6.20 mmol) in 1,4-dioxane (30 mL) and water (10 mL) were added osmium tetraoxide (16 mg, 0.06 mmol) and sodium periodate (2.66 g, 12.4 mmol). After stirring for 2 hours at room temperature, the reaction mixture was diluted with water (20 mL) and extracted with ethyl acetate (3×30 mL). The combined organic layers were washed with brine, dried over anhydrous sodium sulfate, filtered and concentrated under vacuum. The residue was purified by column chromatography (ethyl acetate/petroleum ether, 1/4) to afford the title compound as a racemic mixture isolates as a yellow oil (800 mg, 47%). LCMS (Method D): m/z=277.2 [M+H]$^+$, 0.761 min.

6-(2,2-difluoroethyl)-3-(3-fluorophenyl)-6-methyl-1,2,3,7-tetrahydropyrazolo[1,2-a]pyrazol-5-one: To a stirring mixture of 2-[3-(3-fluorophenyl)-6-methyl-5-oxo-1,2,3,7-tetrahydropyrazolo[1,2-a]pyrazol-6-yl]acetaldehyde (200 mg, 0.72 mmol) in dichloromethane (1 mL) was added Bis(2-methoxyethyl)aminosulfur trifluoride (1.59 g, 7.20 mmol). After stirring for 0.5 hour at room temperature, the reaction mixture was quenched by the addition of water (20 mL) and extracted with ethyl acetate (3×30 mL). The combined organic layers were washed with brine, dried over anhydrous sodium sulfate, filtered and concentrated under vacuum. The residue was purified by Prep-HPLC with the following conditions: Column: XBridge Prep C18, 5 μm, 19×150 mm; Mobile Phase A: water (0.1% NH$_4$HCO$_3$), Mobile Phase B: ACN; Flow rate: 20 mL/min; Gradient: 22% B to 55% B over 8 min; UV 254 & 220 nm; Rt: 7.78 min to afford the title compound as a racemic mixture. $^1$H NMR (400 MHz, CD$_3$OD) δ 7.40-7.32 (m, 1H), 7.15-7.10 (m, 1H), 7.06-6.96 (m, 2H), 6.30-5.97 (m, 1H), 5.01 (t, J=8.0 Hz, 1H), 3.53 (d, J=9.6 Hz, 1H), 3.46-3.34 (m, 1H), 3.02-2.87 (m, 2H), 2.65-2.51 (m, 1H), 2.33-1.99 (m, 3H), 1.43 (s, 3H). LC-MS (Method J): m/z=299.0 [M+H]$^+$, 1.238 min.

Example 28

2-(3-(3-fluorophenyl)-6-methyl-5-oxo-1,2,3,7-tetrahydropyrazolo[1,2-a]pyrazol-6-yl)acetonitrile

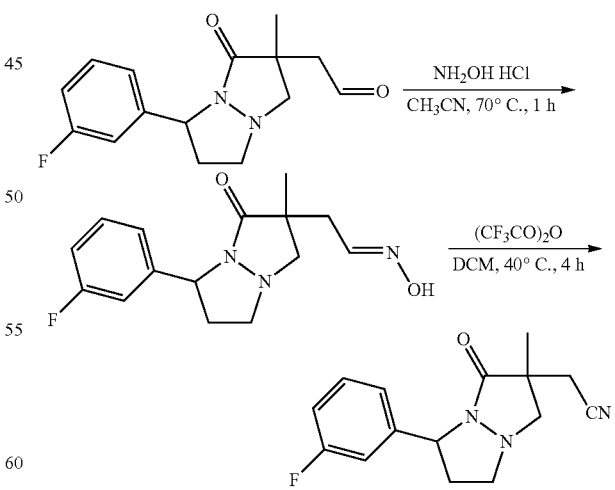

2-[3-(3-fluorophenyl)-6-methyl-5-oxo-1,2,3,7-tetrahydropyrazolo[1,2-a]pyrazol-6-yl]acetaldehyde oxime: Hydroxylamine hydrochloride (45 mg, 0.65 mmol) was added to a mixture of 2-[3-(3-fluorophenyl)-6-methyl-5-oxo-1,2,3,7-tetrahydropyrazolo[1,2-a]pyrazol-6-yl]acetaldehyde (150 mg, 0.54 mmol) in acetonitrile (8 mL). The resulting mixture was stirred for 1 hour at 70° C. After cooling to room temperature, the reaction mixture was quenched by the addition of water (20 mL) and extracted with ethyl acetate (3×20 mL). The combined organic layers were washed with brine, dried over anhydrous sodium sulfate, and filtered. The filtrate was concentrated under vacuum to afford the title compound (125 mg crude) as a yellow oil. LCMS (Method K): m/z=292.15 [M+H]$^+$, 0.842 min.

2-[3-(3-fluorophenyl)-6-methyl-5-oxo-1,2,3,7-tetrahydropyrazolo[1,2-a]pyrazol-6-yl]acetonitrile: Trifluoroacetic anhydride (451 mg, 2.15 mmol) was added to a mixture of 2-(7-(3-fluorophenyl)-2-methyl-1-oxo-hexahydropyrazolo[1,2-a]pyrazol-2-yl)acetaldehyde oxime (125 mg, 0.43 mmol) in dichloromethane (6 mL). After stirring for 4 hours at 40° C., the reaction mixture was quenched by the addition of water (20 mL) and extracted with dichloromethane (3×20 mL). The combined organic layers were washed with brine, dried over anhydrous sodium sulfate, filtered and concentrated under vacuum. The residue was purified by column chromatography (ethyl acetate/petroleum ether, 2/1) to afford the racemate as a yellow oil. LCMS (Method F): m/z=274.25 [M+H]$^+$, 0.721 min. The racemate was separated by Prep-Chiral-HPLC with the following conditions: Column: CHIRALPAK IG UL001, 20×250 mm, 5 µm; Mobile Phase A: Hexane, Mobile Phase B: EtOH; Flow rate: 20 mL/min; Gradient: 50% B to 50% B over 20 min; UV 254 & 220 nm; Rt: 17.149 min to afford the title compound as the second eluting enantiomer. $^1$H NMR (300 MHz, Methanol-d$_4$) δ 7.39 (td, J=7.9, 5.8 Hz, 1H), 7.18-7.10 (m, 1H), 7.11-6.99 (m, 2H), 5.04 (t, J=7.9 Hz, 1H), 3.62 (d, J=9.5 Hz, 1H), 3.45 (t, J=7.9 Hz, 1H), 3.07-2.92 (m, 2H), 2.87-2.69 (m, 2H), 2.67-2.54 (m, 1H), 2.36-2.19 (m, 1H), 1.46 (s, 3H). LC-MS (Method I): m/z=274.1 [M+H]$^+$, 1.129 min.

sulfonate: Trifluoromethanesulfonic anhydride (55.8 mg, 0.20 mmol) and pyridine (17.1 mg, 0.22 mmol) were added to solution of 6-ethyl-3-(3-fluorophenyl)-6-(hydroxymethyl)-1,2,3,7-tetrahydropyrazolo[1,2-a]pyrazol-5-one (50 mg, 0.18 mmol) in DCM (2 mL). The reaction mixture was stirred at rt overnight. The reaction mixture was concentrated to dryness and the residue was taken up in EtOAc (25 mL), washed with 2×10 mL water and 1×10 mL saturated brine solution. The organics were separated and dried over MgSO$_4$ before concentrating under reduced pressure. The resulting residue was purified by flash column chromatography eluting with 25% EtOAc in hexanes to yield the title compound as a racemic mixture isolated as a colorless solid (15 mg, 21%). LCMS (Method C): m/z=411.3 [M+H]$^+$.

6-(chloromethyl)-6-ethyl-3-(3-fluorophenyl)-1,2,3,7-tetrahydropyrazolo[1,2-a]pyrazol-5-one: LiCl (8.5 mg, 0.2 mmol) was added to a solution of [6-ethyl-3-(3-fluorophenyl)-5-oxo-1,2,3,7-tetrahydropyrazolo[1,2-a]pyrazol-6-yl]methyl trifluoromethanesulfonate (44 mg, 0.11 mmol) in DCM (2 mL). The reaction mixture was stirred at rt for 3 h and then concentrated to dryness. The resulting residue was taken up in EtOAc (25 mL) and washed with 2×20 mL water and 1×25 mL saturated brine solution. The organics were then separated and dried over MgSO$_4$ before concentrating to dryness. The crude material was purified by flash column chromatography eluting with 50% EtOAc in hexanes to yield the title compound as a racemic mixture. $^1$H-NMR (400 MHz; CDCl$_3$): δ 7.35-7.31 (m, 1H), 7.15-7.13 (m, 1H), 7.08-7.05 (m, 1H), 7.00-6.97 (m, 1H), 5.10-5.06 (m, 1H), 3.84 (d, J=11.3 Hz, 1H), 3.70-3.65 (m, 1H), 3.54 (d, J=11.3 Hz, 1H), 3.49-3.43 (m, 1H), 3.31-3.27 (m, 1H), 2.91-2.83 (m, 1H), 2.73-2.68 (m, 1H), 2.38-2.31 (m, 1H), 1.90-1.79 (m, 2H), 1.11 (t, J=7.5 Hz, 3H). LCMS (Method C): m/z=297.1, 299.1 [M+H]$^+$.

Example 29

6-(chloromethyl)-6-ethyl-3-(3-fluorophenyl)-1,2,3,7-tetrahydropyrazolo[1,2-a]pyrazol-5-one Example 30

6-Ethyl-6-(fluoromethyl)-3-(3-fluorophenyl)-1,2,3,7-tetrahydropyrazolo[1,2-a]pyrazol-5-one

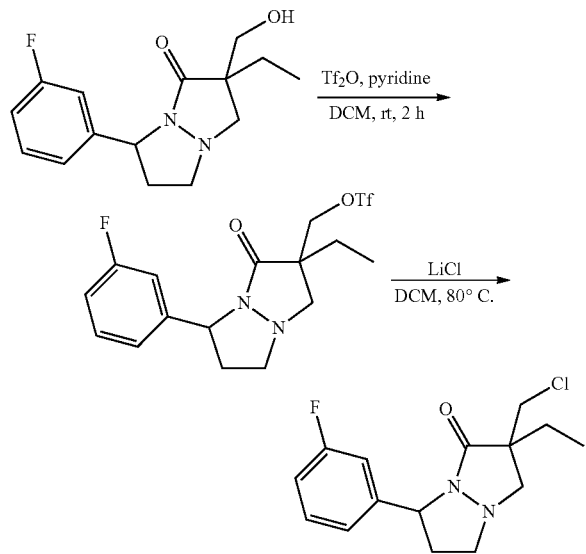

[6-ethyl-3-(3-fluorophenyl)-5-oxo-1,2,3,7-tetrahydropyrazolo[1,2-a]pyrazol-6-yl]methyl trifluoromethane-

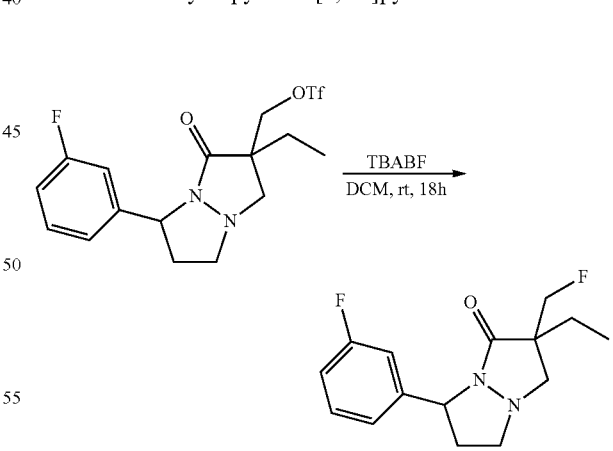

TBABF (36 mg, 0.13 mmol) was added to a solution of [6-ethyl-3-(3-fluorophenyl)-5-oxo-1,2,3,7-tetrahydropyrazolo[1,2-a]pyrazol-6-yl]methyl trifluoromethanesulfonate (44 mg, 0.11 mmol) in DCM (2 mL). The reaction mixture was stirred at rt for 3 h and then concentrated to dryness. The resulting residue was taken up in EtOAc (25 mL) and washed with 2×20 mL water and 1×25 mL saturated brine solution. The organics were separated and dried over MgSO$_4$ before concentrating to dryness. The crude product was purified by flash column chromatography eluting with 50% EtOAc in hexanes to provide the title compound as a racemic mixture. ¹H-NMR (400 MHz; CDCl₃): δ 7.32 (dt, J=8.0, 4.0 Hz, 1H), 7.13-7.10 (m, 1H), 7.07-7.03 (m, 1H), 6.99-6.93 (m, 1H), 5.10-5.06 (m, 1H), 4.69 (dd, J=47.1, 9.2 Hz, 1H), 4.31-4.17 (m, 1H), 3.72-3.63 (m, 1H), 3.41-3.35 (m, 1H), 3.28-3.23 (m, 1H), 2.87-2.80 (m, 1H), 2.63-2.56 (m, 1H), 2.37-2.22 (m, 1H), 1.75-1.60 (m, 2H), 1.12-1.05 (m, 3H). LCMS (Method C): m/z=281.1, [M+H]⁺.

Examples 31 and 32

3-fluoro-5-(6-(difluoromethyl)-6-ethyl-5-oxo-1,2,3,7-tetrahydropyrazolo[1,2-a]pyrazol-3-yl)benzonitrile

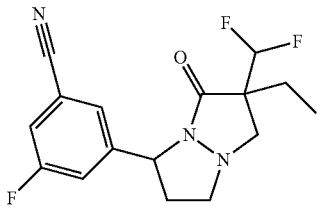 [SMILES: CCC1(C(F)F)CN2CCC(c3cc(F)cc(C#N)c3)N2C1=O]

Prepared according to Procedure B and purified by flash chromatography to provide the two diastereomeric title compounds.

3-Fluoro-5-(6-(difluoromethyl)-6-ethyl-5-oxo-1,2,3,7-tetrahydropyrazlo[1,2-a]pyrazol-3-yl)benzonitrile as the first eluting diastereomer (Example 31). ¹H-NMR (400 MHz; CDCl₃): δ 7.43 (td, J=1.3, 0.3 Hz, 1H), 7.31-7.29 (m, 2H), 5.96 (dd, J=56.6, 56.1 Hz, 1H), 5.07 (dd, J=8.2, 7.9 Hz, 1H), 3.59-3.42 (m, 2H), 3.36 (t, J=7.8 Hz, 1H), 2.87 (dddd, J=12.6, 8.8, 6.7, 1.2 Hz, 1H), 2.60 (dddd, J=11.1, 8.4, 6.9, 1.5 Hz, 1H), 2.21 (ddt, J=12.5, 11.2, 7.2 Hz, 1H), 1.92 (dq, J=14.3, 7.2 Hz, 1H), 1.76 (ddd, J=13.9, 7.5, 1.2 Hz, 1H), 1.12 (t, J=7.5 Hz, 3H). LCMS (Method C): m/z=324.3 [M+H]⁺. e.e.=90%.

3-Fluoro-5-(6-(difluoromethyl)-6-ethyl-5-oxo-1,2,3,7-tetrahydropyrazlo[1,2-a]pyrazol-3-yl)benzonitrile as the second eluting diastereomer (Example 32). ¹H-NMR (400 MHz; CDCl₃): δ 7.41 (t, J=1.3 Hz, 1H), 7.30-7.29 (m, 1H), 7.28-7.27 (m, 1H), 6.08-5.80 (m, 1H), 5.07-5.03 (m, 1H), 3.97 (d, J=11.3 Hz, 1H), 3.40-3.35 (m, 1H), 3.00-2.91 (m, 2H), 2.61-2.55 (m, 1H), 2.28 (ddt, J=12.7, 10.1, 6.9 Hz, 1H), 1.93-1.85 (m, 1H), 1.77-1.67 (m, 2H), 1.06 (t, J=7.5 Hz, 3H). LCMS (Method C): m/z=324.3 [M+H]⁺. e.e.=90%.

Examples 33 and 34

6-(difluoromethyl)-6-ethyl-3-(5-fluoro-3-pyridyl)-1,2,3,7-tetrahydropyrazolo[1,2-a]pyrazol-5-one

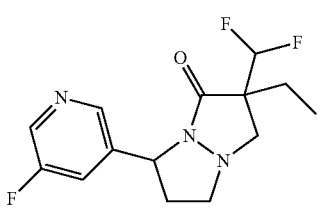 [SMILES: CCC1(C(F)F)CN2CCC(c3cncc(F)c3)N2C1=O]

Prepared according to Procedure B and purified by flash chromatography (0-70% ethyl acetate in hexanes) to provide the two diastereomeric title compounds.

6-(Difluoromethyl)-6-ethyl-3-(5-fluoro-3-pyridyl)-1,2,3,7-tetrahydropyrazolo[1,2-a]pyrazol-5-one as the second eluting diastereomer isolated as a mixture of enantiomers (Example 33). ¹H-NMR (400 MHz; CDCl₃): δ 8.43-8.42 (m, 1H), 8.41 (d, J=2.8 Hz, 1H), 7.39 (dddd, J=9.1, 2.7, 1.9, 0.7 Hz, 1H), 5.97 (t, J=56.3 Hz, 1H), 5.15-5.11 (m, 1H), 3.55 (d, J=2.1 Hz, 1H), 3.44 (d, J=11.9 Hz, 1H), 3.38 (t, J=7.7 Hz, 1H), 2.88 (dddd, J=12.6, 8.8, 6.7, 1.2 Hz, 1H), 2.64-2.57 (m, 1H), 2.32-2.22 (m, 1H), 1.91 (dt, J=14.1, 7.2 Hz, 1H), 1.75 (ddd, J=14.4, 7.0, 1.2 Hz, 1H), 1.11 (t, J=7.5 Hz, 3H). LCMS (Method C): m/z=300.1 [M+H]⁺.

6-(Difluoromethyl)-6-ethyl-3-(5-fluoro-3-pyridyl)-1,2,3,7-tetrahydropyrazolo[1,2-a]pyrazol-5-one as the first eluting diastereomer isolated as a mixture of enantiomers (Example 34). ¹H-NMR (400 MHz; CDCl₃): δ 8.40 (dd, J=4.6, 2.2 Hz, 2H), 7.39 (dddd, J=9.1, 2.6, 1.9, 0.7 Hz, 1H), 5.93 (t, J=55.9 Hz, 1H), 5.11-5.08 (m, 1H), 3.95 (dd, J=11.1, 0.5 Hz, 1H), 3.38-3.33 (m, 1H), 3.00-2.92 (m, 2H), 2.63-2.56 (m, 1H), 2.32 (ddt, J=12.7, 9.8, 6.8 Hz, 1H), 1.89 (dt, J=14.5, 7.3 Hz, 1H), 1.75-1.71 (m, 1H), 1.06 (t, J=7.5 Hz, 3H). LCMS (Method C): m/z=300.1 [M+H]⁺.

Example 35

3-fluoro-5-(6-(cyclopropylmethyl)-6-methyl-5-oxo-1,2,3,7-tetrahydropyrazolo[1,2-a]pyrazol-3-yl)benzonitrile

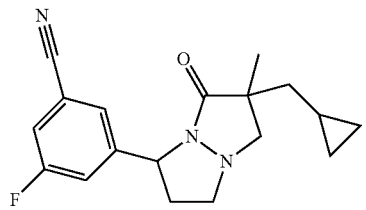 [SMILES: CC1(CC2CC2)CN2CCC(c3cc(F)cc(C#N)c3)N2C1=O]

Prepared according to Procedure B and purified by flash chromatography (0-70% ethyl acetate in hexanes) to provide the title compound as the first eluting diastereomer (a racemic mixture of a single diastereomer). ¹H-NMR (400 MHz; CDCl₃): δ 7.41 (t, J=1.3 Hz, 1H), 7.30-7.29 (m, 1H), 7.28-7.27 (m, 1H), 5.00-5.05 (m, 1H), 3.45-3.49 (m, 1H), 3.38-3.36 (m, 1H), 3.03-3.00 (m, 1H), 2.90-2.80 (m, 1H), 2.52-2.48 (m, 1H), 2.34-2.28 (m, 1H), 1.60-1.40 (m, 2H), 1.46 (s, 3H), 0.70-0.60 (m, 1H), 0.55-0.45 (m, 2H), 0.20-0.10 (m, 2H). LCMS (Method C): m/z=314.3 [M+H]⁺.

Examples 36, 37, 38 and 39

5-[6-(1,1-difluoroethyl)-6-methyl-5-oxo-1,2,3,7-tetrahydropyrazolo[1,2-a]pyrazol-3-yl]pyridine-3-carbonitrile and 5-[6-(difluoromethyl)-6-methyl-5-oxo-1,2,3,7-tetrahydropyrazolo[1,2-a]pyrazol-3-yl]pyridine-3-carbonitrile

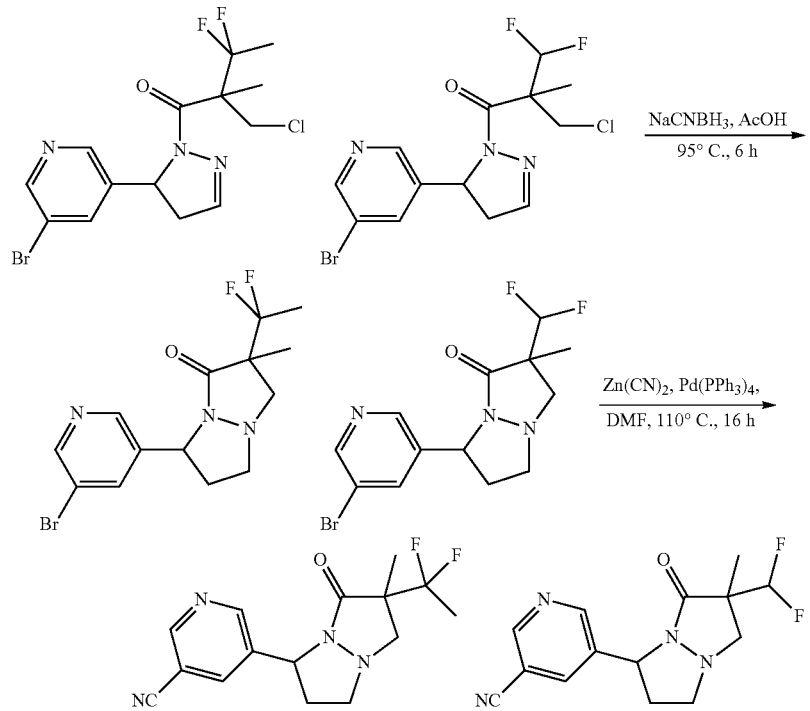

3-(5-bromo-3-pyridyl)-6-(1,1-difluoroethyl)-6-methyl-1,2,3,7-tetrahydropyrazolo[1,2-a]pyrazol-5-one and 3-(5-bromo-3-pyridyl)-6-(difluoromethyl)-6-methyl-1,2,3,7-tetrahydropyrazolo[1,2-a]pyrazol-5-one: Prepared according to Procedure B to give a mixture of 3-(5-bromo-3-pyridyl)-6-(1,1-difluoroethyl)-6-methyl-1,2,3,7-tetrahydropyrazolo[1,2-a]pyrazol-5-one. LC-MS (Method O): m/z=360.1 362.1 [M+H]$^+$, 1.180 min and 3-(5-bromo-3-pyridyl)-6-(difluoromethyl)-6-methyl-1,2,3,7-tetrahydropyrazolo[1,2-a]pyrazol-5-one. LC-MS (Method O): m/z=346.1, 348.1 [M+H]$^+$, 1.133 min as a light yellow oil. The crude residue was used without purification in the next step.

5-[6-(1,1-difluoroethyl)-6-methyl-5-oxo-1,2,3,7-tetrahydropyrazolo[1,2-a]pyrazol-3-yl]pyridine-3-carbonitrile and 5-[6-(difluoromethyl)-6-methyl-5-oxo-1,2,3,7-tetrahydropyrazolo[1,2-a]pyrazol-3-yl]pyridine-3-carbonitrile: Prepared according to Procedure C and purified by Prep-HPLC with the following conditions: column: Agela Durashell C18 150 mm×25 mm 5 μm; mobile phase A: water (10 mM NH$_4$HCO$_3$), mobile phase B: ACN; 10%-35% B over 10.5 min to provide the title compounds, which were further purified by Prep-TLC (SiO$_2$, PE:EtOAc=1:1) to yield pure products.

5-[6-(1,1-difluoroethyl)-6-methyl-5-oxo-1,2,3,7-tetrahydropyrazolo[1,2-a]pyrazol-3-yl]pyridine-3-carbonitrile as the second eluting product (89% ee). This compound was further purified by SFC with the following conditions: Instrument: Thar SFC80 preparative SFC; Column: Chiralpak AD-H 250 mm×30 mm i.d. 5 μm; Mobile phase A: CO$_2$ Mobile phase B: MeOH (0.1% NH$_3$H$_2$O); Gradient: B %=30%; Flow rate: 65 g/min; Wavelength: 220 nm; Column temperature: 40° C.; System back pressure: 100 bar to provide the first eluting isomer as a single enantiomer (Example 36). $^1$H NMR (400 MHz, CDCl$_3$): δ 8.81 (d, J=1.9 Hz, 1H), 8.77 (d, J=2.1 Hz, 1H), 7.90 (t, J=2.0 Hz, 1H), 5.10 (t, J=7.8 Hz, 1H), 4.16 (br d, J=10.2 Hz, 1H), 3.41 (br s, 1H), 3.01-2.84 (m, 2H), 2.59 (br s, 1H), 2.33-2.22 (m, 1H), 1.76 (t, J=19.5 Hz, 3H), 1.44 (s, 3H). LC-MS (Method N): m/z=307.3 [M+H]$^+$, 1.235 min.

5-[6-(1,1-difluoroethyl)-6-methyl-5-oxo-1,2,3,7-tetrahydropyrazolo[1,2-a]pyrazol-3-yl]pyridine-3-carbonitrile as the fourth eluting product (89% ee). This compound was further purified by SFC with the following conditions: Instrument: Thar SFC80 preparative SFC; Column: Chiralpak AD-H 250 mm×30 mm i.d. 5 μm; Mobile phase A: CO$_2$ Mobile phase B: MeOH (0.1% NH$_3$H$_2$O); Gradient: B %=40%; Flow rate: 70 g/min; Wavelength: 220 nm; Column temperature: 40° C.; System back pressure: 100 bar to afford the second eluting isomer as a single enantiomer (Example 37). $^1$H NMR (400 MHz, CDCl$_3$): δ 8.80 (d, J=1.9 Hz, 1H), 8.77 (d, J=2.1 Hz, 1H), 7.91 (t, J=2.0 Hz, 1H), 5.09 (t, J=8.0 Hz, 1H), 3.49 (s, 2H), 3.37 (t, J=7.8 Hz, 1H), 2.92 (dddd, J=12.7, 8.5, 6.9, 1.1 Hz, 1H), 2.70-2.62 (m, 1H), 2.27 (tdd, J=12.6, 10.9, 7.2 Hz, 1H), 1.84 (t, J=20.0 Hz, 3H), 1.52 (s, 3H). LC-MS (Method N): m/z=307.3 [M+H]$^+$, 1.291 min.

5-[6-(difluoromethyl)-6-methyl-5-oxo-1,2,3,7-tetrahydropyrazolo[1,2-a]pyrazol-3-yl]pyridine-3-carbonitrile as the first eluting product (88% ee) (Example 38). $^1$H NMR (400 MHz, CDCl$_3$) δ 8.81 (d, J=2.0 Hz, 1H), 8.77 (s, 1H), 7.91 (t, J=2.1 Hz, 1H), 5.87 (t, J=56 Hz, 1H), 5.06-5.15 (m, 1H), 4.06 (br d, J=11.3 Hz, 1H), 3.41 (br s, 1H), 2.97 (dddd, J=12.8, 8.8, 6.7, 2.1 Hz, 1H), 2.90 (br d, J=11.7 Hz, 1H), 2.60 (br s, 1H), 2.24-2.34 (m, 1H), 1.42 (s, 3H). LC-MS (Method N): m/z=293.3 [M+H]$^+$, 1.154 min.

5-[6-(difluoromethyl)-6-methyl-5-oxo-1,2,3,7-tetrahydropyrazolo[1,2-a]pyrazol-3-yl]pyridine-3-carbonitrile as the third eluting product (85% ee) (Example 39). ¹H NMR (400 MHz, CDCl₃) δ 8.82 (d, J=2.0 Hz, 1H), 8.78 (d, J=2.0 Hz, 1H), 7.93 (t, J=1.9 Hz, 1H), 5.92 (t, J=56 Hz, 1H), 5.10 (t, J=8.0 Hz, 1H), 3.42-3.57 (m, 2H), 3.37 (t, J=7.8 Hz, 1H), 2.84-2.98 (m, 1H), 2.58-2.71 (m, 1H), 2.25 (tdd, J=12.7, 11.0, 7.1 Hz, 1H), 1.51 (s, 3H). LC-MS (Method N): m/z=293.3 [M+H]⁺, 1.208 min.

Examples 40, 41, 42 and 43

3-[6-(1,1-difluoroethyl)-6-methyl-5-oxo-1,2,3,7-tetrahydropyrazolo[1,2-a]pyrazol-3-yl]-5-fluoro-benzonitrile and 3-[6-(difluoromethyl)-6-methyl-5-oxo-1,2,3,7-tetrahydropyrazolo[1,2-a]pyrazol-3-yl]-5-fluoro-benzonitrile

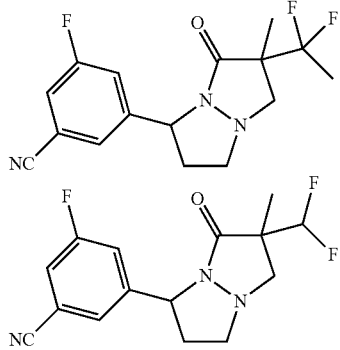

Prepared according to Procedure B and purified by Prep-TLC (SiO₂, PE:EtOAc=1:1) followed by purification by Prep-HPLC with the following conditions: column: Agela Durashell C18 150 mm×25 mm 5 μm; mobile phase: [A: water (0.1% TFA)—B: ACN]; Flow rate: 25 mL/min; Gradient: B % 20%-50% over 10.5 min to afford the title compounds.

3-[6-(difluoromethyl)-6-methyl-5-oxo-1,2,3,7-tetrahydropyrazolo[1,2-a]pyrazol-3-yl]-5-fluoro-benzonitrile as the first eluting product (76% ee) (Example 40). ¹H NMR (400 MHz, CDCl₃) δ 7.42 (s, 1H), 7.29 (s, 1H), 7.27-7.28 (m, 1H), 5.92 (t, J=56.4 Hz, 1H), 5.03 (t, J=7.9 Hz, 1H), 3.40-3.54 (m, 2H), 3.35 (t, J=7.8 Hz, 1H), 2.87 (dddd, J=12.6, 8.6, 7.0, 1.3 Hz, 1H), 2.56-2.65 (m, 1H), 2.23 (tdd, J=12.6, 11.1, 7.3 Hz, 1H), 1.51 (s, 3H). LC-MS (Method N): m/z=310.3 [M+H]⁺, 1.420 min.

3-[6-(difluoromethyl)-6-methyl-5-oxo-1,2,3,7-tetrahydropyrazolo[1,2-a]pyrazol-3-yl]-5-fluoro-benzonitrile as the second eluting product (78% ee) (Example 41). ¹H NMR (400 MHz, CDCl₃) δ 7.40 (s, 1H), 7.29 (s, 1H), 7.27 (d, J=1.1 Hz, 1H), 5.89 (t, J=56 Hz, 1H), 5.00-5.08 (m, 1H), 4.05 (br d, J=11.3 Hz, 1H), 3.38 (br s, 1H), 2.81-3.00 (m, 2H), 2.56 (br d, J=7.1 Hz, 1H), 2.20-2.33 (m, 1H), 1.41 (s, 3H). LC-MS (Method N): m/z=310.3 [M+H]⁺, 1.362 min.

3-[6-(1,1-difluoroethyl)-6-methyl-5-oxo-1,2,3,7-tetrahydropyrazolo[1,2-a]pyrazol-3-yl]-5-fluoro-benzonitrile as the third eluting product. This compound was further purified by SFC (column: IC (250 mm×30 mm, 10 μm); Mobile phase A: CO₂; Mobile phase B: MeOH; B %: 10%-10% over 10 min) to provide the second eluting isomer (Rt=5.5 min) as a single enantiomer (Example 42). ¹H NMR (400 MHz, CDCl₃) δ 7.41 (s, 1H), 7.28 (d, J=0.9 Hz, 1H), 7.26 (d, J=1.3 Hz, 1H), 5.03 (t, J=8.0 Hz, 1H), 3.42-3.52 (m, 2H), 3.35 (t, J=7.8 Hz, 1H), 2.88 (dddd, J=12.7, 8.5, 6.9, 1.3 Hz, 1H), 2.62 (td, J=10.7, 7.8 Hz, 1H), 2.24 (tdd, J=12.6, 11.0, 7.2 Hz, 1H), 1.85 (t, J=20.0 Hz, 3H), 1.53 (s, 3H). LC-MS (Method N): m/z=324.3 [M+H]⁺, 1.499 min.

3-[6-(1,1-difluoroethyl)-6-methyl-5-oxo-1,2,3,7-tetrahydropyrazolo[1,2-a]pyrazol-3-yl]-5-fluoro-benzonitrile as the fourth eluting product. Further purification by SFC (column: AD (250 mm×30 mm, 5 μm); Mobile phase A: CO₂; Mobile phase B: MeOH; B %: 15%-15% over 10 min) provided the second eluting isomer (Rt=8 min) as a single enantiomer (Example 43). ¹H NMR (400 MHz, CDCl₃) δ 7.40 (s, 1H), 7.23-7.30 (m, 2H), 5.04 (t, J=7.9 Hz, 1H), 4.14 (br d, J=11.5 Hz, 1H), 3.38 (br s, 1H), 2.79-2.98 (m, 2H), 2.46-2.62 (m, 1H), 2.18-2.32 (m, 1H), 1.76 (t, J=19.5 Hz, 3H), 1.44 (s, 3H). LC-MS (Method N): m/z=324.3 [M+H]⁺, 1.422 min.

Example 44

5-(6-(difluoromethyl)-6-ethyl-7-oxohexahydropyrazolo[1,2-a]pyrazol-1-yl)nicotinonitrile

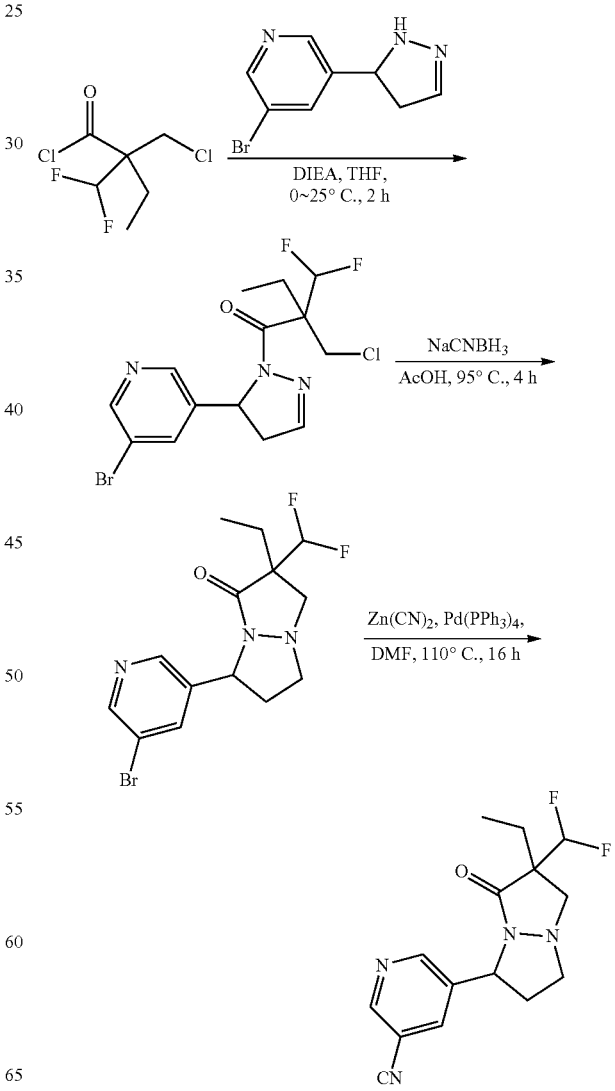

1-(5-(5-bromopyridin-3-yl)-4,5-dihydro-1H-pyrazol-1-yl)-2-(chloromethyl)-2-(difluoromethyl)butan-1-one: To a solution of 3-bromo-5-[4,5-dihydro-1H-pyrazol-5-yl]pyridine (1.43 g, 6.34 mmol) in THF (15 mL) was added DIPEA (1.64 g, 12.68 mmol) and a solution of 2-(chloromethyl)-2-(difluoromethyl)butanoyl chloride (1.3 g, 6.34 mmol) in THF (10 mL) at 0° C. under N$_2$. The reaction solution was stirred at 25° C. for 2 h. The mixture was poured into water (60 mL). The aqueous phase was extracted with EtOAc (3×20 mL). The combined organic phase was washed with brine (20 mL), dried over anhydrous Na$_2$SO$_4$, filtered and concentrated under reduced pressure. The residue was purified by silica gel column chromatography (PE:EtOAc=1:1) to give 1-(5-(5-bromopyridin-3-yl)-4,5-dihydro-1H-pyrazol-1-yl)-2-(chloromethyl)-2-(difluoromethyl)butan-1-one (the first eluting racemic diastereomer) and 1-(5-(5-bromopyridin-3-yl)-4,5-dihydro-1H-pyrazol-1-yl)-2-(chloromethyl)-2-(difluoromethyl)butan-1-one (the second eluting racemic diastereomer). LCMS (Method N): m/z=394.1, 396.0 [M+H]$^+$, 1.308 min.

7-(5-bromopyridin-3-yl)-2-(difluoromethyl)-2-ethyltetrahydropyrazolo[1,2-a]pyrazol-1(5H)-one: Prepared from 1-(5-(5-bromopyridin-3-yl)-4,5-dihydro-1H-pyrazol-1-yl)-2-(chloromethyl)-2-(difluoromethyl)butan-1-one (the first eluting racemic diastereomer) (330 mg, 836.20 μmol) using Procedure B and purified by silica gel column chromatography (PE:EtOAc=5:1 to 1:1) to provide the title compound. LCMS (Method O): m/z=360.1, 362.1 [M+H]$^+$, 1.145 min.

5-(6-(difluoromethyl)-6-ethyl-7-oxohexahydropyrazolo[1,2-a]pyrazol-1-yl)nicotinonitrile: Prepared according to Procedure C and purified by prep-HPLC with the following conditions: column: Nano-micro Kromasil C18 100 mm×30 mm 5 μm; Mobile phase A: water (0.1% TFA); Mobile phase B: ACN; B %: 20%-45% B over 10 min followed by neutralization. Further purification by SFC with the following conditions: Instrument: Thar SFC80 preparative SFC; Column: Chiralpak AS-H 250 mm×30 mm i.d. 5 μm; Mobile phase A: CO$_2$; Mobile phase B: MeOH; Gradient: B %=20%; Flow rate: 55 g/min; Wavelength: 220 nm; Column temperature: 40° C.; System back pressure: 100 bar provided the title compound as a single enantiomer (second eluting enantiomer). $^1$H NMR (400 MHz, CDCl$_3$): δ 8.81 (d, J=2.01 Hz, 1H), 8.78 (d, J=2.3 Hz, 1H), 7.91 (t, J=2.0 Hz, 1H), 5.81-6.13 (m, 1H), 5.12 (t, J=8.0 Hz, 1H), 3.54-3.62 (m, 1H), 3.42-3.48 (m, 1H), 3.37 (t, J=7.8 Hz, 1H), 2.90 (dt, J=12.7, 7.3 Hz, 1H), 2.57-2.67 (m, 1H), 2.22 (tt, J=11.9, 7.3 Hz, 1H), 1.85-1.96 (m, 1H), 1.74 (dq, J=14.3, 7.1 Hz, 1H), 1.09 (t, J=7.5 Hz, 3H). LCMS (Method N): m/z=307.3 [M+H]$^+$, 1.264 min.

Examples 45, 46 and 47

6-(1,1-difluoroethyl)-3-(5-fluoro-3-pyridyl)-6-methyl-1,2,3,7-tetrahydropyrazolo[1,2-a]pyrazol-5-one, and 6-(difluoromethyl)-3-(5-fluoro-3-pyridyl)-6-methyl-1,2,3,7-tetrahydropyrazolo[1,2-a]pyrazol-5-one

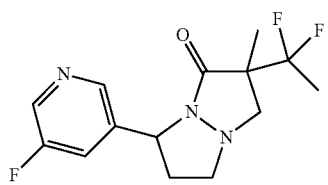

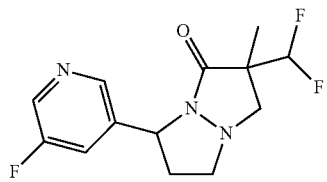

Prepared according to procedure B and purified by Prep-HPLC with the following conditions: Column: Agela Durashell C18 150 mm×25 mm 5 μm; mobile phase A: water (10 mM NH$_4$HCO$_3$) mobile phase B: ACN; Flow rate: 25 mL/min; B %: 15%-35% over 10.5 min to give four product peaks, which were further purified by prep-TLC (SiO$_2$, PE:EtOAC=1:1) to give pure product.

6-(difluoromethyl)-3-(5-fluoro-3-pyridyl)-6-methyl-1,2,3,7-tetrahydropyrazolo[1,2-a]pyrazol-5-one was obtained as the second eluting product (Example 45). $^1$H NMR (400 MHz, CDCl$_3$) δ 8.36-8.46 (m, 2H), 7.38 (td, J=9.0, 2.1 Hz, 1H), 5.92 (t, J=56 Hz, 1H), 5.09 (t, J=7.9 Hz, 1H), 3.39-3.56 (m, 2H), 3.36 (br t, J=7.7 Hz, 1H), 2.83-2.94 (m, 1H), 2.55-2.67 (m, 1H), 2.29 (tdd, J=12.6, 11.0, 7.1 Hz, 1H), 1.50 (m, 3H). LC-MS (Method N): m/z=286.3 [M+H]$^+$, 1.195 min.

6-(1,1-difluoroethyl)-3-(5-fluoro-3-pyridyl)-6-methyl-1,2,3,7-tetrahydropyrazolo[1,2-a]pyrazol-5-one was obtained as the third eluting product. Further purification by SFC (column: IC-H (250 mm×30 mm i.d., 5 μm); Mobile phase A: CO$_2$; Mobile phase B: MeOH; B %: 20%-20% over 10 min) provided the first eluting isomer as a single enantiomer (Example 46). $^1$H NMR (400 MHz, CDCl$_3$) δ 8.39 (d, J=2.8 Hz, 2H), 7.37 (td, J=9.1, 2.1 Hz, 1H), 5.09 (br t, J=7.8 Hz, 1H), 4.13 (br d, J=8.2 Hz, 1H), 3.38 (br s, 1H), 2.78-2.98 (m, 2H), 2.56 (br s, 1H), 2.24-2.37 (m, 1H), 1.76 (t, J=19.5 Hz, 3H), 1.44 (s, 2H), 1.440 (m, 1H). LC-MS (Method N): m/z=300.3 [M+H]$^+$, 1.182 min.

6-(1,1-difluoroethyl)-3-(5-fluoro-3-pyridyl)-6-methyl-1,2,3,7-tetrahydropyrazolo[1,2-a]pyrazol-5-one was obtained as the fourth eluting product and was further purified by SFC (Column: Chiralpak AD-H 250 mm×30 mm i.d. 5 μm; Mobile phase A: CO$_2$; Mobile phase B: MeOH; Gradient: B %=20%-20% over 10 mim) to provide the first eluting isomer as a single enantiomer (Example 47). $^1$H NMR (400 MHz, CDCl$_3$) δ 8.34-8.45 (m, 2H), 7.37 (td, J=9.0, 2.1 Hz, 1H), 5.07 (t, J=8.0 Hz, 1H), 3.40-3.51 (m, 2H), 3.36 (br t, J=7.7 Hz, 1H), 2.89 (dddd, J=12.7, 8.5, 6.9, 1.4 Hz, 1H), 2.57-2.68 (m, 1H), 2.30 (tdd, J=12.7, 10.9, 7.2 Hz, 1H), 1.85 (t, J=20.0 Hz, 3H), 1.51 (s, 3H). LC-MS (Method N): m/z=300.3 [M+H]$^+$, 1.247 min.

Examples 48, 49, 50 and 51

6-(difluoromethyl)-3-(5-fluoro-3-pyridyl)-6-(2,2,2-trifluoroethyl)-1,2,3,7-tetrahydropyrazolo[1,2-a]pyrazol-5-one and 3-(5-fluoro-3-pyridyl)-6-methyl-6-(2,2,2-trifluoroethyl)-1,2,3,7-tetrahydropyrazolo[1,2-a]pyrazol-5-one

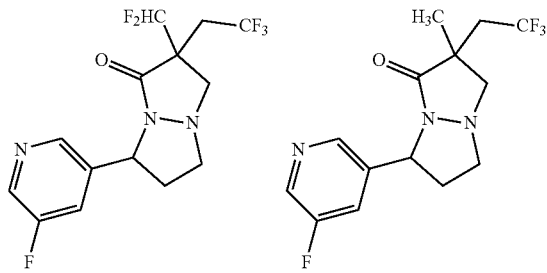 [SMILES: O=C1N2C(c3cncc(F)c3)CCN2CC1(CC(F)(F)F)C(F)F ; CC1(CC(F)(F)F)CN2CCC(c3cncc(F)c3)N2C1=O]

Prepared according to Procedure B and purified by prep-HPLC using the following conditions: column: Agela Durashell C18 150 mm×25 mm 5 μm; mobile phase A: water (10 mM NH$_4$HCO$_3$) mobile phase B: ACN; B %: 25%-45% over 10.5 min to provide the title compounds.

6-(difluoromethyl)-3-(5-fluoro-3-pyridyl)-6-(2,2,2-trifluoroethyl)-1,2,3,7-tetrahydropyrazolo[1,2-a]pyrazol-5-one as the fourth eluting product (82% ee) (Example 48). $^1$H NMR (400 MHz, CDCl$_3$) δ 8.45-8.35 (m, 2H), 7.42-7.31 (m, 1H), 5.81-6.19 (t, J=56 Hz, 1H), 5.11 (t, J=8.0 Hz, 1H), 3.82 (br d, J=1 1.8 Hz, 1H), 3.44 (br d, J=11.8 Hz, 1H), 3.39 (br t, J=7.2 Hz, 1H), 2.97-2.88 (m, 1H), 2.78-2.71 (m, 1H), 2.71-2.65 (m, 1H), 2.65-2.58 (m, 1H), 2.39-2.27 (m, 1H). LCMS (Method N): m/z=354.3 [M+H]$^+$, 1.371 min.

6-(difluoromethyl)-3-(5-fluoro-3-pyridyl)-6-(2,2,2-trifluoroethyl)-1,2,3,7-tetrahydropyrazolo[1,2-a]pyrazol-5-one as the third eluting product (Example 49). $^1$H NMR (400 MHz, CDCl$_3$) δ 8.45-8.36 (m, 2H), 7.36 (td, J=8.9, 2.1 Hz, 1H), 6.16-5.84 (t, J=56 Hz, 1H), 5.11 (t, J=7.8 Hz, 1H), 4.01 (d, J=11.7 Hz, 1H), 3.44 (br t, J=7.2 Hz, 1H), 3.20 (br d, J=11.7 Hz, 1H), 3.03-2.91 (m, 1H), 2.85-2.65 (m, 2H), 2.64-2.56 (m, 1H), 2.42-2.30 (m, 1H). LCMS (Method N): m/z=354.3 [M+H]$^+$, 1.351 min.

3-(5-fluoro-3-pyridyl)-6-methyl-6-(2,2,2-trifluoroethyl)-1,2,3,7-tetrahydropyrazolo[1,2-a]pyrazol-5-one as the second eluting product (79% ee) (Example 50). $^1$H NMR (400 MHz, CDCl$_3$) δ 8.40 (d, J=2.4 Hz, 2H), 7.35 (td, J=9.0, 2.2 Hz, 1H), 5.05 (t, J=7.9 Hz, 1H), 3.64 (br d, J=9.5 Hz, 1H), 3.45 (br t, J=7.4 Hz, 1H), 2.94 (dddd, J=12.7, 8.4, 6.5, 1.8 Hz, 1H), 2.86 (br d, J=9.5 Hz, 1H), 2.58-2.68 (m, 1H), 2.47-2.57 (m, 1H), 2.30-2.45 (m, 2H), 1.50 (s, 3H). LCMS (Method N): m/z=318.3 [M+H]$^+$, 1.318 min.

3-(5-fluoro-3-pyridyl)-6-methyl-6-(2,2,2-trifluoroethyl)-1,2,3,7-tetrahydropyrazolo[1,2-a]pyrazol-5-one as the first eluting product (Example 51). $^1$H NMR (400 MHz, CDCl$_3$) δ 8.36-8.44 (m, 2H), 7.35 (td, J=9.0, 2.1 Hz, 1H), 5.04 (br t, J=7.5 Hz, 1H), 3.73 (br s, 1H), 3.29 (br s, 1H), 2.82-3.01 (m, 2H), 2.71 (br s, 1H), 2.39-2.62 (m, 2H), 2.33 (tdd, J=12.9, 8.9, 6.6 Hz, 1H), 1.40 (d, J=0.9 Hz, 3H). LCMS (Method N): m/z=318.3 [M+H]$^+$, 1.283 min.

Examples 52 and 53

6-(cyclopropylmethyl)-6-(difluoromethyl)-3-(5-fluoro-3-pyridyl)-1,2,3,7-tetrahydropyrazolo[1,2-a]pyrazol-5-one

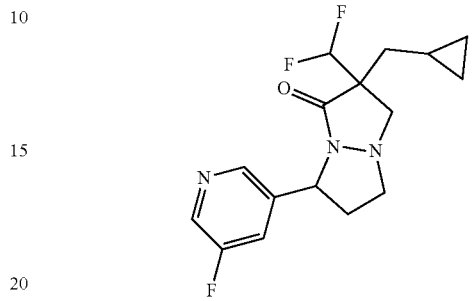

Prepared according to Preparation 6 and purified by prep-TLC (SiO$_2$, PE:EtOAc=1:1) to provide 2-(chloromethyl)-2-(cyclopropylmethyl)-3,3-difluoro-1-[3-(5-fluoro-3-pyridyl)-3,4-dihydropyrazol-2-yl]propan-1-one as the faster eluting isomer (0.2 g, 15%) as a yellow oil, LC-MS (Method O): m/z=360.2 [M+H]$^+$, 1.299 min and 2-(chloromethyl)-2-(cyclopropylmethyl)-3,3-difluoro-1-[3-(5-fluoro-3-pyridyl)-3,4-dihydropyrazol-2-yl]propan-1-one as the slower eluting isomer (0.27 g, 21%) as a yellow oil, LC-MS (Method O): m/z=360.2 [M+H]$^+$, 1.272 min.

6-(cyclopropylmethyl)-6-(difluoromethyl)-3-(5-fluoro-3-pyridyl)-1,2,3,7-tetrahydropyrazolo[1,2-a]pyrazol-5-one: Prepared from 2-(chloromethyl)-2-(cyclopropylmethyl)-3,3-difluoro-1-[3-(5-fluoro-3-pyridyl)-3,4-dihydropyrazol-2-yl]propan-1-one (faster eluting isomer) according to Procedure B and purified by prep-TLC (SiO$_2$, PE:EtOAc=1:3) to provide the title compound (97% ee) (Example 52). $^1$H NMR (400 MHz, CDCl$_3$) δ 8.46-8.35 (m, 2H), 7.40 (td, J=9.1, 2.1 Hz, 1H), 6.17-5.85 (t, J=56 Hz, 1H), 5.13 (t, J=8.0 Hz, 1H), 3.72 (dd, J=11.7, 2.0 Hz, 1H), 3.43 (d, J=11.7 Hz, 1H), 3.37 (t, J=7.8 Hz, 1H), 2.92-2.83 (m, 1H), 2.66-2.57 (m, 1H), 2.33-2.22 (m, 1H), 1.92 (dd, J=14.2, 5.4 Hz, 1H), 1.55-1.46 (m, 1H), 0.97-0.86 (m, 1H), 0.63-0.45 (m, 2H), 0.23-0.10 (m, 2H). LC-MS (Method N): m/z=326.3 [M+H]$^+$, 1.407 min.

6-(cyclopropylmethyl)-6-(difluoromethyl)-3-(5-fluoro-3-pyridyl)-1,2,3,7-tetrahydropyrazolo[1,2-a]pyrazol-5-one: Prepared from 2-(chloromethyl)-2-(cyclopropylmethyl)-3,3-difluoro-1-[3-(5-fluoro-3-pyridyl)-3,4-dihydropyrazol-2-yl]propan-1-one (slower eluting isomer) according to Procedure B and purified by prep-TLC (SiO$_2$, EtOAc) to provide the title compound (94% ee) (Example 53). $^1$H NMR (400 MHz, CDCl$_3$) δ 8.39 (d, J=2.4 Hz, 2H), 7.38 (td, J=9.1, 2.1 Hz, 1H), 6.13-5.80 (t, J=56 Hz, 1H), 5.14-5.06 (m, 1H), 3.96 (br d, J=11.4 Hz, 1H), 3.25 (d, J=11.3 Hz, 1H), 2.94 (dddd, J=12.8, 8.9, 6.7, 2.3 Hz, 1H), 2.64 (br d, J=7.4 Hz, 1H), 2.38-2.25 (m, 1H), 1.83-1.74 (m, 1H), 1.83-1.58 (m, 2H), 0.88-0.75 (m, 1H), 0.65-0.48 (m, 2H), 0.28-0.12 (m, 2H). LC-MS (Method N): m/z=326.3 [M+H]$^+$, 1.353 min.

Example 54

5-(6-(difluoromethyl)-7-oxo-6-propylhexahydropyrazolo[1,2-a]pyrazol-1-yl)nicotinonitrile

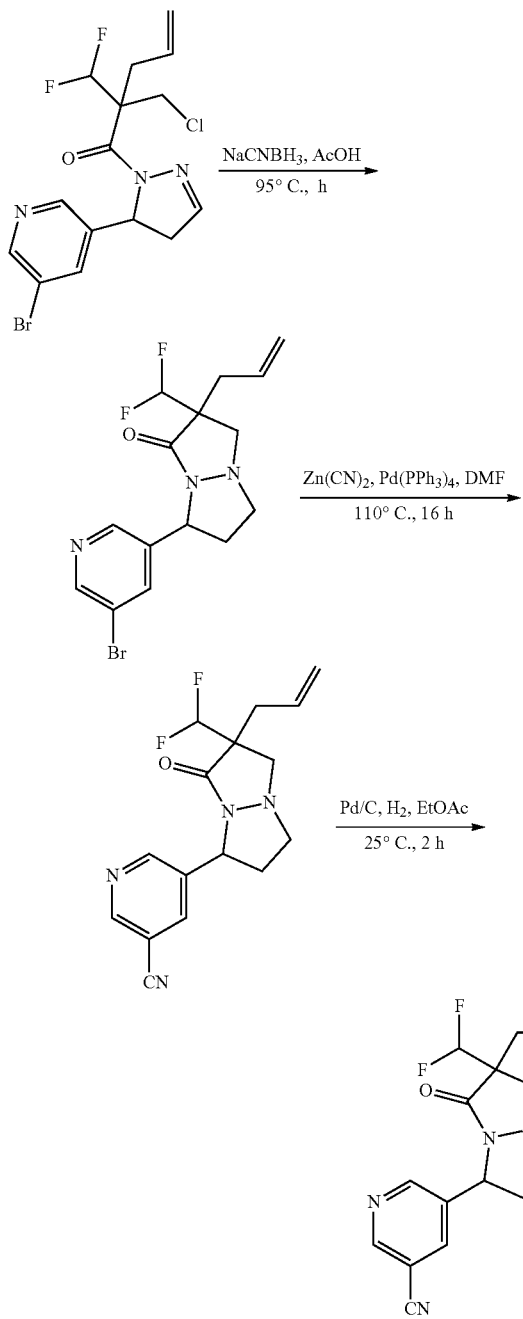

2-allyl-7-(5-bromopyridin-3-yl)-2-(difluoromethyl)tetrahydropyrazolo[1,2-a]pyrazol-1(5H)-one: Prepared from 1-[3-(5-bromo-3-pyridyl)-3,4-dihydropyrazol-2-yl]-2-(chloromethyl)-2-(difluoromethyl)pent-4-en-1-one (1 g, 2.46 mmol) using Procedure B and purified by silica gel column chromatography (PE:EtOAc=1:1) to provide the title compound (0.6 g, 66%) as a yellow oil.

5-(6-allyl-6-(difluoromethyl)-7-oxohexahydropyrazolo[1,2-a]pyrazol-1-yl)nicotinonitrile: Prepared from 2-allyl-7-(5-bromopyridin-3-yl)-2-(difluoromethyl)tetrahydropyrazolo[1,2-a]pyrazol-1(5H)-one using Procedure C and purified by silica gel column chromatography (PE:EtOAc=1:1 to 0:1) to provide the title compound as a light yellow solid.

5-(6-(difluoromethyl)-7-oxo-6-propylhexahydropyrazolo[1,2-a]pyrazol-1-yl)nicotinonitrile: To a solution of 5-(6-allyl-6-(difluoromethyl)-7-oxohexahydropyrazolo[1,2-a]pyrazol-1-yl)nicotinonitrile (400 mg, 402.11 umol) in EtOAc (5 mL) was added 10% Pd/C (43 mg) in one portion at 25° C. The mixture was stirred for 2 h under $H_2$ at 15 psi. The mixture was filtered through a pad of celite. The filtrate was concentrated under vacuum. The residue was purified by prep-HPLC with the following conditions: column: Waters Xbridge 150 mm×25 mm 5 μm; Mobile phase A: water (0.05% HCl); Mobile phase B: ACN; B %: 20%-40% over 12 min to provide the title compound as a mixture of enantiomers. $^1$H NMR (400 MHz, CDCl$_3$): δ 8.79 (d, J=1.8 Hz, 1H), 8.77 (d, J=2.0 Hz, 1H), 7.93-7.87 (m, 1H), 6.08-5.76 (t, J=56 Hz, 1H), 5.10 (t, J=8.0 Hz, 1H), 3.56 (dd, J=12.1, 2.0 Hz, 1H), 3.46-3.40 (m, 1H), 3.35 (t, J=7.8 Hz, 1H), 2.92-2.83 (m, 1H), 2.65-2.55 (m, 1H), 2.21 (m, 1H), 1.84-1.73 (m, 1H), 1.68-1.54 (m, 2H), 1.41-1.26 (m, 1H), 0.98 (t, J=7.3 Hz, 3H). HPLC (Method T): Retention Time: 2.049 min, m/z=321.2 [M+H]$^+$.

Examples 55 and 56

(8R)-2-(difluoromethyl)-2-ethyl-5-(3-fluorophenyl)-5,6,7,8-tetrahydro-1H-pyrrolizin-3-one

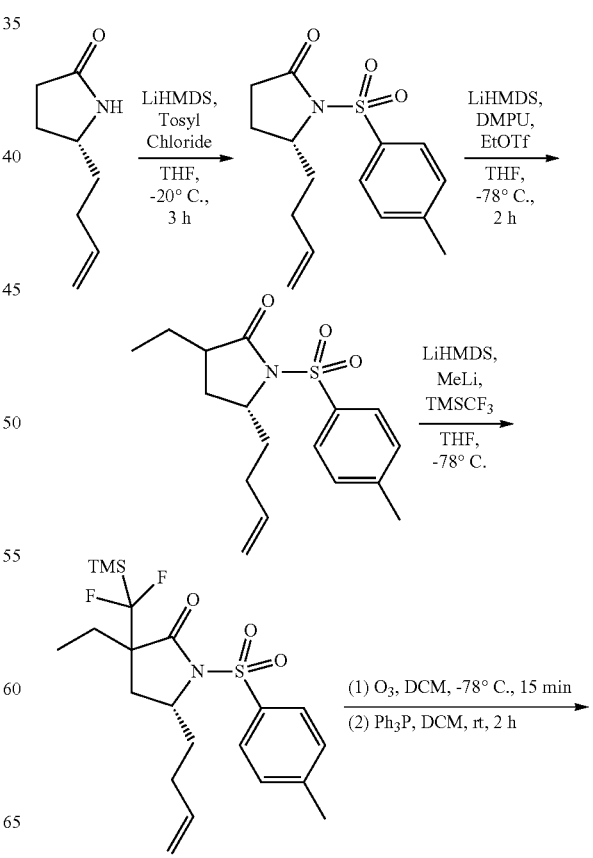

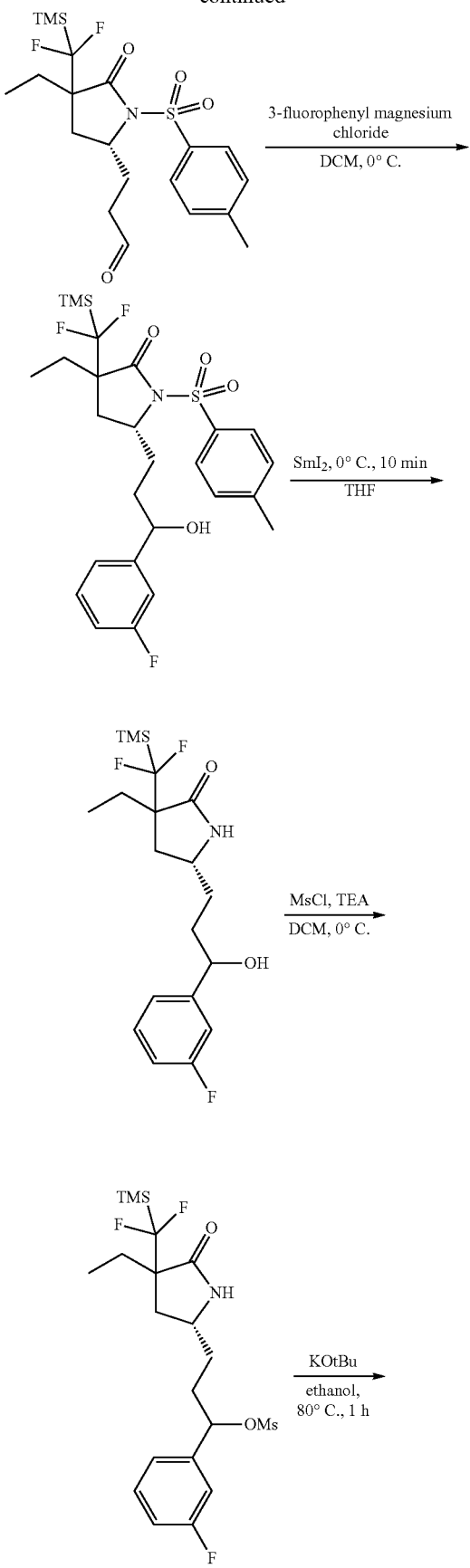

-continued

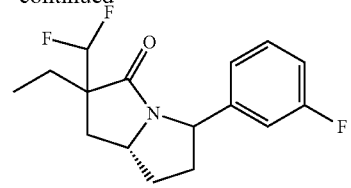

(5R)-5-but-3-enyl-1-(p-tolylsulfonyl)pyrrolidin-2-one: LiHMDS (1M in methyl tert-butyl ether) (39.51 mL, 39.51 mmol) was added to a solution of (5R)-5-but-3-enylpyrrolidin-2-one (5 g, 35.92 mmol) in THF (100 mL) at −20° C. The reaction mixture was stirred at −20° C. for 30 min before p-toluenesulfonyl chloride (7.53 g, 39.51 mmol) was added. The reaction mixture was stirred at rt overnight. The reaction mixture was concentrated to dryness and the residue was taken up in EtOAc (100 mL). The organic layer was washed with 2×50 mL water then 1×50 mL saturated brine solution. The organics were then separated and dried (MgSO$_4$) before concentration to dryness. The crude was then purified by flash column chromatography eluting with 0-100% EtOAc in hexane. The desired fractions were concentrated to dryness in vacuo. $^1$H-NMR (400 MHz; CDCl$_3$): δ 7.97 (d, J=8.4 Hz, 2H), 7.35 (dd, J=8.6, 0.6 Hz, 2H), 5.83 (ddt, J=17.0, 10.4, 6.5 Hz, 1H), 5.09-5.03 (m, 2H), 4.46-4.41 (m, 1H), 2.55 (ddd, J=17.7, 11.2, 9.1 Hz, 1H), 2.37 (ddd, J=17.7, 9.5, 2.3 Hz, 1H), 2.25-2.09 (m, 4H), 1.93-1.86 (m, 1H), 1.79-1.74 (m, 1H). LCMS (Method C): m/z=294.4 [M+H]$^+$, 1.98 min.

(5R)-5-but-3-enyl-3-ethyl-1-(p-tolylsulfonyl)pyrrolidin-2-one: LiHMDS (1M in methyl tert-butyl ether) (22.25 mL, 22.25 mmol) was added to a solution of (5R)-5-but-3-enyl-1-(p-tolylsulfonyl)pyrrolidin-2-one (6.1 g, 20.79 mmol) in THF (100 mL) and DMPU (2.53 mL, 20.79 mmol). The reaction mixture was stirred at −78° C. for 90 min. before ethyl trifluoromethanesulfonate (3.5 mL, 27.03 mmol) was added. The reaction mixture was stirred at −78° C. for 1 h before warming to rt and stirring for 2 h. The reaction mixture was poured carefully into 100 mL of ice-water. The mixture was extracted with EtOAc (100 mL) and the organics were washed with 2×50 mL water and 1×100 mL saturated brine solution. The organics were dried (MgSO$_4$) before concentration to dryness. The crude was then purified by flash column chromatography eluting with 60% EtOAc in hexane. The desired fractions were concentrated to dryness in vacuo. LC-MS (Method C): m/z=322.4 [M+H]$^+$, 1.92 min.

(5R)-5-but-3-enyl-3-[difluoro(trimethylsilyl)methyl]-3-ethyl-1-(p-tolylsulfonyl)pyrrolidin-2-one: To a solution of (5R)-5-but-3-enyl-3-ethyl-1-(p-tolylsulfonyl)pyrrolidin-2-one (2.3 g, 7.16 mmol) in THF (100 mL) was added a solution of LiHMDS (1M in methyl tert-butyl ether) (7.3 mL, 7.3 mmol) at −78° C. The reaction mixture was stirred at 0° C. for 30 min then cooled to −78° C. Methyl lithium (1.6 M in diethyl ether) (4.47 mL, 7.16 mmol) was added and the mixture was stirred at −78° C. for 10 min before trimethyl(trifluoromethyl)silane (5.29 mL, 35.78 mmol) was added. The reaction mixture was warmed to rt and stirred at rt for 18 h. The reaction mixture was poured carefully into ice-water (100 mL) and then extracted with EtOAc (150 mL). The organic layer was separated and washed with water (2×100 mL) then saturated brine solution (1×150 mL). The organics were then separated and dried over MgSO$_4$ before concentration to dryness. The crude was then purified by flash column chromatography eluting with 20% EtOAc in heptanes. The desired fractions were concentrated to dryness in vacuo. LC-MS (Method C): m/z=444.4 [M+H]$^+$, 2.32 min.

3-[(2R)-4-[difluoro(trimethylsilyl)methyl]-4-ethyl-5-oxo-1-(p-tolylsulfonyl)pyrrolidin-2-yl]propanal: Ozone was bubbled through a cooled (−78° C.) solution of (5R)-5-but-3-enyl-3-[difluoro(trimethylsilyl)methyl]-3-ethyl-1-(p-tolylsulfonyl)pyrrolidin-2-one (2.5 g, 5.64 mmol) in DCM (100 mL) until a light blue color appeared. Oxygen was then bubbled through the solution for 10 min followed by argon for 30 min. Triphenylphosphine (2.22 g, 8.45 mmol) was added and the mixture was stirred at rt for 3 h. The reaction mixture was concentrated and purified by flash chromatography to yield the title compound (1.3 g, 2.92 mmol, 52% yield). LC-MS (Method C): m/z=446.4 [M+H]$^+$, 2.01 min.

(5R)-3-[difluoro(trimethylsilyl)methyl]-3-ethyl-5-[3-(3-fluorophenyl)-3-hydroxy-propyl]-1-(p-tolylsulfonyl)pyrrolidin-2-one: 3-Fluorophenylmagnesium chloride in THF solution (0.57 mL, 0.57 mmol) was added to a solution of 3-[(2R)-4-[difluoro(trimethylsilyl)methyl]-4-ethyl-5-oxo-1-(p-tolylsulfonyl)pyrrolidin-2-yl]propanal (240 mg, 0.54 mmol) in DCM (20 mL). The reaction mixture was stirred at rt overnight before quenching by adding 5 mL of 1.0 N HCl. The reaction mixture was taken up in 50 mL of ethyl acetate, washed with water and brine and then dried over MgSO$_4$ before concentration in vacuo. The crude product was purified by flash chromatography to yield the title compound (110 mg, 37.7% yield). LC-MS (Method C): m/z=542.4 [M+H]$^+$, 1.95 min.

(5R)-3-[difluoro(trimethylsilyl)methyl]-3-ethyl-5-[3-(3-fluorophenyl)-3-hydroxy-propyl]pyrrolidin-2-one: To a solution of (5R)-3-[difluoro(trimethylsilyl)methyl]-3-ethyl-5-[3-(3-fluorophenyl)-3-hydroxy-propyl]-1-(p-tolylsulfonyl)pyrrolidin-2-one (40 mg, 0.07 mmol) in THF (5 mL) at 0° C. was added a solution of SmI$_2$ (0.1 M, 3.69 mL, 0.37 mmol). The reaction mixture was stirred at 0° C. for 10 min then quenched by adding water (10 mL). The mixture was taken up in ethyl acetate (50 mL) then washed with water (50 mL) and brine (50 mL). The organic layer was collected and dried over MgSO$_4$ before concentration. The crude product was purified by flash chromatography to provide the title compound (22.5 mg, 78.6%). LC-MS (Method C): m/z=388.4 [M+H]$^+$, 1.92 min.

[3-[(2R)-4-[difluoro(trimethylsilyl)methyl]-4-ethyl-5-oxo-pyrrolidin-2-yl]-1-(3-fluorophenyl)propyl]methanesulfonate: To a solution of (5R)-3-[difluoro(trimethylsilyl)methyl]-3-ethyl-5-[3-(3-fluorophenyl)-3-hydroxy-propyl]pyrrolidin-2-one (46 mg, 0.12 mmol) in DCM (5 mL) at −10° C. was added triethylamine (0.02 mL, 0.18 mmol) followed by methanesulfonyl chloride (0.01 mL, 0.14 mmol). The mixture was stirred at −10° C. for 30 min, concentrated and used directly in the next step. LC-MS (Method C): m/z=466.4 [M+H]$^+$, 2.15 min.

(8R)-2-(difluoromethyl)-2-ethyl-5-(3-fluorophenyl)-5,6,7,8-tetrahydro-1H-pyrrolizin-3-one: Potassium tert-butoxide (72.3 mg, 0.54 mmol) was added to a solution of [3-[(2R)-4-[difluoro(trimethylsilyl)methyl]-4-ethyl-5-oxopyrrolidin-2-yl]-1-(3-fluorophenyl)propyl]methanesulfonate (30 mg, 0.056 mmol) in ethanol (2 mL). The reaction mixture was stirred at 80° C. for 1 h heated by microwave. The reaction mixture was poured into ice-water (20 mL) and then extracted with ethyl acetate (25 mL×2). The organic layers were combined and washed with brine (50 mL) before concentration. The residue was purified by flash chromatography eluting with 0-100% EtOAc/hexanes to provide the title compounds.

Second and third eluting isomers isolated as a mixture (Example 55). $^1$H-NMR (400 MHz; CDCl$_3$): δ 7.33-7.29 (m, 1H), 7.00-6.93 (m, 2H), 6.92-6.88 (m, 1H), 6.05-5.60 (m, 1H), 4.99-4.65 (m, 1H), 4.10-4.00 (m, 1H), 2.75-2.57 (m, 1H), 2.46-2.30 (m, 1H), 2.16-2.08 (m, 1H), 2.06-1.96 (m, 2H), 1.84-1.74 (m, 2H), 1.72-1.48 (m, 1H), 1.12-1.08 (m, 3H). LC-MS (Method C): m/z=298.3 [M+H]$^+$, 1.74 min.

Fourth eluting isomer isolated as a single stereoisomer (Example 56): $^1$H-NMR (400 MHz; CDCl$_3$): δ 7.31 (dd, J=8.0, 5.9 Hz, 1H), 7.00-6.93 (m, 2H), 6.90 (dt, J=9.9, 2.1 Hz, 1H), 5.94 (t, J=56.4 Hz, 1H), 4.66 (d, J=9.2 Hz, 1H), 4.11-4.03 (m, 1H), 2.69-2.58 (m, 1H), 2.42 (dd, J=13.2, 8.9 Hz, 1H), 2.14-2.03 (m, 3H), 1.86-1.66 (m, 3H), 1.08 (t, J=7.5 Hz, 3H). LC-MS (Method C): m/z=298.3 [M+H]$^+$, 1.73 min.

Examples 57 and 58

(8S)-2-(difluoromethyl)-2-ethyl-5-(3-fluorophenyl)-5,6,7,8-tetrahydro-1H-pyrrolizin-3-one

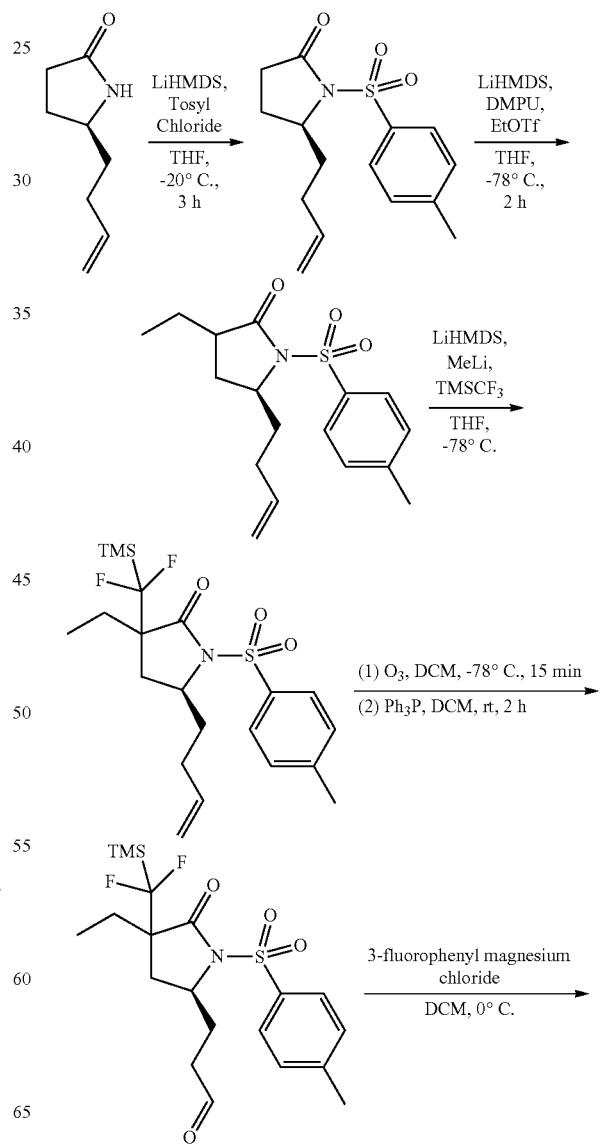

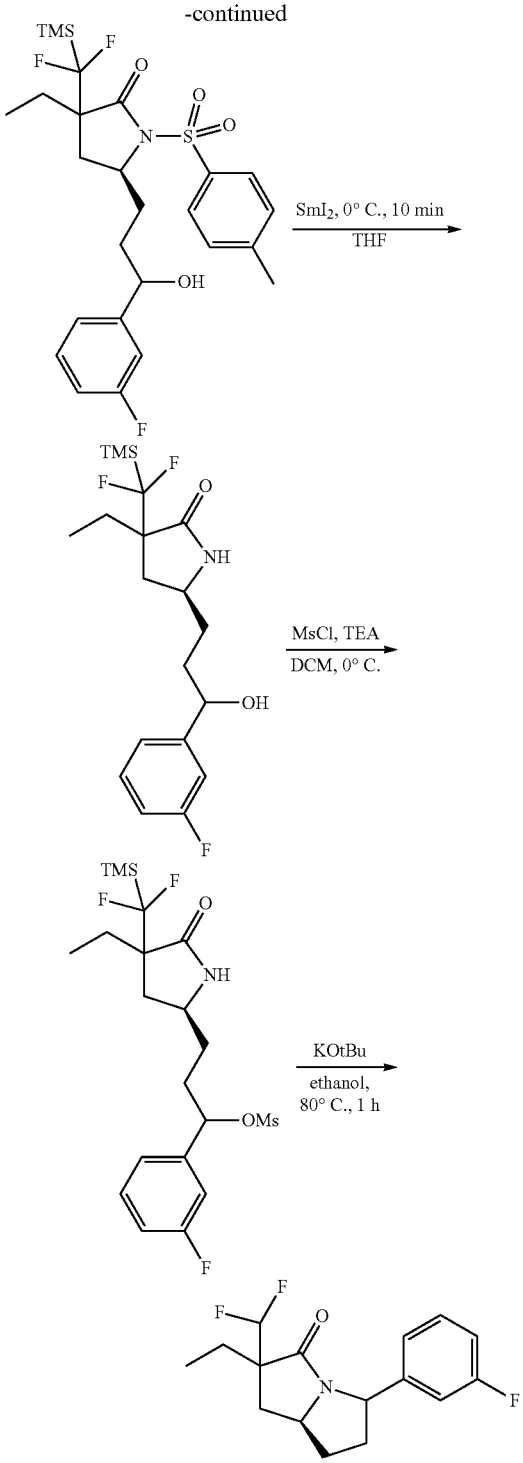

The title compounds were prepared using (5S)-5-but-3-enylpyrrolidin-2-one employing the procedures described for the synthesis of Examples 55 and 56 followed by purification by flash chromatography eluting with 0-100% EtOAc/hexanes.

The first eluting isomer isolated as a single stereoisomer (Example 57). $^1$H-NMR (400 MHz; CDCl$_3$): δ 7.33-7.29 (m, 1H), 7.02 (ddt, J=7.7, 1.6, 0.8 Hz, 1H), 6.97-6.91 (m, 2H), 5.98 (t, J=56.5 Hz, 1H), 4.99-4.95 (m, 1H), 4.08-4.01 (m, 1H), 2.75-2.67 (m, 1H), 2.31 (dd, J=14.0, 5.9 Hz, 1H), 2.20-2.14 (m, 2H), 2.04-1.96 (m, 1H), 1.89 (td, J=14.2, 6.8 Hz, 1H), 1.77-1.70 (m, 1H), 1.57-1.47 (m, 1H), 1.11 (t, J=7.5 Hz, 3H). LC-MS (Method C): m/z=298.3 [M+H]$^+$, 1.81 min.

The second and third eluting isomers isolated as a mixture (Example 58). $^1$H-NMR (400 MHz; CDCl$_3$): δ 7.33-7.29 (m, 1H), 7.00-6.93 (m, 2H), 6.92-6.88 (m, 1H), 6.05-5.60 (m, 1H), 4.99-4.65 (m, 1H), 4.10-4.00 (m, 1H), 2.75-2.57 (m, 1H), 2.46-2.30 (m, 1H), 2.16-2.08 (m, 1H), 2.06-1.96 (m, 2H), 1.84-1.74 (m, 2H), 1.72-1.48 (m, 1H), 1.12-1.08 (m, 3H). LC-MS (Method C): m/z=298.3 [M+H]$^+$, 1.77 min.

Other compound(s) shown above in Table 1 were prepared according to the Examples above and/or general procedures described herein.

In Vitro Assay 1

Receptor Interacting Protein Kinase 1 Inhibition by Compounds of Formula I

Fluorescent Polarization Binding (FP Binding) assay (Berger S. B. et al. (2015) *Cell Death Discovery*, 1: 15009; Maki J. L. et al. (2012) *Anal Biochem.*, 427(2): 164-174) was performed in polystyrene low volume 384-well black plate, at Room Temperature (RT) in a final volume of 10.1 μL/well using 10 nM of GST-human receptor interacting protein kinase 1 fusion (8-327) enzyme and 5 nM of fluorescent-labeled ligand (14-(2-{[3-({2-{[4-(cyanomethyl)phenyl]amino}-6-[(5-cyclopropyl-1H-pyrazol-3-yl)amino]-4-pyrimidinyl}amino) propyl]amino}-2-oxoethyl)-16,16,18,18-tetramethyl-6,7,7a,8a,9,10,16,18-octahydrobenzo[2",3"]indolizino[8",7":5',6']pyrano[3',2':3,4]pyrido[1,2-a]indol-5-ium-2-sulfonate.

Test compounds were serially diluted in DMSO at 100 fold final concentrations in the assay (1% DMSO final). In each well of a 384-well Plate were dispensed 0.1 μL of compound solution (or DMSO for controls) followed by 5 μL of GST-human receptor interacting protein kinase 1 fusion (8-327) enzyme at twice the final concentrations in assay buffer (50 mM HEPES pH 7.5, 10 mM NaCl, 50 mM MgCl$_2$, 0.02% CHAPS, 0.5 mM DTT and 0.01% Pluronic F127). For negative control the enzyme addition was replaced by assay buffer only.

After addition of 5 μL of fluorescent-labeled ligand at twice the final concentrations in assay buffer, the plate was incubated at RT for 30 min. At the end, the binding was measured as FP value with the Envision (PerkinElmer) plate reader using filter for an excitation λ=531 nm FP and an emission λ=595 nm FP (S & P-pol).

Test compound inhibition was expressed as percent inhibition of internal assay controls. For concentration response curves, normalized data is fit and IC$_{50}$ determined using XL-fit (IDBS) for Excel. IC$_{50}$ were averaged to determine a mean value, for a minimum of two independent experiments.

Receptor interacting protein kinase 1 activity of exemplary compounds was determined according to the above general procedures. Results are summarized in Table 3.

TABLE 3

| No | IC$_{50}$ |
|---|---|
| 1 | +++ |
| 2 | ++ |
| 3 | +++ |
| 4 | ++ |
| 5 | +++ |

TABLE 3-continued

| No | IC$_{50}$ |
|---|---|
| 6 | +++ |
| 7 | +++ |
| 8 | ++ |
| 9 | ++ |
| 10 | +++ |
| 11 | +++ |
| 12 | +++ |
| 13 | +++ |
| 14 | +++ |
| 15 | ++ |
| 16 | +++ |
| 17 | +++ |
| 18 | +++ |
| 19 | +++ |
| 20 | +++ |
| 21 | +++ |
| 22 | +++ |
| 23 | +++ |
| 24 | +++ |
| 25 | +++ |
| 26 | ++ |
| 27 | +++ |
| 28 | +++ |
| 29 | +++ |
| 30 | +++ |
| 31 | +++ |
| 32 | +++ |
| 33 | +++ |
| 34 | ++ |
| 35 | +++ |
| 36 | ++ |
| 37 | +++ |
| 38 | ++ |
| 39 | +++ |
| 40 | +++ |
| 41 | ++ |
| 42 | +++ |
| 43 | ++ |
| 44 | +++ |
| 45 | +++ |
| 46 | ++ |
| 47 | +++ |
| 48 | ++ |
| 49 | ++ |
| 50 | +++ |
| 51 | ++ |
| 52 | +++ |
| 53 | ++ |
| 54 | +++ |
| 55 | +++ |
| 56 | +++ |
| 57 | +++ |
| 58 | +++ |

+++ indicates IC$_{50}$ < 1 µM
++ indicates 1 µM ≤ IC$_{50}$ < 30 µM
+ indicates IC$_{50}$ ≥ 30 µM Although various embodiments of the disclosure are disclosed herein, many adaptations and modifications may be made within the scope of the disclosure in accordance with the common general knowledge of those skilled in this art. Such modifications include the substitution of known equivalents for any aspect of the disclosure in order to achieve the same result in substantially the same way. Numeric ranges are inclusive of the numbers defining the range. The word "comprising" is used herein as an open-ended term, substantially equivalent to the phrase "including, but not limited to" and the word "comprises" has a corresponding meaning. As used herein, the singular forms "a", "an" and "the" include plural referents unless the context clearly dictates otherwise. Thus, for example, reference to "a thing" includes more than one such thing. Citation of references herein is not an admission that such references are prior art to the present disclosure. Any priority document(s) and all publications, including but not limited to patents and patent applications, cited in this specification are incorporated herein by reference as if each individual publication were specifically and individually indicated to be incorporated by reference herein and as though fully set forth herein. The disclosure includes all embodiments and variations substantially as hereinbefore described and with reference to the examples and drawings.

The invention claimed is:

1. A compound of Formula I:

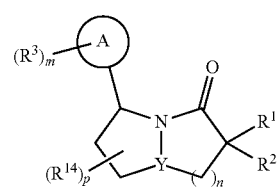

or a pharmaceutically acceptable salt, stereoisomer, or mixture of stereoisomers thereof, wherein:

Y is N or CH;

n is 1 or 2;

m is 0, 1, 2, 3, 4, or 5;

p is 0, 1, 2, or 3;

A is aryl, heteroaryl, $C_{3-10}$ cycloalkyl, or heterocyclyl;

each of $R^1$ and $R^2$ is independently hydrogen, deuterium, halo, $C_{1-12}$ alkyl, $C_{1-12}$ alkenyl, $C_{1-12}$ alkynyl, $C_{1-12}$ alkoxy, $C_{1-12}$ haloalkyl, $C_{1-12}$ haloalkoxy, $C_{3-10}$ cycloalkyl, heterocyclyl, heteroaryl or aryl;

wherein each $C_{1-12}$ alkyl, $C_{1-12}$ alkenyl, $C_{1-12}$ alkynyl, $C_{1-12}$ alkoxy, $C_{1-12}$ haloalkyl, $C_{1-12}$ haloalkoxy, $C_{3-10}$ cycloalkyl, heterocyclyl, heteroaryl, and aryl is optionally substituted with one, two, three, four, or five $Z^1$; or $R^1$ and $R^2$ taken together with the atoms to which they are attached form a $C_{3-10}$ cycloalkyl;

wherein the $C_{3-10}$ cycloalkyl is optionally substituted with one, two, three, four, or five $Z^2$;

$R^3$ in each instance is independently deuterium, halo, hydroxy, cyano, nitro, azido, oxo, $C_{1-12}$ alkyl, —OR$^5$, $C_{1-12}$ alkoxy, $C_{2-12}$ alkenyl, $C_{2-12}$ alkynyl, $C_{1-12}$ haloalkyl, $C_{1-12}$ haloalkoxy, $C_{3-10}$ cycloalkyl, heterocyclyl, aryl, heteroaryl, —C(=O)R$^4$, —C(=O)OR$^4$, —OC(=O)OR$^4$, —OC(=O)R$^4$, —C(=O)NR$^4$R$^5$, —OC(=O)NR$^4$R$^5$, —NR$^4$C(=O)NR$^5$R$^6$, —S(=O)$_{1-2}$R$^4$, —S(=O)$_{1-2}$OR$^4$, —OS(=O)$_{1-2}$R$^4$, —S(=O)$_{1-2}$NR$^4$, —NR$^4$S(=O)$_{1-2}$R$^5$, —NR$^4$S(=O)$_{1-2}$NR$^4$R$^5$, —NR$^4$R$^5$, —NR$^4$C(=O)R$^5$, or —NR$^4$C(=O)OR$^5$;

wherein each $C_{1-12}$ alkyl, $C_{1-12}$ alkoxy, $C_{2-12}$ alkenyl, $C_{2-12}$ alkynyl, $C_{1-12}$ haloalkyl, $C_{1-12}$ haloalkoxy, $C_{3-10}$ cycloalkyl, heterocyclyl, aryl, and heteroaryl is optionally substituted with one, two, three, four, or five $Z^3$;

$R^4$, $R^5$, and $R^6$ in each instance are independently $C_{1-12}$ alkyl, $C_{1-12}$ alkenyl, $C_{1-12}$ alkynyl, $C_{1-12}$ haloalkyl, $C_{3-10}$ cycloalkyl, heterocyclyl, heteroaryl, or aryl;

wherein each $C_{1-12}$ alkyl, $C_{1-12}$ alkenyl, $C_{1-12}$ alkynyl, $C_{1-12}$ haloalkyl, $C_{3-10}$ cycloalkyl, heterocyclyl, heteroaryl, and aryl is optionally substituted with one, two, three, four, or five $Z^4$; or two of $R^4$, $R^5$, and $R^6$ taken together with the atoms to which they are attached form a heterocyclyl;

wherein the heterocyclyl is optionally substituted with one, two, three, four, or five $Z^5$;

$R^{14}$ is bonded to either ring of the fused bicyclic ring and, in each instance, is independently halo or haloalkyl, or two $R^{14}$ bonded to the same carbon atom may be taken together with the atom to which they are attached to form a $C_{3-10}$ cycloalkyl or heterocyclyl;

wherein the $C_{3-10}$ cycloalkyl or heterocyclyl is optionally substituted with one, two, three, four, or five $Z^6$;

each of $Z^1$, $Z^2$, $Z^3$, $Z^4$, $Z^5$, and $Z^6$ are independently deuterium, halo, hydroxy, cyano, nitro, azido, $C_{1-12}$ alkyl, $C_{1-12}$ alkenyl, $C_{1-12}$ alkynyl, $C_{1-12}$ alkoxy, $C_{1-12}$ haloalkyl, $C_{1-12}$ haloalkoxy, $C_{3-10}$ cycloalkyl, heterocyclyl, aryl, heteroaryl, —C(=O)$R^{11}$, —C(=O)O$R^{11}$, —OC(=O)O$R^{11}$, —OC(=O)$R^{11}$, —C(=O)N$R^{11}R^{12}$, —OC(=O)N$R^{11}R^{12}$, —N$R^{11}$C(=O)N$R^{12}R^{13}$, —S(=O)$_{1-2}R^{11}$, —S(=O)$_{1-2}$O$R^{11}$, —S(=O)$_{1-2}$N$R^{11}$, —N$R^{11}$S(=O)$_{1-2}R^{12}$, —N$R^{11}$S(=O)$_{1-2}$N$R^{12}R^{13}$, —N$R^{11}R^{12}$, —N$R^{11}$C(=O)$R^{12}$, or —N$R^{11}$C(=O)O$R^{12}$;

wherein each $C_{1-12}$ alkyl, $C_{1-12}$ alkenyl, $C_{1-12}$ alkynyl, $C_{1-12}$ alkoxy, $C_{1-12}$ haloalkyl, $C_{1-12}$ haloalkoxy, $C_{3-10}$ cycloalkyl, heterocyclyl, aryl, and heteroaryl is optionally substituted with one, two, or three substituents independently selected from deuterium, halo, hydroxy, cyano, amino, nitro, azido, oxo, $C_{1-12}$ alkyl, $C_{1-12}$ alkoxy, $C_{1-12}$ haloalkyl, $C_{1-12}$ haloalkoxy, $C_{2-12}$ alkenyl, $C_{2-12}$ alkynyl, $C_{3-10}$ cycloalkyl, heterocyclyl, aryl, and heteroaryl; and $R^{11}$, $R^{12}$, and $R^{13}$ in each instance are independently $C_{1-12}$ alkyl, $C_{1-12}$ alkenyl, $C_{1-12}$ alkynyl, $C_{1-12}$ alkoxy, $C_{3-10}$ cycloalkyl, heterocyclyl, heteroaryl, or aryl;

wherein each $C_{1-12}$ alkyl, $C_{1-12}$ alkenyl, $C_{1-12}$ alkynyl, $C_{1-12}$ alkoxy, $C_{3-10}$ cycloalkyl, heterocyclyl, heteroaryl, and aryl is optionally substituted with one, two, three, four, or five $Z^{11}$; or two of $R^{11}$, $R^{12}$, and $R^{13}$ are taken together with the atoms to which they are attached to form a heterocyclyl; wherein the heterocyclyl is optionally substituted with one, two, three, four or five $Z^{12}$;

wherein each of $Z^{11}$ and $Z^{12}$ is independently deuterium, halo, hydroxy, cyano, oxo, amino or $C_{1-12}$ alkyl; wherein the $C_{1-12}$ alkyl is optionally substituted with one, two or three halo, hydroxyl, amino or oxo, provided that when n is 1, Y is CH, and both of $R^1$ and $R^2$ are hydrogen, then A is not heterocyclyl substituted with oxo; and when n is 2, Y is CH and one of $R^1$ or $R^2$ is iodo, or both of $R^1$ or $R^2$ are hydrogen, then A is not 4-chlorophenyl, 2,6-difluoropyridin-3-yl, phenyl, or phenyl substituted with 1, 2 or 3 fluoro; and the compound is not chosen from (3R,8aR)-6-chloro-3-(4-fluorophenyl)hexahydroindolizin-5(1H)one; (3R,6S,8aS)-6-methyl-3-phenylhexahydroindolizin-5(1H)-one; hexahydro-6-methyl-3-phenyl-5(1H)-indolizinone; and 6-[(2-bromo-1H-indol-3-yl)methyl]hexahydro-3-(4-hydroxyphenyl)-5(1H)-indolizinone.

2. The compound of claim 1, wherein Y is N.
3. The compound of claim 1, wherein Y is CH.
4. The compound of claim 1, wherein n is 1.
5. The compound of claim 1, wherein n is 2.
6. The compound of claim 1, wherein each of $R^1$ and $R^2$ is independently hydrogen, deuterium, $C_{1-12}$ haloalkyl, or $C_{1-12}$ alkyl.

7. The compound of claim 6, wherein each of $R^1$ and $R^2$ is independently $C_{1-12}$ haloalkyl or $C_{1-12}$ alkyl.

8. The compound of claim 7, wherein one of $R^1$ and $R^2$ is methyl and the other of $R^1$ and $R^2$ is ethyl.

9. The compound of claim 7, wherein $R^1$ and $R^2$ are both methyl.

10. The compound of claim 1, wherein m is 1, 2, or 3.

11. The compound of claim 1, wherein $R^3$ in each instance is independently deuterium, halo, hydroxy, cyano, nitro, or $C_{1-12}$ alkyl.

12. The compound of claim 1, wherein m is 1 or 2, and $R^3$ in each instance is independently deuterium, halo, hydroxy, cyano, nitro, or $C_{1-12}$ alkyl.

13. The compound of claim 1, wherein $R^3$ in each instance is independently halo or cyano.

14. The compound of claim 13, wherein $R^3$ in each instance is independently fluoro or cyano.

15. The compound of claim 1, wherein m is 0.

16. A compound selected from:

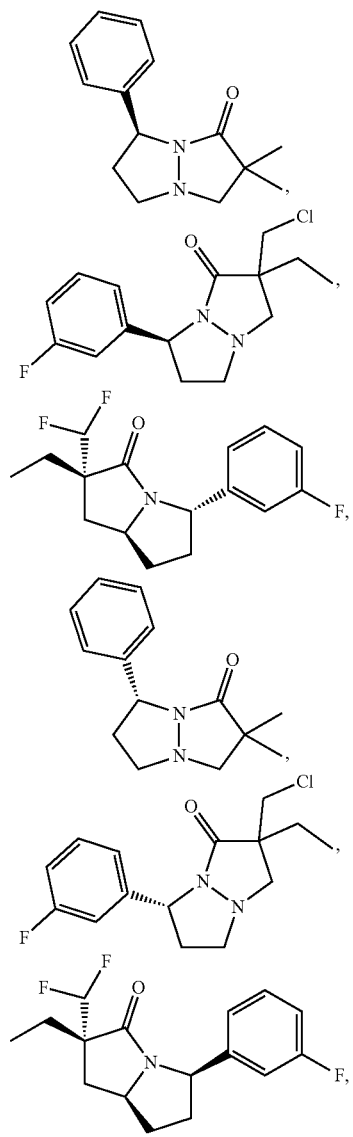

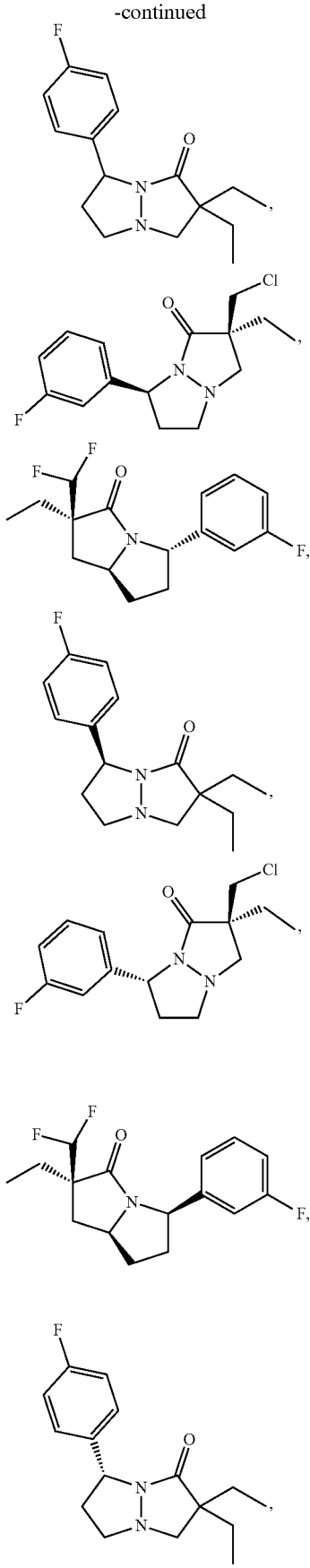
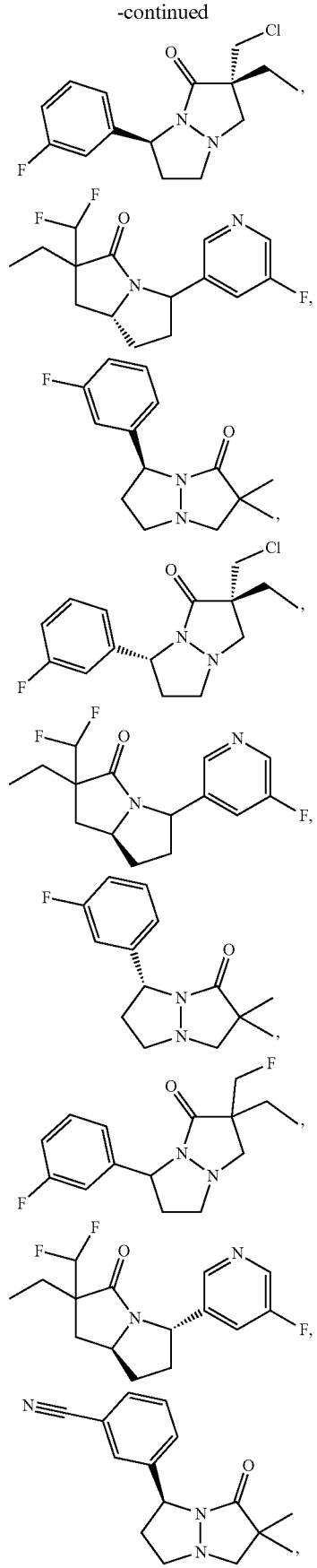

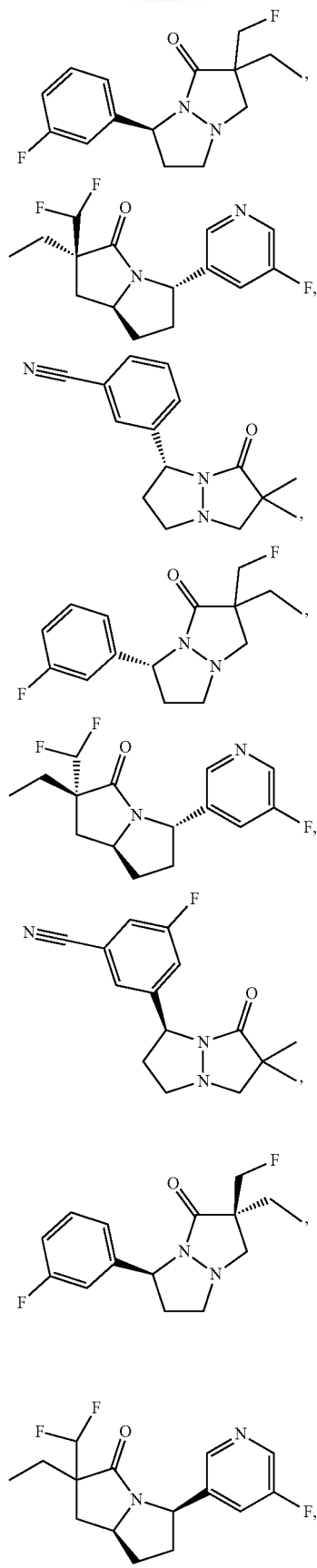
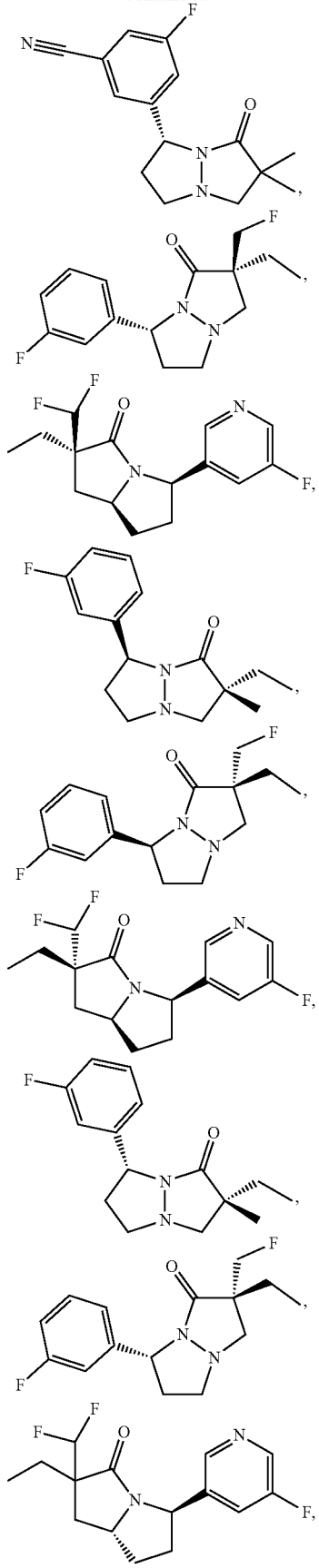

185
-continued
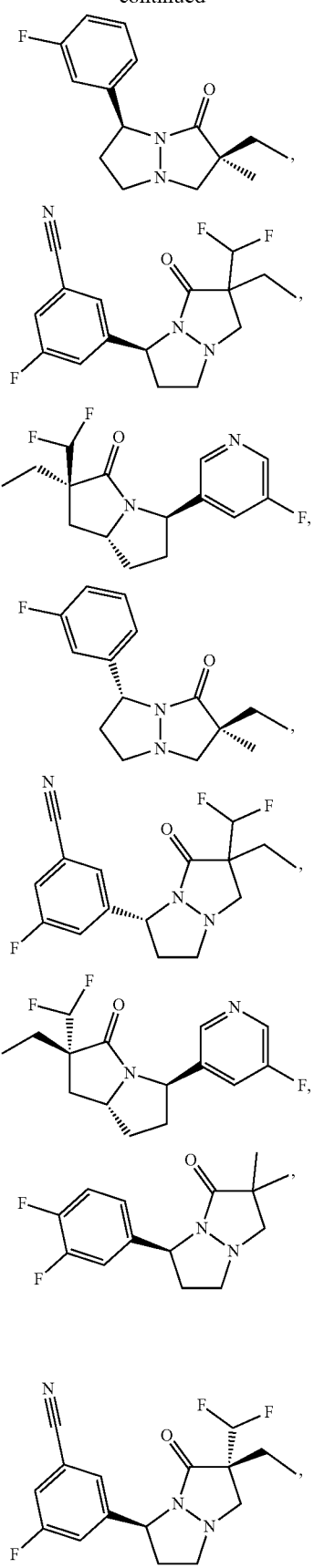
186
-continued
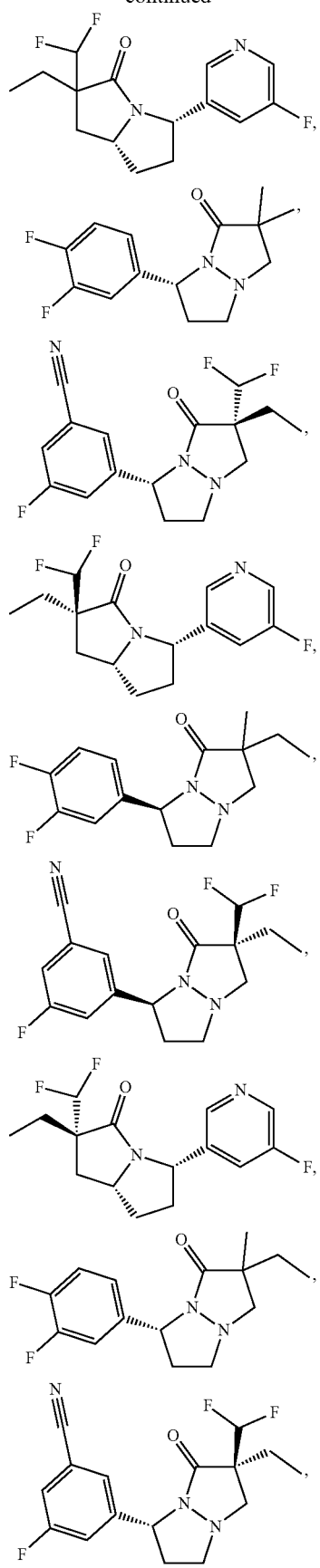

187
-continued
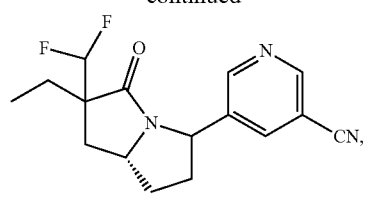
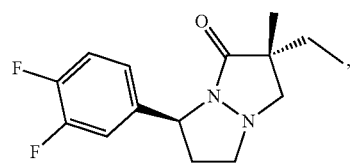
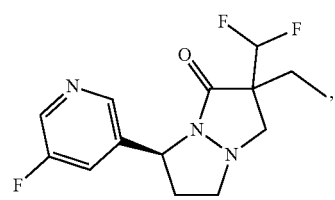
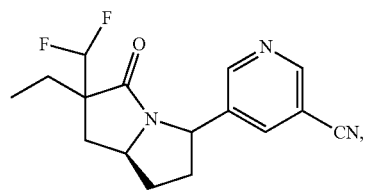
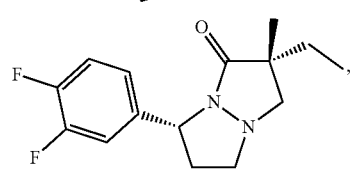
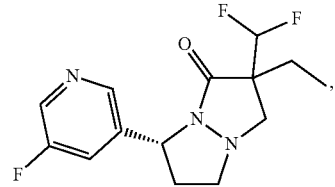
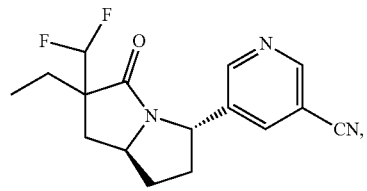
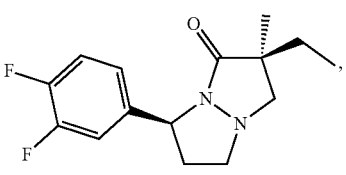
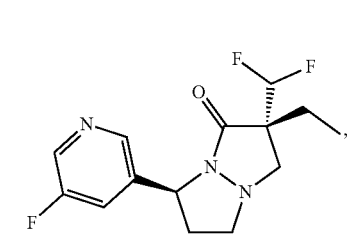
188
-continued
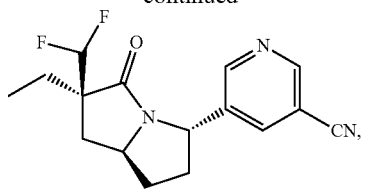
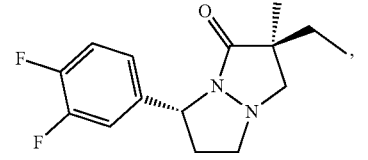
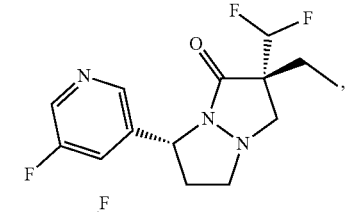
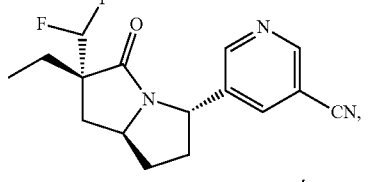
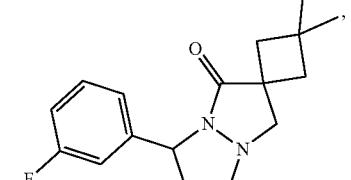
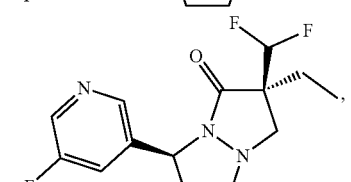
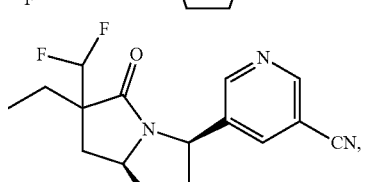
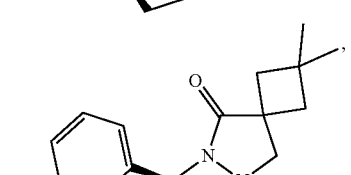
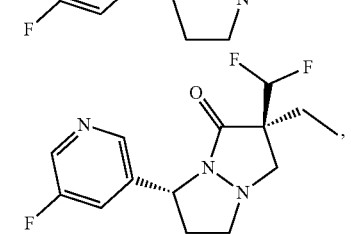

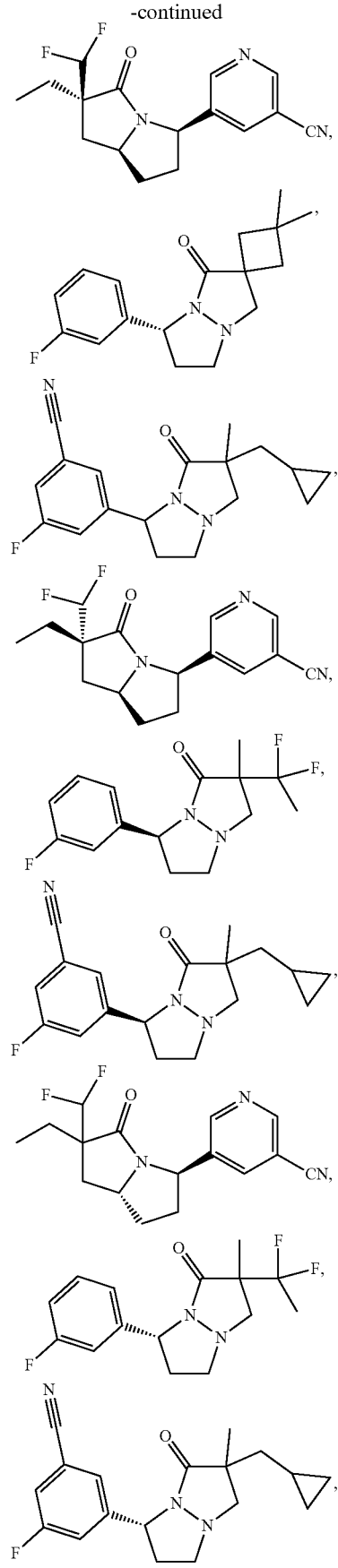
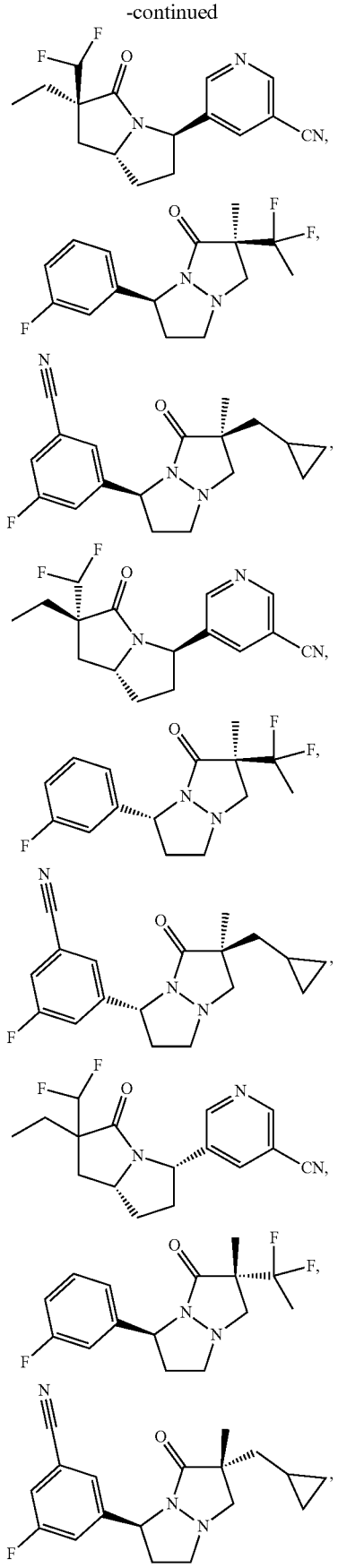

191
-continued
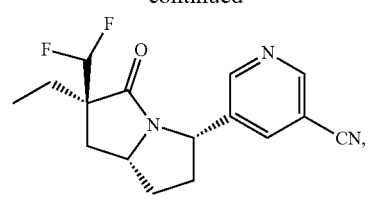
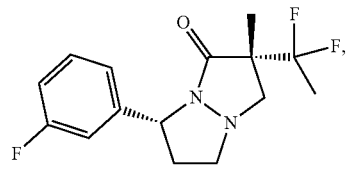
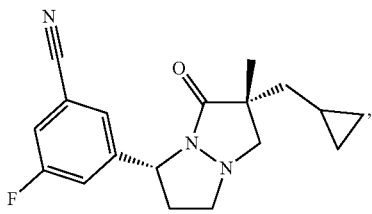
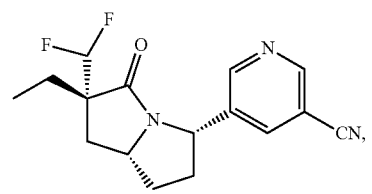
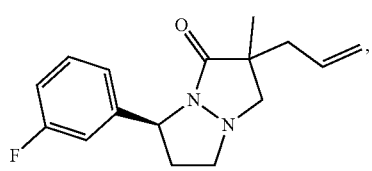
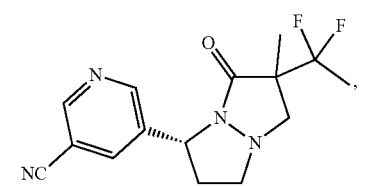
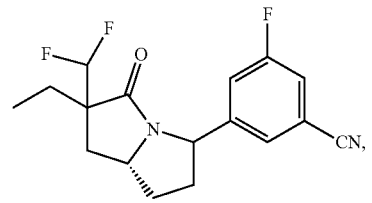
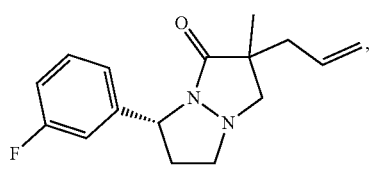
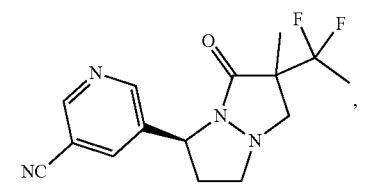
192
-continued
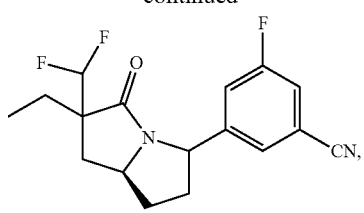
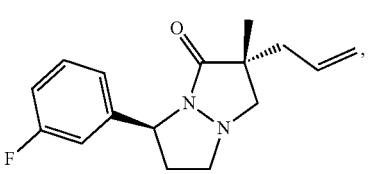
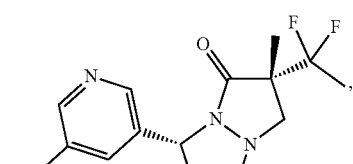
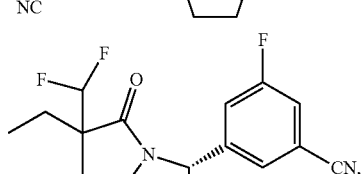
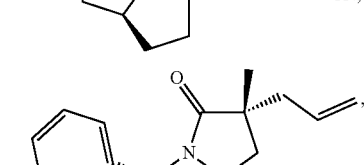
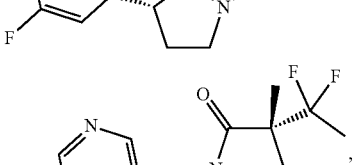
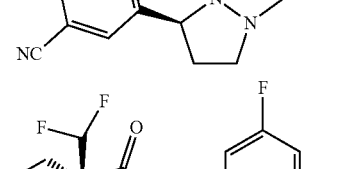
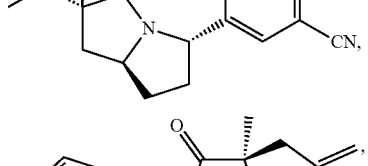
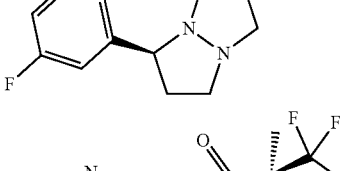
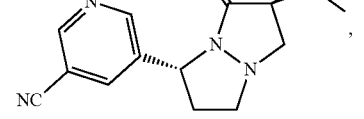

193
-continued
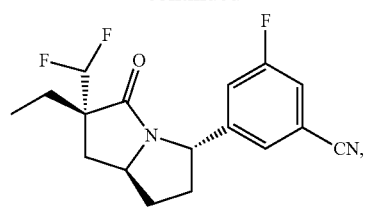
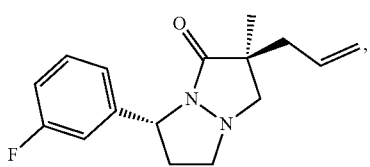
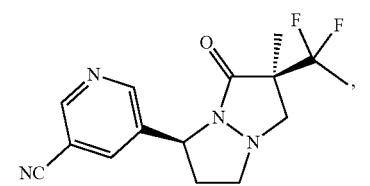
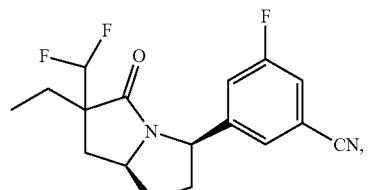
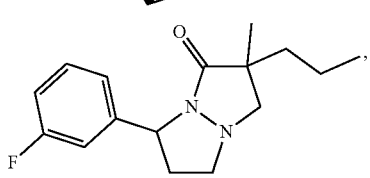
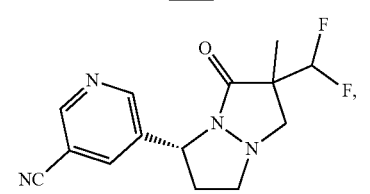
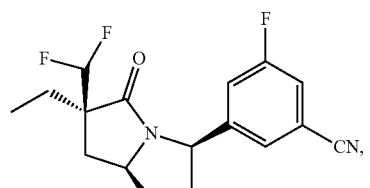
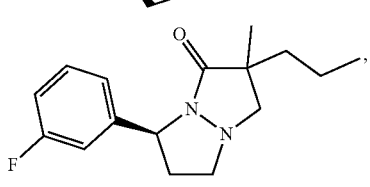
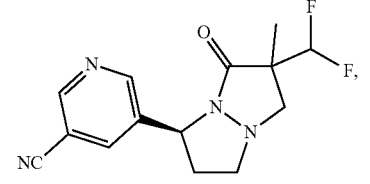
194
-continued
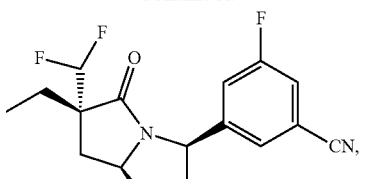
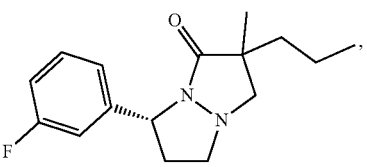
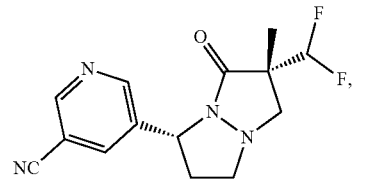
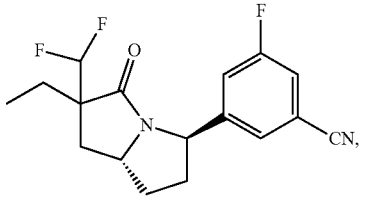
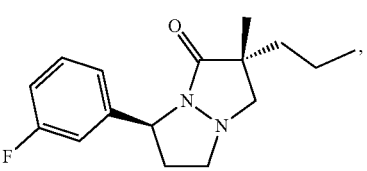
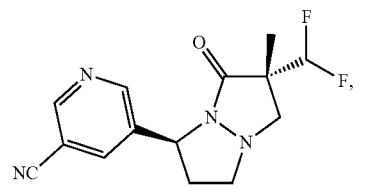
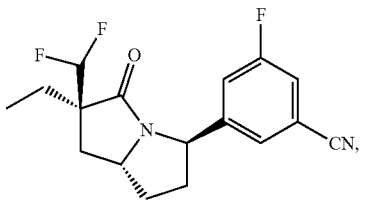
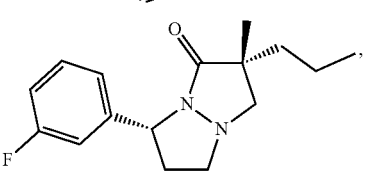
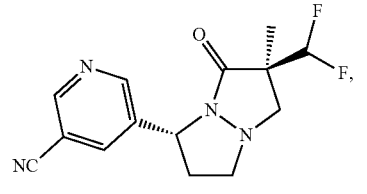

-continued
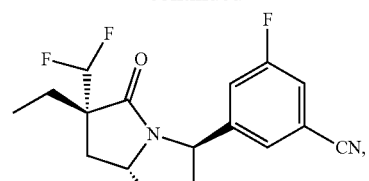
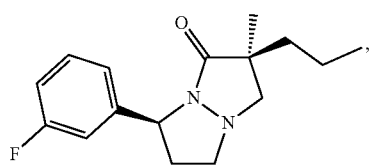
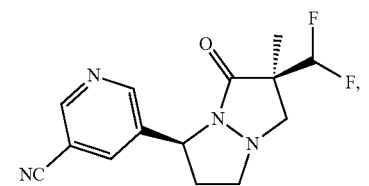
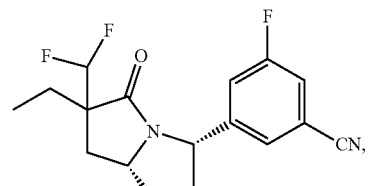
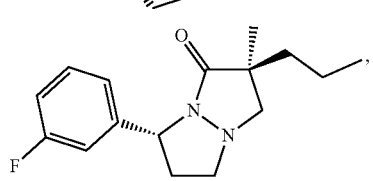
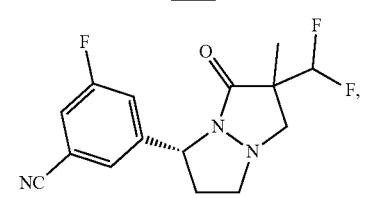
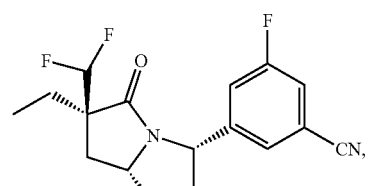
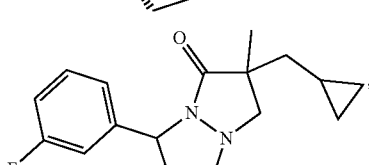
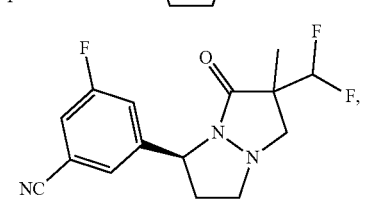
-continued
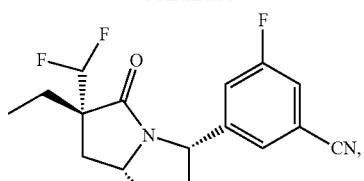
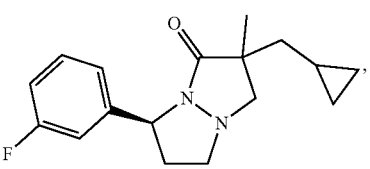
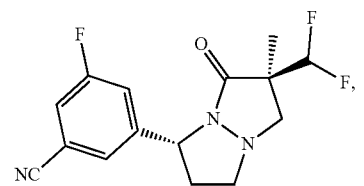
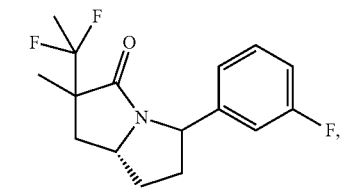
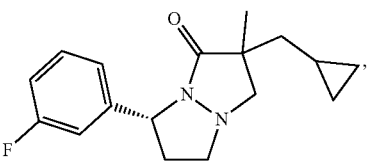
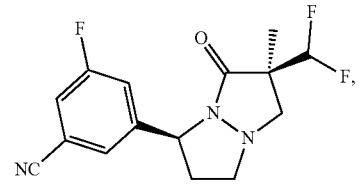
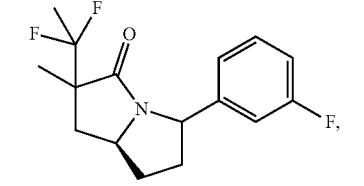
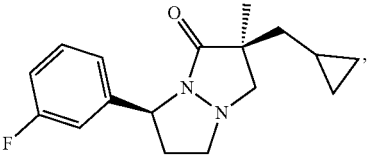
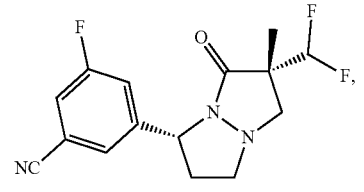

197
-continued
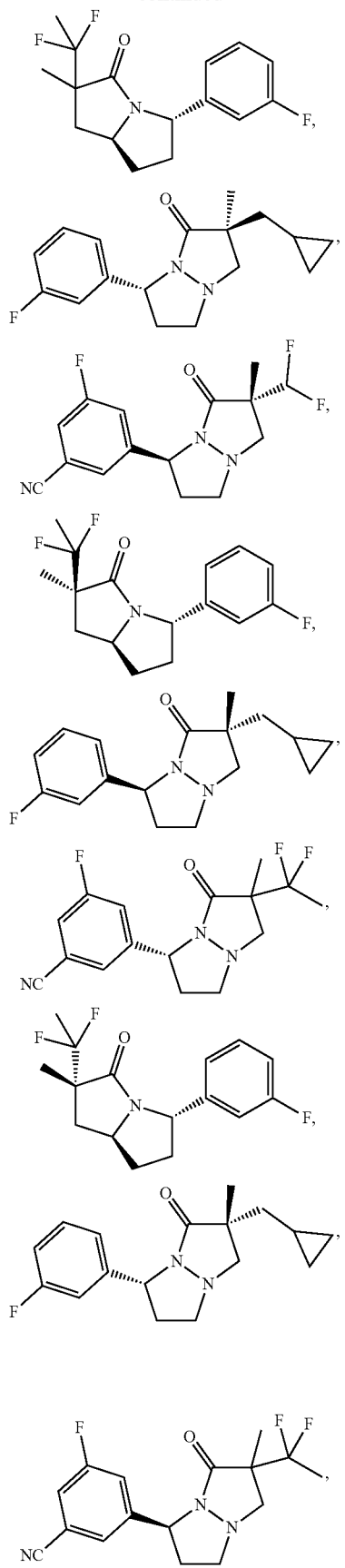
198
-continued
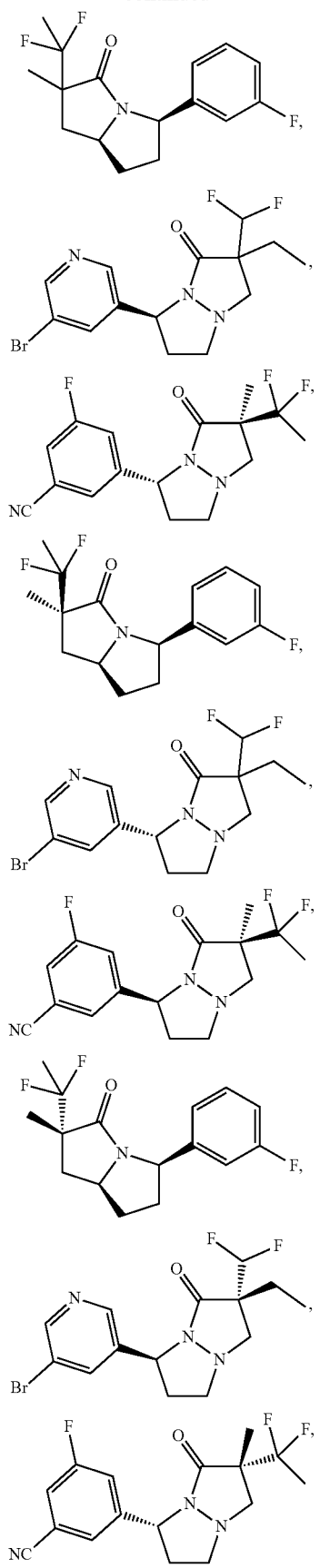

199
-continued
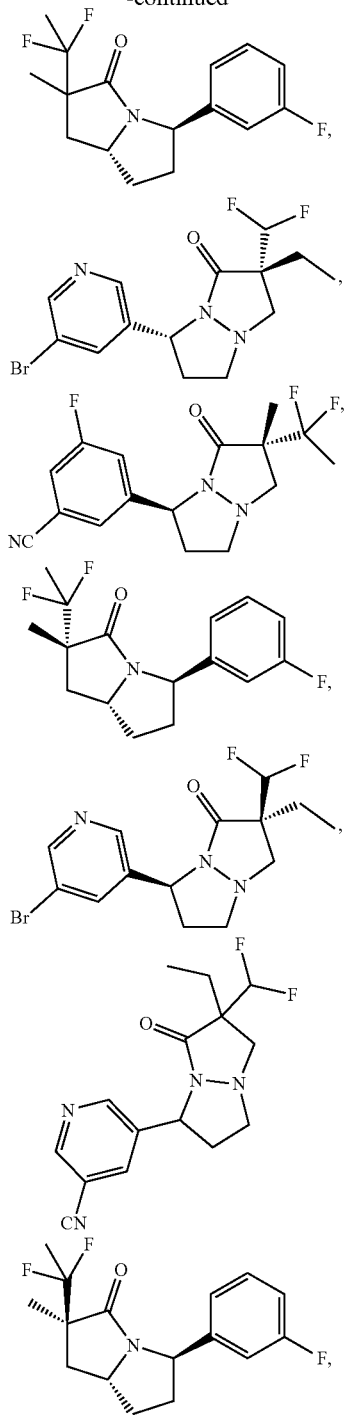
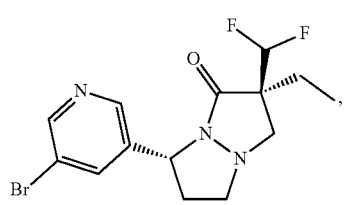
second eluting enantiomer,
200
-continued
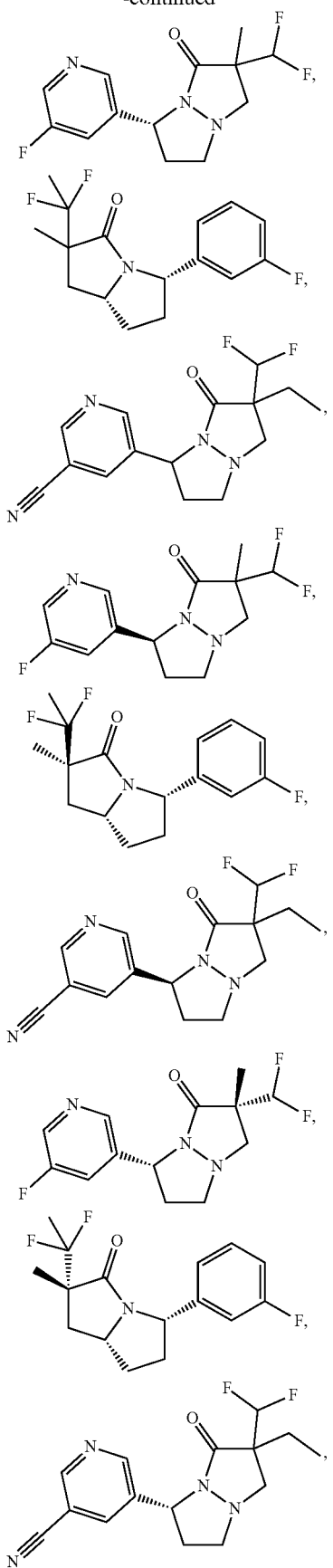

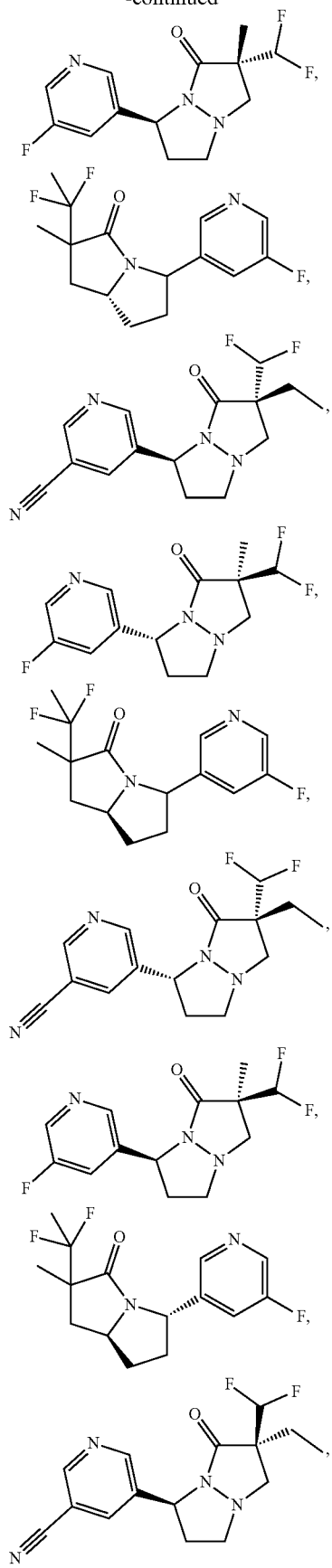
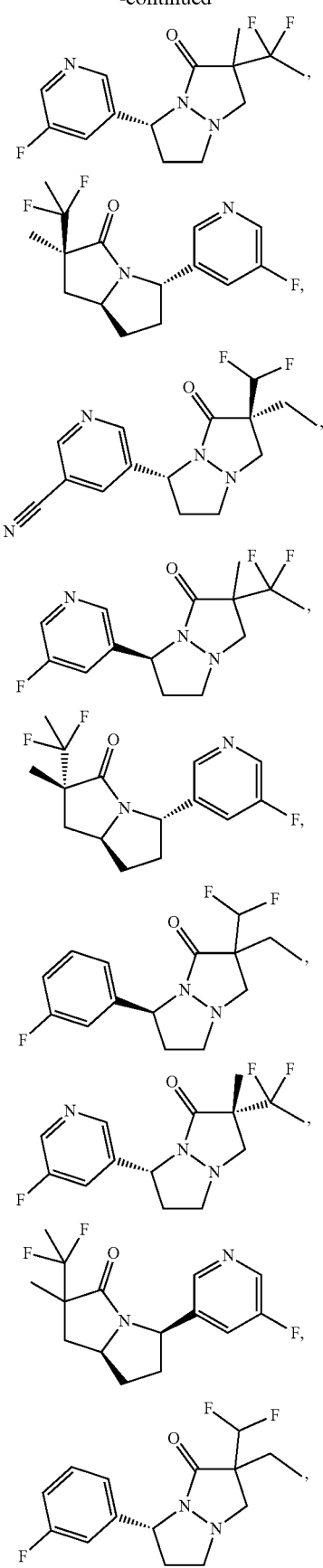

203
-continued
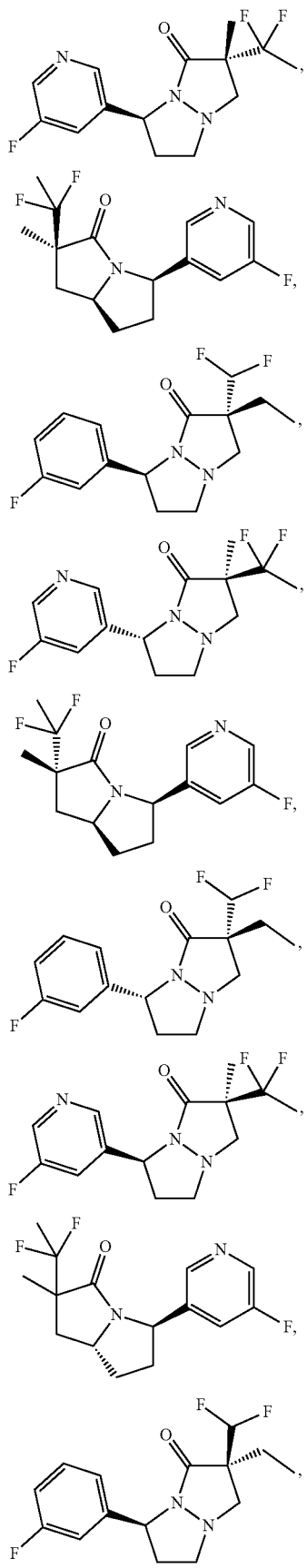
204
-continued
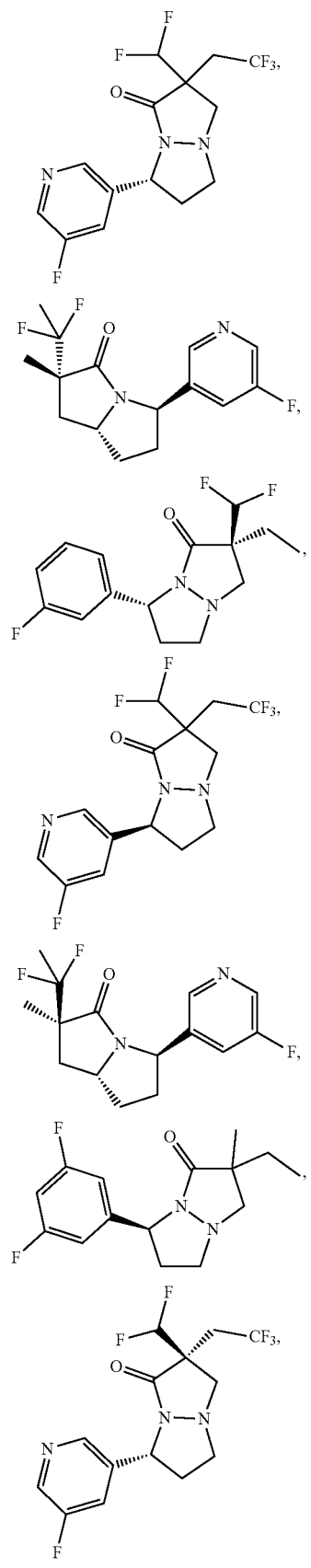

205
-continued
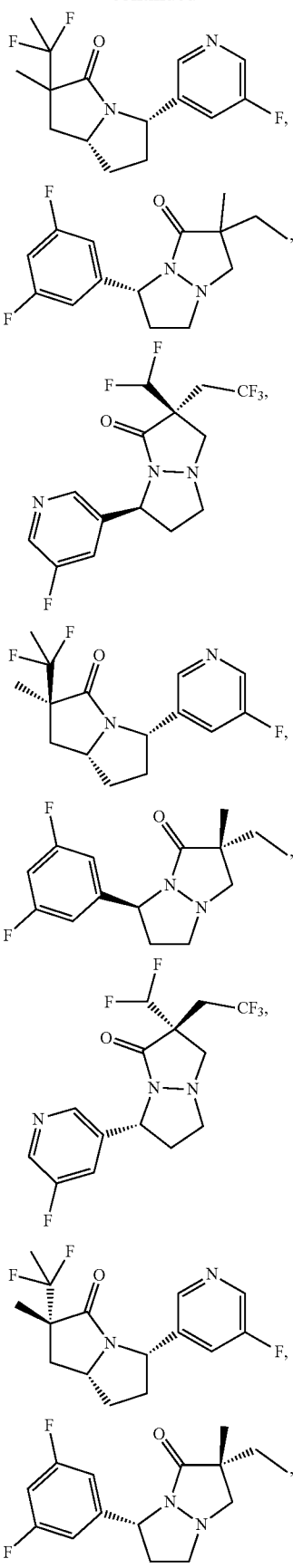
206
-continued
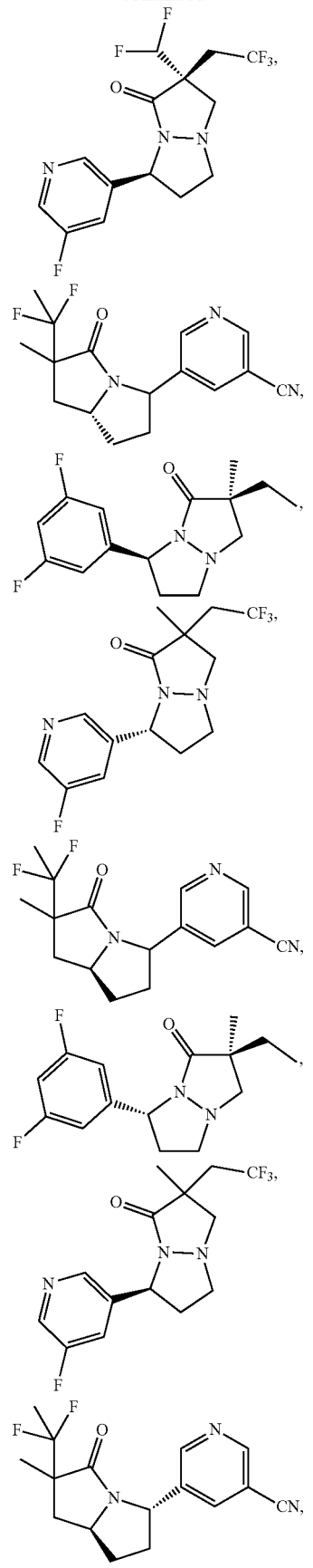

207
-continued
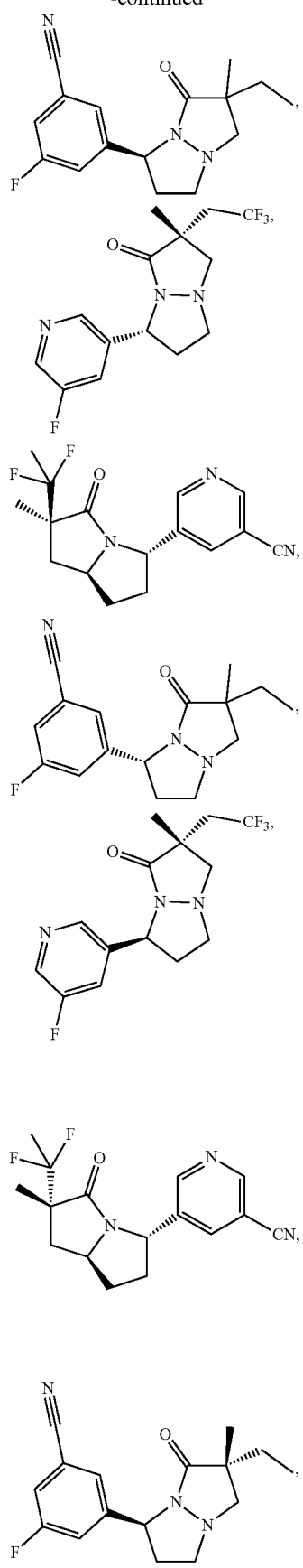
208
-continued
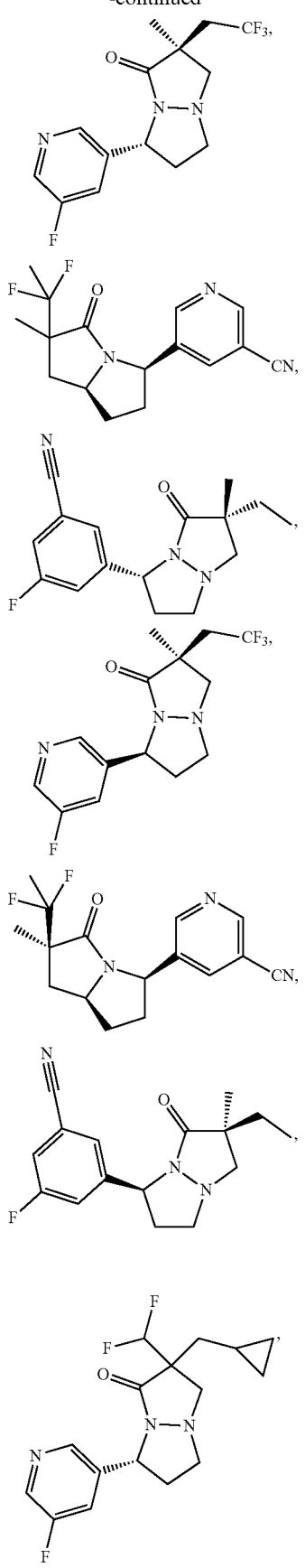

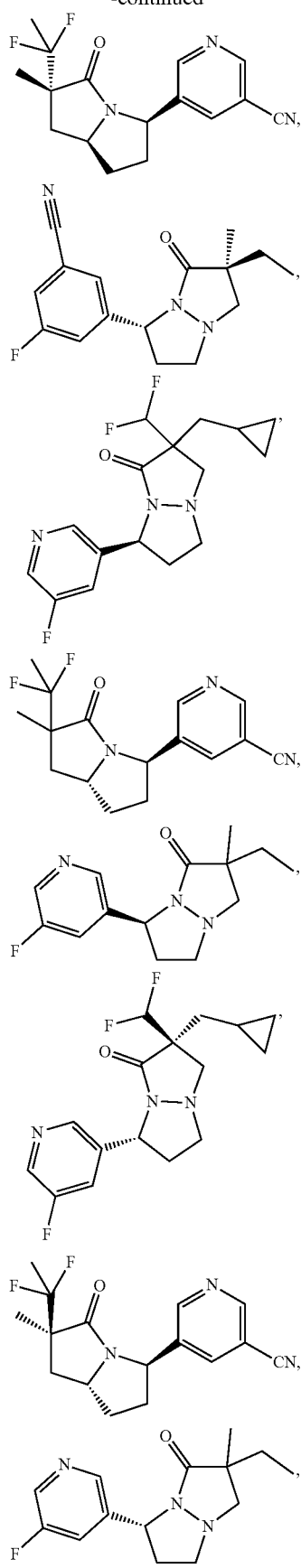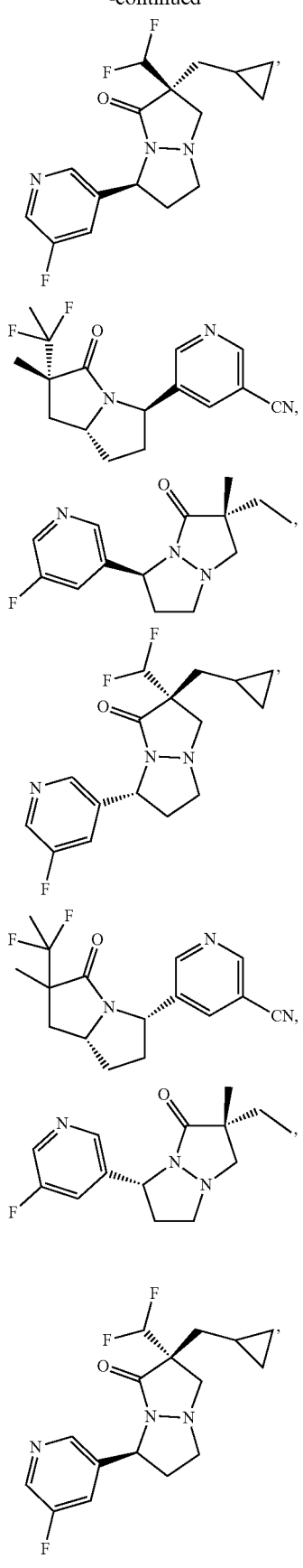

-continued
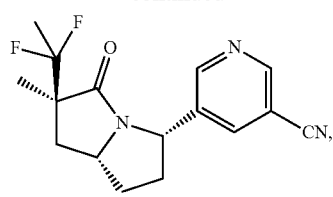
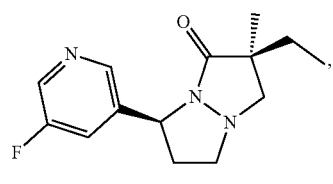
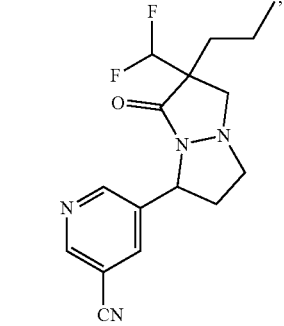
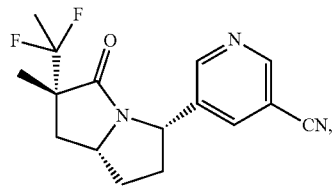
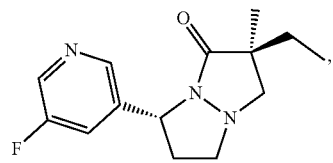
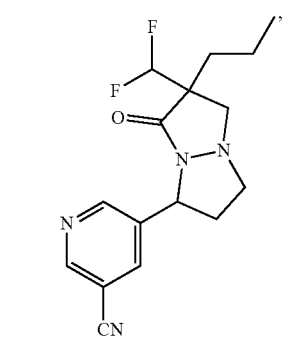
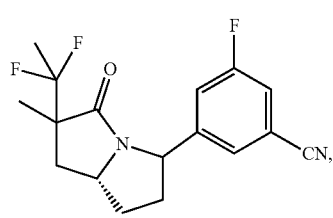
-continued
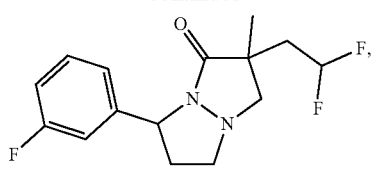
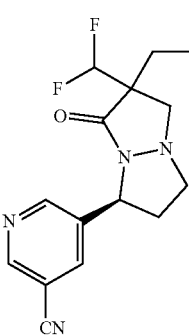
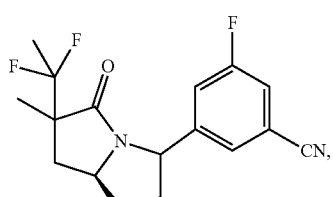
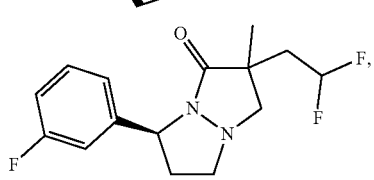
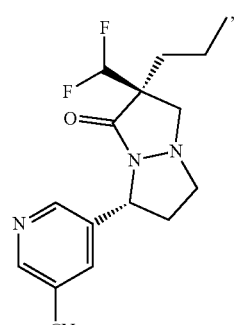
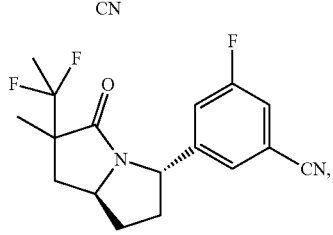
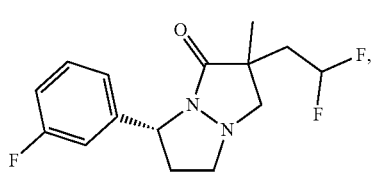

213
-continued
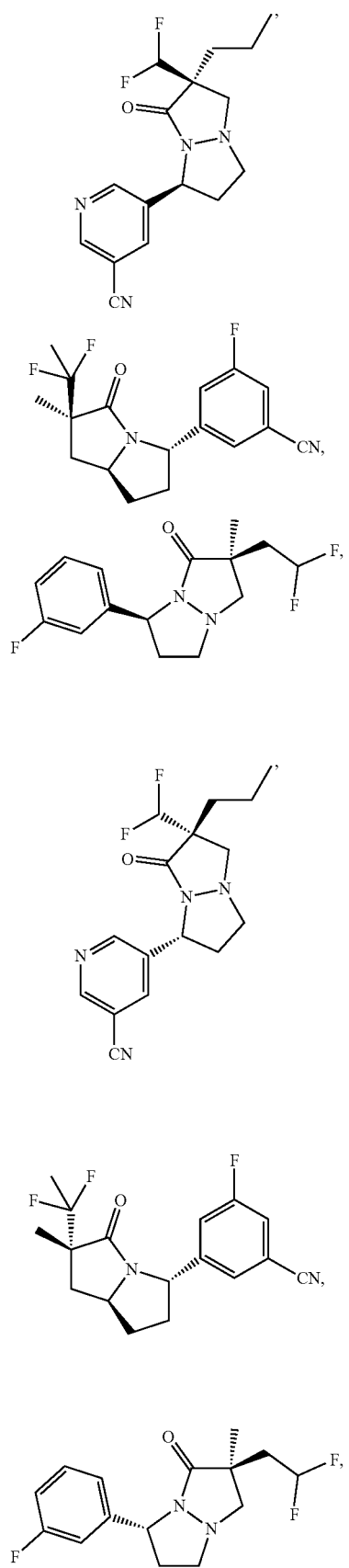
214
-continued
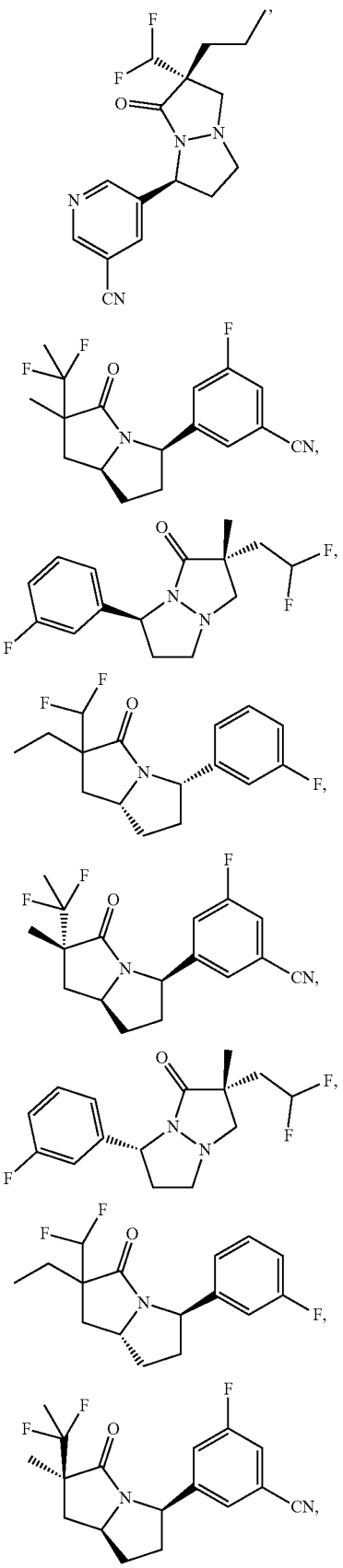

215
-continued
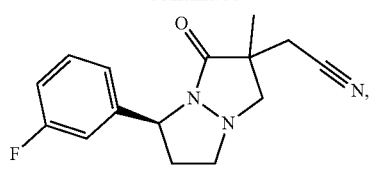
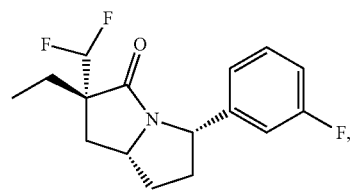
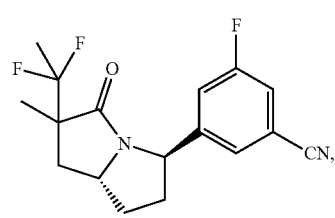
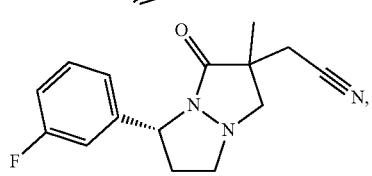
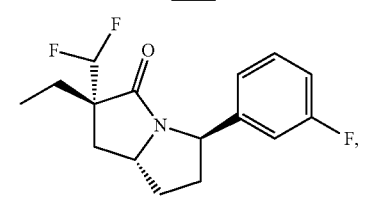
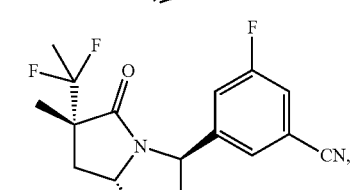
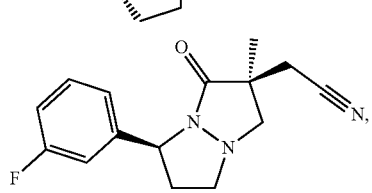
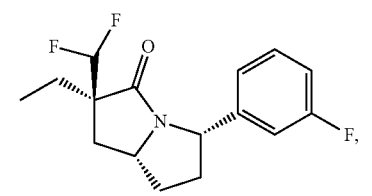
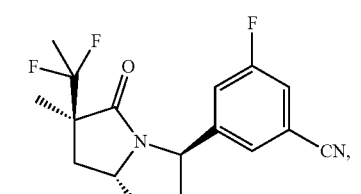
216
-continued
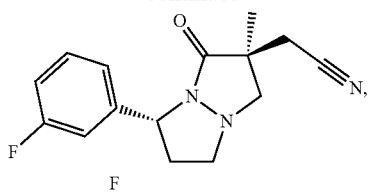
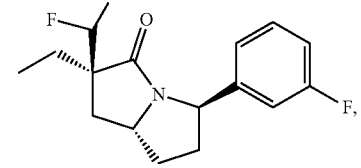
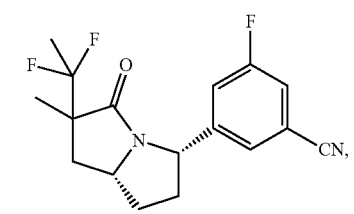
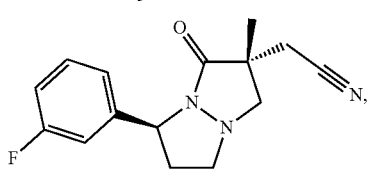
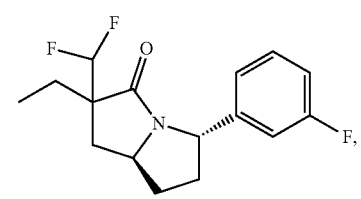
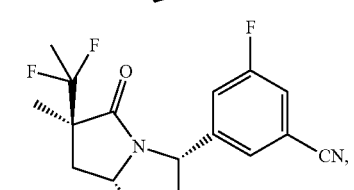
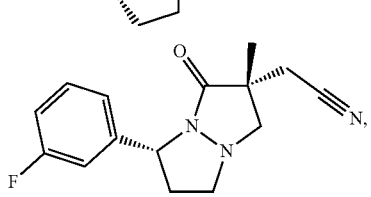
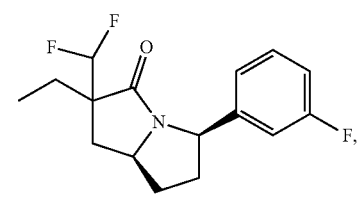
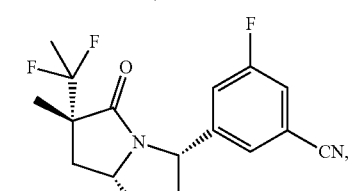

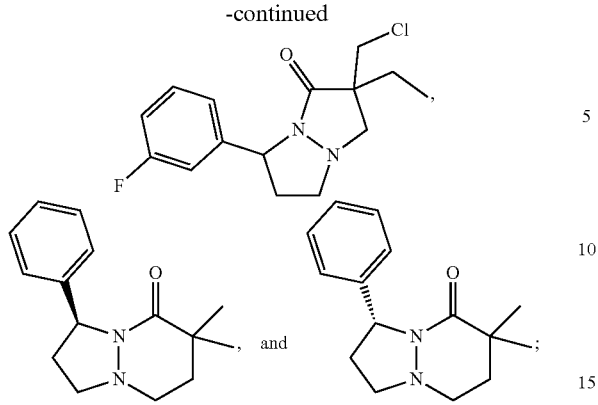
and pharmaceutically acceptable salts, stereoisomers, and mixtures of stereoisomers thereof.
17. A pharmaceutical composition comprising a pharmaceutically acceptable carrier and a compound of claim 1.
* * * * *